United States Patent
Qiao et al.

(10) Patent No.: US 9,493,412 B2
(45) Date of Patent: *Nov. 15, 2016

(54) PYRROLINONE CARBOXAMIDE COMPOUNDS USEFUL AS ENDOTHELIAL LIPASE INHIBITORS

(71) Applicant: BRISTOL-MYERS SQUIBB COMPANY, Princeton, NJ (US)

(72) Inventors: Jennifer X. Qiao, Princeton, NJ (US); Heather Finlay, Skillman, NJ (US); Ji Jiang, West Windsor, NJ (US); John Lloyd, Yardley, PA (US); Carol Hui Hu, New Hope, PA (US); Zulan Pi, Pennington, NJ (US); George O. Tora, Langhorne, PA (US); James Neels, Newtown, PA (US); Jon J. Hangeland, Morrisville, PA (US); Todd J. Friends, Bordentown, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/346,751

(22) PCT Filed: Sep. 24, 2012

(86) PCT No.: PCT/US2012/056824
§ 371 (c)(1),
(2) Date: Mar. 24, 2014

(87) PCT Pub. No.: WO2013/048928
PCT Pub. Date: Apr. 4, 2013

(65) Prior Publication Data
US 2014/0228321 A1 Aug. 14, 2014

Related U.S. Application Data

(60) Provisional application No. 61/539,643, filed on Sep. 27, 2011.

(51) Int. Cl.
| | | |
|---|---|---|
| *C07D 207/38* | (2006.01) | |
| *C07D 409/12* | (2006.01) | |
| *C07D 471/04* | (2006.01) | |
| *C07D 401/12* | (2006.01) | |
| *C07D 413/12* | (2006.01) | |
| *C07D 417/12* | (2006.01) | |
| *C07D 403/12* | (2006.01) | |
| *C07D 401/04* | (2006.01) | |
| *C07D 405/12* | (2006.01) | |
| *C07F 7/08* | (2006.01) | |

(52) U.S. Cl.
CPC ........... *C07D 207/38* (2013.01); *C07D 401/04* (2013.01); *C07D 401/12* (2013.01); *C07D 403/12* (2013.01); *C07D 405/12* (2013.01); *C07D 409/12* (2013.01); *C07D 413/12* (2013.01); *C07D 417/12* (2013.01); *C07D 471/04* (2013.01); *C07F 7/0812* (2013.01)

(58) Field of Classification Search
None
See application file for complete search history.

(56) References Cited

U.S. PATENT DOCUMENTS

| | | | |
|---|---|---|---|
| 6,727,275 B2 | 4/2004 | Zou et al. | |
| 6,936,633 B2 | 8/2005 | Zou et al. | |
| 7,109,186 B2 * | 9/2006 | Walker et al. | 514/91 |
| 7,179,839 B2 * | 2/2007 | Strobel | C07C 233/58 514/465 |
| 7,217,727 B2 | 5/2007 | Eacho et al. | |
| 7,595,403 B2 | 9/2009 | Eacho et al. | |
| 8,952,180 B2 * | 2/2015 | Abell | C07D 403/12 546/112 |
| 2004/0229909 A1 | 11/2004 | Kiyama et al. | |
| 2005/0004180 A1 | 1/2005 | Zou et al. | |
| 2006/0211755 A1 | 9/2006 | Eacho et al. | |
| 2006/0281949 A1 | 12/2006 | Weber et al. | |
| 2008/0287448 A1 | 11/2008 | Zoller et al. | |
| 2009/0054478 A1 | 2/2009 | Zoller et al. | |
| 2009/0076068 A1 | 3/2009 | Zoller et al. | |
| 2010/0105719 A1 | 4/2010 | Zoller et al. | |

FOREIGN PATENT DOCUMENTS

| | | |
|---|---|---|
| DE | 19535842 A1 | 3/1997 |
| WO | WO99/32611 A1 | 7/1999 |

(Continued)

OTHER PUBLICATIONS

Bevilacqua, M. et al., "Selectins", J. Clinical Invest., vol. 91, pp. 379-387 (1993).

(Continued)

*Primary Examiner* — Rita Desai
*Assistant Examiner* — Ben S Michelson
(74) *Attorney, Agent, or Firm* — Jing G. Sun; Barry H. Jacobsen; Yong Lu

(57) ABSTRACT

The present invention provides compounds of Formula (I): (I), as defined in the specification and compositions comprising any of such novel compounds. These compounds are endothelial lipase inhibitors which may be used as medicaments.

(I)

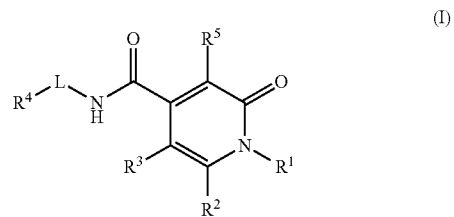

7 Claims, No Drawings

(56) References Cited

FOREIGN PATENT DOCUMENTS

| WO | WO 02/064545 A1 | 8/2002 |
|---|---|---|
| WO | WO03/030897 A1 | 4/2003 |
| WO | WO 2004/004657 A2 | 1/2004 |
| WO | WO2004/093872 A1 | 11/2004 |
| WO | WO2004/094393 A1 | 11/2004 |
| WO | WO2004/094394 A1 | 11/2004 |
| WO | WO2007/042178 A1 | 4/2007 |
| WO | WO2007/110215 A1 | 10/2007 |
| WO | WO2007/110216 A1 | 10/2007 |
| WO | WO2009/123164 A1 | 10/2009 |
| WO | WO2009/133834 A1 | 11/2009 |

OTHER PUBLICATIONS deLemos, A. et al., "Identification of Genetic Variants in Endothelial Lipase in Persons With Elevated High-Density Lipoprotein Cholesterol", Circulation, vol. 106, pp. 1321-1326 (2002).
Emerson, D. et al., "Ring Opening Reactions of 6-Oxo-substituted Spiro-pyrrolidinediones: Synthesis of 4-Substituted-1,5-Dihydro-3-Hydroxy-2-oxo-1,5-diphenyl-2H-pyrroles", J. Heterocyclic Chem., vol. 35, pp. 611-617 (1998).
Folkman, J. et al., "Angiogenic Factors", Science, vol. 235, pp. 442-447 (1987).
Folkman, J. et al., "Angiogenesis" *Minireview*. The J. of Biological Chemistry, vol. 267(16) pp. 10931-10934 (1992).
Gein, V.L. et al., "Five-Membered 2, 3-Dioxoheterocycles. XXI.* Synthesis of 1, 5-Diaryl-4-Tert-Butoxycarbonyl-3-Hydroxy-2, 5-Dihydro-2-Pyrrolones and Their Reaction with Arylamines and o-Phenylenediamine", Russian J. of General Chemistry, vol. 62(8) pp. 1722-1729 1992.
Gein, V.L. et al., "Five-Membered 2,3-Dioxo Heterocycles.21.* Reaction of 1,5-Diaryl-4-Ethoxycarbonyl-tetrahydropyrrole-2,3-diones with 2-aminopyridine", Russian J. of General Chemistry, vol. 62(8), pp. 27-30 (1992).
Gein, V.L. et al., "Five-Membered 2,3-Dioxoheterocycles. XXII.* Reactions of 1,5-Diaryl-3-Hydroxy-2-Oxo-3-Pyrroline-4-Carboxylic Acids and their Functional Derivatives with Diphenyldiazomethane and the Thermolysis of Products of the Reactions", Russian J. of General Chemistry, vol. 62(8), pp. 1559-1564 (1992).
Gein, V.L. et al., "Five-Membered 2,3-Dioxoheterocycles XXX. Cyclization of 1,5-Diaryl- and 1-Methyl-5-Phenyl-4-Ethoxalylacetyltetrahydropyrrole-2,3-Diones and Their Arylamino Derivatives", Russian J. of General Chemistry, vol. 62(8), pp. 1710-1715 (1992).
Gein, V.L. et al., "Five-Membered 2,3-Dioxoheterocycles. XXXI.* Reactions of 1,5-Diaryl-3-Hydroxy-4-*tert*-Butoxycarbonyl-3-Pyrrolin-2-ones with Hydrazine Derivatives", Russian J. of General Chemistry, vol. 63(10), pp. 1613-1616 (1993).
Gordon, D.J. et al., "High-Density Lipoprotein-The Clinical Implications of Recent studies", New England J. of Medicine, vol. 321(19), pp. 1311-1316 (1989).
Gordon, D.J. et al., "High-Density Lipoprotein Cholesterol and Cardiovascular Disease", Circulation, vol. 79, pp. 8-15 (1989).
Hirata, K. et al., "Cloning of a Unique Lipase from Endothelial Cells Extends the Lipase Gene Family", The J. of Biological Chemistry, vol. 274(20), pp. 14170-14175 (1999).
Janssens, S.P. et al., "Cloning and Expression of a cDNA Encoding Human Endothelium-derived Relaxing Factor/Nitric Oxide Synthase", The J. of Biological Chemistry, vol. 267(21), pp. 14519-14522 (1992).
Jaye, M. et al., "A novel endothelial-derived lipase that modulates HDL metabolism", Nature Genetics, vol. 21, pp. 424-428 (1999).
Jin, W. et al., "Lipases and HDL metabolism" TRENDS in Endocrinology& Metabolism, vol. 13(4), pp. 174-178 (2002).
Kadin, Saul B., "Synthesis and Antiinflammatory Properties of N-Substituted 4,5-Dioxopyrrolidine-3-carboxanilides", J. of Medicinal Chemistry, vol. 19 (1), pp. 172-173 (1976).
Lamas, S. et al., "Endothelial nitric oxide synthase: Molecular cloning and characterization of a distinct constitutive enzyme isoform", PNAS, vol. 89, pp. 6348-6352 (1992).
Lüscher, T.F. et al., "Endothelium-Derived Contracting Factors", Hypertension, vol. 19, pp. 117-130 (1992).
McCoy, M.G. et al., "Characterization of the lipolytic activity of endothelial lipase", Journal of Lipid Research, vol. 43, pp. 921-929 (2002).
Pace, P. et al., "4-Hydroxy-5-pyrrolinone-3-carboxamide HIV-1 integrase inhibitors", Bioorganic & Medicinal Chemistry Letters, vol. 18, pp. 3865-3869 (2008).
Ross, R., "The pathogenesis of atherosclerosis: a perspective for the 1990s" Nature, vol. 362(80), pp. 801-809 (1993).
Saalfrank, R. W. et al., "Synthesis and Reactions of 4-Acyl/Carbamoyl-N-aryl-3-chloro-pyrrol-2,5-diones: Crystal Structure of a Supramolecular Ribbon Based on Hydrogen Bonds [1]", Z. Naturforsch, vol. 51, pp. 1084-1098 (1996).
Southwick, P.L. et al., "1-Carbamoyl- and 1-Aminomethyl-1, 4-dihydropyrrolo[3,4-b]indole Derivatives. Indole Formation by Fragmentation of Strain-Barrier Stabilized 2-Aminoindoline Derivatives", J. of Organic Chemistry, vol. 33(5), pp. 2051-2056 (1968).
Strauss, J.G. et al., "Endothelial cell-derived lipase mediates uptake and binding of high-density lipoprotein (HDL) particles and the selective uptake of HDL-associated cholesterol esters independent of its enzymic activity", Biochem. J., vol. 368, pp. 69-79 (2002).
Sugden, J.K. et al., "Antiinflammatory activity of some N-substituted-3-carboxamido-4-hydroxy-5-oxo-3-pyrrolines", Eur. J. Med. Chem-Chimica Therapeutica, vol. 14(2), pp. 189-190 (1979).
Wei, Han-Xun et al., "Experimental Support for Planar Pseudopericyclic Transition States in Thermal Cheletropic Decarbonylations", Organic Letters, vol. 6(23), pp. 4289-4292 (2004).
Williams, T.J. et al., "Adhesion Molecules Involved in the Microvascular Inflammatory Response", Am Rev. Respir. Disease, vol. 146, pp. S45-S50 (1992).
Wong, H. et al., "The lipase gene family", Journal of Lipid Research, vol. 43, pp. 993-999 (2002).
Vaughan, W. et al., "1,5-Diaryl-2,3-pyrrolidinediones. XII. Enamines and the Pseudo-pyrrolidinediones", J. of the American Chemical Society, vol. 82 (16), pp. 4370-4376 (1960).
Yanagisawa, M. et al., "A novel potent vasoconstrictor peptide produced by vascular endothelial cells", Nature, vol. 332, pp. 411-415 (1988).

* cited by examiner

PYRROLINONE CARBOXAMIDE COMPOUNDS USEFUL AS ENDOTHELIAL LIPASE INHIBITORS

CROSS-REFERENCE TO RELATED APPLICATIONS

The present application is a 371 application of PCT/US2012/056824 filed Sep. 24, 2012, which claims priority benefit of U.S. Provisional Application Ser. No. 61/539,643, filed Sep. 27, 2011; each of which is fully incorporated by reference herein.

FIELD OF THE INVENTION

The present invention provides novel pyrrolinone carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, *Nature*, 362(80):1-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon et al., *N. Engl. J. Med.*, 321:1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin et al., *Trends Endocrinol. Metab.*, 13:174-178 (2002); Wong et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata et al., *J. Biol. Chem.*, 274:14170-14175 (1999); Jaye et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides novel pyrrolinone carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

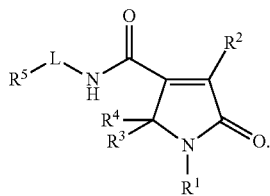

(I)

In a first embodiment of the first aspect, the present disclosure provides a compound of Formula (I), or a stereoisomer, a tautomer, a pharmaceutically acceptable salt, or a solvate thereof, wherein:

$R^1$ is independently selected from the group consisting of: H, $C_{1-6}$ alkyl substituted with 0-3 $R^a$, $C_{2-6}$ alkenyl substituted with 0-3 $R^a$, and —$(CH_2)_n$—W—$(CH_2)_m$—$R^{1a}$;

W is independently selected from the group consisting of: a bond, NH, O, S, N($C_{1-4}$ alkyl), CO, CONH, CON($C_{1-4}$ alkyl), NHCO, $SO_2$, $NHSO_2$, $SO_2NH$, $NHCO_2$, and $CHR^f$;

$R^{1a}$ is independently selected from the group consisting of: $C_{3-10}$ carbocycle and a 5- to 10-membered heterocycle comprising: carbon atoms and 1-4 heteroatoms selected from N, $NR^e$, O, and $S(O)_p$; and wherein said carbocycle and heterocycle are substituted with 0-3 $R^c$;

$R^2$ is independently selected from the group consisting of: $OR^6$, CN, and $NR^7R^8$;

$R^3$ is independently selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, —$CO_2(C_{1-4}$ alkyl), —$SO_2$(phenyl), —$(CH_2)_n$—($C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^4$ is independently selected from the group consisting of: H and $C_{1-4}$ alkyl;

$R^5$ is independently selected from the group consisting of: $C_{3-10}$ carbocycle and a 5- to 10-membered heterocycle comprising: carbon atoms and 1-4 heteroatoms selected from N, $NR^e$, O, and $S(O)_p$; wherein said carbocycle and heterocycle are substituted with 0-3 $R^d$;

$R^6$ is independently selected from the group consisting of: H and $C_{1-6}$ alkyl substituted with 0-1 $CO_2H$;

$R^7$ is independently selected from the group consisting of: H, $C_{1-6}$ alkyl substituted with 0-1 $R^a$, —$(CH_2)_n$-(phenyl substituted with 0-3 $R^b$), and —$(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: H and $C_{1-6}$ alkyl;

alternatively, $NR^7R^8$ is a 5- to 6-membered heterocycle comprising: carbon atoms and 1-4 heteroatoms selected from N, $NR^e$, O, and $S(O)_p$;

L is $X_1$—Y—$X_2$;

$X_1$, and $X_2$ are, independently at each occurrence, selected from the group consisting of: a bond, a hydrocarbon linker and a hydrocarbon-heteroatom linker;

wherein said hydrocarbon linker and hydrocarbon-heteroatom linker may be substituted with 0-2 $R^g$; said hydrocarbon linker has one to five carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-10}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from the group consisting of: halogen, OH, $C_{1-4}$ alkyl, $C_{1-4}$ haloalkyl, and $C_{1-4}$ alkyoxy;

alternatively, $R^4$-L- is

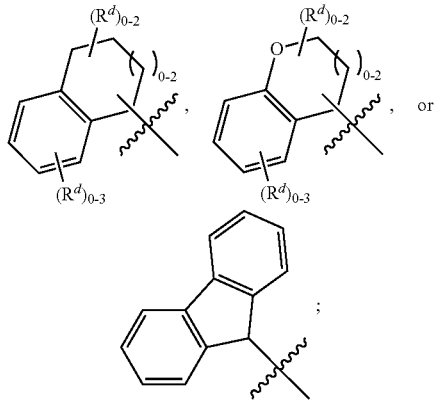

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, NH($C_{1-4}$ alkyl), N($C_{1-4}$ alkyl)$_2$, $CO_2H$, $CO_2(C_{1-4}$ alkyl), NHCO($C_{1-4}$ alkyl substituted with 0-1 $NH_2$), N($C_{1-4}$ alkyl)CO($C_{1-4}$ alkyl), $NHCO_2(C_{1-4}$ alkyl), $CONHSO_2(C_{1-4}$ alkyl), $SO_2(C_{1-4}$ alkyl), $CONH_2$, CONH($C_{1-4}$ alkyl), $NHSO_2(C_{1-4}$ alkyl), N($C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, NH($C_{1-4}$ alkyl), N($C_{1-4}$ alkyl)$_2$, $CO_2H$, $CO_2(C_{1-4}$ alkyl), $CONH_2$, CONH($C_{1-4}$ alkyl), CON($C_{1-4}$ alkyl)$_2$, $NHCO_2(C_{1-4}$ alkyl), $NHSO_2(C_{1-4}$ alkyl), N($C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, NH($C_{1-4}$ alkyl), N($C_{1-4}$ alkyl)$_2$, $CO_2H$, $CO_2(C_{1-4}$ alkyl), CO($C_{1-4}$ alkyl), NHCO($C_{1-4}$ alkyl), —$CH_2NHCO$($C_{1-4}$ alkyl), $CONH_2$, CONH($C_{1-4}$ alkyl), CON($C_{1-4}$ alkyl)$_2$, $SO_2(C_{1-4}$ alkyl), $SO_2NH_2$, —$SO_2NH(C_{1-4}$ alkyl), —$SO_2NH$($C_{3-6}$ cycloalkyl), —$NHSO_2(C_{1-4}$ alkyl), —$CH_2NHSO_2$($C_{1-4}$ alkyl), Si($C_{1-4}$ alkyl)$_3$, and phenyl optionally substituted with one or two substituents independently selected from: halogen, OH, $C_{1-4}$ alkyl, $C_{1-4}$ haloalkyl, $C_{1-4}$ alkyoxy, and NHCO($C_{1-4}$ alkyl);

$R^e$ is, independently at each occurrence, selected from the group consisting of: H, $C_{1-4}$ alkyl, CO($C_{1-4}$ alkyl), $CO_2(C_{1-4}$ alkyl), $CO_2$(benzyl), and —$(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

m is, independently at each occurrence, selected from 0, 1, and 2;

n is, independently at each occurrence, selected from 0, 1, 2, 3, and 4; and p is, independently at each occurrence, selected from 0, 1, and 2.

In a second embodiment of the first aspect, the present disclosure provides a compound of Formula (I), or a stereoisomer, a tautomer, a pharmaceutically acceptable salt, or a solvate thereof, within the scope of the above embodiments, wherein:

$R^1$ is independently selected from the group consisting of: $C_{1-6}$ alkyl substituted with 0-2 $R^a$, $C_{2-6}$ alkenyl substituted with 0-2 $R^a$, and $—(CH_2)_n—W—R^{1a}$;

W is independently selected from the group consisting of: a bond, NH, N($C_{1-4}$ alkyl), CO, CONH, CON($C_{1-4}$ alkyl), $SO_2$, $NHCO_2$, and $CHR^f$;

$R^{1a}$ is independently selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^2$ is independently selected from the group consisting of: OH, $O(C_{1-4}$ alkyl substituted with 0-1 $CO_2H$), CN, and $NR^7R^8$;

$R^3$ is independently selected from the group consisting of: H, halogen, $CF_3$, $OCF_3$, $C_{1-6}$ alkyl substituted with 0-2 $R^a$, $C_{2-6}$ alkenyl substituted with 0-2 $R^a$, $—CO_2(C_{1-4}$ alkyl), $—SO_2$(phenyl), $—(CH_2)_n—(C_{3-6}$ cycloalkyl substituted with 0-3 $R^c$), $—(CH_2)_n$-(phenyl substituted with 0-3 $R^b$), $—(CH_2)_n$-(naphthyl substituted with 0-3 $R^b$), and $—(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^5$ is independently selected from the group consisting of: $C_{3-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

L is $X_1—Y—X_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-7}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

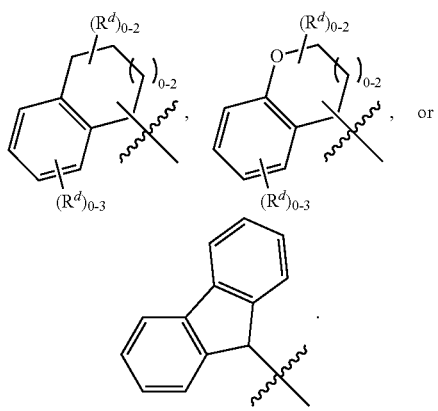

In a third embodiment of the first aspect, the present disclosure provides a compound of Formula (I), or a stereoisomer, a tautomer, a pharmaceutically acceptable salt, or a solvate thereof, within the scope of the above embodiments, wherein:

$R^2$ is $OR^6$;

$R^3$ is independently selected from the group consisting of: H, $C_{1-6}$ alkyl substituted with $R^a$, $—(CH_2)_n—C_{3-6}$ cycloalkyl substituted with 0-3 $R^b$, and $—(CH_2)_n$-phenyl substituted with 0-3 $R^c$; and $R^4$ is H.

In a fourth embodiment of the first aspect, the present disclosure provides a compound of Formula (I), or a stereoisomer, a tautomer, a pharmaceutically acceptable salt, or a solvate thereof, within the scope of the above embodiments, wherein:

$R^5$ is independently selected from the group consisting of: $C_{3-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

L is $X_1—Y—X_2$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to four carbon atoms and may be saturated or unsaturated; and said hydrocarbon-heteroatom linker may be saturated or unsaturated and has zero to three carbon atoms and one group selected from O, —CO—, S, —SO—, —$SO_2$—, NH, and N($C_{1-4}$ alkyl);

$X_2$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to five carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-6}$ cycloalkylene, $C_{4-6}$ cycloalkenylene, phenylene, naphthylene, tetrahydronaphthylene, and a 5- to 10 membered heterocycle comprising: carbon atoms and 1-4 heteroatoms selected from N, $NR^e$, O, and $S(O)_p$; wherein each moiety may be optionally substituted with one or two substituents independently selected from: halogen, OH, CN, $C_{1-4}$ alkyl, $C_{1-4}$ haloalkyl, and $C_{1-4}$ alkyoxy; and alternatively, $R^5$-L- is

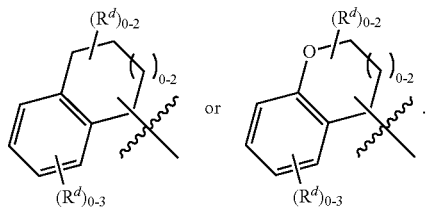

In a fifth embodiment of the first aspect, the present disclosure provides a compound of Formula (I), wherein $R^2$ is OH, and $R^3$ and $R^4$ are hydrogen, further characterized by Formula (II):

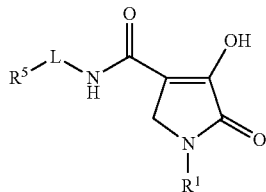

(II)

or a stereoisomer, a tautomer, a pharmaceutically acceptable salt, or a solvate thereof, within the scope of any of the above aspects, wherein: $R^1$ is independently selected from the group consisting of: $C_{1-6}$ alkyl substituted with 0-2 $R^a$, —$(CH_2)_2N(C_{1-4}$ alkyl)(—CH═CHCF$_3$), and —$(CH_2)_n$—W—$R^{1a}$;

W is independently selected from the group consisting of: a bond, NH, N($C_{1-4}$ alkyl), CO, CONH, CON($C_{1-4}$ alkyl), SO$_2$, NHCO$_2$, and CHR$^f$;

$R^{1a}$ is independently selected from the group consisting of: $C_{3-6}$ cycloalkyl substituted with 0-2 $R^c$, phenyl substituted with 0-2 $R^b$, naphthyl substituted with 0-2 $R^b$, dihydroindenyl substituted with 0-2 $R^c$, and a 5- to 6-membered heterocycle comprising: carbon atoms and 1-4 heteroatoms selected from N, NR$^e$, O, and S(O)$_p$; and wherein said heterocycle is substituted with 0-2 $R^c$;

$R^5$ is independently selected from the group consisting of: $C_{5-6}$ cycloalkyl, phenyl, thienyl, pyrazolyl, imidazolyl, thiazolyl, tetrahydropyranyl, piperidinyl, pyridyl, and benzothiazolyl; and wherein each moiety is substituted with 0-2 $R^d$;

L is $X_1$—Y—$X_2$;

$X_1$ is independently selected from the group consisting of: a bond, —CH═CH—, O, NH, —CH$_2$O—, —CO—, —SO$_2$—;

$X_2$ is independently selected from the group consisting of: —CH$_2$—, —(CH$_2$)$_2$—, —(CH$_2$)$_3$—, —(CH$_2$)$_4$—, —CH(C$_{1-4}$ alkyl)-, —O(CH$_2$)$_2$—, and —O(CH$_2$)$_3$—;

Y is independently selected from the group consisting of: $C_{3-6}$ cycloalkylene, $C_{4-6}$ cycloalkenylene, phenylene, pyridylene, piperidinylene, oxadiazolylene,

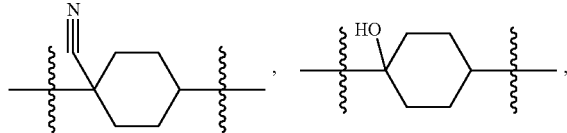

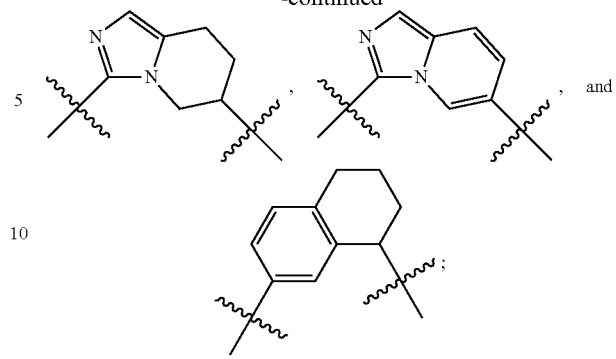

and alternatively, $R^5$-L- is

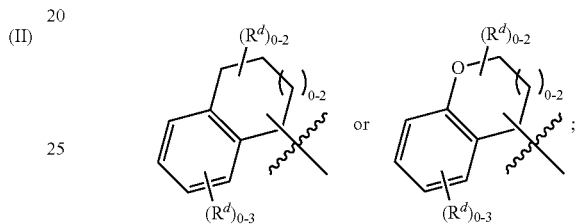

$R^a$ is, independently at each occurrence, selected from the group consisting of: halogen, CF$_3$, CF$_2$CF$_3$, OCH$_2$CF$_3$, NH($C_{1-4}$ alkyl), CONH$_2$, CONH($C_{1-4}$ alkyl), NHSO$_2$($C_{1-4}$ alkyl), and N($C_{1-4}$ alkyl)SO$_2$($C_{1-4}$ alkyl);

$R^b$ is, independently at each occurrence, selected from the group consisting of: halogen, $C_{1-4}$ alkyl, CF$_3$, OCF$_3$, CONH$_2$, and CONH($C_{1-4}$ alkyl);

$R^c$ is, independently at each occurrence, selected from the group consisting of: ═O and $R^b$;

$R^d$ is, independently at each occurrence, selected from the group consisting of: halogen, OH, $C_{1-4}$ alkyl, $C_{1-4}$ alkoxy, CF$_3$, OCF$_3$, CN, NH$_2$, NH($C_{1-4}$ alkyl), N($C_{1-4}$ alkyl)$_2$, CO($C_{1-4}$ alkyl), CO$_2$($C_{1-4}$ alkyl), NHCO($C_{1-4}$ alkyl), —CH$_2$NHCO($C_{1-4}$ alkyl), CONH$_2$, CONH($C_{1-4}$ alkyl), CON($C_{1-4}$ alkyl)$_2$, SO$_2$($C_{1-4}$ alkyl), SO$_2$NH$_2$, —SO$_2$NH($C_{1-4}$ alkyl), —SO$_2$NH($C_{3-6}$ cycloalkyl), —NHSO$_2$($C_{1-4}$ alkyl), —CH$_2$NHSO$_2$($C_{1-4}$ alkyl), and Si($C_{1-4}$ alkyl)$_3$;

$R^e$ is, independently at each occurrence, selected from the group consisting of: H, $C_{1-4}$ alkyl, CO$_2$($C_{1-4}$ alkyl), CO$_2$(benzyl), phenyl, and benzyl;

$R^f$ is, independently at each occurrence, selected from the group consisting of: $C_{1-4}$ alkyl, CO$_2$($C_{1-4}$ alkyl), and CONH$_2$;

n is, independently at each occurrence, selected from 0, 1, 2, and 3; and p is, independently at each occurrence, selected from 0, 1, and 2.

In a sixth embodiment of the first aspect, the present disclosure provides a compound of Formula (II), or a stereoisomer, a tautomer, a pharmaceutically acceptable salt, or a solvate thereof, within the scope of the above embodiments, wherein:

$R^1$ is independently selected from the group consisting of: $C_{1-4}$ alkyl substituted with 0-1 $R^a$, 4-halo-phenyl, 2-halo-4-halo-phenyl, —CH(Ph)CONH$_2$, —CH(Bn)CONH$_2$, —(CH$_2$)$_2$N($C_{1-4}$ alkyl)(—CH═CHCF$_3$), —(CH$_2$)$_2$NH(Ph), —(CH$_2$)$_2$N($C_{1-4}$ alkyl)(Ph), —(CH$_2$)$_2$NH(4-halo-Ph), —(CH$_2$)$_2$N($C_{1-4}$ alkyl)(3-$C_{1-4}$ alkyl-Ph), —(CH$_2$)$_2$CONH (4-halo-Ph), —(CH$_2$)$_2$NHCO$_2$Bn, —(CH$_2$)$_2$SO$_2$Ph, —(CH$_2$)$_2$NHSO$_2$(4-C$_{1-4}$ alkyl-Ph), —CH$_2$CONH(2-naphthyl),

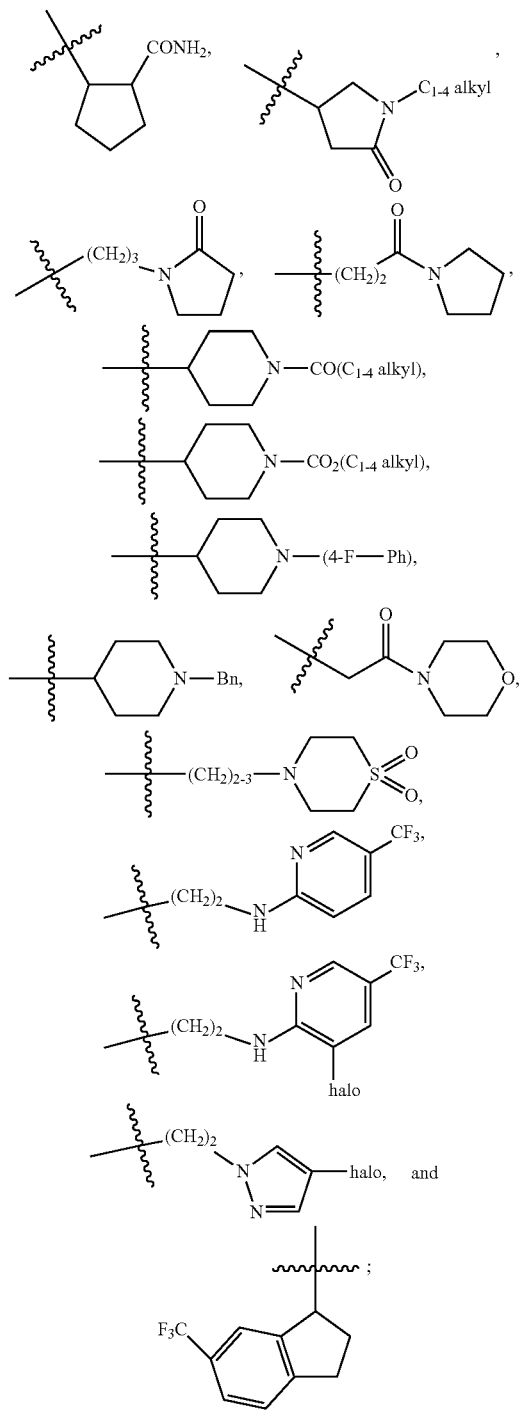

R$^5$ is independently selected from the group consisting of: C$_{5-6}$ cycloalkyl, phenyl, 2-C$_{1-4}$ alkyl-phenyl, 3-C$_{1-4}$ alkyl-phenyl, 4-C$_{1-4}$ alkyl-phenyl, 2-C$_{1-4}$ alkoxy-phenyl, 3-C$_{1-4}$ alkoxy-phenyl, 4-C$_{1-4}$ alkoxy-phenyl, 2-halo-phenyl, 3-halo-phenyl, 4-halo-phenyl, 3-CF$_3$-phenyl, 4-CF$_3$-phenyl, 2-OCF$_3$-phenyl, 3-OCF$_3$-phenyl, 4-OCF$_3$-phenyl, 2-CN-phenyl, 3-CN-phenyl, 4-CN-phenyl, 3-CO(C$_{1-4}$ alkyl)-phenyl, 4-CO(C$_{1-4}$ alkyl)-phenyl, 3-CO$_2$(C$_{1-4}$ alkyl)-phenyl, 3-N(C$_{1-4}$ alkyl)-2-phenyl, 2-NHCO(C$_{1-4}$ alkyl)-phenyl, 4-NHCO(C$_{1-4}$ alkyl)-phenyl, 3-CH$_2$NHCO(C$_{1-4}$ alkyl)-phenyl, 4-CH$_2$NHCO(C$_{1-4}$ alkyl)-phenyl, 2-CONH$_2$-phenyl, 3-CONH$_2$-phenyl, 3-CONH(C$_{1-4}$ alkyl)-phenyl, 3-CON(C$_{1-4}$ alkyl)-2-phenyl, 4-CON(C$_{1-4}$ alkyl)-2-phenyl, 2-SO$_2$(C$_{1-4}$ alkyl)-phenyl, 3-SO$_2$(C$_{1-4}$ alkyl)-phenyl, 4-SO$_2$(C$_{1-4}$ alkyl)-phenyl, 3-SO$_2$NH$_2$-phenyl, 4-SO$_2$NH(cyclopropyl)-phenyl, 4-NHSO$_2$(C$_{1-4}$ alkyl)-phenyl, 3-CH$_2$NHSO$_2$(C$_{1-4}$ alkyl)-phenyl, 4-CH$_2$NHSO$_2$(C$_{1-4}$ alkyl)-phenyl, 3-Si(Me)-3-phenyl, 2-C$_{1-4}$ alkyl-4-C$_{1-4}$ alkyl-phenyl, 2-C$_{1-4}$ alkyl-6-C$_{1-4}$ alkyl-phenyl, 2-halo-4-halo-phenyl, 2-halo-5-halo-phenyl, 3-halo-4-halo-phenyl, 3-halo-5-halo-phenyl, 2-OH-4-halo-phenyl, 3-halo-4-CF$_3$-phenyl, 2-CF$_3$-6-halo-phenyl, 3-CF$_3$-4-C$_{1-4}$ alkyl-phenyl, 3,5-di(CF$_3$)-phenyl, thien-3-yl, 5-C$_{1-4}$ alkyl-thien-2-yl, 5-halo-thien-2-yl, 1H-pyrazol-4-yl, 1-C$_{1-4}$ alkyl-pyrazol-5-yl, 1-C$_{1-4}$ alkyl-imidazol-5-yl, 2-C$_{1-4}$ alkyl-4-C$_{1-4}$ alkyl-thiazol-5-yl, tetrahydro-2H-pyran-4-yl, piperidin-1-yl, pyrid-2-yl, pyrid-3-yl, pyrid-4-yl, 2-C$_{1-4}$ alkyl-pyrid-4-yl, 2-C$_{1-4}$ alkoxy-pyrid-3-yl, 6-C$_{1-4}$ alkoxy-pyrid-3-yl, 3-halo-pyrid-4-yl, 6-halo-pyrid-3-yl, 5-CF$_3$-pyrid-3-yl, 4-halo-6-halo-pyrid-3-yl, and benzothiazol-2-yl;

L is independently selected from the group consisting of: 1,2-phenylene-CH$_2$—, 1,3-phenylene-CH$_2$—, 1,4-phenylene-CH$_2$—, 1,3-phenylene-CH(C$_{1-4}$ alkyl)-, —CH=CH-1,3-phenylene-CH$_2$—, —O-(1,2-phenylene)-CH$_2$—, —O-(1,3-phenylene)-CH$_2$—, —O-(1,4-phenylene)-CH$_2$—, —O-(1,4-phenylene)-(CH$_2$)$_2$—, —O-(1,4-phenylene)-(CH$_2$)$_3$—, —CH$_2$O-(1,4-phenylene)-CH$_2$—, —O-(1,3-phenylene)-O(CH$_2$)$_3$—, —O-(1,4-phenylene)-O(CH$_2$)$_3$—, —CO-(1,4-phenylene)-CH$_2$—,

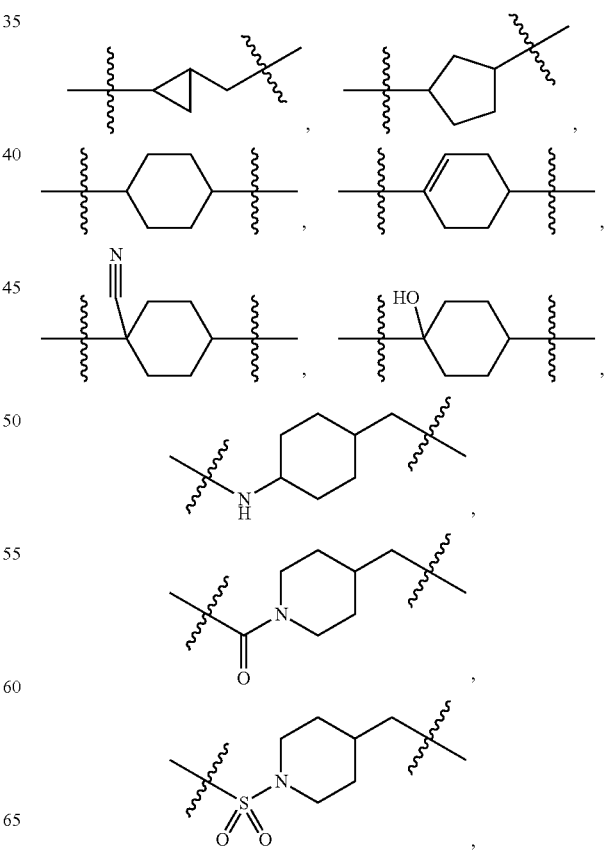

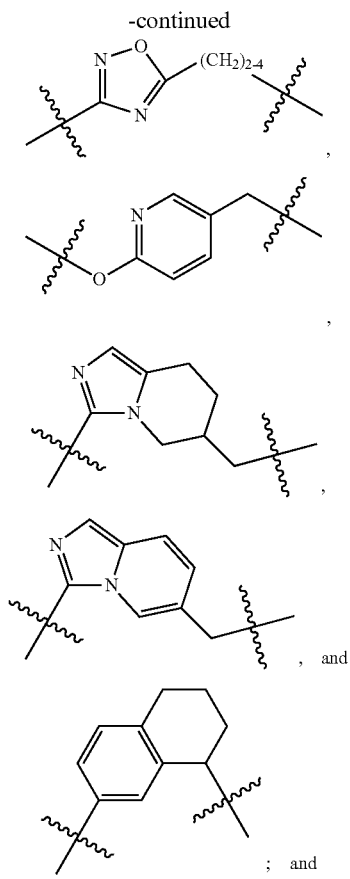

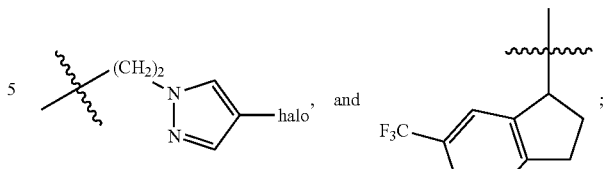

$R^a$ is, independently at each occurrence, selected from the group consisting of: $CF_3$, $CF_2CF_3$, $OCH_2CF_3$, $NH(C_{1-4}$ alkyl), $CONH_2$, $CONH(C_{1-4}$ alkyl), $NHSO_2(C_{1-4}$ alkyl), and $N(C_{1-4}$ alkyl)$SO_2(C_{1-4}$ alkyl).

In a seventh embodiment of the first aspect, the present disclosure provides a compound of Formula (II), or a stereoisomer, a tautomer, a pharmaceutically acceptable salt, or a solvate thereof, within the scope of the above embodiments, wherein:

$R^1$ is independently selected from the group consisting of: $C_{1-4}$ alkyl substituted with 0-1 $R^a$, 4-halo-phenyl, 2-halo-4-halo-phenyl, —$(CH_2)_2NH(4$-halo-Ph), —$(CH_2)_2N(C_{1-4}$ alkyl)(3-$C_{1-4}$ alkyl-Ph), —$(CH_2)_2CONH(4$-Cl-Ph), —$CH_2CONH(2$-naphthyl),

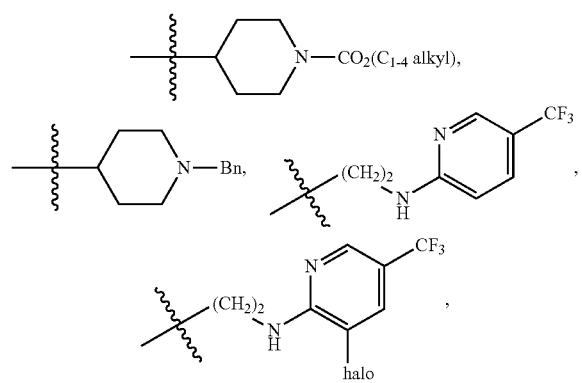

$R^5$ is independently selected from the group consisting of: $C_{5-6}$ cycloalkyl, phenyl, 2-$C_{1-4}$ alkyl-phenyl, 3-$C_{1-4}$ alkyl-phenyl, 4-$C_{1-4}$ alkyl-phenyl, 2-$C_{1-4}$ alkoxy-phenyl, 3-$C_{1-4}$ alkoxy-phenyl, 4-$C_{1-4}$ alkoxy-phenyl, 2-halo-phenyl, 3-halo-phenyl, 4-halo-phenyl, 3-$CF_3$-phenyl, 4-$CF_3$-phenyl, 2-$OCF_3$-phenyl, 3-$OCF_3$-phenyl, 4-$OCF_3$-phenyl, 2-CN-phenyl, 3-CN-phenyl, 4-CN-phenyl, 3-CO($C_{1-4}$ alkyl)-phenyl, 4-CO($C_{1-4}$ alkyl)-phenyl, 3-$CO_2(C_{1-4}$ alkyl)-phenyl, 3-N($C_{1-4}$ alkyl)-2-phenyl, 4-NHCO($C_{1-4}$ alkyl)-phenyl, 3-$CH_2NHCO(C_{1-4}$ alkyl)-phenyl, 4-$CH_2NHCO(C_{1-4}$ alkyl)-phenyl, 3-$CONH_2$-phenyl, 3-CONH($C_{1-4}$ alkyl)-phenyl, 3-CON($C_{1-4}$ alkyl)-2-phenyl, 4-CON($C_{1-4}$ alkyl)-2-phenyl, 3-$SO_2(C_{1-4}$ alkyl)-phenyl, 4-$SO_2(C_{1-4}$ alkyl)-phenyl, 4-$SO_2NH$(cyclopropyl)-phenyl, 4-$NHSO_2(C_{1-4}$ alkyl)-phenyl, 3-$CH_2NHSO_2(C_{1-4}$ alkyl)-phenyl, 4-$CH_2NHSO_2(C_{1-4}$ alkyl)-phenyl, 3-Si(Me)-3-phenyl, 2-$C_{1-4}$ alkyl-4-$C_{1-4}$ alkyl-phenyl, 2-$C_{1-4}$ alkyl-6-$C_{1-4}$ alkyl-phenyl, 2-halo-4-halo-phenyl, 2-halo-5-halo-phenyl, 3-halo-4-halo-phenyl, 3-halo-5-halo-phenyl, 2-OH-4-halo-phenyl, 3-halo-4-$CF_3$-phenyl, 2-$CF_3$-6-halo-phenyl, 3-$CF_3$-4-$C_{1-4}$ alkyl-phenyl, 3,5-di($CF_3$)-phenyl, thien-3-yl, 5-$C_{1-4}$ alkyl-thien-2-yl, 5-halo-thien-2-yl, 1H-pyrazol-4-yl, 1-$C_{1-4}$ alkyl-pyrazol-5-yl, 2-$C_{1-4}$ alkyl-4-$C_{1-4}$ alkyl-thiazol-5-yl, tetrahydro-2H-pyran-4-yl, pyrid-3-yl, pyrid-4-yl, 2-$C_{1-4}$ alkyl-pyrid-4-yl, 2-$C_{1-4}$ alkoxy-pyrid-3-yl, 6-$C_{1-4}$ alkoxy-pyrid-3-yl, 3-halo-pyrid-4-yl, 5-$CF_3$-pyrid-3-yl, 4-halo-6-halo-pyrid-3-yl, and benzothiazol-2-yl;

L is independently selected from the group consisting of: 1,2-phenylene-$CH_2$—, 1,3-phenylene-$CH_2$—, 1,4-phenylene-$CH_2$—, 1,3-phenylene-$CH(C_{1-4}$ alkyl)-, —CH=CH-1,3-phenylene-$CH_2$—, —O-(1,2-phenylene)-$CH_2$—, —O-(1,3-phenylene)-$CH_2$—, —O-(1,4-phenylene)-$CH_2$—, —O-(1,4-phenylene)-$(CH_2)_2$—, —O-(1,4-phenylene)-$(CH_2)_3$—, -(1,3-phenylene)-O$(CH_2)_3$—, -(1,4-phenylene)-O$(CH_2)_3$—, —$CH_2$O-(1,4-phenylene)-$CH_2$—, —O-(1,4-phenylene)-O$(CH_2)_2$—, —O-(1,3-phenylene)-O$(CH_2)_3$—, —O-(1,4-phenylene)-O$(CH_2)_3$—,

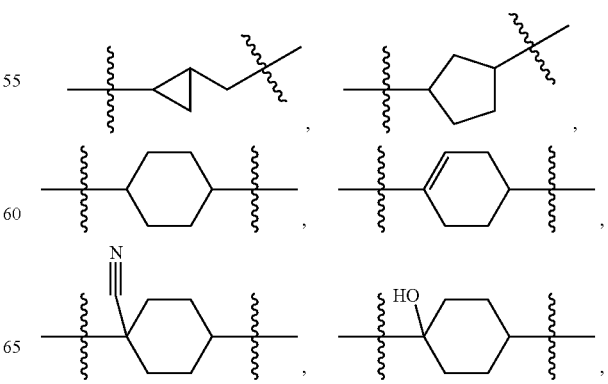

-continued

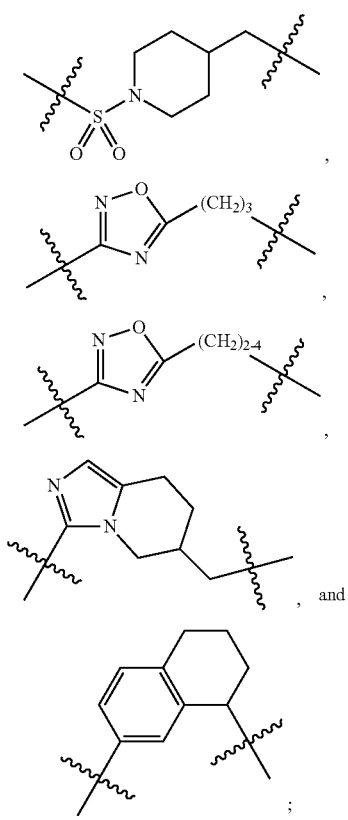

and $R^a$ is, independently at each occurrence, selected from the group consisting of: $CF_3$ and $CONH_2$.

In an eighth embodiment of the first aspect, the present disclosure provides a compound of Formula (II), or a stereoisomer, a tautomer, a pharmaceutically acceptable salt, or a solvate thereof, within the scope of the above embodiments, wherein:

$R^1$ is independently selected from the group consisting of: $C_{1-4}$ alkyl substituted with 0-1 $CF_3$, 4-halo-phenyl, 2-halo-4-halo-phenyl, —$(CH_2)_2NH$(4-halo-Ph), —$(CH_2)_2N(C_{1-4}$ alkyl)(3-$C_{1-4}$ alkyl-Ph),

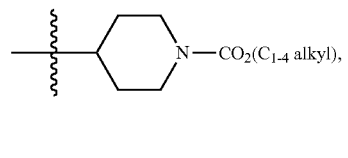

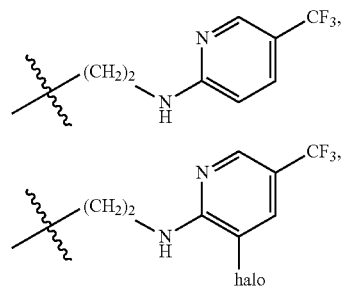

-continued

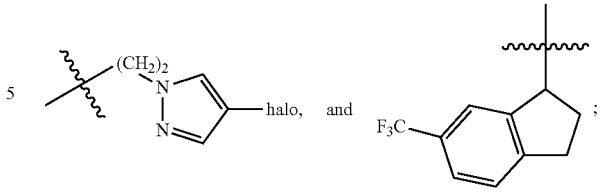

$R^5$ is independently selected from the group consisting of: $C_{5-6}$ cycloalkyl, phenyl, 2-$C_{1-4}$ alkyl-phenyl, 3-$C_{1-4}$ alkyl-phenyl, 4-$C_{1-4}$ alkyl-phenyl, 2-$C_{1-4}$ alkoxy-phenyl, 3-$C_{1-4}$ alkoxy-phenyl, 4-$C_{1-4}$ alkoxy-phenyl, 2-halo-phenyl, 3-halo-phenyl, 4-halo-phenyl, 3-$CF_3$-phenyl, 4-$CF_3$-phenyl, 2-$OCF_3$-phenyl, 3-$OCF_3$-phenyl, 4-$OCF_3$-phenyl, 3-CN-phenyl, 4-CN-phenyl, 3-CO($C_{1-4}$ alkyl)-phenyl, 4-CO($C_{1-4}$ alkyl)-phenyl, 3-$CO_2$($C_{1-4}$ alkyl)-phenyl, 3-N($C_{1-4}$ alkyl)-2-phenyl, 4-NHCO($C_{1-4}$ alkyl)-phenyl, 3-$CH_2$NHCO($C_{1-4}$ alkyl)-phenyl, 4-$CH_2$NHCO($C_{1-4}$ alkyl)-phenyl, 3-$CONH_2$-phenyl, 3-$CONH(C_{1-4}$ alkyl)-phenyl, 3-$CON(C_{1-4}$ alkyl)-2-phenyl, 4-$CON(C_{1-4}$ alkyl)-2-phenyl, 3-$SO_2(C_{1-4}$ alkyl)-phenyl, 4-$SO_2(C_{1-4}$ alkyl)-phenyl, 4-$SO_2NH$(cyclopropyl)-phenyl, 4-$NHSO_2(C_{1-4}$ alkyl)-phenyl, 3-$CH_2NHSO_2(C_{1-4}$ alkyl)-phenyl, 4-$CH_2NHSO_2(C_{1-4}$ alkyl)-phenyl, 2-$C_{1-4}$ alkyl-4-$C_{1-4}$ alkyl-phenyl, 2-$C_{1-4}$ alkyl-6-$C_{1-4}$ alkyl-phenyl, 2-halo-4-halo-phenyl, 2-halo-5-halo-phenyl, 3-halo-4-halo-phenyl, 3-halo-5-halo-phenyl, 2-OH-4-halo-phenyl, 3-halo-4-$CF_3$-phenyl, 3-$CF_3$-4-$C_{1-4}$ alkyl-phenyl, 3,5-di($CF_3$)-phenyl, thien-3-yl, 5-$C_{1-4}$ alkyl-thien-2-yl, 5-halo-thien-2-yl, 1H-pyrazol-4-yl, 1-$C_{1-4}$ alkyl-pyrazol-5-yl, 2-$C_{1-4}$ alkyl-4-$C_{1-4}$ alkyl-thiazol-5-yl, tetrahydro-2H-pyran-4-yl, pyrid-3-yl, 2-$C_{1-4}$ alkyl-pyrid-4-yl, 2-$C_{1-4}$ alkoxy-pyrid-3-yl, 6-$C_{1-4}$ alkoxy-pyrid-3-yl, 5-$CF_3$-pyrid-3-yl, and 4-halo-6-halo-pyrid-3-yl; and L is independently selected from the group consisting of: 1,2-phenylene-$CH_2$—, 1,3-phenylene-$CH_2$—, 1,4-phenylene-$CH_2$—, 1,3-phenylene-$CH(C_{1-4}$ alkyl)-, —CH═CH-1,3-phenylene-$CH_2$—, —O-(1,2-phenylene)-$CH_2$—, —O-(1,3-phenylene)-$CH_2$—, —O-(1,4-phenylene)-$CH_2$—, —O-(1,4-phenylene)-$(CH_2)_2$—, —O-(1,4-phenylene)-$(CH_2)_3$—, -(1,3-phenylene)-$O(CH_2)_3$—, -(1,4-phenylene)-$O(CH_2)_3$—, —$CH_2$O-(1,4-phenylene)-$CH_2$—, —O-(1,4-phenylene)-$O(CH_2)_2$—, —O-(1,3-phenylene)-$O(CH_2)_3$—, —O-(1,4-phenylene)-$O(CH_2)_3$—, —CO-(1,4-phenylene)-$CH_2$—,

15

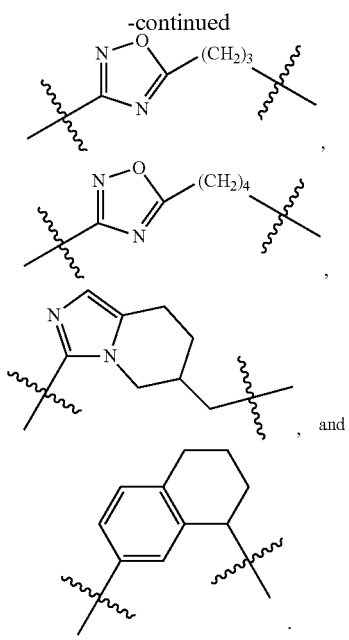

, and

In a ninth embodiment of the first aspect, the present disclosure provides a compound of Formula (II), or a stereoisomer, a tautomer, a pharmaceutically acceptable salt, or a solvate thereof, within the scope of the above embodiments, wherein:

$R^1$ is independently selected from the group consisting of: methyl, ethyl, i-butyl, —$CH_2CF_3$, —$(CH_2)_3CF_3$, 4-F-phenyl, 2,4-diF-phenyl, —$(CH_2)_2NH$(4-Cl-Ph), —$(CH_2)_2N$(Et)(3-Me-Ph),

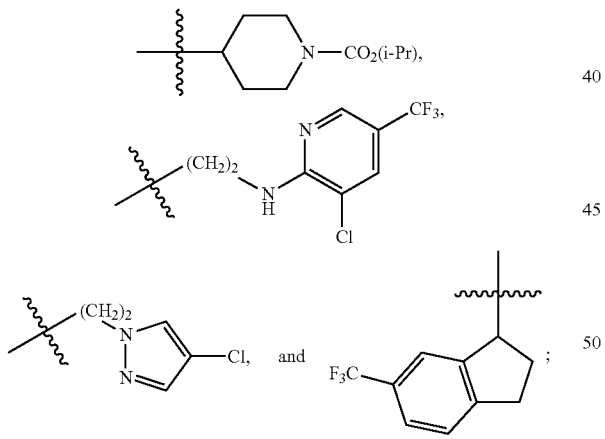

$R^5$ is independently selected from the group consisting of: cyclopentyl, cyclohexyl, phenyl, 2-Me-phenyl, 3-Me-phenyl, 4-Me-phenyl, 2-OMe-phenyl, 3-OMe-phenyl, 4-OMe-phenyl, 2-F-phenyl, 3-F-phenyl, 4-F-phenyl, 2-Cl-phenyl, 3-Cl-phenyl, 4-Cl-phenyl, 3-$CF_3$-phenyl, 4-$CF_3$-phenyl, 2-$OCF_3$-phenyl, 3-$OCF_3$-phenyl, 4-$OCF_3$-phenyl, 3-CN-phenyl, 4-CN-phenyl, 3-COMe-phenyl, 4-COMe-phenyl, 3-$CO_2$Me-phenyl, 3-$CO_2$Et-phenyl, 3-N(Me)-2-phenyl, 4-NHCOMe-phenyl, 3-$CH_2$NHCOMe-phenyl, 4-$CH_2$NHCOMe-phenyl, 3-$CONH_2$-phenyl, 3-CONH(t-Bu)-phenyl, 3-CON(Me)-2-phenyl, 4-CON(Me)-2-phenyl, 3-$SO_2$Me-phenyl, 4-$SO_2$Me-phenyl, 4-$SO_2$NH(cyclopropyl)-phenyl, 4-$NHSO_2$Me-phenyl, 3-$CH_2NHSO_2$Me-phenyl, 4-$CH_2NHSO_2$Me-phenyl, 2,4-diMe-phenyl, 2,6-diMe-phenyl, 2,4-diCl-phenyl, 2,5-diCl-phenyl, 3,4-diCl-phenyl, 3,5-diCl-phenyl, 2-OH-4-F-phenyl, 4-Cl-3-F-phenyl, 3-$C_{1-4}$-$CF_3$-phenyl, 3-$CF_3$-4-Me-phenyl, 3,5-di($CF_3$)-phenyl, thien-3-yl, 5-Me-thien-2-yl, 5-Cl-thien-2-yl, 1H-pyrazol-4-yl, 1-Me-pyrazol-5-yl, 2,4,-di-Me-thiazol-5-yl, tetrahydro-2H-pyran-4-yl, pyrid-3-yl, 2-Me-pyrid-4-yl, 2-OMe-pyrid-3-yl, 6-OMe-pyrid-3-yl, 5-$CF_3$-pyrid-3-yl, and 4,6-diCl-pyrid-3-yl; and L is independently selected from the group consisting of: 1,2-phenylene-$CH_2$—, 1,3-phenylene-$CH_2$—, 1,4-phenylene-$CH_2$—, 1,3-phenylene-CHMe-, —CH=CH-1,3-phenylene-$CH_2$—, —O-(1,2-phenylene)-$CH_2$—, —O-(1,3-phenylene)-$CH_2$—, —O-(1,4-phenylene)-$CH_2$—, —O-(1,4-phenylene)-$(CH_2)_2$—, —O-(1,4-phenylene)-$(CH_2)_3$—, —$CH_2$O-(1,4-phenylene)-$CH_2$—, —O-(1,3-phenylene)-O$(CH_2)_3$—, —O-(1,4-phenylene)-O$(CH_2)_3$—,

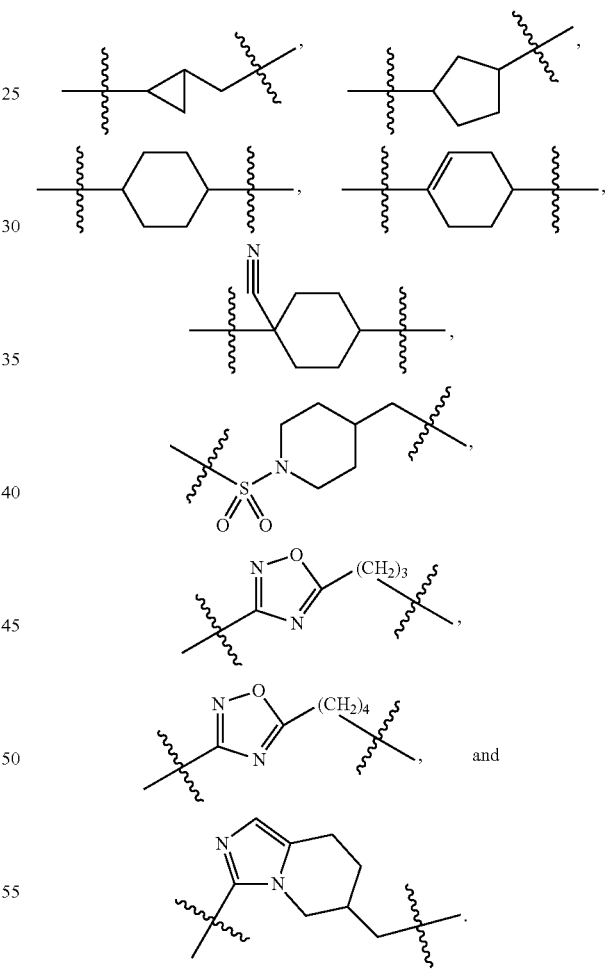

In a tenth embodiment of the first aspect, the present disclosure provides a compound of Formula (II), or a stereoisomer, a tautomer, a pharmaceutically acceptable salt, or a solvate thereof, within the scope of the above embodiments, wherein:

$R^1$ is independently selected from the group consisting of: methyl, ethyl, i-butyl, —$(CH_2)_3CF_3$, 2,4-diF-phenyl, and

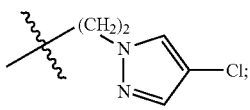

R⁵ is independently selected from the group consisting of: cyclohexyl, phenyl, 3-Me-phenyl, 4-Me-phenyl, 4-OMe-phenyl, 2-F-phenyl, 3-F-phenyl, 4-F-phenyl, 4-Cl-phenyl, 3-CF₃-phenyl, 4-CF₃-phenyl, 2-OCF₃-phenyl, 3-OCF₃-phenyl, 4-NHCOMe-phenyl, 3-CONH₂-phenyl, 4-NHSO₂Me-phenyl, 2,4-diMe-phenyl, 2,4-diCl-phenyl, 3,4-diCl-phenyl, 5-Me-thien-2-yl, and 6-OMe-pyrid-3-yl; and L is independently selected from the group consisting of: 1,2-phenylene-CH₂—, 1,3-phenylene-CH₂—, 1,4-phenylene-CH₂—, 1,3-phenylene-CHMe-, —O-(1,3-phenylene)-CH₂—, —O-(1,4-phenylene)-CH₂—, —O-(1,4-phenylene)-(CH₂)₂—, —O-(1,4-phenylene)-(CH₂)₃—, —O-(1,3-phenylene)-O(CH₂)₃—, —O-(1,4-phenylene)-O(CH₂)₃—,

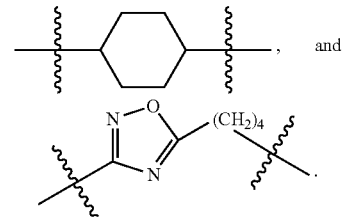

, and

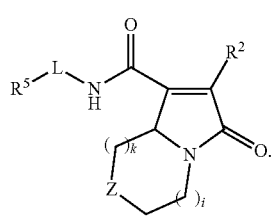

.

In a second aspect, the present disclosure provides compounds of Formula (III):

$$\text{(III)}$$

[structure shown]

In a first embodiment of the second aspect, the present disclosure provides a compound of Formula (III), or a stereoisomer, a tautomer, a pharmaceutically acceptable salt, or a solvate thereof, wherein:

R² is independently selected from the group consisting of: OR⁶, CN, and NR⁷R⁸;

R⁵ is independently selected from the group consisting of: $C_{3-10}$ carbocycle and a 5- to 10-membered heterocycle comprising: carbon atoms and 1-4 heteroatoms selected from N, NR^e, O, and $S(O)_p$; wherein said carbocycle and heterocycle are substituted with 0-3 R^d;

R⁶ is independently selected from the group consisting of: H and $C_{1-6}$ alkyl substituted with 0-1 CO₂H;

R⁷ is independently selected from the group consisting of: H, $C_{1-6}$ alkyl substituted with 0-1 R^a, —(CH₂)ₙ-(phenyl substituted with 0-3 R^b), and —(CH₂)ₙ-(5- to 6-membered heterocycle comprising: carbon atoms and 1-4 heteroatoms selected from N, NR^e, O, and $S(O)_p$); and wherein said heterocycle is substituted with 0-3 R^c;

R⁸ is independently selected from the group consisting of: H and $C_{1-6}$ alkyl;

alternatively, NR⁷R⁸ is a 5- to 6-membered heterocycle comprising: carbon atoms and 1-4 heteroatoms selected from N, NR^e, O, and $S(O)_p$;

L is X₁—Y—X₂;

X₁, and X₂ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-2 R^g; said hydrocarbon linker has one to five carbon atoms and may be saturated or unsaturated; and said hydrocarbon-heteroatom linker may be saturated or unsaturated and has one to four carbon atoms and one group selected from O, —CO—, S, —SO—, —SO₂—, NH, and N($C_{1-4}$ alkyl);

Y is independently selected from the group consisting of: $C_{3-10}$ carbocycle and a 4- to 10-membered heterocycle comprising: carbon atoms and 1-4 heteroatoms selected from N, NR^e, O, and $S(O)_p$; wherein each said carbocycle and heterocycle may be optionally substituted with one, two or three substituents independently selected from the group consisting of: halogen, OH, $C_{1-4}$ alkyl, $C_{1-4}$ haloalkyl, and $C_{1-4}$ alkyoxy;

alternatively, R⁴-L- is

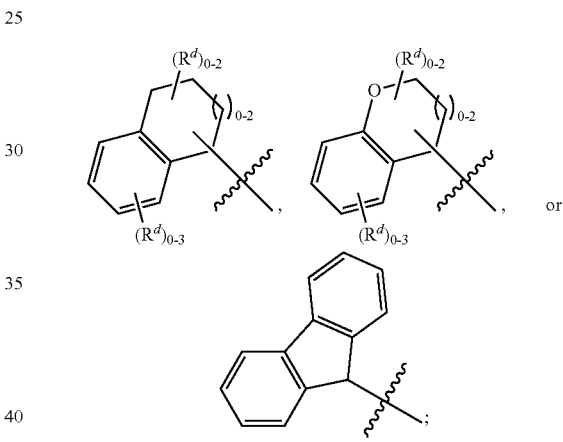

Z is independently selected from the group consisting of: CH₂, CH($C_{1-4}$ alkyl), C($C_{1-4}$ alkyl)₂, O, CO, S, SO, SO₂, NH, N($C_{1-4}$ alkyl), NHCO, CONH, SO₂NH, and NHSO₂;

R^a is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF₃, OCF₃, CN, NH₂, NO₂, NH($C_{1-4}$ alkyl), N($C_{1-4}$ alkyl)₂, CO₂H, CO₂($C_{1-4}$ alkyl), NHCO($C_{1-4}$ alkyl substituted with 0-1 NH₂), N($C_{1-4}$ alkyl)CO($C_{1-4}$ alkyl), NHCO₂($C_{1-4}$ alkyl), CONHSO₂($C_{1-4}$ alkyl), SO₂($C_{1-4}$ alkyl), CONH₂, CONH($C_{1-4}$ alkyl), NHSO₂($C_{1-4}$ alkyl), N($C_{1-4}$ alkyl)SO₂($C_{1-4}$ alkyl), and phenoxy;

R^b is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF₃, OCF₃, OCF₂CHF₂, OCH₂CF₃, CN, NH₂, NO₂, NH($C_{1-4}$ alkyl), N($C_{1-4}$ alkyl)₂, CO₂H, CO₂($C_{1-4}$ alkyl), CONH₂, CONH($C_{1-4}$ alkyl), CON($C_{1-4}$ alkyl)₂, NHCO₂($C_{1-4}$ alkyl), NHSO₂($C_{1-4}$ alkyl), N($C_{1-4}$ alkyl)SO₂($C_{1-4}$ alkyl), SO₂($C_{1-4}$ alkyl), SO₂NH₂, phenyl, benzyl, and phenoxy;

R^c is, independently at each occurrence, selected from the group consisting of: =O and R^b;

R^d is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, CF₃, OCF₃, OCF₂CF₂H, OCH₂CF₃, CN, NH₂, NO$_2$, NH(C$_{1-4}$ alkyl), N(C$_{1-4}$ alkyl)$_2$, CO$_2$H, CO$_2$(C$_{1-4}$ alkyl), CO(C$_{1-4}$ alkyl), NHCO(C$_{1-4}$ alkyl), —CH$_2$NHCO(C$_{1-4}$ alkyl), CONH$_2$, CONH(C$_{1-4}$ alkyl), CON(C$_{1-4}$ alkyl)$_2$, SO$_2$(C$_{1-4}$ alkyl), SO$_2$NH$_2$, —SO$_2$NH(C$_{1-4}$ alkyl), —SO$_2$NH(C$_{3-6}$ cycloalkyl), —NHSO$_2$(C$_{1-4}$ alkyl), —CH$_2$NHSO$_2$(C$_{1-4}$ alkyl), Si(C$_{1-4}$ alkyl)$_3$, and phenyl optionally substituted with one or two substituents independently selected from: halogen, OH, C$_{1-4}$ alkyl, C$_{1-4}$ haloalkyl, C$_{1-4}$ alkyoxy, and NHCO(C$_{1-4}$ alkyl);

R$^e$ is, independently at each occurrence, selected from the group consisting of: H, C$_{1-4}$ alkyl, CO(C$_{1-4}$ alkyl), CO$_2$(C$_{1-4}$ alkyl), CO$_2$(benzyl), and —(CH$_2$)$_n$-(phenyl optionally substituted with 0-2 halogens);

R$^g$ is, independently at each occurrence, selected from the group consisting of: halogen, OH, C$_{1-4}$ alkyl, C$_{2-4}$ alkenyl, C$_{1-4}$ haloalkyl, C$_{1-4}$ alkyoxy, CO$_2$(C$_{1-4}$ alkyl), C$_{3-6}$ cycloalkyl, and phenyl;

i is 0, 1, or 2;
k is 1 or 2;
n is, independently at each occurrence, selected from 0, 1, 2, 3, and 4; and
p is, independently at each occurrence, selected from 0, 1, and 2.

In a second embodiment of the second aspect, the present disclosure provides a compound of Formula (III), or a stereoisomer, a tautomer, a pharmaceutically acceptable salt, or a solvate thereof, wherein:
R$^2$ is OH;
R$^5$-L- is

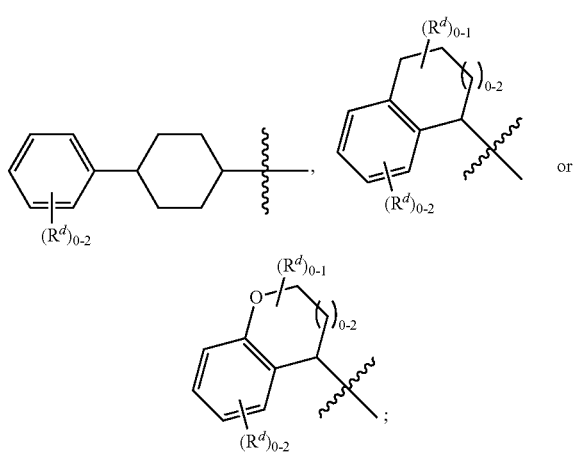

Z is independently selected from the group consisting of: CH$_2$ and NHCO;
i is 1 or 2; and
k is 1.

In a third embodiment of the second aspect, the present disclosure provides a compound of Formula (III), or a stereoisomer, a tautomer, a pharmaceutically acceptable salt, or a solvate thereof, wherein:
R$^2$ is OH;
R$^5$-L- is

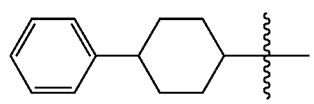 or

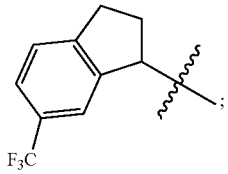;

Z is CH$_2$;
i is 1 or 2; and
k is 1.

In another embodiment, the present invention includes a compound of Formula (I), (II) or (III), or a stereoisomer, a tautomer, a pharmaceutically acceptable salt, or a solvate thereof, within the scope of any of the above embodiments of the first or second aspect wherein:
R$^5$-L- is

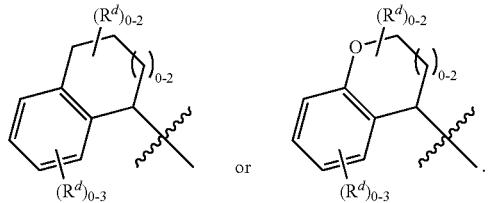

In another embodiment, the present invention includes a compound of Formula (I), (II) or (III), or a stereoisomer, a tautomer, a pharmaceutically acceptable salt, or a solvate thereof, within the scope of any of the above embodiments of the first or second aspect wherein:
R$^5$-L- is

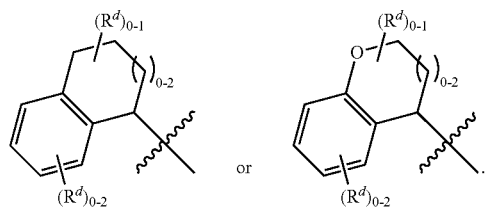

In another embodiment, the present invention includes a compound of Formula (I), (II) or (III), or a stereoisomer, a tautomer, a pharmaceutically acceptable salt, or a solvate thereof, within the scope of any of the above embodiments of the first or second aspect wherein:
R$^5$-L- is selected from the group consisting of:

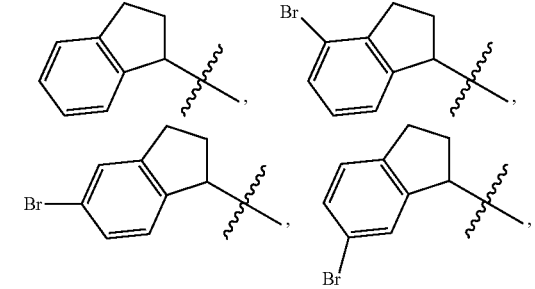

-continued

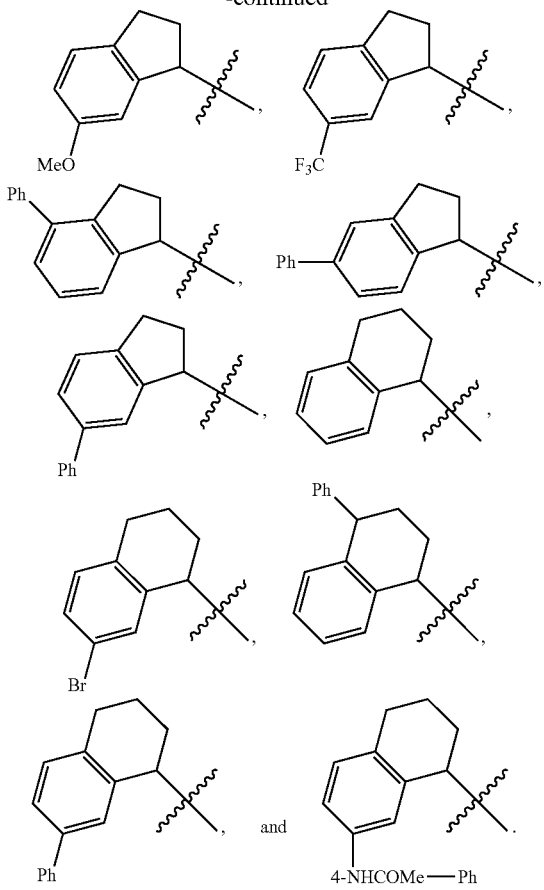

In another embodiment, the present invention includes a compound of Formula (I), (II) or (III), or a stereoisomer, a tautomer, a pharmaceutically acceptable salt, or a solvate thereof, within the scope of any of the above embodiments of the first or second aspect wherein:

$R^5$-L- is selected from the group consisting of:

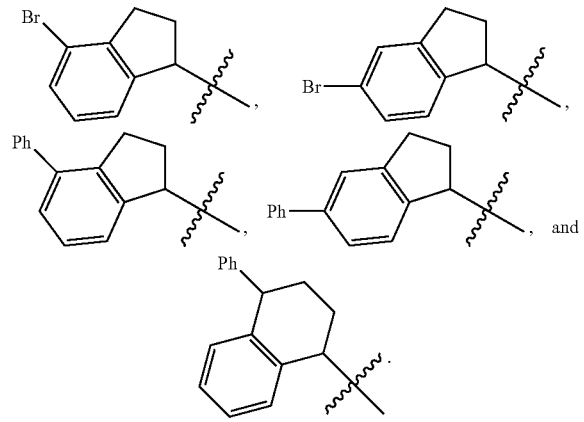

In a third aspect, the present invention provides a compound selected from the exemplified examples or a stereoisomer, a tautomer, a pharmaceutically acceptable salt, or a solvate thereof.

In another aspect, the present invention provides a compound selected from any subset list of the exemplified examples or any one of the exemplified examples or a stereoisomer, a tautomer, a pharmaceutically acceptable salt, or a solvate thereof, within the scope of the third aspect.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyll" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl," "$C_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C═O) group in a molecule may tautomerize to its enol form (—C═C—OH), as shown in the following equation:

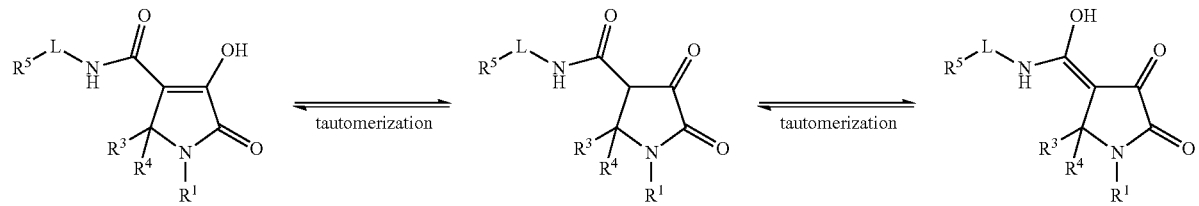

Likewise, an imine (—CH—C═NHR) group in a molecule may tautomerize to its enamine form (—C═C—NHR), as shown in the following equation:

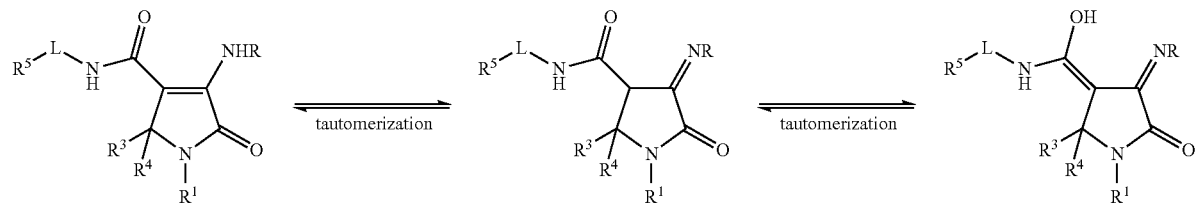

Thus, this disclosure is intended to cover all possible tautomers even when a structure depicts only one of them.

As a person of ordinary skill in the art would be able to understand, when $R^3$ and $R^4$ are different in a compound of Formula (I) or Formula (II), the carbon atom to which both $R^3$ and $R^4$ are attached would be a stereogenic center. The same principle applies to Formula (III) when $R^3$ is not hydrogen. Absent other stereogenic centers on other R groups, the compound would have two enantiomers. For example, when $R^3$ is methyl and $R^4$ is hydrogen, the two enantiomers can be represented by the following (R—) and (S—) configurations:

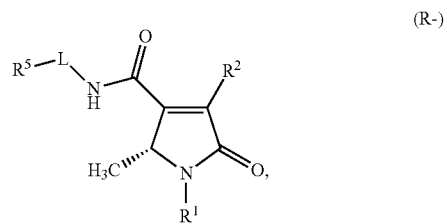

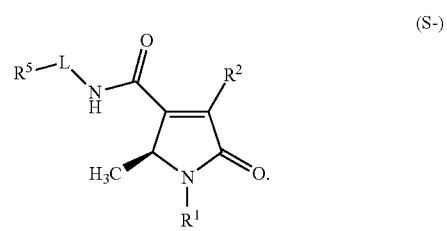

Likewise, a compound of Formula (IV) may exist in the following two different configurations with respect to the stereogenic center indicated:

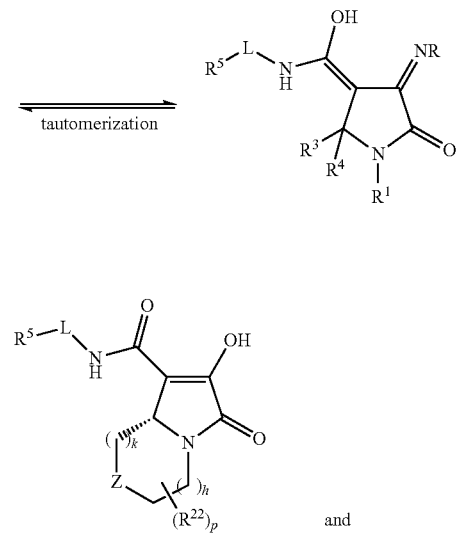

and

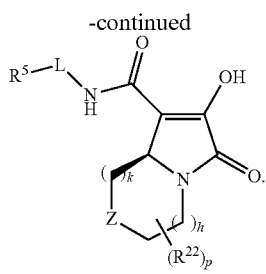

The same principle also applies to the stereogenic centers that may exist in the R groups of the compounds. When two or more stereogenic centers exist in a compound, the compound may exist as enantiomers or diastereomers. Thus, this disclosure is intended to cover all possible stereoisomers even when a single stereoisomer, or no stereochemistry, is described in a structure.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I), Formula (II), Formula (III), or Formula (IV) may have prodrug forms. Any compound that will be converted in vivo to provide the bioactive agent (i.e., a compound of Formula (I), Formula (II), Formula (III), or Formula (IV)) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mw" for microwave, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$AlCl_3$ aluminum chloride
$BBr_3$ boron tribromide
$BCl_3$ boron trichloride
BOP reagent benzotriazol-1-yloxytris(dimethylamino)phosphonium hexafluorophosphate
Cbz carbobenzyloxy
$CH_2Cl_2$ dichloromethane
$CH_3CN$ or ACN acetonitrile
$CDCl_3$ deutero-chloroform
$CDCl_3$ chloroform
mCPBA or m-CPBA meta-chloroperbenzoic acid
$Cs_2CO_3$ cesium carbonate
$Cu(OAc)_2$ copper (II) acetate
DCE 1,2 dichloroethane
DCM dichloromethane
DEA diethylamine
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimthylaminopropyl)-N'-ethylcarbodiimide
EDTA ethylenediaminetetraacetic acid
$Et_3N$ or TEA triethylamine
EtOAc ethyl acetate
$Et_2O$ diethyl ether
EtOH ethanol
HCl hydrochloric acid
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
NIS N-iodosuccinimide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PS-Pd(Ph$_3$)$_4$ tetrakis(triphenylphosphine)palladium (0) on polystyrene support
i-PrOH or IPA isopropanol
PS polystyrene
PyBOP (benzotriazol-1-yloxy)tripyrrolidinophosphonium hexafluorophosphate
$SiO_2$ silica oxide
$SnCl_2$ tin(II) chloride
TBAF tetra-n-butylammonium fluoride
TBAI tetra-n-butylammonium iodide
TEA triethylamine
TFA trifluoroacetic acid
THF tetrahydrofuran
$TMSCHN_2$ trimethylsilyldiazomethane

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The Compounds of the present invention may be prepared by the exemplary processes described in the following schemes and working examples, as well as relevant published literature procedures that are used by one skilled in the art. Exemplary reagents and procedures for these reactions appear hereinafter and in the working examples. Protection and de-protection of functional groups in the processes below may be carried out by procedures generally known in the art (see, for example, Greene, T. W. et al., *Protecting Groups in Organic Synthesis,* 3rd Edition, John Wiley & Sons, Inc., New York (1999)). General methods of organic synthesis and functional group transformations are found in: *Comprehensive Organic Synthesis: Selectivity, Strategy & Efficiency in Modern Organic Chemistry*, B. M. Trost et al., eds., Pergamon Press, New York, N.Y. (1991); March, J., *Advanced Organic Chemistry: Reactions, Mechanisms, and Structure*, 4th Edition, Wiley & Sons, New York, N.Y. (1992); *Comprehensive Organic Functional Groups Transformations*, 1st Edition, A. R. Katritzky et al., eds. Elsevier Science Inc. Tarrytown, N.Y. (1995); Larock, R. C., *Comprehensive Organic Transformations*, VCH Publishers, Inc., New York, N.Y. (1989); and references therein.

Solvents, temperatures, pressures, and other reaction conditions may readily be selected by one of ordinary skill in the art. Starting materials are commercially available or can be readily prepared by one of ordinary skill in the art using known methods. For all of the schemes and compounds described below the variables are as described above, unless otherwise indicated. The following are the definitions of symbols used throughout Schemes 1 through 14:

PG: suitable nitrogen protecting group, exemplified by benzyl- (Bn), tert-butoxycarbonyl-(Boc), phthalimide (Phth), tert-butyldimethylsilyl-(TBDMS).

LG: leaving group exemplified by halogen (Cl, Br, I) and sulfonates (—OS(O)$_2$-aryl (e.g., —OS(O)$_2$Ph or —OS(O)$_2$ C$_6$H$_4$—CH$_{3-p}$), or —OS(O)$_2$-alkyl (e.g., —OS(O)$_2$CH$_3$ or —OS(O)$_2$CF$_3$)).

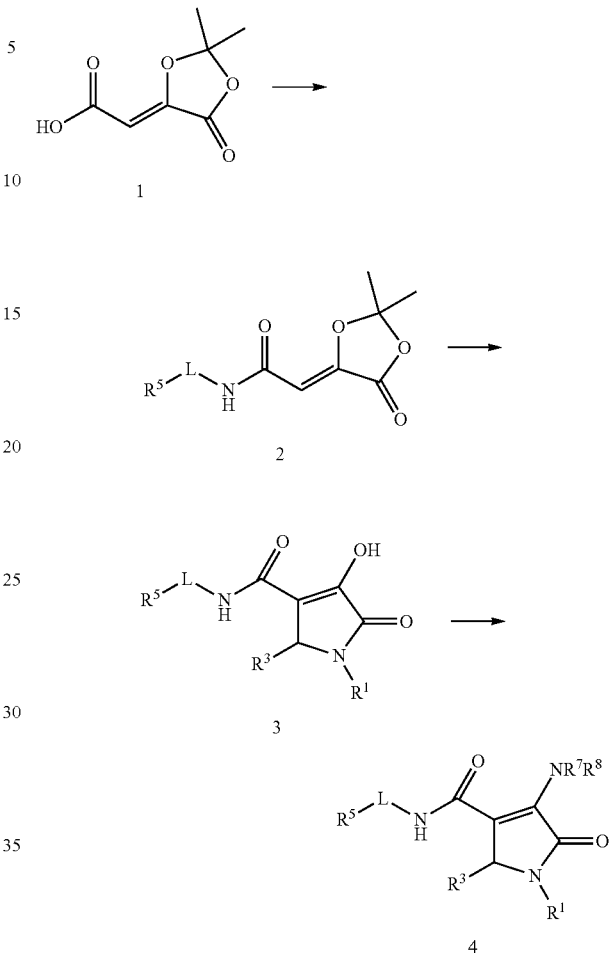

Compounds of formula 4 and of formula 3, wherein L R$^1$, R$^3$, R$^5$, R$^7$, and R$^8$, as defined above, may be synthesized according to Scheme 1. (Z)-2-(2,2-dimethyl-5-oxo-1,3-dioxolan-4-ylidene)acetic acid (1), which is synthesized according to methods described in WO 2004/004657, is condensed with an amine, R$^5$-L-NH$_2$, using standard peptide coupling protocols. The protocols include, but are not limited to, formation of the acid chloride of 1 using oxalyl chloride and catalytic DMF in the presence of a suitable solvent such as methylene chloride, followed by addition of R$^5$-L-NH$_2$ in the presence of a base such as TEA, DIPEA or N-methylmorpholine or formation of the active ester of 1 using EDC, HOBt and a base, such as TEA, DIPEA or N-methylmorpholine, in the presence of R$^5$-L-NH$_2$. The amides thus formed are combined with the Schiff base formed by the combination of an amine (R$^1$NH$_2$) and an aldehyde (R$^3$CHO) in a suitable solvent such as methanol, and heated to effect condensation of the Schiff base with intermediates of formula 2 to form compounds of formula 3. Typically, the reactions are heated to 100° C. using microwave irradiation. Compounds of formula 4 may be synthesized by heating compounds of formula 3 with an amine NHR$^7$R$^8$ and an acid, such as HOAc, in a suitable solvent such as EtOH to 140° C. using microwave irradiation. Other temperatures and methods of heating may be employed.

Scheme 2

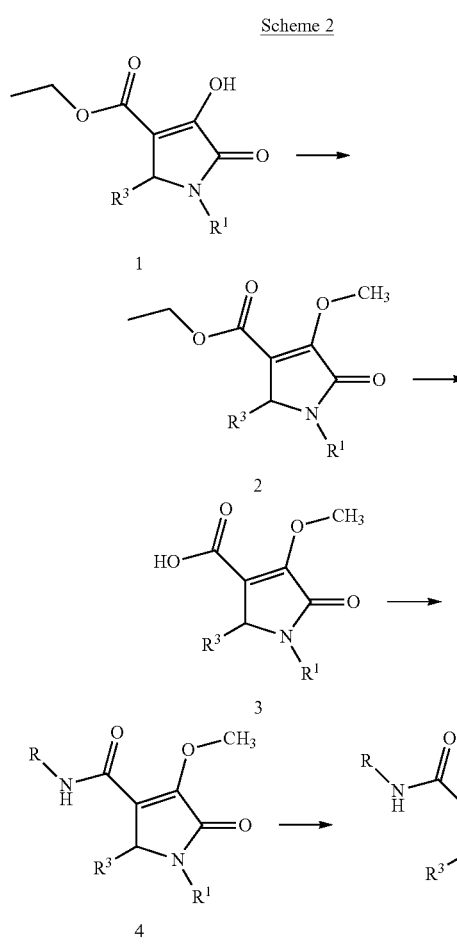

Compounds of formula 5 may also be synthesized according to Scheme 2. Thus, compounds of formula 2 may be accessed by O-alkylation of compounds of formula 1 using, for example, trimethylsilyldiazomethane in a suitable solvent such as acetonitrile at room temperature. Hydrolysis of the ester moiety of compounds of formula 2 using, for example, sodium hydroxide or lithium hydroxide in a suitable solvent such as methanol or THF containing water at room temperature provides carboxylic acids of formula 3, which can be condensed with amines to form amides of formula 4 using standard amide coupling conditions (e.g., EDC, HOBt and a base such as TEA, DIPEA or N-methylmorpholine in, for example, DMF or DCM). Demethylation of the methoxy group of compounds of formula 4 provides compounds of formula 5 may be achieved using, for example, boron tribromide or boron trichloride in a suitable solvent such as dichloromethane at room temperature.

Scheme 3

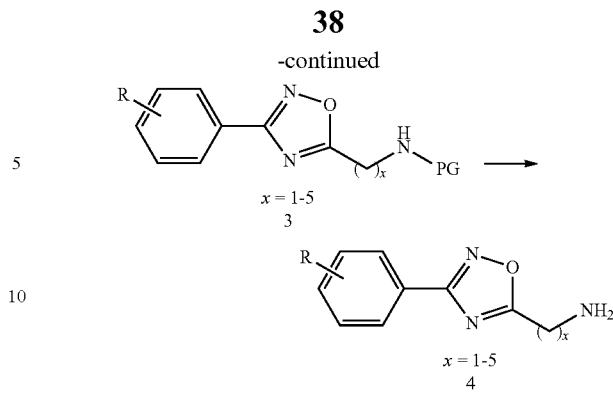

Amines of formula 4 may be synthesized according to Scheme 3. N-hydroxybenzimidic acids of formula 1 may be coupled to carboxylic acids of formula 2 using, for example, DIC and DMAP in a suitable solvent such as DMF. The intermediate thus formed is dehydrated to give oxadiazoles of formula 3 by stirring in, for example, pyridine while heating to 145° C. using microwave irradiation. Other temperatures, solvents and methods of heating may be employed. Deprotection of the amine of compounds of formula 3 using, for example, 10% TFA in $CH_2Cl_2$ when Boc is used as the amine protecting group provides amines of formula 4.

Scheme 4

Amines of formula 4, where A is selected from aryl, heteroaryl and cycloalkyl groups, wherein each moiety may be optionally substituted, may be synthesized according to Scheme 4. Thus, compounds of formula 1 are combined with benzonitriles of formula 2 suitably substituted with a leaving group para to the nitrile. Leaving groups include, for example, bromine. The nitrile moiety of compounds of formula 3 are reduced to provide compounds of formula 4 using a reducing reagent such as, for example, $LiAlH_4$ in a suitable solvent such as THF. Other reducing reagents and solvents known to those skilled in the art may be employed.

Scheme 5

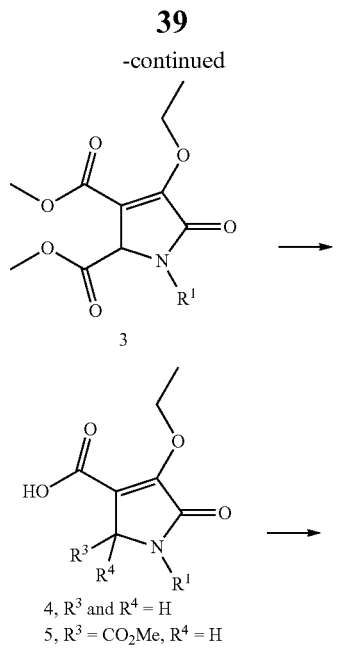

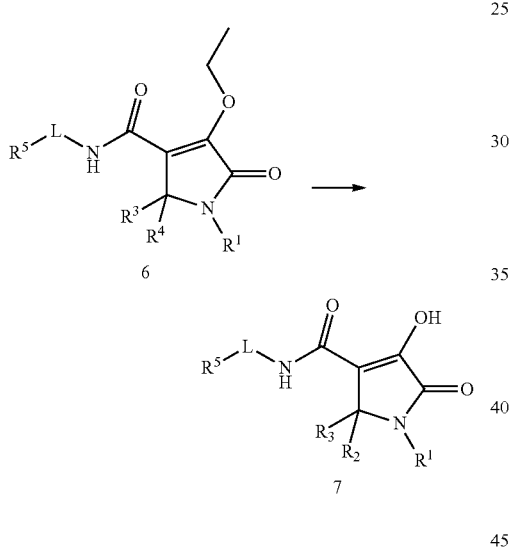

4, $R^3$ and $R^4$ = H
5, $R^3$ = $CO_2Me$, $R^4$ = H

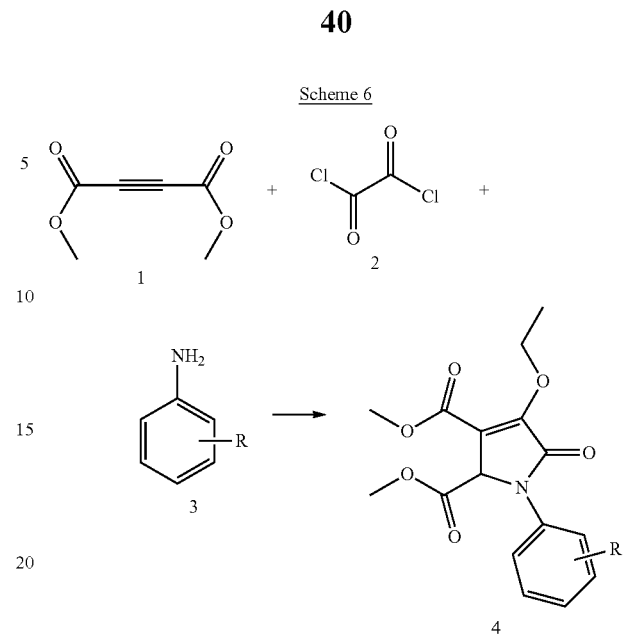

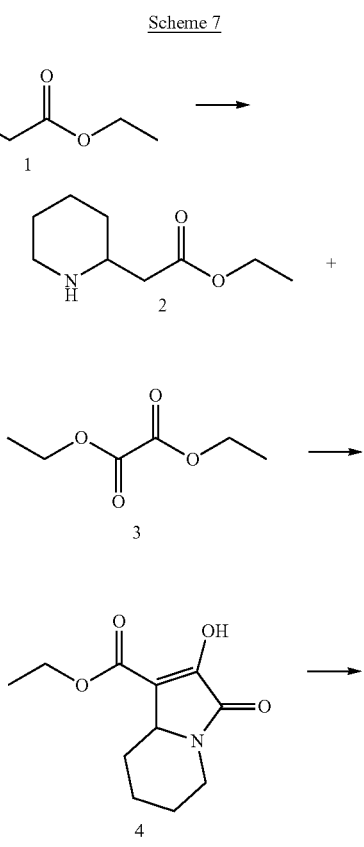

Alternatively to Scheme 5, compounds of formula 4 may also be synthesized according to Scheme 6, using the modified protocols described in Anary-Abbasinejad, M. et al, *Journal of Chemical research*, 574-576 (2007), from commercially available triphenylphosphine, dimethyl but-2-ynedioate, oxalyl dichloride, and anilines, where R could be any substitution, in a suitable solvent, such as DCM.

Compounds of formula 7 may be synthesized according to Scheme 5. Compounds of formula 2, where $R^1$ is alkyl or aryl or heteroaryl, wherein each moiety may be optionally substituted, can be synthesized from ethyl oxalylchloride and aliphatic or aromatic amines by using methods generally known in the art. Compounds of formula 3, which can be synthesized according to modified methods described in Yavari, Issa et al, *Synthetic Communications*, 2527-2534 (2002), from triphenylphosphine, dimethyl but-2-ynedioate, and compounds of formula 2 in a variety of solvents, such as methylene chloride, 1,2-dichloroethane, ethyl acetate, DMSO, etc., at 0-80° C. Saponification and decarboxylation of compounds of formula 3 by heating with aqueous LiOH or NaOH in MeOH and/or THF can give compounds of formula 4 (where $R^3$ and $R^4$=H), or compounds of formula 5 (where $R^3$=$CO_2Me$, $R^4$=H). The monoacids of formula 4 or 5 can be condensed with an amine, using standard peptide protocols, to afford amides of formula 6. The removal of ethoxy group by standard deprotection procedures known to those skilled in the art gives the compounds of formula 7.

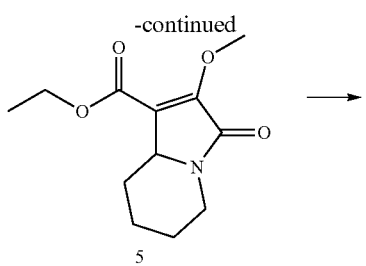

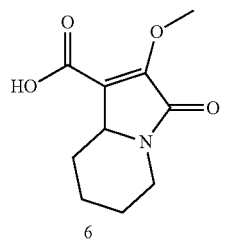

Compounds of formula 1, which can either be commercially available or synthesized according to methods known in the art of organic synthesis, can be hydrogenated over either rhodium on alumina catalyst or platinum (IV) oxide to afford the amino ester 2. Compound 2 can be combined with diethyl oxalate, compound 3, to afford the monocycle 4, which is methylated using conditions generally known in the art. Saponification of the ethyl ester using known methods can afford acid of formula 6.

Scheme 8

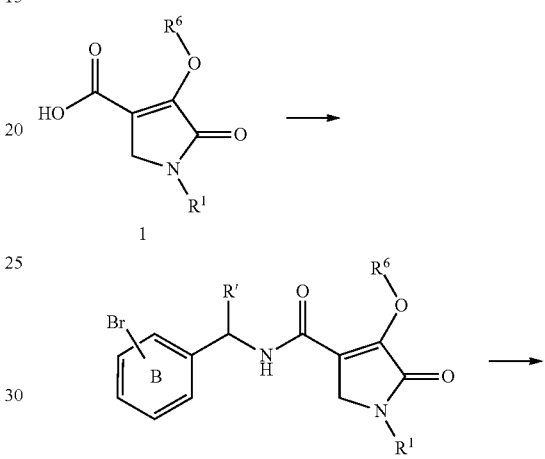

Compounds of formula 5 can also be synthesized by an extension of the imine addition method using modified conditions described by B. M. Goldschmidt, *J. Org. Chem.*, 27, 4057 (1962). Compounds of formula 1, which can either be commercially available or synthesized according to methods known in the art of organic synthesis, can be condensed with ester 2 to afford the monocycle of formula 3, which can be methylated using conditions generally known in the art to give compounds of formula 4. Saponification of the ethyl ester using known methods can afford the acid of formula 5.

Scheme 9

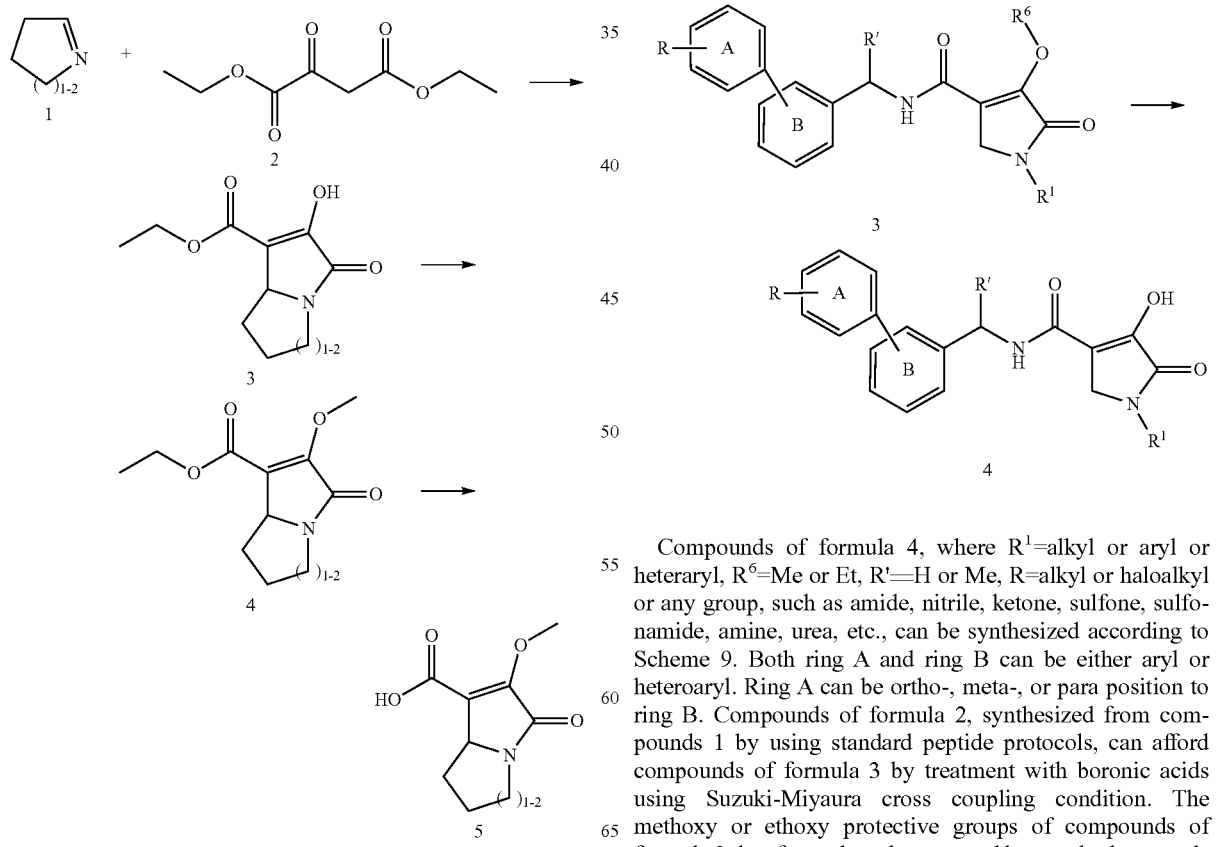

Compounds of formula 4, where $R^1$=alkyl or aryl or heteraryl, $R^6$=Me or Et, R'=H or Me, R=alkyl or haloalkyl or any group, such as amide, nitrile, ketone, sulfone, sulfonamide, amine, urea, etc., can be synthesized according to Scheme 9. Both ring A and ring B can be either aryl or heteroaryl. Ring A can be ortho-, meta-, or para position to ring B. Compounds of formula 2, synthesized from compounds 1 by using standard peptide protocols, can afford compounds of formula 3 by treatment with boronic acids using Suzuki-Miyaura cross coupling condition. The methoxy or ethoxy protective groups of compounds of formula 3 thus formed can be removed by standard protocols to give the compounds of formula 4.

Scheme 10

L = boronic acid or ester

Scheme 10 illustrates a method of synthesis of ketones of formula 7 where R is selected from groups consisting of: $C_{3-6}$ cycloalkyl, phenyl, naphthyl, and a 5- to 10-membered heterocycle and R can be optionally substituted. The vinyl intermediates of formula 6 can be readily synthesized by reaction between alkyl, heteroaryl or aryl halides (X=Br or I) of formula 1 and boronic acids or esters of formula 3, or alternatively, between boronic acids or esters of formula 2 and vinyl triflates of formula 4. All these starting materials are either commercially available or can be readily synthesized via methodology known to one skilled in the art of organic synthesis. Subsequent hydrogenation of the double bond in formula 5 and hydrolysis of ketal in formula 6 under acidic condition yields the ketones of formula 7.

Scheme 11

Amines of formula 4 may be synthesized according to Scheme 11. Phenols (X=O) or thiols (X=S) of formula 1 may be coupled to amines of formula 2, where R'=H or Me, suitably protected with, for example, phthalimide or Boc, and containing a leaving group (LG) such as bromide. The reaction takes place in the presence of a base such as $Cs_2CO_3$ in a suitable solvent such as DMF. Removal of the protecting group from compounds of formula 3 provides amines of formula 4. When the protecting group is a phthalimide, the typical deprotection procedure employs hydrazine monohydrate in a suitable solvent such as EtOH. When a Boc group is employed as the protecting group, it is typically removed using, for example, 10% TFA in a suitable solvent such as DCM.

Scheme 12

Scheme 12 outlines preparation of amine intermediates of formula 4, wherein on a cycloalkyl ring, $R^5$ is selected from groups consisting of: $C_{3-6}$ cycloalkyl, phenyl, naphthyl, and a 5- to 10-membered heterocycle comprising carbon atoms and 1-4 heteroatoms selected from N, O, and $S(O)_p$; and $R^5$ may be optionally substituted. Reductive amination of the cyclic ketone of formula 1 with diphenylmethanamine followed by separation of the cis and trans isomers using silica gel chromatography and subsequent hydrogenation can provide the desired cis or trans amines of formula 4.

Scheme 13

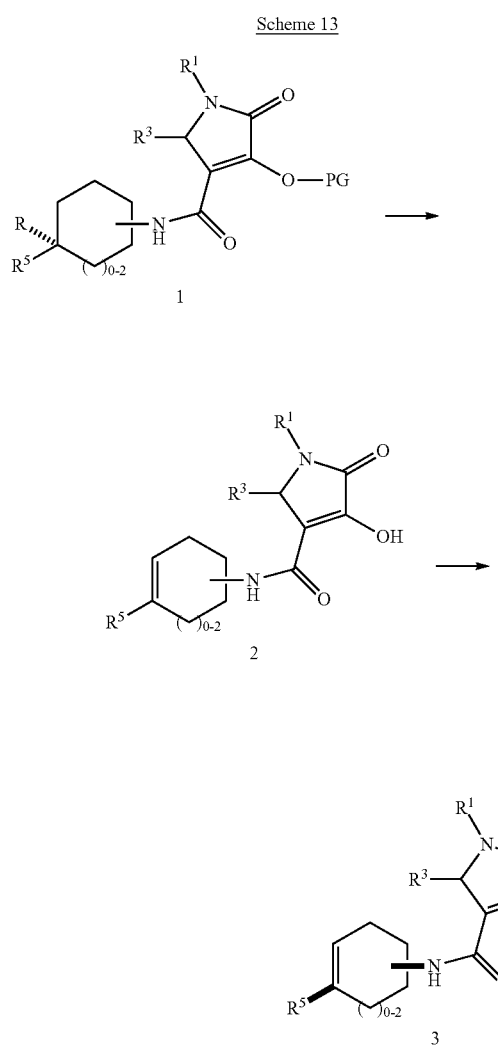

When R in Scheme 13 equals OH or OMe, during deprotection step to remove alkyloxy protection group, R can be eliminated to give the vinyl product as compounds of formula 2. Hydrogenation of compound 2 with Pd/C in ethanol can afford both cis and trans isomers of formula 3, which can be separated using prep HPLC separation techniques.

Scheme 14

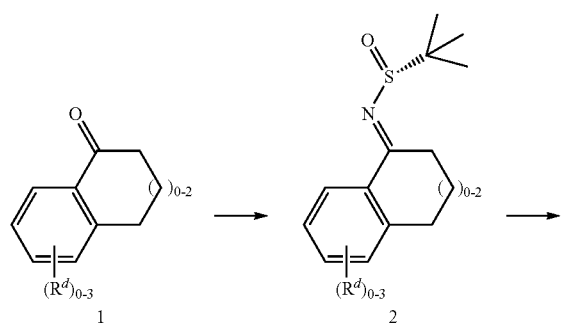

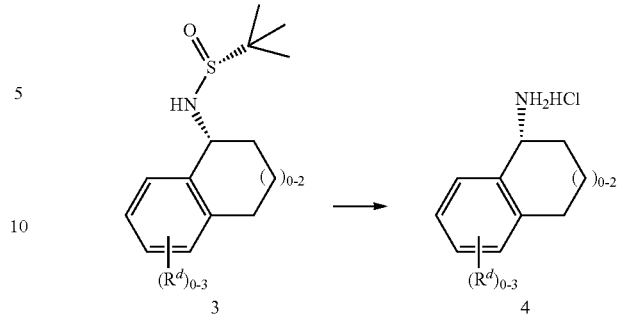

Scheme 14 illustrates bicyclic amines of formula 4 ($R^5$-L-$NH_2$) wherein $R^5$-L is an indane or a tetralin or a 6,7,8,9-tetrahydro-5H-benzo[7]annulene ring. The ketone starting material of formula 1 is either commercially available or can be readily prepared from commercially available materials by methods known to one skilled in the art of organic synthesis, for example, Friedel-Crafts reaction or by intramolecular cyclization. The desired diastereomers can be obtained by using Ellman's t-butylsulfinamide methodology (Ellman, J. A. *J. Org. Chem.* 2007, 72, 626-629). Reduction of sulfinamides of formula 2 with either $NaBH_4$ or L-selectride at low temperature (for examples, −40 to −50° C.) in THF can afford the diastereomers of formula 3 after silica gel column chromatography. Compound 3 can be hydrolyzed to give the desired enantiopure amines of formula 4.

GENERAL METHODS

The following methods were used in the exemplified Examples, except where noted otherwise.

Analytical HPLC and LC/MS Methods Employed in Characterization of Examples and Preparative HPLC Methods Employed in Purification of Examples Reverse phase analytical HPLC/MS was performed on Shimadzu LC10AS systems coupled with Waters ZMD Mass Spectrometers (Methods A-C, E and F) or Waters Aquity system coupled with a Waters Micromass ZQ Mass Spectrometer (Method D). Chiral analytical LC was performed on a Berger Analytical SFC instrument (Method G).

Method A: Linear gradient of 0 to 100% B over 4 min, with 1 min hold at 100% B;
UV visualization at 220 nm
Column: Phenomenex Luna C18 4.6×50 mm
Flow rate: 4 mL/min
Solvent A: 0.1% trifluoroacetic acid, 90% water, 10% acetonitrile
Solvent B: 0.1% trifluoroacetic acid, 90% acetonitrile, 10% water.

Method B: Linear gradient of 0 to 100% B over 4 min, with 1 min hold at 100% B;
UV visualization at 220 nm
Column: Phenomenex Luna C18 4.6×50 mm
Flow rate: 4 mL/min
Solvent A: 10 mM ammonium acetate, 90% water, 10% acetonitrile
Solvent B: 10 mM ammonium acetate, 90% acetonitrile, 10% water.

Method C: Linear gradient of 0 to 100% B over 4 min, with 1 min hold at 100% B;
UV visualization at 220 nm
Column: Phenomenex Luna C18 4.6×50 mm
Flow rate: 4 mL/min Solvent A: 0.1% trifluoroacetic acid, 90% water, 10% methanol
Solvent B: 0.1% trifluoroacetic acid, 90% methanol, 10% water.
Method D: Linear gradient of 0 to 100% B over 2 min, with 1 min hold at 100% B;
UV visualization at 220 nm
Column: Phenomenex Luna C18 2.0×30 mm
Flow rate: 1 mL/min
Solvent A: 0.1% trifluoroacetic acid, 90% water, 10% methanol
Solvent B: 0.1% trifluoroacetic acid, 90% methanol, 10% water.
Method E: Linear gradient of 0 to 100% B over 4 min, with 1 min hold time at 100% B;
UV visualization at 220 nm;
Column: Ascentis Express 4.6×50 C18 at 45° C.;
Flow rate: 4 mL/min;
Solvent A: 10 mM ammonium acetate, 5% ACN, 95% water;
Solvent B: 10 mM ammonium acetate, 95% ACN, 5% water.
Method F: Linear gradient of 0 to 100% B over 8 min, with 1 min hold at 100% B;
UV visualization at 220 nm;
Column: PHENOMENEX® Luna C18 4.6×75 mm;
Flow rate: 2.5 mL/min.
Solvent A: 10 mM ammonium acetate, 90% water, 10% methanol;
Solvent B: 10 mM ammonium acetate, 90% methanol, 10% water.
Method G: Isocratic 80/20 $CO_2$/MeOH containing 0.1% DEA;
UV visualization at 220 nm;
Column: CHIRALPAK® AC, 250×4.6 mm, 10 μM;
Flow rate: 3.0 mL/min.
Method H (Preparative HPLC method): Linear gradient of 0 to 100% B over 10 min, with 5 min hold time at 100% B; Shimadzu LC-8A binary pumps; Waters ZQ mass spectrometer using Waters Masslynx 4.0 SP4 MS software;
UV visualization at 220 nm;
Column: Waters SunFire 19×100 mm 5 μm C18;
Flow rate: 20 mL/min;
Peak collection triggered by mass spectrometry;
Solvent A: 0.1% TFA, 10% ACN, 90% water;
Solvent B: 0.1% TFA, 90% ACN, 10% water.
Method I (Preparative HPLC method): Linear gradient of 20 to 100% B over 10 min, with 5 min hold time at 100% B; Shimadzu LC-8A binary pumps; Shimadzu SPD-20A UV detector;
UV visualization at 220 nm;
Column: PHENOMENEX® Luna AXIA 21.1×100 mm 5 μm C18;
Flow rate: 20 mL/min;
Peak collection triggered by UV absorbance;
Solvent A: 0.1% TFA, 10% MeOH, 90% water;
Solvent B: 0.1% TFA, 90% MeOH, 10% water.
Method J (Preparative HPLC method): Linear gradient of 20 to 100% B over 10 min, with 2 min hold time at 100% B; Shimadzu LC-8A binary pumps; Shimadzu SPD-10A UV detector;
UV visualization at 220 nm;
Column: PHENOMENEX® Luna AXIA 21.1×100 mm 5 μm C18;
Flow rate: 20 mL/min;
Peak collection triggered by UV absorbance;
Solvent A: 0.1% TFA, 10% ACN, 90% water;
Solvent B: 0.1% TFA, 90% ACN, 10% water.

Method K (Preparative HPLC method): Isocratic 80/20 $CO_2$/$CH_3OH$ containing 0.1% DEA; Berger Multigram II SFC instrument;
UV visualization at 220 nm;
Column: CHIRALPAK® AD-H 250×21 cm ID, 5 μm;
Flow rate: 65 mL/min;
Peak collection triggered by UV absorbance.
Method L: Linear gradient of 0 to 100% B over 2 min, with 1 min hold at 100% B;
UV visualization at 220 nm;
Column: Phenomenex Luna C18 2.0×30 mm;
Flow rate: 1 mL/min;
Solvent A: 0.1% trifluoroacetic acid, 90% water, 10% methanol;
Solvent B: 0.1% trifluoroacetic acid, 90% methanol, 10% water.
Method M: Linear gradient of 0 to 100% B over 2 min, with 1 min hold at 100% B;
UV visualization at 220 nm;
Column: Phenomenex Luna C18 2.0×30 mm;
Flow rate: 1 mL/min;
Solvent A: 0.1% trifluoroacetic acid, 90% water, 10% acetonitrile;
Solvent B: 0.1% trifluoroacetic acid, 90% acetonitrile, 10% water.
Method N: Linear gradient of 0 to 100% B over 4 min, with 1 min hold at 100% B;
UV visualization at 220 nm;
Column: PHENOMENEX® Luna C18 4.6×50 mm;
Flow rate: 4 mL/min;
Solvent A: 0.1% trifluoroacetic acid, 90% water, 10% MeOH;
Solvent B: 0.1% trifluoroacetic acid, 90% MeOH, 10% water.
Method O: Linear gradient of 0 to 100% B over 2 min, with 1 min hold at 100% B;
UV visualization at 220 nm
Column: Phenomenex Luna C18 2.0×30 mm
Flow rate: 1 mL/min
Solvent A: 0.1% formic acid, 90% water, 10% methanol
Solvent B: 0.1% formic acid, 90% methanol, 10% water.
Method P: Linear gradient of 0 to 100% B over 4 min, with 1 min hold at 100% B;
UV visualization at 220 nm
Column: Mac-Mod Halo C18, 4.6×50 mm
Flow rate: 4 mL/min
Solvent A:
10 mM ammonium acetate, 95% water, 5% ACN
Solvent B: 10 mM ammonium acetate, 95% ACN, 5% water
Method Q: Linear gradient of 0 to 100% B over 4 min, with 1 min hold at 100% B;
UV visualization at 220 nm;
Column: Waters XBridge C18, 4.6×50 mm, 5 μm;
Flow rate: 4 mL/min;
Solvent A: 0.05% trifluoroacetic acid, 95% water, 5% MeOH;
Solvent B: 0.05% trifluoroacetic acid, 95% MeOH, 5% water.
Method R: Linear gradient of 0 to 100% B over 2 min, with 1 min hold at 100% B;
UV visualization at 220 nm;
Column: PHENOMENEX® Luna C18 4.6×50 mm;
Flow rate: 5 mL/min;
Solvent A: 10 mM ammonium acetate, 90% water, 10% methanol;
Solvent B: 10 mM ammonium acetate, 90% methanol, 10% water.

Method S (Preparative HPLC method): Linear gradient of
20 to 100% B over 20 min;
UV visualization at 220 nm;
Column: Axia Luna 5 µm C18 30×100 mm;
Flow rate: 40 mL/min;
Solvent A: 0.1% TFA, 10% ACN, 90% water;
Solvent B: 0.1% TFA, 90% ACN, 10% water.
Method T (Preparative HPLC method): Linear gradient of
20 to 100% B over 10 min, with 2 min hold time at 100% B;
UV visualization at 220 nm;
Column: YMC Sunfire, 5 µm, C18 column, 30×100 mm;
Flow rate: 40 mL/min;
Solvent A: 0.1% TFA, 10% MeOH, 90% water;
Solvent B: 0.1% TFA, 90% MeOH, 10% water.
Method U (Preparative HPLC method): Linear gradient of
20 to 100% B over 10 min;
UV visualization at 220 nm;
Column: Axia Luna 5 µm C18 30×100 mm;
Flow rate: 40 mL/min;
Solvent A: 0.1% TFA, 10% ACN, 90% water;
Solvent B: 0.1% TFA, 90% ACN, 10% water.
Method V: Linear gradient of 0 to 100% B over 2 min, with
1 min hold at 100% B;
UV visualization at 220 nm;
Column: Phenomenex Luna C18 2.0×30 mm;
Flow rate: 1 mL/min;
Solvent A: 0.1% trifluoroacetic acid, 90% water, 10% methanol;
Solvent B: 0.1% trifluoroacetic acid, 90% methanol, 10% water.
Method W
Linear gradient of 0 to 100% B over 3.75 min, with 1.5 min
hold at 100% B;
UV visualization at 220 nm;
Column: Waters XBridge C18, 4.6×50 mm, 5 µm;
Flow rate: 4 mL/min;
Solvent A: 10 mM ammonium acetate, 95% water, 5% acetonitrile;
Solvent B: 10 mM ammonium acetate, 95% acetonitrile, 5% water.
NMR Employed in Characterization of Examples $^1$H NMR spectra were obtained with Bruker or JEOL fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman et al., *Science*, 235:442-447 (1987); Yanagisawa et al., *Nature*, 332:411-415 (1988); Folkman et al., *J. Biol. Chem.*, 267:10931-10934 (1992); Janssens et al., *J. Biol. Chem.*, 267:14519-14522 (1992); Lamas et al., *Proc. Natl. Acad. Sci. U.S.A.*, 89:6348-6352 (1992); Luscher et al., *Hypertension*, 19:117-130 (1992); Williams et al., *Am. Rev. Respir. Dis.*, 146:545-S50 (1992); and Bevilacqua et al., *J. Clin. Invest.*, 91:379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation*, 79:8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos et al., *Circulation*, 106:1321-1326 (2002)). Notably, the endothelial lipase-mediated binding and uptake of HDL particles and the selective uptake of HDL-derived cholesterol esters have been reported to be independent of its enzymatic lipolytic activity (Strauss et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 uL of 1 mM DMPG in a 1:1 mixture of MeOH and CHCl$_3$ with 15 uL of 1 mM A10070 in a 1:1 mixture of MeOH and CHCl$_3$. The mixture was dried under nitrogen and resuspended in 150 uL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 uL of assay buffer (50 mM HEPES pH 8.0, 50 mM NaCl and 1 mM CaCl$_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 uL of a 1:4 dilution of vesicles. The final total reaction volume was 100 uL. The reaction rates were measured on a Gemini plate reader with an excitation wavelength of 488 nm and a emission of 530 nm. Readings were taken every 20 seconds for 10 min with agitation between each reading. The slope of the linear portion of the readout was used to calculate the rate of the reaction.

The exemplified examples disclosed in the present invention were tested in the EL assay described above and found having EL inhibitory activity. The EL IC$_{50}$ values measured for the following examples are listed in Table 1.

TABLE 1

| Ex. No. | HLE_EL_CRC IC$_{50}$ (nM) |
|---|---|
| 2 | 43.05 |
| 8 | 49.45 |
| 9 | 27.05 |
| 18 | 27.00 |
| 21 | 15.38 |
| 22 | 270.4 |
| 24 | 9295 |
| 29 | 22.08 |
| 34 | 32.12 |
| 48 | 27.08 |
| 62 | 246.30 |
| 63 | 249.50 |
| 66 | 285.00 |
| 83 | 256.60 |
| 85 | 241.30 |
| 91 | 270.90 |
| 92 | 245.80 |
| 96 | 277.30 |
| 103 | 49.64 |
| 104 | 253.50 |
| 146 | 49.99 |
| 157 | 4842 |
| 168 | 252.10 |
| 169 | 7169.00 |
| 172 | 4724.00 |
| 173 | 8468.00 |
| 178 | 9919.00 |
| 179 | 3094.00 |
| 181 | 5733.00 |
| 196 | 8254.00 |
| 210 | 6570.00 |
| 212 | 8276.00 |
| 214 | 460.4 |
| 218 | 43.54 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent (s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1

2-(3-phenyl-1,2,4-oxadiazol-5-yl)ethanamine

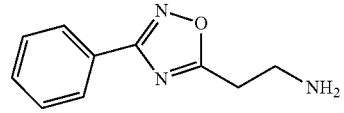 [SMILES: NCCc1nc(-c2ccccc2)no1]

Intermediate 1A

Tert-butyl 2-(3-phenyl-1,2,4-oxadiazol-5-yl)ethylcarbamate

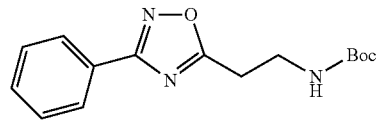 [SMILES: CC(C)(C)OC(=O)NCCc1nc(-c2ccccc2)no1]

To a solution of 3-(tert-butoxycarbonylamino)propanoic acid (1.0 g, 5.3 mmol), (Z)—N'-hydroxybenzimidamide (0.86 g, 6.3 mmol) and DMAP (0.65 g, 5.3 mmol) in DMF (20 mL) was added DIC (0.823 mL, 5.29 mmol). The reaction mixture was stirred at rt for 16 h. The reaction was then divided into 2 equal portions, diluted with pyridine (7.0 mL), and heated to 145° C. for 20 min using microwave irradiation. After cooling to rt, the reaction mixtures were combined, diluted with EtOAc (400 mL), the organic portions washed with 1N HCl (50 mL), saturated aqueous NaCl, dried over MgSO$_4$, filtered and evaporated to dryness in vacuo. The residue was purified via silica gel chromatography to obtained 1.2 g (78% yield) of Intermediate 1A. HPLC/MS (Method C) RT=3.26 min, [M+H]$^+$ 290.

Intermediate 1

To a suspension of Intermediate 1A (1.2 g, 4.2 mmol) in DCM (11 mL) was added TFA (11 mL). The reaction mixture was stirred at rt for several hours. The reaction mixture was diluted with CH$_2$Cl$_2$, and washed with saturated NaHCO$_3$ then brine. The aqueous phases were extracted with CH$_2$Cl$_2$ (3×), and the combined organic portions dried over Na$_2$SO$_4$, filtered, and concentrated to give Intermediate 1 (623 mg, 79% yield). HPLC/MS (Method C) retention time=1.43 min, [M+H]$^+$ 190.2; $^1$H NMR (500 MHz, chloroform-d) (δ ppm): 1.63 (br s, 2 H), 3.09 (t, J=6.32 Hz, 2 H), 3.25 (t, J=6.32 Hz, 2 H), 7.46-7.53 (m, 3 H), 8.08 (d, J=6.05 Hz, 2 H).

Intermediate 2

(4-(3,4-dichlorophenoxy)phenyl)methanamine

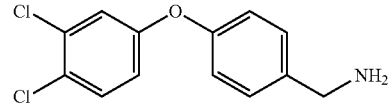 [SMILES: NCc1ccc(Oc2ccc(Cl)c(Cl)c2)cc1]

Intermediate 2A 4-(3,4-Dichlorophenoxy)benzonitrile

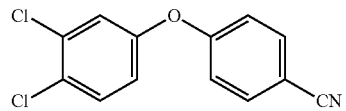 [SMILES: N#Cc1ccc(Oc2ccc(Cl)c(Cl)c2)cc1]

To a solution of 4-bromobenzonitrile (500 mg, 2.8 mmol), 3,4-dichlorophenol (896 mg, 5.50 mmol), and 2,2,6,6-tetramethyl-3,5-heptanedione (0.06 mL, 0.3 mmol), $Cs_2CO_3$ (1.8 g, 5.5 mmol) in N-methyl-2-pyrrolidinone (10 mL) stirring under Ar was added CuCl (136 mg, 1.4 mmol). The reaction vessel was evacuated and backfilled with Ar. The reaction mixture was heated to 120° C. for 1.75 h. The reaction mixture was allowed to cool to rt, diluted with EtOAc (50 mL) and filtered. The resulting blue solid was washed with 2×20 mL of EtOAc. The combined filtrates were washed with 2 M aqueous HCl, 0.3 M aqueous HCl, and 2 M aqueous NaOH. The organic layer was dried over $Na_2SO_4$, filtered and evaporated in vacuo. The product was purified by silica gel chromatography (40 g silica gel; linear gradient 0-20% EtOAc in hexanes over 15 min) to give 196 mg (27%) of Intermediate 2A. HPLC/MS (Method D) RT=0.91 min, $[M+1]^+$ 264.2.

Intermediate 2

To a solution of Intermediate 2A (196 mg, 0.74 mmol) in anhydrous THF (8 mL) stirring at rt under argon was added by dropwise addition $LiAlH_4$ (0.37 mL, 0.74 mmol). The reaction mixture was stirred at rt for 1 h. The reaction mixture was cooled to 0° C. and quenched by dropwise addition of 1N aqueous NaOH. The mixture was concentrated to dryness in vacuo and the solid residue washed with EtOAc. The solid was removed by filtration. The filtrate was washed with 3 N aqueous HCl. The combined acidic aqueous extracts were made basic with excess 3 N aqueous NaOH, and then extracted with EtOAc. The combined organic layers were dried over $Na_2SO_4$, filtered and concentrated in vacuo. $^1$H NMR ($CDCl_3$): δ: 1 mixture of the desired product and the mono chloro derivative. Include the separation conditions for intermediate 2 Obtained 79 mg (32% yield) of Intermediate 2. HPLC/MS (Method D) RT=0.82 min, $[M-NH_2+1]^+$ 251; $^1$H NMR (400 MHz, chloroform-d) (δ ppm): 1.65 (s, 2 H), 3.87 (s, 2 H), 6.83 (dd, J=8.78, 2.76 Hz, 1 H), 6.94-7.01 (m, 2 H), 7.05 (d, J=2.76 Hz, 1 H), 7.26-7.37 (m, 3 H).

Intermediate 3

(Z)-2-(2,2-dimethyl-5-oxo-1,3-dioxolan-4-ylidene)-N-(2-phenoxybenzyl)acetamide

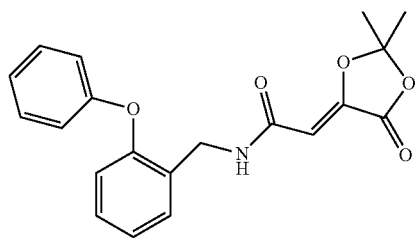 [SMILES: CC1(C)OC(=O)/C(=C/C(=O)NCc2ccccc2Oc2ccccc2)O1]

To a solution of (2-phenoxyphenyl)methanamine, HCl (100 mg, 0.424 mmol), HOBT (84 mg, 0.552 mmol) and EDC (106 mg, 0.552 mmol) in DMF (2 mL) was added N-methylmorpholine (0.187 mL, 1.70 mmol). The mixture was stirred for 2 h at rt. The reaction mixture was diluted with ethyl acetate (10 mL), and washed with 3×20 mL of 1:1 brine/$H_2O$. The organic portion was dried over sodium sulfate and concentrated to dryness under reduced pressure. The residue was purified by flash chromatography (12 g silica gel), eluting with 0-100% ethyl acetate/hexanes over 15 min to give the Intermediate 3 (114 mg, 76% yield). HPLC/MS (Method D) RT=1.02 min; $[M+H]^+$ 354.3.

Intermediate 4

1-ethyl-4,5-dioxopyrrolidine-3-carboxylic acid

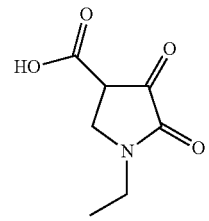

A solution of ethyl 1-ethyl-4,5-dioxopyrrolidine-3-carboxylate (150 mg, 0.753 mmol) and LiOH (43.3 mg, 1.81 mmol) in THF (0.5 mL) and $H_2O$ (0.5 mL) was heated at 80° C. for 1 h using microwave irradiation. The reaction solution was concentrated under reduced pressure and acidified with 1 N aqueous HCl, whereupon a precipitate formed. $CH_2Cl_2$ was added to the suspension and the precipitate was collected by filtration, which was dried in vacuo to provide Intermediate 4 (92.1 mg, 71.4% yield). HPLC/MS (Method D) RT=0.48 min, $[M+H]^+$ 172.1; $^1$H NMR (400 MHz, Solvent) (δ ppm): 1.11-1.24 (m, 3 H), 3.53 (q, J=7.28 Hz, 2 H), 3.84 (s, 0.47 H), 4.04 (s, 1.53 H).

Intermediate 5

1-ethyl-4-methoxy-5-oxo-2,5-dihydro-1H-pyrrole-3-carboxylic acid

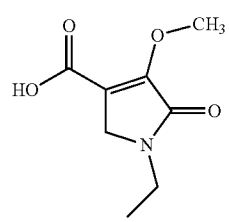

Intermediate 5A

Ethyl 1-ethyl-4-methoxy-5-oxo-2,5-dihydro-1H-pyrrole-3-carboxylate

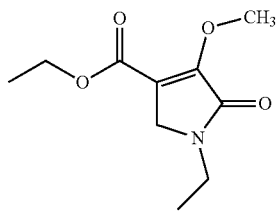

To a solution of ethyl 1-ethyl-4,5-dioxopyrrolidine-3-carboxylate (200 mg, 1.0 mmol) and DIPEA (0.18 mL, 1.0 mmol) in ACN (1.8 mL) and MeOH (0.2 mL) was added TMS-CH$_2$N$_2$ (2.0 M in Et$_2$O; 0.5 mL, 1.0 mmol). The reaction mixture was stirred at rt for 3.5 h, then evaporated in vacuo. The product was purified by silica gel chromatography (40 g silica gel; linear gradient of 0-50% MeOH:EtOAc (10:1) in hexanes over 15 min) to obtain Intermediate 5A (203 mg, 95% yield). HPLC/MS (Method D) RT=0.73 min, [M+H]$^+$ 214.2.

Intermediate 5

A solution of Intermediate 5A (20 mg, 0.094 mmol) and NaOH (9.8 mg, 0.24 mmol) in MeOH (0.12 mL) and H$_2$O (0.12 mL) was stirred at 70° C. for 1 h. The reaction mixture was concentrated and the residue was dissolved in CH$_2$Cl$_2$ and acidified using concentrated HCl. LCMS indicated aqueous layer contains small amount of product. The reaction mixture was lyophilized to give Intermediate 5 (29.1 mg, 0.094 mmol, 101% yield). HPLC/MS (Method D) RT=0.53, [M+H]$^+$ 186.1; $^1$H NMR (400 MHz, MeOH-d$_4$) (δ ppm): 4.21 (3 H, s), 4.08 (2 H, s), 3.51 (2 H, q, J=7.28 Hz), 1.20 (3 H, m).

Intermediate 6

1-(2,4-difluorophenyl)-4-ethoxy-5-oxo-2,5-dihydro-1H-pyrrole-3-carboxylic acid

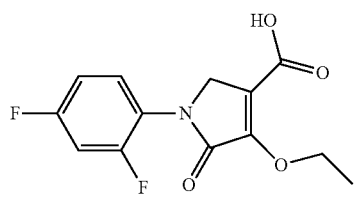 [SMILES: CCOC1=C(C(=O)O)CN(c2ccc(F)cc2F)C1=O]

Intermediate 6A

Ethyl 2-(2,4-difluorophenylamino)-2-oxoacetate

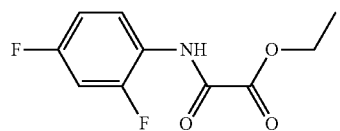

To a solution of 2,4-difluoroaniline (10 g, 77 mmol) and triethylamine (12.95 mL, 93.00 mmol) in tetrahydrofuran (50 mL) was added ethyl 2-chloro-2-oxoacetate (9.05 mL, 81.0 mmol) drop wise at 0° C. A white solid precipitated instantly. The reaction mixture was stirred at rt for 1 h. The solvent was evaporated under reduced pressure, and Et$_2$O was added. The organic layer was washed with 1N HCl (20 mL), saturated NaHCO$_3$ and then brine, dried over MgSO$_4$, filtered and concentrated to give Intermediate 6A (15.8 g, 68.9 mmol, 89.0% yield) as a white crystalline solid. HPLC/MS (Method L) RT=1.58 min, [M+H]$^+$ 230.0.

Intermediate 6B

Dimethyl 1-(2,4-difluorophenyl)-4-ethoxy-5-oxo-2,5-dihydro-1H-pyrrole-2,3-dicarboxylate

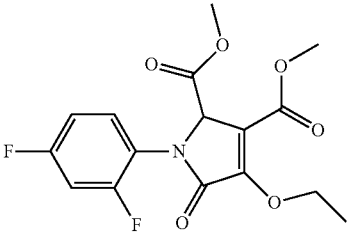 [SMILES: CCOC1=C(C(=O)OC)C(C(=O)OC)N(c2ccc(F)cc2F)C1=O]

To a stirred solution of triphenylphosphine (629 mg, 2.40 mmol) and

Intermediate 6A (458 mg, 2.00 mmol) in Cl CH$_2$CH$_2$Cl (1 mL) was added dimethyl but-2-ynedioate (0.26 mL, 2.1 mmol) drop wise at rt. The reaction mixture was stirred at 80° C. in a capped vial for 18 h. The reaction mixture was allowed to cool to rt, loaded on to a 40 g silica gel column and purified with 0-100% EtOAc/Hex to give Intermediate 6B (560 mg, 1.58 mmol, 79.0% yield) as slightly tan viscous oil. HPLC/MS (Method L) retention time=1.77 min, [M+H]$^+$ 356.0.

Intermediate 6

To a mixture of Intermediate 6B (1.6 g, 4.5 mmol) in MeOH (3 mL) and tetrahydrofuran (9 mL) was added 1N LiOH (13.51 mL, 13.51 mmol). The reaction mixture was stirred at reflux for 0.5 h then concentrated. To the residue was added 1N HCl to acidify pH to 2. The aqueous layer was extracted with DCM three times. The combined organic layers were dried over Na$_2$SO$_4$, filtered and concentrated to give a light yellow solid as Intermediate 6 (1.28 g, 4.52 mmol, 100% yield). HPLC/MS (Method L) RT=1.62 min, [M+H]$^+$ 284.0.

Intermediate 7

4-ethoxy-2-(methoxycarbonyl)-5-oxo-1-phenyl-2,5-dihydro-1H-pyrrole-3-carboxylic acid

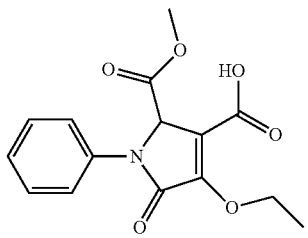 [SMILES: CCOC1=C(C(=O)O)C(C(=O)OC)N(c2ccccc2)C1=O]

To a mixture of dimethyl 4-ethoxy-5-oxo-1-phenyl-2,5-dihydro-1H-pyrrole-2,3-dicarboxylate (240 mg, 0.750 mmol), which was synthesized according to similar methods as described for Intermediate 6B, in MeOH (1 mL) was added 1N NaOH (1.50 mL, 1.50 mmol). The reaction mixture was heated at 80° C. for 2 h, allowed to cool to rt, and then concentrated under reduced pressure. To the residue was added 1N HCl to acidify pH to 2. The solvent was removed to afford crude Intermediate 7 as a gray solid. HPLC/MS (Method L) RT=1.59 min, [M+H]$^+$ 306.0.

Intermediate 8

(R)—N-(1-(3-bromophenyl)ethyl)-1-(2,4-difluorophenyl)-4-ethoxy-5-oxo-2,5-dihydro-1H-pyrrole-3-carboxamide

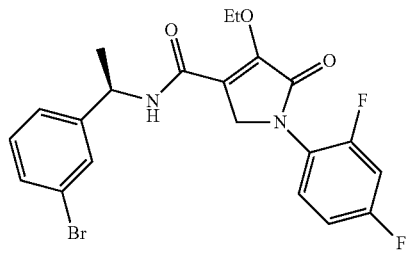 [SMILES: CCOC1=C(C(=O)N[C@H](C)c2cccc(Br)c2)CN(c2ccc(F)cc2F)C1=O]

Intermediate 8A 1-(2,4-difluorophenyl)-4-ethoxy-5-oxo-2,5-dihydro-1H-pyrrole-3-carbonyl chloride

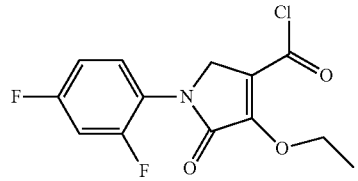 [SMILES: CCOC1=C(C(=O)Cl)CN(c2ccc(F)cc2F)C1=O]

To a solution of Intermediate 6 (0.14 g, 0.50 mmol) in DCM (2 mL) was added oxalyl chloride (0.38 mL, 0.75 mmol) and one drop of DMF. The reaction mixture was stirred at rt for 1.5 h. This crude product was used directly for next step. HPLC/MS (Method L) RT=1.79 min, [M-Cl+OMe+H]$^+$ 298.0.

Intermediate 8

To a solution of Intermediate 8A (648 mg, 2.15 mmol) in DCM (2 mL) was added TEA (0.90 mL, 6.4 mmol) and (R)-1-(3-bromophenyl)ethanamine (430 mg, 2.15 mmol). The reaction mixture was stirred at rt for 18 h, diluted with DCM. The organic layer was washed with 1N HCl and brine, dried over Na$_2$SO$_4$, filtered and concentrated. The residue was purified by flash chromatography (0-40% EtOAc/Hexanes) to give Intermediate 8 (605 mg, 1.30 mmol, 61.0% yield) as a yellow oil. HPLC/MS (Method L) RT=2.25 min, [M+H]$^+$ 465.0.

Intermediate 9

4-ethoxy-1-(4-fluorophenyl)-5-oxo-2,5-dihydro-1H-pyrrole-3-carbonyl chloride

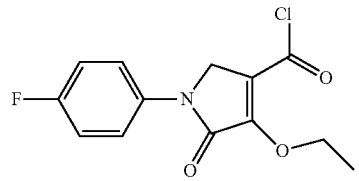 [SMILES: CCOC1=C(C(=O)Cl)CN(c2ccc(F)cc2)C1=O]

Intermediate 9 was prepared in similar procedure as described in Intermediate 8A. HPLC/MS (Method N) RT=3.29 min, [M-Cl+OMe+H]$^+$ 280.1.

Intermediate 10

1-ethyl-4-methoxy-5-oxo-N-(prop-2-ynyl)-2,5-dihydro-1H-pyrrole-3-carboxamide

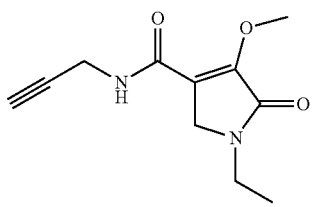 [SMILES: C#CCNC(=O)C1=C(OC)C(=O)N(CC)C1]

To a solution of prop-2-yn-1-amine (0.360 mL, 6.53 mmol), 1-ethyl-4-methoxy-5-oxo-2,5-dihydro-1H-pyrrole-3-carboxylic acid (1.1 g, 5.94 mmol) and PyBOP (3.40 g, 6.53 mmol) in DMF (50 mL) was added DIEA (3.11 mL, 17.82 mmol). The reaction was then stirred at rt for 2 h. The reaction mixture was concentrated under reduced pressure and purified by flash chromatography (4 g cartridge, 0 to 100% EtOAc/Hex) to afford Intermediate 10 (0.84 g, 3.78 mmol, 63.6% yield). HPLC/MS (Method L) RT=1.19 min, [M+1]$^+$ 223.1.

Intermediate 11

Tert-butyl (1-(3,4-dichlorobenzoyl)piperidin-4-yl)methylcarbamate

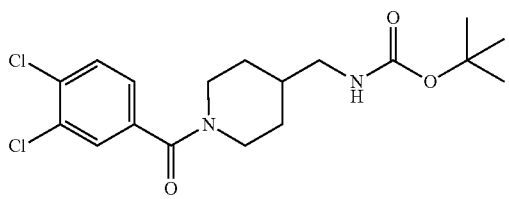 [SMILES: CC(C)(C)OC(=O)NCC1CCN(C(=O)c2ccc(Cl)c(Cl)c2)CC1]

A mixture of tert-butyl piperidin-4-ylmethylcarbamate (100 mg, 0.467 mmol), 3,4-dichlorobenzoic acid (98 mg, 0.51 mmol), HOBT (93 mg, 0.61 mmol) and EDC (116 mg, 0.607 mmol) in DMF (3 mL) was stirred for 5 min at rt and then N-methylmorpholine (0.205 mL, 1.87 mmol) was added. The reaction was stirred at rt for 14 h. The mixture was diluted with ethyl acetate (20 mL) and washed with 2×40 mL of brine. The organic portion was dried over sodium sulfate, concentrated and purified by flash chromatography (12 g silica gel), eluting with 0-100% ethyl acetate/hexanes to give Intermediate 11 (163 mg, 90%) as a white solid. HPLC/MS (Method D) RT=1.03 min, [M+1]$^+$ 409. $^1$H NMR (400 MHz, chloroform-D) δ ppm 1.03-1.30 (m, 2 H) 1.37-1.48 (m, 9 H) 1.63-1.88 (m, 3 H) 2.69-3.14 (m, 4 H) 3.57-3.83 (m, 1 H) 4.54-4.74 (m, 2 H) 7.21 (dd, J=8.21, 1.89 Hz, 1 H) 7.44-7.49 (m, 2 H).

Intermediate 12

(1-(3,4-dichlorophenylsulfonyl)piperidin-4-yl)methanamine

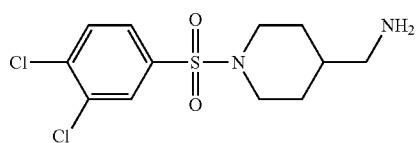 [SMILES: NCC1CCN(S(=O)(=O)c2ccc(Cl)c(Cl)c2)CC1]

Intermediate 12A

Tert-butyl (1-(3,4-dichlorophenylsulfonyl)piperidin-4-yl)methylcarbamate

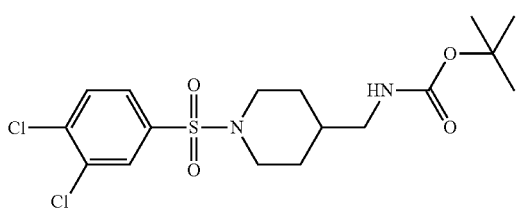 [SMILES: CC(C)(C)OC(=O)NCC1CCN(S(=O)(=O)c2ccc(Cl)c(Cl)c2)CC1]

To a solution of 3,4-dichlorobenzene-1-sulfonyl chloride (470 mg, 1.91 mmol) was added tert-butyl piperidin-4-ylmethylcarbamate (410 mg, 1.91 mmol), followed by triethylamine (0.27 mL, 1.9 mmol). The reaction mixture was stirred at rt for 18 h then diluted with DCM. The organic phase was washed with 1N HCl, H$_2$O, and brine, dried over Na$_2$SO$_4$, and then filtered. The solvent was evaporated under reduced pressure and the residue was purified on a 24 g cartridge using 0 to 100% EtOAc in Hexane and then 0 to 20% MeOH in DCM to yield Intermediate 12A (800 mg, 1.89 mmol, 99.0% yield). HPLC/MS (Method L) retention time=1.55 min, [M+H-Boc] 324.1.

Intermediate 12

To a solution of Intermediate 12A (100 mg, 0.240 mmol) in DCM (1 mL) was added HCl (0.12 mL, 0.47 mmol). The reaction mixture was stirred at rt for 16 h. The reaction mixture was concentrated and the residue was titurated with Et$_2$O. The solid was collected by filtration and dried to give Intermediate 12 (75 mg, 0.23 mmol, 98% yield). HPLC/MS (Method N) RT=2.74 min, [M+H]$^+$ 324.1.

Intermediate 13

(R)-6-(trifluoromethyl)-2,3-dihydro-1H-inden-1-amine hydrochloride

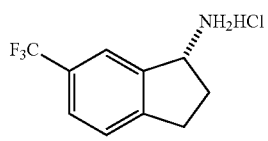

Intermediate 13A (R)-2-methyl-N-(6-(trifluoromethyl)-2,3-dihydro-1H-inden-1-ylidene)propane-2-sulfinamide

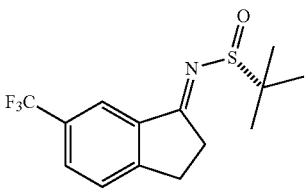 [SMILES: CC(C)(C)[S@@](=O)/N=C1\CCc2ccc(C(F)(F)F)cc21]

To a stirred solution of (R)-2-methylpropane-2-sulfinamide (578 mg, 4.77 mmol) and 6-(trifluoromethyl)-2,3-dihydro-1H-inden-1-one (1.0 g, 5.0 mmol) in THF (4 mL) at rt was added tetraethoxytitanium (1.88 mL, 9.08 mmol). The reaction mixture was heated at 75° C. for 18 h. The reaction mixture was allowed to cool and used directly in the next step. HPLC/MS (Method L), RT=2.20 min, [M+1]$^+$ 304.0.

Intermediate 13B (R)-2-methyl-N-((R)-6-(trifluoromethyl)-2,3-dihydro-1H-inden-1-yl)propane-2-sulfinamide

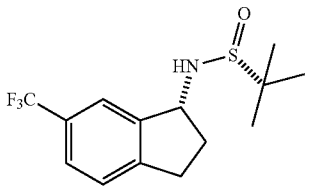 [SMILES: CC(C)(C)[S@@](=O)N[C@@H]1CCc2ccc(C(F)(F)F)cc21]

Sodium borohydride (756 mg, 20.0 mmol) was stirred in a round-bottomed flask under argon at −40 to −50° C. The reaction mixture of Intermediate 13A was added drop wise to the flask, and THF was added to the reaction mixture (ca. 0.6 M). The resulting mixture was allowed to warm up to 0° C. during 1.5 h period. The reaction mixture was cooled in dry ice and MeOH was added dropwise until gas evolution stopped. The mixture was stirred at rt for 20 min, filtered through Celite® and the Celite® rinsed with EtOAc then $CH_2Cl_2$. The filtrate was washed with brine twice and dried over $MgSO_4$, filtered and concentrated. The residue was purified on flash chromatography (hexanes/EtOAc) to give Intermediate 13B (370 mg, 1.21 mmol, 27.0% yield) as colorless crystals. HPLC/MS (ESI) (Method L), RT=2.10 min, $[M+1]^+$ 306.0.

Intermediate 13

To a solution of Intermediate 13B (370 mg, 1.21 mmol) in MeOH (5 mL) at rt was added 4N HCl in dioxane (2 mL). The resulting mixture was stirred at rt for 20 min. The solvents were evaporated and $CH_2Cl_2$ was added and evaporated for three times. The resulting white solid was vacuum dried for 1 h to give Intermediate 13 (84 mg, 0.35 mmol, 29% yield) as a crude salt. HPLC/MS (ESI) (Method L), RT=1.30 min, $[M+1]^+$185.0; $^1$H NMR (400 MHz, MeOD) δ ppm 7.57 (1 H, d, J=7.8 Hz), 7.47 (1 H, d, J=7.6 Hz), 7.25 (1 H, t, J=7.8 Hz), 4.88 (1 H, dd, J=7.8, 4.8 Hz), 3.09-3.23 (1 H, m), 2.90-3.08 (1 H, m), 2.64 (1 H, dddd, J=14.1, 8.5, 8.3, 5.7 Hz), 2.01-2.23 (1 H, m, J=14.1, 8.7, 5.3, 5.3 Hz).

Intermediate 14

Cis-4-phenylcyclohexanamine

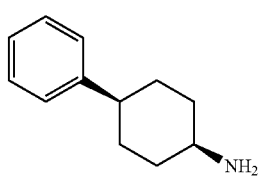 [SMILES: N[C@H]1CC[C@@H](c2ccccc2)CC1]

Intermediate 14A

Cis-N-benzhydryl-4-phenylcyclohexanamine

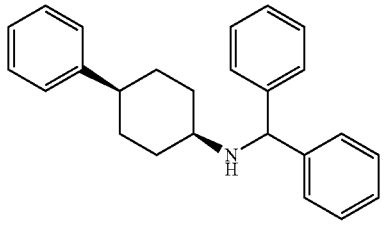 [SMILES: c1ccc(C(N[C@H]2CC[C@@H](c3ccccc3)CC2)c2ccccc2)cc1]

To a solution of 4-phenylcyclohexanone (500 mg, 2.87 mmol) and diphenylmethanamine (526 mg, 2.87 mmol) in DCE (4 mL) at 0° C. was slowly added sodium triacetoxyborohydride (912 mg, 4.30 mmol) portionwise. A white suspension formed and was stirred for 5 min before the ice-water bath was removed. The reaction mixture was stirred at rt for 1.5 h, quenched with water carefully, then saturated $NaHCO_3$ was added carefully and the aqueous layer was extracted with DCM three times. The organic layers were combined, washed with brine, dried over $Na_2SO_4$, filtered and concentrated. The residue was purified by flash chromatography (hexane/EtOAc) to give Intermediate 14A (734 mg, 2.15 mmol, 75.0% yield) and trans-N-benzhydryl-4-phenylcyclohexanamine (191 mg, 0.560 mmol, 19.0% yield). HPLC/MS (Method L), retention time=1.76 min, $[M+1]^+$ 342.1; $^1$H NMR (400 MHz, CHLOROFORM-d) δ ppm 7.37 (4 H, d, J=7.33 Hz), 7.23-7.31 (6 H, m), 7.11-7.23 (5 H, m), 4.91 (1 H, s), 2.80-2.88 (1 H, m), 2.46-2.56 (1 H, m), 1.74-1.90 (4 H, m), 1.60-1.70 (2 H, m), 1.47-1.59 (2 H, m).

Intermediate 14

To a solution of Intermediate 14A (714 mg, 2.09 mmol) in MeOH (20 mL) and EtOAc (5 mL) were added 10% palladium on carbon (71.4 mg, 0.0700 mmol) and acetic acid (0.120 mL, 2.09 mmol). The reaction mixture was stirred under $H_2$ balloon for 3 h, filtered through Celite® and the Celite® rinsed with EtOAc. The filtrate was concentrated, re-dissolved in DCM, and the organic layer was extracted with 1N HCl. The aqueous layer was basified with 1N NaOH and extracted with DCM three times. The combined organic layers were washed with brine, dried over $Na_2SO_4$, decanted, and concentrated to give Intermediate 14 (321 mg, 1.83 mmol, 88.0% yield) as a colorless wax. HPLC/MS (Method L), RT=1.43 min, $[M+1]^+$ 176.1 $^1$H NMR (400 MHz, DMSO-d) δ ppm 7.24-7.30 (4 H, m), 7.13-7.18 (1 H, m), 3.10-3.16 (1 H, m), 2.42-2.50 (1 H, m), 1.80-1.93 (2H, m), 1.60-1.66 (4H, m), 1.44-1.54 (2 H, m).

Intermediate 15

Cis-4-(3-(trifluoromethoxy)phenyl)cyclohexanamine

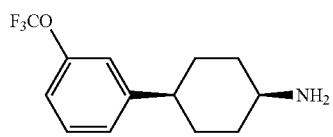 [SMILES: N[C@H]1CC[C@@H](c2cccc(OC(F)(F)F)c2)CC1]

Intermediate 15A 8-(3-(trifluoromethoxy)phenyl)-1,4-dioxaspiro[4.5]dec-7-ene

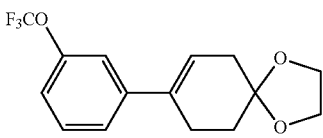 [SMILES: FC(F)(F)Oc1cccc(C2=CCC3(CC2)OCCO3)c1]

To a solution of 4,4,5,5-tetramethyl-2-(1,4-dioxaspiro[4.5]dec-7-en-8-yl)-1,3,2-dioxaborolane (150 mg, 0.560 mmol) in dioxane (2.5 mL) was added 1-iodo-3-(trifluoromethoxy)benzene (195 mg, 0.680 mmol), bis(triphenylphosphine)palladium (II) chloride (20 mg, 0.028 mmol) and a solution of sodium carbonate (179 mg, 1.69 mmol) in water (1.127 mL). The reaction mixture was degassed, refilled with Ar three times, subject to microwave irradiation at 110° C. for 90 min. The reaction mixture was diluted with H$_2$O and the aqueous phase extracted with DCM twice. The combined organic portions were dried over MgSO$_4$, filtered, concentrated under reduced pressure and purified by flash chromatography (EtOAc/Hexanes 0-50% over 20 min, column 4 g, flow rate 40 mL/min) to give Intermediate 15A (119 mg, 0.400 mmol, 70.0% yield) as a clear oil. $^1$H NMR (400 MHz, CHLOROFORM-d) δ ppm 1.93 (2 H, t, J=6.4 Hz), 2.48 (2 H, d, J=3.8 Hz), 2.59-2.71 (2 H, m), 4.02 (4 H, s), 5.96-6.11 (1 H, m), 7.03-7.11 (1 H, m), 7.22 (1 H, s), 7.27-7.36 (2H, m).

Intermediate 15B 8-(3-(trifluoromethoxy)phenyl)-1,4-dioxaspiro[4.5]decane

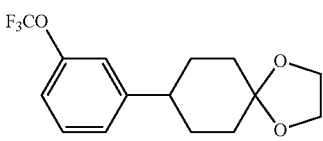 [SMILES: FC(F)(F)Oc1cccc(C2CCC3(CC2)OCCO3)c1]

To a solution of Intermediate 15A (119 mg, 0.400 mmol) in MeOH (1 mL) was added Pd/C (4.2 mg, 0.040 mmol). The mixture was degassed and refilled with hydrogen three times and then subject to balloon hydrogenation for 18 h. The catalyst was filtered and the filtrate was concentrated to give Intermediate 15B (120 mg, 0.400 mmol, 100% crude) as a crude product. It is taken directly to next step without further purification. HPLC/MS (Method D) RT=1.13 min, [M+1]$^+$ 303.1.

Intermediate 15C 4-(3-(trifluoromethoxy)phenyl)cyclohexanone

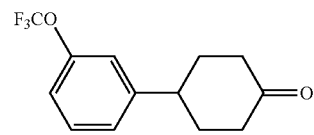 [SMILES: O=C1CCC(c2cccc(OC(F)(F)F)c2)CC1]

To a solution of Intermediate 15B (0.12 g, 0.40 mmol) in DCM (1 mL) was added trifluoroacetic acid (0.20 mL, 2.6 mmol) and the reaction mixture was stirred at rt from 1 h. The reaction mixture was diluted with DCM, washed with saturated NaHCO$_3$, dried over MgSO$_4$, filtered and concentrated under reduced pressure to give Intermediate 15C (103 mg, 0.400 mmol, 100% crude). HPLC/MS (Method D) RT=1.01 min, [M+1]$^+$ 259.1.

Intermediate 15

By appropriate application of the method described in Intermediate 14, Intermediate 15C (103 mg, 0.400 mmol) and diphenylmethanamine (73 mg, 0.40 mmol) were converted to Intermediate 15 (31 mg, 0.12 mmol, 30% yield for two steps. HPLC/MS (Method D) RT=0.75 min, [M+1]$^+$ 260.3.

Intermediate 16

N-(trans-4-(aminomethyl)cyclohexyl)pyridin-2-amine

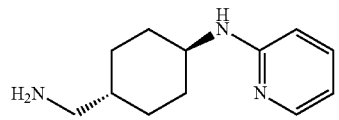 [SMILES: NC[C@H]1CC[C@H](Nc2ccccn2)CC1]

Intermediate 16A

Benzyl(trans-4-aminocyclohexyl)methylcarbamate, HCl

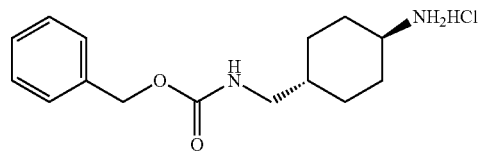

To a solution of benzyl(trans-4-amino-Boc-cyclohexyl)methylcarbamate (1.00 g, 2.76 mmol) in MeOH (19 mL) was added HCl (3.45 mL, 13.8 mmol) dropwise and the reaction mixture was stirred at rt for 18 h. Removal of solvent under reduced pressure gave Intermediate 16A (835 mg, 100%) as a white solid. HPLC/MS (Method D) RT=0.66 min, [M+1]$^+$ 263.

Intermediate 16B

Benzyl(trans-4-(pyridin-2-ylamino)cyclohexyl)methylcarbamate

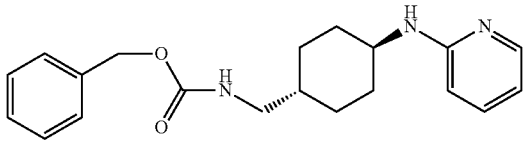 [SMILES: O=C(NC[C@H]1CC[C@H](Nc2ccccn2)CC1)OCc1ccccc1]

The mixture of Intermediate 16A (835 mg, 2.79 mmol), Hunig's Base (0.49 mL, 2.8 mmol) and 2-fluoropyridine (11.0 mL, 128 mmol) was heated at reflux for 18 h and then concentrated. The residue was diluted with DCM (50 mL) and washed with saturated NaHCO$_3$ (30 mL), dried over Na$_2$SO$_4$, filtered and concentrated. The residue was purified by flash chromatography (ethyl acetate/hexane 0-100%; column 40 g) to give Intermediate 16B (161 mg, 0.470 mml, 17.0%). HPLC/MS (method D) RT=0.75 min, [M+1]$^+$=340.

Intermediate 16

To a solution of Intermediate 16B (161 mg, 0.470 mmol) in MeOH (5 mL) was added palladium on carbon (15 mg, 0.014 mmol) under argon. The reaction mixture was subject to balloon hydrogenation for 2 h. The reaction mixture was filtered and concentrated under reduced pressure to give Intermediate 16 (73 mg, 0.36 mmol, 75%) as a colorless oil. HPLC/MS (Method D) RT=0.43 min [M+1]$^+$=206; $^1$H NMR (400 MHz, CHLOROFORM-D) δ ppm 0.99-1.36 (m, 5 H) 1.81-1.89 (m, 2 H) 2.09-2.19 (m, 2 H) 2.55 (d, J=6.27 Hz, 2 H) 3.42-3.54 (m, 2 H) 6.33 (d, J=8.53 Hz, 1 H) 6.49-6.53 (m, 1 H) 7.33-7.40 (m, 1 H) 8.02-8.06 (m, 1 H).

Intermediate 17

2-methoxy-3-oxo-3,5,6,7,8,8a-hexahydroindolizine-1-carboxylic acid

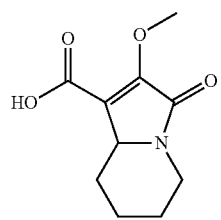

Intermediate 17A

Ethyl 2-(piperidin-2-yl)acetate

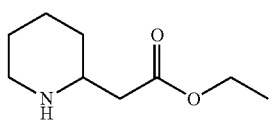

At rt a mixture of ethyl 2-(pyridin-2-yl)acetate (3.0 g, 18 mmol) and platinum (IV) oxide (0.825 g, 3.63 mmol) in methanol (25 mL) was subject to hydrogenation at 50 psi for 18 h. After filtration, the filtrate was concentrated under reduced pressure to afford Intermediate 17A (3.0 g, 96%) as a clear oil. HPLC/MS (Method L) RT=0.99 min, [M+1]$^+$ 172.2.

Intermediate 17B

Ethyl 2-(2-(2-ethoxy-2-oxoethyl)piperidin-1-yl)-2-oxoacetate

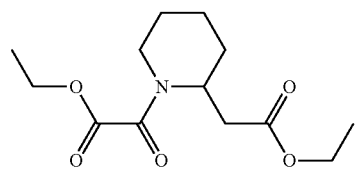 [SMILES: CCOC(=O)CC1CCCCN1C(=O)C(=O)OCC]

At 0° C. to a solution of Intermediate 17A (3.00 g, 17.5 mmol) and TEA (4.9 mL, 35 mmol) in DCM (100 mL) was added mono-ethyl oxalyl chloride (1.96 mL, 17.5 mmol) and the reaction mixture was stirred at rt for 2 h. The reaction mixture was quenched by addition of a few drops of MeOH and concentrated. The residue was purified by flash chromatography (ethyl acetate/hexanes 0-100%, column 80 g) to give Intermediate 17B (3.8 g, 95%) as a clear oil. HPLC/MS (Method L) RT=1.45 min, [M+1]$^+$ 272.1.

Intermediate 17C

Ethyl 2-hydroxy-3-oxo-3,5,6,7,8,8a-hexahydroindolizine-1-carboxylate

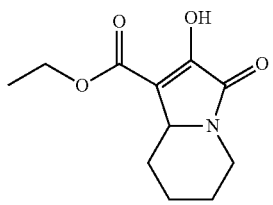 [SMILES: CCOC(=O)C1=C(O)C(=O)N2CCCCC12]

Intermediate 17B (3.75 g, 13.8 mmol) was suspended in toluene (100 mL) and treated with potassium ethoxide (5.42 mL, 24% in methanol, 13.8 mmol). The clear mixture was heated at 100° C. for 4 h. After cooling to rt, the solvent was evaporated and the residue was dissolved in ethyl acetate. The organic layer was washed with 10% citric acid twice, brine twice, dried over Na$_2$SO$_4$, filtered and concentrated to afford Intermediate 17C (2.0 g, 64%) as a clear oil. $^1$H NMR (400 MHz, CHLOROFORM-d) δ ppm 1.28 (3 H, td, J=7.2, 1.8 Hz), 1.46-1.87 (5 H, m), 2.19 (1 H, br. s.), 3.12-3.51 (1 H, m), 4.09-4.23 (2 H, m), 4.27-4.42 (2 H, m).

Intermediate 17D

Ethyl 2-methoxy-3-oxo-3,5,6,7,8,8a-hexahydroindolizine-1-carboxylate

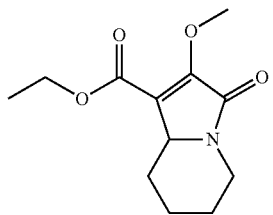 [SMILES: CCOC(=O)C1=C(OC)C(=O)N2CCCCC12]

At 0° C. to a solution of Intermediate 17C (30 mg, 0.13 mmol) and N,N-diisopropylethylamine (35 μL, 0.20 mmol) in methanol (0.15 mL) and acetonitrile (1.35 mL) was added (trimethylsilyl)diazomethane (0.10 mL, 2.0 M in diethyl ether, 0.20 mmol). The reaction mixture was stirred at rt for 2 h, concentrated and the residue was purified by flash chromatography (ethyl acetate/hexane 0-100%, column, 4 g) to afford Intermediate 17D (20 mg, 63%). ¹ H NMR (400 MHz, CHLOROFORM-d) δ ppm 1.25-1.41 (5 H, m), 1.50-1.61 (1 H, m), 1.76-1.98 (2 H, m), 2.44-2.52 (1 H, m), 2.79-2.90 (1 H, m), 3.95 (1 H, dd, J=11.4, 3.6 Hz), 4.23-4.38 (6 H, m).

Intermediate 17

The mixture of Intermediate 17D (50 mg, 0.21 mmol) and a solution of lithium hydroxide (0.25 mL, 0.25 mmol) in methanol (0.5 mL) and water (0.5 mL) was stirred for 30 min, then neutralized with a 1 N hydrochloric acid (0.25 mL, 0.25 mmol). The solvent was removed in vacuo to afford Intermediate 17 (44.0 mg, 100% crude) as a black solid. HPLC/MS (Method L) RT=1.13 min, [M+1]⁺ 212.2.

Intermediate 18

(4-(cyclopentyloxy)phenyl)methanamine

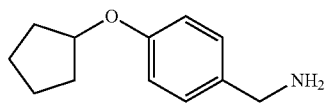 [SMILES: NCc1ccc(OC2CCCC2)cc1]

Intermediate 18A 4-(cyclopentyloxy)benzonitrile

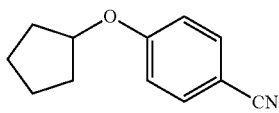 [SMILES: N#Cc1ccc(OC2CCCC2)cc1]

Under argon sodium hydride (0.40 g, 9.9 mmol, 60 wt. %) was suspended in DMF (15 mL) and cyclopentanol (0.60 mL, 6.6 mmol) was added dropwise to the mixture, followed by the addition of 4-bromobenzonitrile (1.0 g, 5.5 mmol) in one portion. The reaction mixture was heated at 70° C. for 1.5 h and then allowed to cool to rt. The reaction mixture was diluted with ethyl acetate (100 mL), washed with water (200 mL) and brine (200 mL). The organic layer was separated, dried over Na₂SO₄, filtered and the filtrate was concentrated to dryness in vacuo. The resulting residue was purified by flash chromatography (EtOAc/Hexanes 0-50% over 14 min, column 40 g, flow rate 40 mL/min) to give Intermediate 18A (414 mg, 2.14 mmol, 40.0% yield) as a colorless oil. HPLC/MS (Method D) RT=1.06 min, [M+H]⁺ 188.2.

Intermediate 18B

Tert-butyl 4-(cyclopentyloxy)benzylcarbamate

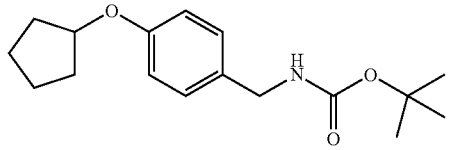 [SMILES: CC(C)(C)OC(=O)NCc1ccc(OC2CCCC2)cc1]

To a solution of Intermediate 18A (414 mg, 2.21 mmol) in MeOH (12 mL) and HCl (2.43 mL, 2.43 mmol) was added 10% Pd/C (235 mg, 0.220 mmol) and the reaction mixture was subject to hydrogenation (1 atm) at rt for 2.5 h. The catalyst was removed by filtration and the resulting filtrate was concentrated to dryness. The residue was dissolved in ethyl acetate (30 mL) and washed with saturated NaHCO₃ (10 mL). The aqueous layer was extracted with ethyl acetate (30 mL) and the combined organic layers were dried over Na₂SO₄, filtered and concentrated. The residue was dissolved in DCM (11 mL) and triethylamine (0.15 mL, 1.1 mmol) was added followed by the addition of di-tert-butyl dicarbonate (0.243 mL, 1.05 mmol). The reaction mixture was stirred under argon for 2 h, diluted with DCM (20 mL) and washed with saturated NaHCO₃ (10 mL) and brine (10 mL). The organic layer was dried over Na₂SO₄, filtered and concentrated. The residue was purified by flash chromatography (EtOAc/Hexanes 0-40% over 14 min, column 40 g, flow rate 40 mL/min) to give Intermediate 18B (147 mg, 0.510 mmol, 52.0% yield) as a colorless oil. HPLC/MS (Method D) RT=1.13 min, [M+1-C₄H₉]⁺=236.2.

Intermediate 18

To a solution of Intermediate 18B (98 mg, 0.34 mmol) in MeOH (2 mL) was added HCl (0.42 mL, 1.7 mmol) dropwise and the reaction mixture was stirred at rt for 2.5 h. The solvent was removed to give Intermediate 18 (HCl salt, (71 mg, 76% yield)). HPLC/MS (Method D) RT=0.70 min, [M+1-C₄H₉]⁺=175.1. ¹H NMR (400 MHz, methanol-d₃) d ppm 1.56-2.02 (m, 8 H) 4.02 (s, 2 H) 4.81-4.85 (m, 1 H) 6.90-6.97 (m, 2 H) 7.31-7.37 (m, 2 H).

Intermediate 19

(6-(cyclohexyloxy)pyridin-3-yl)methanamine

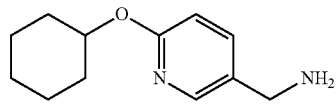 [SMILES: NCc1ccc(OC2CCCCC2)nc1]

Intermediate 19A 6-(cyclohexyloxy)nicotinonitrile

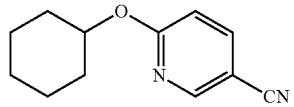 [SMILES: N#Cc1ccc(OC2CCCCC2)nc1]

To a solution of cyclohexanol (0.84 mL, 7.9 mmol) in THF (15 mL) was added sodium bis(trimethylsilyl)amide) (10.8 mL, 1.00M, 10.8 mmol). The amber solution was stirred at rt for 0.5 h and then 6-chloronicotinonitrile (1.00 g, 7.22 mmol) in THF (5 mL) was added dropwise. The reaction mixture was stirred at rt for 18 h and quenched by addition of saturated NaHCO$_3$ (100 mL). Ethyl acetate (3×100 mL) was added and the organic layer was washed with brine (100 mL), dried over Na$_2$SO$_4$, filtered and concentrated. The residue was purified by flash chromatography (EtOAc/Hexanes 0-50% over 14 min, column 40 g, flow rate 40 mL/min) to give Intermediate 19A (365 mg, 1.81 mmol, 25.0% yield) as a white solid. HPLC/MS (Method D) RT=1.09 min, [M+1]$^+$=203.2.

Intermediate 19

Under argon to a solution of Intermediate 19A (134 mg, 0.660 mmol) in THF (850 µL) was added dropwise borane tetrahydrofuran complex in THF (1.99 mL, 1.00M, 1.99 mmol) and the reaction mixture was stirred at rt for 1 h. At 0° C., the reaction mixture was slowly quenched into 5N HCl (5 mL) and the mixture was stirred at 0° C. for 10 min, concentrated. The residue was dissolved in MeOH (3 mL) and loaded onto an Agilent SCX (1000 mg) column that had been previously conditioned with methanol. The column was washed with 4 column volumes of methanol and then 4 column volumes of 2N NH$_3$ in methanol. The ammonia fractions were evaporated in vacuo to provide Intermediate 19 (44 mg, 0.21 mmol, 32% yield) as a colorless oil. HPLC/MS (Method D) RT=0.69 min, [M+1]$^+$=207.2; 1H NMR (400 MHz, chloroform-d) δ ppm 1.20-1.62 (m, 8 H) 1.72-1.82 (m, 2 H) 1.95-2.04 (m, 2 H) 3.77 (s, 2 H) 4.93-5.04 (m, 1 H) 6.66 (d, J=8.53 Hz, 1 H) 7.53 (dd, J=8.53, 2.51 Hz, 1 H) 8.03 (d, J=2.01 Hz, 1 H)

Intermediate 20

(3S)-3-(3,4-dichlorophenyl)cyclopentanamine hydrochloride

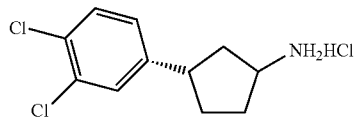

Intermediate 20A (S)-3-(3,4-dichlorophenyl)cyclopentanone

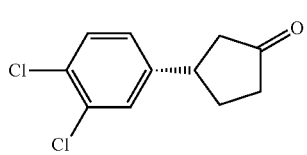

A mixture of 3,4-dichlorophenylboronic acid (488 mg, 2.56 mmol), Bis(norbornadiene)rhodium tetrafluoroborate (14.6 mg, 0.0390 mmol) and S-2,2'-bis(diphenylphosphino)-1,1'-binaphthyl (25.8 mg, 0.0410 mmol) in dioxane (6.6 mL) was sparged with Ar three times and stirred at rt for 2 h. To the reaction mixture was added water (1.015 mL) followed by the addition of cyclopent-2-enone (200 mg, 2.44 mmol) and TEA (0.340 mL, 2.44 mmol). The reaction mixture was stirred at room for 18 h. The reaction mixture was diluted with DCM, washed with H$_2$O, dried over MgSO4, filtered and concentrated. The residue was purified by flash chromatography 40 g using Hexanes/EtOAc (0-100% over 15 min, flow rate 40 mL/min) to give Intermediate 20A (585 mg, 2.55 mmol, 100% yield) as a yellow oil. $^1$H NMR (400 MHz, CHLOROFORM-d) δ ppm 1.86-2.02 (1 H, m), 2.18-2.38 (2 H, m), 2.38-2.55 (2 H, m), 2.67 (1 H, dd, J=18.2, 7.4 Hz), 3.28-3.49 (1 H, m), 7.09 (1 H, dd, J=8.0, 2.5 Hz), 7.34 (1 H, d, J=1.8 Hz), 7.41 (1 H, d, J=8.3 Hz).

Intermediate 20

Ammonium formate (275 mg, 4.36 mmol) was added to a solution of Intermediate 20A (100 mg, 0.436 mmol) in methanol (1 mL). The reaction was stirred at rt for 20 min, then sodium cyanoborohydride (165 mg, 2.62 mmol) was added in portions and the reaction was stirred at rt for 18 h. The reaction mixture was concentrated, diluted with DCM, washed with saturated NaHCO$_3$, dried over MgSO$_4$, filtered and concentrated. The residue was taken into ether, 1N HCl in ether was added and the mixture was stirred for 20 min, solvent was decanted and the precipitate was collected to give Intermediate 20 as a crude white solid. HPLC/MS (Method D) RT=0.73 min, [M+H]$^+$ 231.9.

Intermediate 21

(3-(3,4-dichlorophenyl)imidazo[1,5-a]pyridin-6-yl)methanamine

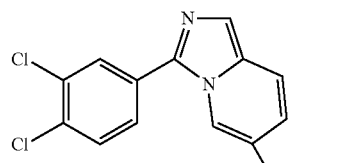

Intermediate 21A

N-((5-bromopyridin-2-yl)methyl)-3,4-dichlorobenzamide

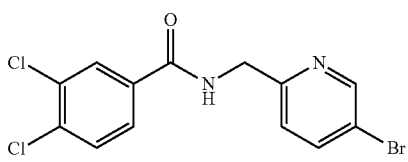 [SMILES: O=C(NCc1ccc(Br)cn1)c1ccc(Cl)c(Cl)c1]

3,4-Dichlorobenzoic acid (0.50 g, 2.6 mmol), (5-bromopyridin-2-yl)methanamine (0.490 g, 2.62 mmol) and PyBOP® (1.5 g, 2.9 mmol) were combined in dimethylformamide (10 mL) and treated with diisopropylethylamine (1.4 mL, 7.9 mmol). The reaction was stirred at rt for 2 h, concentrated and the residue purified on flash chromatography (4 g cartridge, 0 to 100% ethyl acetate/hexanes) to afford 0.52 g of Intermediate 21A (55% yield) as a white solid. LC/MS (HPLC Method M): RT=2.00 min, (M+H)+= 360.8.

Intermediate 21B 6-bromo-3-(3,4-dichlorophenyl)imidazo[1,5-a]pyridine

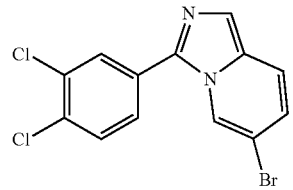 [SMILES: Clc1ccc(-c2ncc3ccc(Br)cn23)cc1Cl]

Intermediate 21A (0.52 g, 1.4 mol) and pyridine (1.2 mL, 14 mmol) were combined in 1,2-dichloroethane (15 mL) and treated with phosphorus oxychloride (0.67 mL, 7.2 mmol). The reaction mixture was heated at reflux for 1 h. After cooling to rt, the solvent was removed in vacuo, and the residue was partitioned between ethyl acetate and water. The product formed as a precipitate which was filtered, washed successively with water and dried in vacuo over night to afford Intermediate 21B (336 mg, 68.0%) as a white solid. LC/MS (HPLC Method M): RT=2.05 min, (M+H)+=342.8.

Intermediate 21C 3-(3,4-dichlorophenyl)imidazo[1,5-a]pyridine-6-carbonitrile

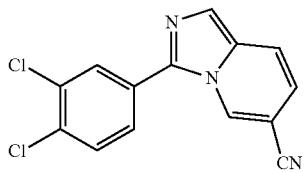 [SMILES: N#Cc1ccc2cnc(-c3ccc(Cl)c(Cl)c3)n2c1]

Intermediate 21B (180 mg, 0.530 mmol), zinc (10 mg, 0.16 mmol), zinc cyanide (46 mg, 0.40 mmol) and bis(tri-t-butylphosphine)palladium(0) (14 mg, 0.030 mmol) were combined in a microwave tube and sealed. The system was back filled with nitrogen and evacuated with vacuum three times. Dimethylformamide (4.0 mL) was introduced and the reaction heated by microwave irradiation for 30 min at 120° C. After cooling to rt, the reaction mixture was poured on ice and the aqueous phase extracted with ethyl acetate (2×). The combined organic portions, washed with brine, dried over magnesium sulfate, filtered and concentrated under reduced pressure. The crude product was purified on flash chromatography (24 g cartridge, 0 to 100% ethyl acetate/hexanes) to afford Intermediate 21C (100 mg, 66%) as a white powder. LC/MS (HPLC Method M): RT=1.89 min, (M+H)+= 287.9.

Intermediate 21

Intermediate 21C (100 mg, 0.35 mmol) was dissolved in methanol (3 mL) and a few drops of conc. hydrochloric acid (to aid solubility). The reaction mixture was purged with nitrogen and raney nickel (in water) (20 mg, 0.35 mmol) was introduced. The flask was flushed with hydrogen and allowed to stir under an atmosphere of hydrogen for 2 h. The reaction mixture was flushed with nitrogen, filtered through Celite® and concentrated to afford Intermediate 21 (100 mg, 100%) as a light yellow oil which was used without further purification. LC/MS (HPLC Method M): RT=1.15 min, (M+H)+=291.9.

Intermediate 22

N-(3-bromobenzyl)-4-methoxy-1-methyl-5-oxo-2,5-dihydro-1H-pyrrole-3-carboxamide

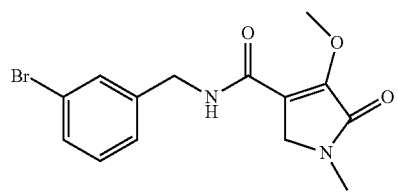 [SMILES: COC1=C(C(=O)NCc2cccc(Br)c2)CN(C)C1=O]

Intermediate 22 was prepared in similar procedure as described in Intermediate 8. HPLC/MS (Method N) RT=3.11 min, [M+H]+ 340.9.

Example 1

4-hydroxy-1-methyl-5-oxo-N-(2-phenoxybenzyl)-2,5-dihydro-1H-pyrrole-3-carboxamide

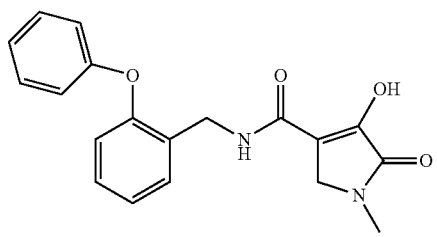 [SMILES: CN1CC(C(=O)NCc2ccccc2Oc2ccccc2)=C(O)C1=O]

Paraformaldehyde (7.05 mg, 0.235 mmol) and a 2M methanol solution of methylamine (0.117 mL, 0.235 mmol) were combined, diluted with MeOH (1 mL) and heated at 60° C. in the microwave for 10 min. The mixture was then added to Intermediate 3 (83 mg, 0.24 mmol) and the mixture was heated at 100° C. in the microwave for 10 min. The reaction mixture was purified by Prep HPLC (Column: YMC Sunfire 5 μm C18 30×100 mm. Mobile Phase A: 90% H$_2$O—10% MeOH—0.1% TFA, Mobile Phase B: 10% H$_2$O—90% MeOH—0.1% TFA, 20-100% B over 10 min, 100% B for 4 min) to give Example 1 (41.3 mg, 50.1%). HPLC/MS (Method D) RT=0.87 min, [M+1]+ 339; $^1$H NMR (400 MHz, chloroform-D) δ ppm 3.07 (s, 3 H) 3.97 (s, 2 H) 4.62 (d, J=6.02 Hz, 2H) 6.86 (d, J=8.28 Hz, 1 H) 6.98 (d, J=7.78 Hz, 2 H) 7.08 (q, J=7.61 Hz, 2 H) 7.17-7.24 (m, 2 H) 7.27-7.34 (m, 2 H) 7.42 (dd, J=7.53, 1.51 Hz, 1 H); Orthogonal HPLC (150×4.6 mm 3.5 μm, 254 nm): Sunfire {RT=7.1 min, 99%}; Xbridge {RT=6.6 min, 96%}.

By appropriate application of the methods described for Example 1, Examples 2-29 were synthesized.

Examples 30-46 were synthesized via parallel synthesis according to the following method. To each microwave vial containing an amine (0.09 mmol) corresponding to the $R^5$ group contained in Examples 30-46 was added a suspension of paraformaldehyde (0.12 M in MeOH, 0.750 mL, 0.09 mmol). The reaction mixtures were heated to 60° C. for 10 min using microwave irradiation, then allowed to cool to rt. To each reaction mixture was added a 0.24 M solution of Intermediate 3 in MeOH (0.25 mL, 0.060 mmol). The resulting reaction mixture was heated to 100° C. for 10 min using microwave irradiation. After cooling to rt, the reaction mixture was diluted with MeOH (0.25 mL). Examples 30-46 were purified from their corresponding solutions by reverse phase preparative HPLC using Method H.

Example 47

N-((4'-fluorobiphenyl-3-yl)methyl)-1-(4-fluorophenyl)-4-hydroxy-5-oxo-2,5-dihydro-1H-pyrrole-3-carboxamide

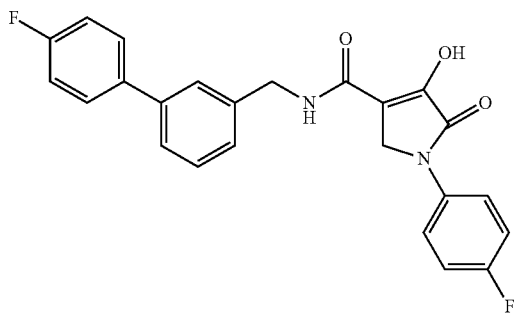 [SMILES: O=C(NCc1cccc(-c2ccc(F)cc2)c1)C1=C(O)C(=O)N(c2ccc(F)cc2)C1]

Example 47A 4-ethoxy-N-((4'-fluorobiphenyl-3-yl)methyl)-1-(4-fluorophenyl)-5-oxo-2,5-dihydro-1H-pyrrole-3-carboxamide

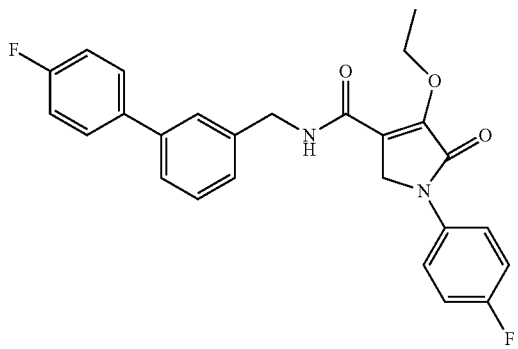 [SMILES: CCOC1=C(C(=O)NCc2cccc(-c3ccc(F)cc3)c2)CN(c2ccc(F)cc2)C1=O]

To a solution of Intermediate 9 (0.037 g, 0.13 mmol) in DCM was added TEA (0.054 mL, 0.390 mmol) and (4'-fluorobiphenyl-3-yl)methanamine, HCl (0.031 g, 0.130 mmol). The reaction was stirred at rt for 14 h. The reaction mixture was filtered and concentrated to give a dark solid, which was used directly for the next step without purification. HPLC/MS (Method N) RT=4.39 min, [M+H]$^+$ 449.0.

Example 47

To a solution of Example 47A (58.3 mg, 0.13 mmol) in dichloromethane (0.5 mL) was added boron trichloride (0.390 mL, 0.390 mmol). The reaction was stirred at rt for 14 h. The reaction was quenched with MeOH and concentrated to give the crude. The crude was purified by prep HPLC (ACN/H$_2$O/TFA, 20-90% B over 12 min) to give Example 47 (3 mg, 6 μmol, 5% yield). HPLC/MS (Method L) RT=2.19 min, [M+H]$^+$ 421.0; Orthogonal HPLC (150× 4.6 mm 3.5 μm, 254 nm): Sunfire {RT=10.61 min, 86.2%}; Xbridge {RT=9.62 min, 83.1%); $^1$H NMR (400 MHz, Acetone) δ ppm 7.86 (2 H, dd, J=9.09, 4.55 Hz), 7.62-7.73 (3 H, m), 7.53 (1 H, d, J=7.33 Hz), 7.34-7.47 (3 H, m), 7.10-7.26 (5H, m), 4.67 (2 H, br. s.), 4.54 (2 H, s).

Example 48

(R)—N-(1-(4'-acetamidobiphenyl-3-yl)ethyl)-1-(2,4-difluorophenyl)-4-hydroxy-5-oxo-2,5-dihydro-1H-pyrrole-3-carboxamide

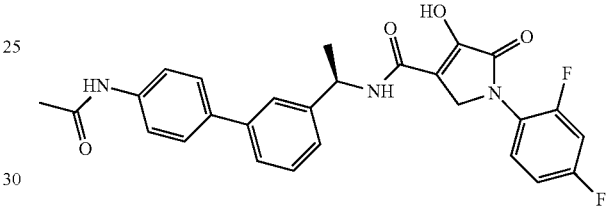

Example 48A (R)—N-(1-(4'-acetamidobiphenyl-3-yl)ethyl)-1-(2,4-difluorophenyl)-4-ethoxy-5-oxo-2,5-dihydro-1H-pyrrole-3-carboxamide

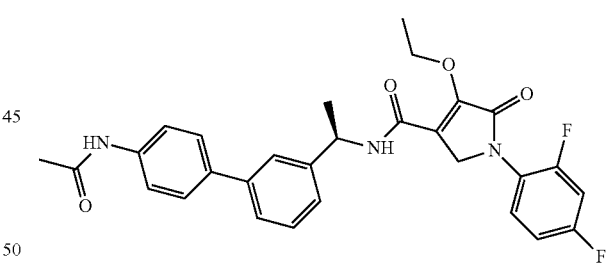

To a solution of Intermediate 8 (50 mg, 0.11 mmol) in DME (1.0 mL) was added 4-acetamidophenylboronic acid (39 mg, 0.22 mmol), 2M sodium carbonate (0.16 mL, 0.32 mmol), and tetrakis(triphenylphosphine)palladium(0) (25 mg, 0.021 mmol) in a microwave vial. The reaction mixture was degassed with argon and heated at 100° C. for 1 h. The reaction mixture was diluted with DCM, dried over MgSO$_4$, filtered and concentrated. The residue was purified by flash chromatography (EtOAc/Hexanes, 0-100% B over 25 min) to give Example 48A as a white solid (43 mg, 77%). HPLC/MS (Method L) RT=2.13 min, [M+H]$^+$ 520.1.

Example 48

To a solution of Example 48A (43 mg, 0.083 mmol) in CHCl$_3$ (1 mL) was added boron trichloride (0.12 mL, 0.12 mmol). The reaction mixture was stirred at rt for 12 h, quenched with MeOH and concentrated. The residue was purified by Prep HPLC (ACN/water/TFA), 0-80% B over 10 min. The product fraction was collected (at Rt=10.02 min) and concentrated to give Example 48 (28 mg, 0.056 mmol, 68% yield) as a white solid. HPLC/MS (Method L) RT=1.99 min, [M+H]$^+$ 514.4; $^1$H NMR (500 MHz, Acetone-d) d ppm 9.26 (1 H, br. s.), 7.73 (2 H, br. s.), 7.69-7.73 (3 H, m), 7.66 (1 H, td, J=8.94, 6.05 Hz), 7.60 (2 H, d, J=8.25 Hz), 7.50-7.54 (1 H, m), 7.37-7.44 (2 H, m), 7.17 (1 H, ddd, J=11.14, 8.67, 2.75 Hz), 7.05-7.12 (1 H, m), 5.28-5.36 (1 H, m, J=7.19, 7.19, 7.08, 6.88 Hz), 4.47 (2 H, s), 2.10 (3 H, s), 2.03-2.07 (1 H, m), 1.60 (3 H, d, J=7.15 Hz).

Examples 49-126 were synthesized following a similar procedure described for Example 48.

Example 127

4-hydroxy-1-methyl-N-(3-(5-methylthiophen-2-yl)benzyl)-5-oxo-2,5-dihydro-1H-pyrrole-3-carboxamide

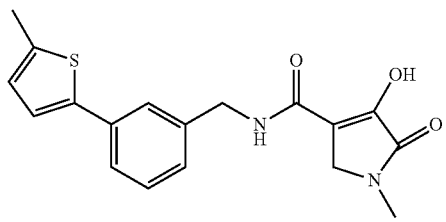 [SMILES: Cc1ccc(-c2cccc(CNC(=O)C3=C(O)C(=O)N(C)C3)c2)s1]

To 6-methyl-2-(5-methylthiophen-2-yl)-1,3,6,2-dioxazaborocane-4,8-dione (38 mg, 0.15 mmol) in 0.5-2 mL microwave vials was added PS-Pd(PPh$_3$)$_4$ (38 mg, 3.8 µmol), potassium phosphate (0.15 mL, 0.45 mmol), and Intermediate 22 (25 mg, 0.075 mmol) in DMF (0.75 mL), followed by addition of ethanol (0.75 mL). The reaction mixture was heated for 15 min at 150° C. with microwave irradiation. The mixture was dissolved in DMF and filtered and the filtrate was concentrated in vacuo. The residue was dissolved in DCM (0.75 mL) and 1M BCl$_3$ (0.15 mL, 0.15 mmol) in DCM was added to the reaction mixture. The reaction mixture was stirred at rt for 18 h, quenched by the addition of MeOH, concentrated under reduced pressure, and purified by Prep (ACN/water/TFA) to give Example 127 (9.4 mg, 36%). HPLC/MS (Method P) RT=1.48 min, [M+H]$^+$ 343.0.

Examples 128-131 were following a similar procedure described for Example 127.

Example 132

1-ethyl-4-hydroxy-5-oxo-N-(3-(4-phenoxyphenyl)propyl)-2,5-dihydro-1H-pyrrole-3-carboxamide

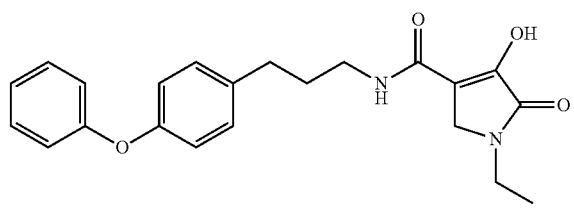 [SMILES: CCN1CC(C(=O)NCCCc2ccc(Oc3ccccc3)cc2)=C(O)C1=O]

Example 132A 1-ethyl-4-hydroxy-5-oxo-N-(3-(4-phenoxyphenyl)prop-2-ynyl)-2,5-dihydro-1H-pyrrole-3-carboxamide

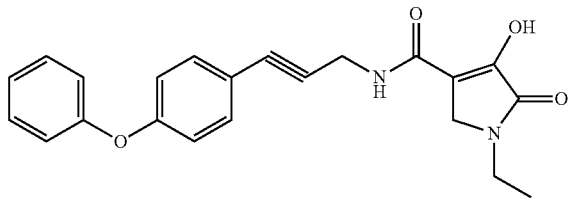 [SMILES: CCN1CC(C(=O)NCC#Cc2ccc(Oc3ccccc3)cc2)=C(O)C1=O]

The mixture of 1-bromo-4-phenoxybenzene (57.2 mg, 0.229 mmol), Intermediate 10 (30 mg, 0.14 mmol), copper (I) iodide (5.1 mg, 0.027 mmol), triphenylphosphine (7.1 mg, 0.027 mmol) and Bis(triphenylphosphine)palladium chloride (9.5 mg, 0.013 mmol) and diethylamine (1.0 mL, 9.57 mmol) in DMF (1 mL) was degassed and refilled with Argon three times. The reaction mixture was subject to microwave irradiation at 120° C. for 20 min, concentrated and the residue was purified by reverse phase preparative HPLC (Method T) to give Example 132A (14 mg, 0.037 mmol, 28% yield). LCMS (Method L) RT=2.013 min, [M+1]$^+$ 377.1.

Example 132

The reaction mixture of Example 132A (14 mg, 0.037 mmol) and Pd/C (2 mg, 2 µmol) in MeOH (1 mL) was subject to balloon hydrogenation for 2 h. The reaction mixture was filtered and the filtrate was concentrated. The residue was purified by reverse phase preparative HPLC (Method T) to afford Example 132 (6.0 mg, 0.014 mmol, 38% yield). LCMS (Method L) RT=2.030 min, [M+1]$^+$ 381.1 $^1$H NMR (400 MHz, MeOD) δ ppm 1.27 (3H, t, J=7.3 Hz), 1.96 (2H, quin, J=7.3 Hz), 2.74 (2 H, t, J=7.7 Hz), 3.44 (2 H, t, J=7.0 Hz), 3.58 (2 H, q, J=7.3 Hz), 4.07 (2 H, s), 6.96 (2 H, m), 6.99 (1 H, s), 7.01 (1 H, d, J=1.0 Hz), 7.13 (1 H, t, J=7.4 Hz), 7.26 (2 H, m, J=8.5 Hz), 7.32-7.45 (2 H, m).

Example 133

N-((3-(3,4-dichlorophenyl)imidazo[1,5-a]pyridin-6-yl)methyl)-1-ethyl-4-hydroxy-5-oxo-2,5-dihydro-1H-pyrrole-3-carboxamide

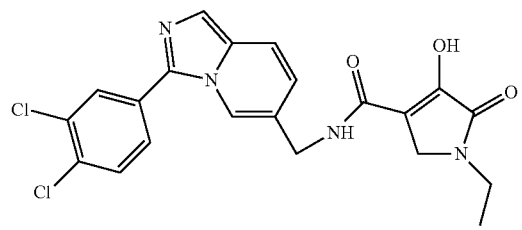 [SMILES: CCN1CC(C(=O)NCc2ccc3cnc(-c4ccc(Cl)c(Cl)c4)n3c2)=C(O)C1=O]

Example 133A

N-((3-(3,4-Dichlorophenyl)imidazo[1,5-a]pyridin-6-yl)methyl)-1-ethyl-4-methoxy-5-oxo-2,5-dihydro-1H-pyrrole-3-carboxamide

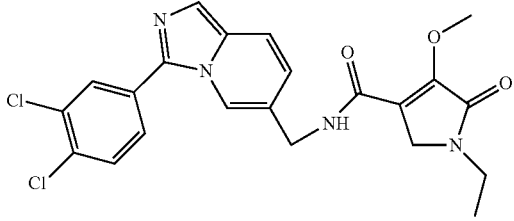 [SMILES: CCN1CC(C(=O)NCc2ccc3cnc(-c4ccc(Cl)c(Cl)c4)n3c2)=C(OC)C1=O]

Intermediate 21 (80 mg, 0.27 mmol), 1-ethyl-4-methoxy-5-oxo-2,5-dihydro-1H-pyrrole-3-carboxylic acid (60.8 mg, 0.33 mmol) and PyBOP® (185 mg, 0.36 mmol) were combined in dimethylformamide (2.5 mL) and treated with diisopropylethyl amine (143 μL, 0.82 mmol). The reaction was stirred at rt for 2 h and concentrated under reduced pressure. The crude product was purified on flash chromatography (40 g cartridge, 0 to 100% ethyl acetate/hexane) to afford Example 133A (0.77 g, 61%) as a clear oil. LC/MS (HPLC Method M): RT=1.60 min, (M+H)$^+$=458.9.

Example 133

To a solution of Example 133A (77 mg, 0.17 mmol) in dichloromethane (2 mL) was added boron tribromide-methyl sulfide complex (503 μL, 0.500 mmol) and the reaction mixture was stirred at rt. After 1 h, methanol was added to the reaction mixture, the resulting reaction mixture stirred for 10 min then concentrated under reduced pressure. The residue was dissolved in methanol and purified by reverse phase preparative HPLC (Method J) to give Example 133 (16 mg, 20%) as a clear oil. $^1$H NMR (400 MHz, MeOD) δ ppm 9.60 (1 H, s), 9.33 (2 H, d, J=7.5 Hz), 9.21 (2 H, dd, J=16.9, 8.9 Hz), 9.07 (1 H, d, J=8.3 Hz), 8.62-8.75 (2 H, m), 5.87 (2 H, d, J=6.3 Hz), 5.38 (2 H, s), 4.82-4.92 (2 H, m), 2.50-2.58 (3 H, m). LC/MS (HPLC Method M): RT=1.60 min, (M+H)$^+$=444.9.

Example 134

(R)-4-hydroxy-5-oxo-1-(2,2,2-trifluoroethyl)-N-(6-(trifluoromethyl)-2,3-dihydro-1H-inden-1-yl)-2,5-dihydro-1H-pyrrole-3-carboxamide

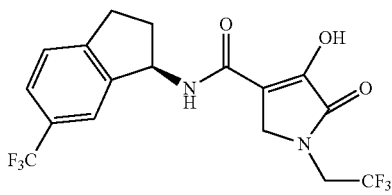 [SMILES: O=C(N[C@@H]1CCc2ccc(C(F)(F)F)cc21)C1=C(O)C(=O)N(CC(F)(F)F)C1]

Example 134A 4-hydroxy-5-oxo-1-(2,2,2-trifluoroethyl)-2,5-dihydro-1H-pyrrole-3-carbonyl chloride

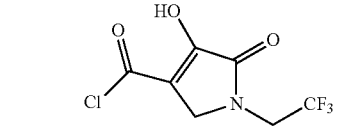 [SMILES: O=C(Cl)C1=C(O)C(=O)N(CC(F)(F)F)C1]

By appropriate application of the methods described for Intermediate 8A, Example 134A was synthesized. HPLC/MS (Method O) RT=1.71 min, [M-Cl+OMe+H]$^+$ 268.4.

Example 134B (R)-4-ethoxy-5-oxo-1-(2,2,2-trifluoroethyl)-N-(6-(trifluoromethyl)-2,3-dihydro-1H-inden-1-yl)-2,5-dihydro-1H-pyrrole-3-carboxamide

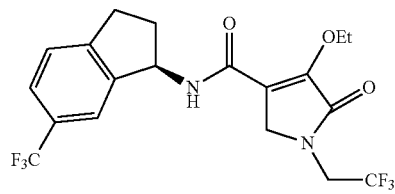 [SMILES: CCOC1=C(C(=O)N[C@@H]2CCc3ccc(C(F)(F)F)cc32)CN(CC(F)(F)F)C1=O]

To a solution of Intermediate 134A (50 mg, 0.184 mmol) in DCM was added TEA (0.077 mL, 0.55 mmol) and (R)-6-(trifluoromethyl)-2,3-dihydro-1H-inden-1-amine, HCl (43.7 mg, 0.184 mmol). The reaction mixture was stirred at rt for 2 h. The reaction mixture was diluted with DCM, washed with 1N HCl and brine, dried over Na$_2$SO$_4$, concentrated and purified by flash chromatography (0-40% EtOAc/Hex) to give Example 134B (52 mg, 0.12 mmol, 65% yield) as a yellow oil. HPLC/MS (Method L) RT=2.21 min, [M+H]$^+$ 437.0.

Example 134

To a solution of Example 134B (52 mg, 0.119 mmol) in DCM (1 mL) was added boron trichloride (0.179 mL, 0.179 mmol). The reaction mixture was stirred at rt for 2 h. The reaction mixture was quenched by the addition of MeOH and concentrated under reduced pressure. The residue was purified by Prep (ACN/water/TFA, 10-90% B over 10 min) to give Example 134 (30 mg, 0.073 mmol, 61% yield) as a white solid. HPLC/MS (Method L) RT=2.07 min, [M+H]$^+$ 409.2; Orthogonal HPLC (150×4.6 mm 3.5 um, 254 nm): Sunfire {RT=9.73 min, 100%}; Xbridge {RT=8.67 min, 99.1%); $^1$H NMR (400 MHz, DMSO-d$_6$) δ ppm 7.88 (1 H, d, J=8.34 Hz), 7.59 (1 H, d, J=7.83 Hz), 7.46-7.55 (2 H, m), 5.50 (1 H, q, J=8.00 Hz), 4.28 (2 H, q, J=9.60 Hz), 4.15 (2 H, s), 2.99-3.11 (1 H, m), 2.84-2.98 (1 H, m), 1.90-2.06 (1 H, m, J=12.54, 8.84, 8.64, 8.64 Hz).

By appropriate application of the methods described for Example 134, Examples 135-153 were synthesized.

Example 154

N-(4-(4-fluorophenyl)cyclohex-3-enyl)-4-hydroxy-5-oxo-1-(2,2,2-trifluoroethyl)-2,5-dihydro-1H-pyrrole-3-carboxamide

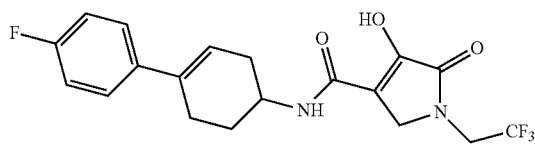 [SMILES: O=C(NC1CC=C(c2ccc(F)cc2)CC1)C1=C(O)C(=O)N(CC(F)(F)F)C1]

Example 154A 4-ethoxy-N-(cis-4-(4-fluorophenyl)-4-methoxycyclohexyl)-5-oxo-1-(2,2,2-trifluoroethyl)-2,5-dihydro-1H-pyrrole-3-carboxamide

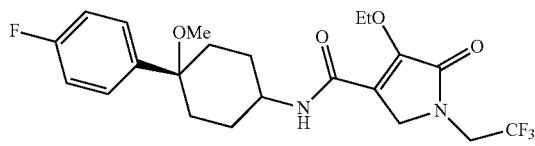

By appropriate application of procedures described in Example 134, Example 154A (53 mg, 63%) was prepared, by replacing the starting materials with cis-4-(4-fluorophenyl)-4-methoxycyclohexanamine (41.1 mg, 0.184 mmol), which was prepared following the procedure described for Intermediate 14, and 4-ethoxy-5-oxo-1-(2,2,2-trifluoroethyl)-2,5-dihydro-1H-pyrrole-3-carbonyl chloride (50 mg, 0.18 mmol), which was prepared following the procedure described for Intermediate 15. LCMS=459.0 [M+H], RT=2.21 min (Method L).

Example 154

To a solution of Example 154A (53 mg, 0.12 mmol) in CHCl₃ (1 mL) was added boron trichloride (0.173 mL, 0.173 mmol). The reaction mixture was stirred at rt for 2 h, quenched with MeOH and concentrated. The residue was purified by Prep HPLC (ACN/water/TFA), 10-90% B over 10 min. The product fraction was collected and concentrated to give Example 154 (16 mg, 0.039 mmol, 34% yield) as a white solid. LCMS=399.0 [M+H] RT=2.14 min {(Method L). $^1$H NMR (400 MHz, CHLOROFORM-d) δ ppm 7.35 (2 H, dd, J=8.46, 5.43 Hz), 7.02 (2 H, t, J=8.59 Hz), 6.44 (1 H, d, J=7.58 Hz), 5.99 (1 H, d, J=1.01 Hz), 4.27-4.40 (1 H, m), 4.22 (2 H, s), 4.10 (2 H, q, J=8.76 Hz), 2.60-2.74 (1 H, m), 2.53-2.60 (1 H, m), 2.07-2.33 (1 H, m), 1.95-2.13 (2 H, m), 1.77-1.94 (1 H, m).

Example 155

N-(cis-4-(4-fluorophenyl)cyclohexyl)-4-hydroxy-5-oxo-1-(2,2,2-trifluoroethyl)-2,5-dihydro-1H-pyrrole-3-carboxamide

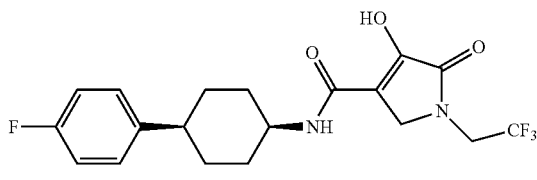

To a solution of Example 154 (7.7 mg, 0.019 mmol) in ethanol (0.2 mL) was added 10% palladium on carbon (4.5 mg, 4.2 μmol). The reaction mixture was stirred under a H₂ balloon for 1 h. The mixture was filtered and purified by prep to give the Example 155 (2.21 mg, 29%) as a white solid. LCMS=401.1 [M+H] RT=1.71 min (Method M).

Example 156

N-((1-(3,4-dichlorophenylsulfonyl)piperidin-4-yl)methyl)-4-hydroxy-1-methyl-5-oxo-2,5-dihydro-1H-pyrrole-3-carboxamide

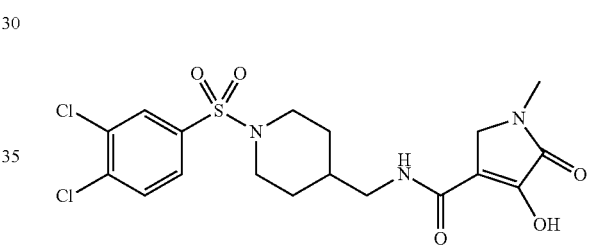

Example 156A

N-((1-(3,4-dichlorophenylsulfonyl)piperidin-4-yl)methyl)-4-methoxy-1-methyl-5-oxo-2,5-dihydro-1H-pyrrole-3-carboxamide

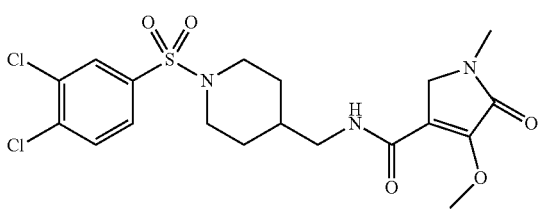 [SMILES: COC1=C(C(=O)NCC2CCN(S(=O)(=O)c3ccc(Cl)c(Cl)c3)CC2)CN(C)C1=O]

To a solution of 4-methoxy-1-methyl-5-oxo-2,5-dihydro-1H-pyrrole-3-carboxylic acid (15 mg, 0.088 mmol) and Intermediate 12 (28 mg, 0.088 mmol) in DCM (2 mL) was added HOBT (16 mg, 0.11 mmol), EDC (25.2 mg, 0.131 mmol) and N-methylmorpholine (0.029 mL, 0.26 mmol). The reaction mixture was stirred at rt for 16 h. The reaction mixture was diluted with DCM, washed with 1N HCl, saturated NaHCO₃, brine, dried over MgSO₄, filtered and concentrated under reduced pressure to give crude Example 156A (36 mg, 0.076 mmol, 86% yield). HPLC/MS (Method L) RT=1.88 min, [M+1]+ 475.9.

Example 156

To a solution of Example 156A (33 mg, 0.070 mmol) in DCM (1 mL) was added boron trichloride-methyl sulfide complex (75 mg, 0.42 mmol). The reaction mixture was stirred at 70° C. for 2 h. The reaction mixture was cooled and quench with MeOH, concentrated and the crude product was purified by Prep HPLC (Method U) to give Example 156 (11 mg, 0.024 mmol, 35% yield). LCMS (Method L) RT=1.95 min [M+1]+=462.1. 1H NMR (400 MHz, CHLOROFORM-d) δ ppm 1.29-1.52 (2 H, m), 1.81 (3 H, br. s.), 2.34 (2 H, d, J=1.8 Hz), 2.37 (2 H, d, J=1.5 Hz), 3.15 (3 H, s), 3.30 (2 H, t, J=6.3 Hz), 3.83 (2 H, d, J=11.9 Hz), 4.07 (2 H, s), 6.83-7.01 (1H, m), 7.54-7.69 (2H, m), 7.86 (1H, d, J=1.5 Hz).

By appropriate application of the methods described for Example 156, Examples 157-176 were synthesized.

Example 177

4-hydroxy-1-methyl-5-oxo-N-((trans-4-(pyridin-2-ylamino)cyclohexyl)methyl)-2,5-dihydro-1H-pyrrole-3-carboxamide

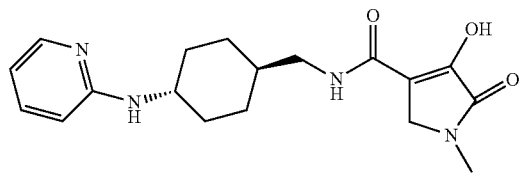 [SMILES: CN1CC(C(=O)NC[C@H]2CC[C@H](Nc3ccccn3)CC2)=C(O)C1=O]

By appropriate application of method described for Example 1, N-(trans-4-(aminomethyl)cyclohexyl)pyridin-2-amine (73 mg, 0.36 mmol) was converted to Example 177 (26 mg, 0.056 mmol, 17% for two steps). HPLC/MS (method D) RT=0.55 min [M+1]=345; 1H NMR (400 MHz, MeOD) δ ppm 1.13-1.27 (m, 2 H) 1.33-1.45 (m, 2 H) 1.55-1.70 (m, 1 H) 1.88-1.96 (m, 2 H) 2.05-2.14 (m, 2 H) 3.06 (s, 3 H) 3.25 (d, J=6.57 Hz, 2 H) 3.47-3.56 (m, 1 H) 3.97-4.02 (m, 2 H) 6.84 (t, J=6.69 Hz, 1 H) 6.99 (d, J=9.09 Hz, 1 H) 7.77 (d, J=6.32 Hz, 1 H) 7.82-7.88 (m, 1 H).

Example 178

4-hydroxy-5-oxo-N-(cis-4-phenylcyclohexyl)-1-(2-((E)-4,4,4-trifluoro-N-methylbut-2-enamido)ethyl)-2,5-dihydro-1H-pyrrole-3-carboxamide

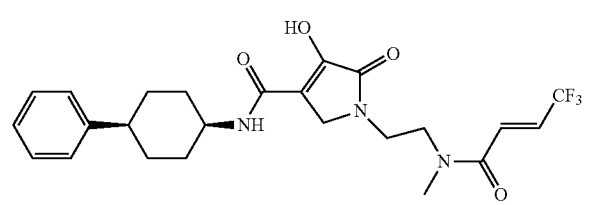 [SMILES: CN(CCN1CC(C(=O)N[C@H]2CC[C@@H](c3ccccc3)CC2)=C(O)C1=O)C(=O)/C=C/C(F)(F)F]

Example 178A 4-hydroxy-1-(2-(methylamino)ethyl)-5-oxo-N-(cis-4-phenylcyclohexyl)-2,5-dihydro-1H-pyrrole-3-carboxamide

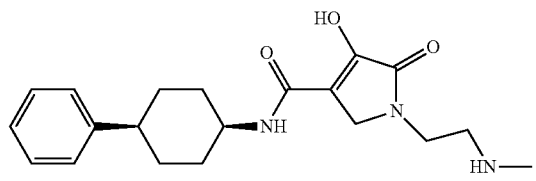 [SMILES: CNCCN1CC(C(=O)N[C@H]2CC[C@@H](c3ccccc3)CC2)=C(O)C1=O]

To a solution of N1-methylethane-1,2-diamine (45.0 mg, 0.607 mmol) in methanol (2 mL) in a microwave vial was added paraformaldehyde (21.9 mg, 0.729 mmol) and Hunig's Base (0.159 mL, 0.911 mmol). The resulting mixture was heated in a microwave reactor at 60° C. for 10 min. To the resulting mixture was added (Z)-2-(2,2-dimethyl-5-oxo-1,3-dioxolan-4-ylidene)-N-(cis-4-phenylcyclohexyl) acetamide (200 mg, 0.607 mmol) and MeOH (3 mL). The resulting mixture was heated in the microwave reactor at 100° C. for 20 min to give a clear orange solution. The reaction mixture was concentrated under reduced pressure to give Example 178A, TFA (242 mg, 0.513 mmol, 85% yield).

Example 178

EDC (25.7 mg, 0.134 mmol), HOBT (20.56 mg, 0.134 mmol) and (E)-4,4,4-trifluorobut-2-enoic acid (13.79 mg, 0.098 mmol) were added to a mixture of Example 178A (32 mg, 0.090 mmol) and DIPEA (0.047 mL, 0.269 mmol) in DCM (1 mL) and DMF (1 mL). The reaction was stirred at rt overnight. The reaction mixture was concentrated. The residue was dissolved in MeOH and purified by reverse phase preparative HPLC(YMC Sunfire, 5 µm, C18 column, 30×100 mm, 10 min gradient from 20-100% B. A=H2O/MeOH/TFA 90/10/0.1. B=MeOH/H2O/TFA 90/10/0.1) to give Example 178 (14 mg, 0.028 mmol, 31% yield) as a yellow solid. HPLC/MS (Method D) RT=2.1 min [M+1]= 480.2. 1H NMR (400 MHz, CHLOROFORM-d) δ ppm 9.64 (2 H, br. s.), 7.14-7.46 (5 H, m), 6.86 (1 H, dd, J=15.43, 1.88 Hz), 6.54-6.75 (1 H, m), 4.27-4.38 (1 H, m), 4.24 (1 H, s), 3.58-3.80 (4 H, m), 2.98-3.13 (3 H, m), 2.50-2.70 (1 H, m), 1.95 (2 H, d, J=13.05 Hz), 1.46-1.90 (6 H, m).

By appropriate application of the methods described for Example 178, Examples 179-210 were synthesized.

Example 211

2-hydroxy-3-oxo-N-((R)-6-(trifluoromethyl)-2,3-dihydro-1H-inden-1-yl)-3,5,6,7,8,8a-hexahydroindolizine-1-carboxamide (Enantiomer A)

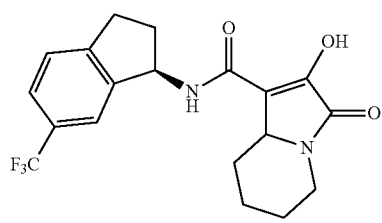 [SMILES: O=C(N[C@@H]1CCc2ccc(C(F)(F)F)cc21)C1=C(O)C(=O)N2CCCCC12]

Example 211A 2-methoxy-3-oxo-N-((R)-6-(trifluoromethyl)-2,3-dihydro-1H-inden-1-yl)-3,5,6,7,8,8a-hexahydroindolizine-1-carboxamide (Enantiomer A)

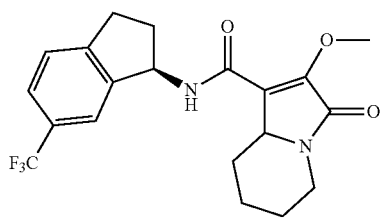 [SMILES: COC1=C(C(=O)N[C@@H]2CCc3ccc(C(F)(F)F)cc32)C2CCCCN2C1=O]

To the mixture of (R)-6-(trifluoromethyl)-2,3-dihydro-1H-inden-1-amine, HCl (33.8 mg, 0.142 mmol), 2-methoxy-3-oxo-3,5,6,7,8,8a-hexahydroindolizine-1-carboxylic acid (30 mg, 0.14 mmol) and PyBOP (81 mg, 0.16 mmol) in DMF (1 mL) was added DIEA (0.074 mL, 0.43 mmol) and the reaction mixture was stirred at rt for 2 h. The reaction mixture was concentrated and purified on flash chromatography (4 g cartridge, 0 to 100% EtOAc/Hex) to afford Example 211A as a racemate. The enantiomers were separated on chiral prep HPLC (chiral AD 10 micron 4.6×250 mm, 15 min 15% isocratic. A=Heptane with 0.1% DEA. B=Isopropyl alcohol with 0.1% DEA) to afford Example 211A (Enantiomer A) (6.0 mg, 0.015 mmol, 11% yield). HPLC/MS (Method L) RT=2.01 min, [M+1]=395.0.

Example 211

By appropriate application of the methods described in Example 156, Example 211A (Enantiomer A) (6 mg, 0.02 mmol) was converted to Example 211 (Enantiomer A) (3.0 mg, 52%) as a clear oil. LC/MS (HPLC Method L): RT=1.97 min, [M+1]$^+$ 381.0. 1H NMR (400 MHz, MeOD) δ ppm 0.82-1.04 (1 H, m), 1.11-1.34 (1 H, m), 1.53 (1 H, d, J=13.1 Hz), 1.72 (1 H, dt, J=13.1, 1.6 Hz), 1.77-1.99 (2 H, m), 2.42-2.65 (2 H, m), 2.79-2.94 (2 H, m), 2.94-3.10 (1 H, m), 3.97 (1 H, td, J=11.7, 3.8 Hz), 4.11 (1 H, dd, J=13.2, 4.9 Hz), 5.47 (1 H, t, J=7.9 Hz), 7.30-7.37 (1 H, m), 7.41-7.48 (2 H, m).

By appropriate application of the methods described for Example 211, Examples 212-213 were synthesized.

Example 214

N-((3-(3,4-Dichlorophenyl)-5,6,7,8-tetrahydroimidazo[1,5-a]pyridin-6-yl)methyl)-1-ethyl-4-hydroxy-5-oxo-2,5-dihydro-1H-pyrrole-3-carboxamide

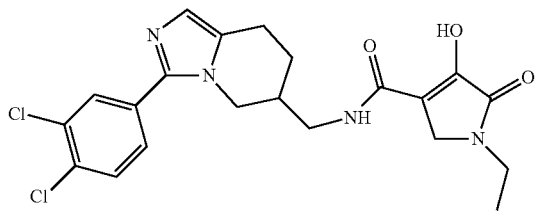 [SMILES: CCN1CC(C(=O)NCC2CCc3cnc(-c4ccc(Cl)c(Cl)c4)n3C2)=C(O)C1=O]

Example 133 (12 mg, 0.030 mmol) in methanol (2 mL) was flushed with nitrogen and treated with palladium (10% on charcoal, 2 mg, 1.9 µmol). The flask was flushed with hydrogen and allowed to stir over a balloon of hydrogen for 2 h. The reaction mixture was flushed with nitrogen, filtered through Celite® and concentrated under reduced pressure. The residue was dissolved in methanol and purified by reverse phase preparative HPLC (Method J) to afford Example 214 (6.2 mg, 47%). $^1$H NMR (400 MHz, MeOD) δ ppm 7.98 (1 H, d, J=2.0 Hz), 7.84-7.88 (1 H, m), 7.69 (1 H, dd, J=8.4, 2.1 Hz), 7.46 (1 H, s), 4.29 (1 H, m), 3.95-4.01 (2H, m), 3.39-3.59 (5 H, m), 3.12-3.23 (1 H, m), 2.90-3.02 (1 H, m), 2.34-2.46 (1 H, m), 2.12-2.23 (1 H, m), 1.73-1.87 (1 H, m), 1.22 (3 H, t, J=7.3 Hz). LC/MS (HPLC Method L): RT=1.47 min, [M+1]$^+$ 449.1.

Example 215

N-(7-(4-acetamidophenyl)-1,2,3,4-tetrahydronaphthalen-1-yl)-1-(2,4-difluorophenyl)-4-hydroxy-5-oxo-2,5-dihydro-1H-pyrrole-3-carboxamide

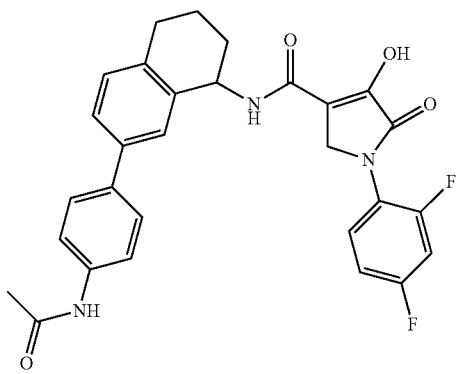 [SMILES: CC(=O)Nc1ccc(-c2ccc3c(c2)C(NC(=O)C2=C(O)C(=O)N(c4ccc(F)cc4F)C2)CCC3)cc1]

Example 215A

N-(7-bromo-1,2,3,4-tetrahydronaphthalen-1-yl)-1-(2,4-difluorophenyl)-4-ethoxy-5-oxo-2,5-dihydro-1H-pyrrole-3-carboxamide

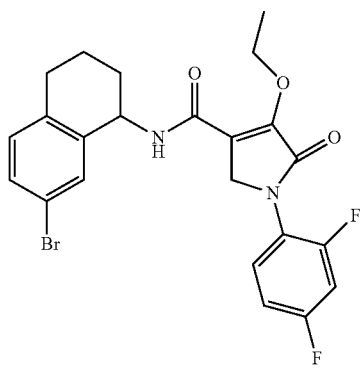 [SMILES: CCOC1=C(C(=O)NC2CCCc3ccc(Br)cc32)CN(c2ccc(F)cc2F)C1=O]

To suspension of 1-(2,4-difluorophenyl)-4-ethoxy-5-oxo-2,5-dihydro-1H-pyrrole-3-carboxylic acid (0.30 g, 1.1 mmol) in DCM (2 mL) was added oxalyl chloride (0.76 mL, 1.5 mmol) and one drop of DMF. The reaction mixture was stirred at rt for 1 h and concentrated under reduced pressure. The residue was dissolved in DCM and TEA was added (0.443 mL, 3.18 mmol) and 7-bromo-1,2,3,4-tetrahydronaphthalen-1-amine (239 mg, 1.059 mmol). The reaction was stirred at rt for 1 h. The reaction was diluted with DCM, washed with 1N HCl and brine, dried over Na₂SO₄, filtered and concentrated. The residue was purified by flash chromatography (0-40% EtOAc/Hex) to give Example 215A (265 mg, 0.539 mmol, 50.9% yield) as a yellow solid. 1H NMR (400 MHz, CHLOROFORM-d) δ ppm 7.49 (1 H, d, J=1.52 Hz), 7.37-7.47 (2 H, m), 7.33 (1 H, dd, J=8.08, 2.02 Hz), 6.91-7.04 (3 H, m), 5.21-5.33 (1 H, m), 4.77 (2 H, q, J=7.07 Hz), 4.50 (2 H, d, J=5.31 Hz), 2.68-2.87 (2 H, m), 2.11-2.22 (1 H, m), 1.75-1.95 (3 H, m), 1.30 (3 H, t, J=7.07 Hz).

Example 215B

N-(7-(4-acetamidophenyl)-1,2,3,4-tetrahydronaphthalen-1-yl)-1-(2,4-difluorophenyl)-4-ethoxy-5-oxo-2,5-dihydro-1H-pyrrole-3-carboxamide To a solution of Example 215A (50 mg, 0.10 mmol) in DME (1.0 mL) was added 4-acetamidophenylboronic acid (36.4 mg, 0.204 mmol), sodium carbonate (0.153 mL, 0.305 mmol), and tetrakis(triphenylphosphine)palladium(0) (23 mg, 0.020 mmol) in a microwave vial. The reaction mixture was degassed and refilled with Argon three times and the reaction mixture was heated at 100° C. for 3 h. The reaction mixture was diluted with DCM, dried over MgSO₄, filtered and concentrated. The residue was purified by flash chromatography (EtOAc/Hex, 0-100% B over 25 min) to give Example 215B (45 mg, 0.082 mmol, 81% yield) as a white solid. LC/MS (HPLC Method L): RT=2.182 min, [M+1]⁺ 546.1.

Example 215

To a solution of Example 215B (45 mg, 0.082 mmol) in CHCl₃ (1 mL) was added boron trichloride (0.124 mL, 0.124 mmol). The reaction mixture was stirred at rt for 18 h., quenched with MeOH and concentrated. The residue was purified by Prep HPLC to give Example 215 (23 mg, 0.044 mmol, 53% yield) as a white solid. LCMS (Method L) RT=2.09 min, [M+Na]=540.5, ¹H NMR (400 MHz, CHLOROFORM-d) δ ppm 7.52 (5 H, br. s.), 7.39-7.45 (2 H, m), 7.20 (1 H, d, J=7.83 Hz), 6.89-6.99 (3 H, m), 5.41 (1 H, t, J=6.95 Hz), 4.51 (2 H, s), 2.76-2.95 (2 H, m), 2.22 (3 H, s), 1.85-1.98 (4 H, m), 1.28 (1 H, br. s.).

By appropriate application of the methods described for Example 215, Examples 216-219 were synthesized. By appropriate application of the methods described for Example 1, Examples 220-222 were synthesized.

Analytical data for Examples 2-46, 49-126, 128-131, 135-153, 157-176, 179-210, 212-213, and 216-222 in Table 2 are reported as follows: compound retention times were recorded using HPLC/MS conditions indicated in the table and the molecular masses of the compounds were determined by MS (ES) by the formula m/z.

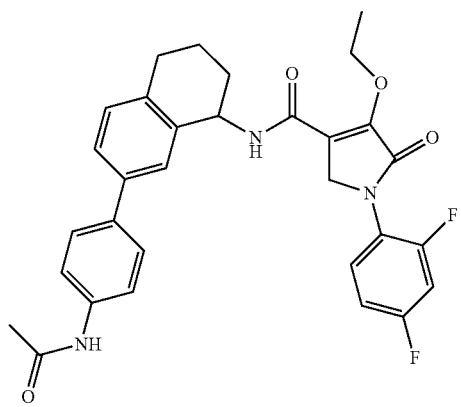 [SMILES: CCOC1=C(C(=O)NC2CCCc3ccc(-c4ccc(NC(C)=O)cc4)cc32)CN(c2ccc(F)cc2F)C1=O]

TABLE 2

| Ex. # | Structure | Name | RT (min) | [M + 1]⁺ | LC/MS Methods |
|---|---|---|---|---|---|
| 2 | 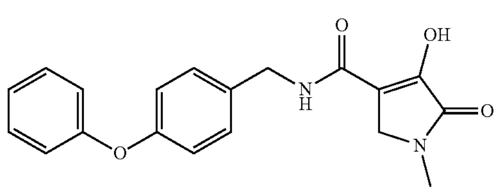 [SMILES: CN1CC(C(=O)NCc2ccc(Oc3ccccc3)cc2)=C(O)C1=O] | 4-hydroxy-1-methyl-5-oxo-N-(4-phenoxybenzyl)-2,5-dihydro-1H-pyrrole-3-carboxamide | 2.50 | 337.3 | C |
| 3 | 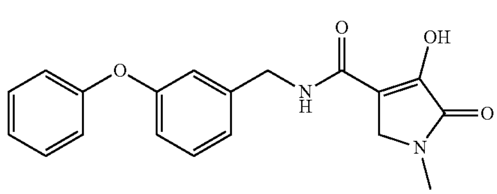 [SMILES: CN1CC(C(=O)NCc2cccc(Oc3ccccc3)c2)=C(O)C1=O] | 4-hydroxy-1-methyl-5-oxo-N-(3-phenoxybenzyl)-2,5-dihydro-1H-pyrrole-3-carboxamide | 0.88 | 339 | D |

TABLE 2-continued

| Ex. # | Structure | Name | RT (min) | [M + 1]+ | LC/MS Methods |
|---|---|---|---|---|---|
| 4 | 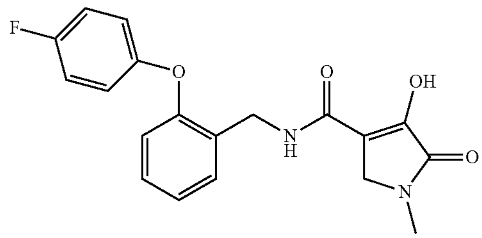 [SMILES: CN1CC(C(=O)NCc2ccccc2Oc2ccc(F)cc2)=C(O)C1=O] | N-(2-(4-fluorophenoxy)benzyl)-4-hydroxy-1-methyl-5-oxo-2,5-dihydro-1H-pyrrole-3-carboxamide | 0.88 | 357 | D |
| 5 | 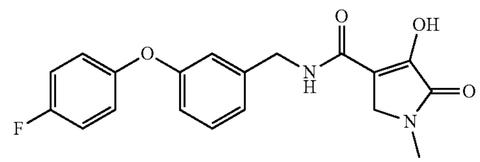 [SMILES: CN1CC(C(=O)NCc2cccc(Oc3ccc(F)cc3)c2)=C(O)C1=O] | N-(3-(4-fluorophenoxy)benzyl)-4-hydroxy-1-methyl-5-oxo-2,5-dihydro-1H-pyrrole-3-carboxamide | 0.89 | 357 | D |
| 6 | 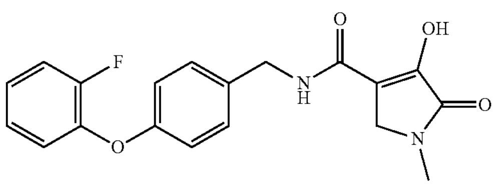 [SMILES: CN1CC(C(=O)NCc2ccc(Oc3ccccc3F)cc2)=C(O)C1=O] | N-(4-(2-fluorophenoxy)benzyl)-4-hydroxy-1-methyl-5-oxo-2,5-dihydro-1H-pyrrole-3-carboxamide | 0.88 | 357 | D |
| 7 | 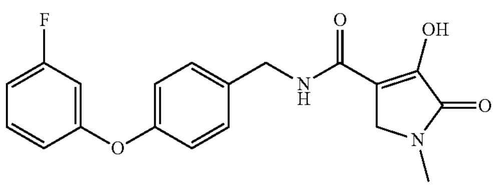 [SMILES: CN1CC(C(=O)NCc2ccc(Oc3cccc(F)c3)cc2)=C(O)C1=O] | N-(4-(3-fluorophenoxy)benzyl)-4-hydroxy-1-methyl-5-oxo-2,5-dihydro-1H-pyrrole-3-carboxamide | 0.90 | 357 | D |
| 8 | 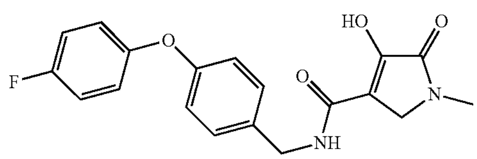 [SMILES: CN1CC(C(=O)NCc2ccc(Oc3ccc(F)cc3)cc2)=C(O)C1=O] | N-(4-(4-fluorophenoxy)benzyl)-4-hydroxy-1-methyl-5-oxo-2,5-dihydro-1H-pyrrole-3-carboxamide | 2.10 | 357 | A |
| 9 | 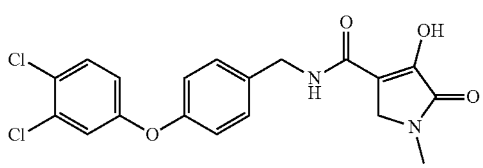 [SMILES: CN1CC(C(=O)NCc2ccc(Oc3ccc(Cl)c(Cl)c3)cc2)=C(O)C1=O] | N-(4-(3,4-dichlorophenoxy)benzyl)-4-hydroxy-1-methyl-5-oxo-2,5-dihydro-1H-pyrrole-3-carboxamide | 3.30 | 264 | D |
| 10 | 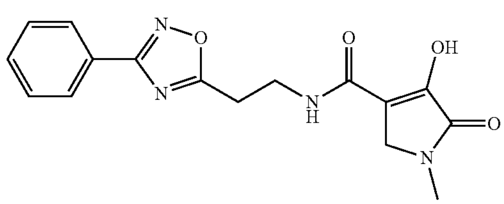 [SMILES: CN1CC(C(=O)NCCc2nc(-c3ccccc3)no2)=C(O)C1=O] | 4-hydroxy-1-methyl-5-oxo-N-(2-(3-phenyl-1,2,4-oxadiazol-5-yl)ethyl)-2,5-dihydro-1H-pyrrole-3-carboxamide | 1.89 | 329.2 | C |
| 11 | 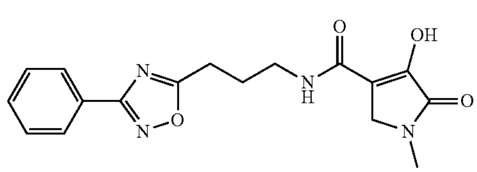 [SMILES: CN1CC(C(=O)NCCCc2nc(-c3ccccc3)no2)=C(O)C1=O] | 4-hydroxy-1-methyl-5-oxo-N-(3-(3-phenyl-1,2,4-oxadiazol-5-yl)propyl)-2,5-dihydro-1H-pyrrole-3-carboxamide | 1.97 | 343.2 | C |

TABLE 2-continued

| Ex. # | Structure | Name | RT (min) | [M + 1]+ | LC/MS Methods |
|---|---|---|---|---|---|
| 12 | 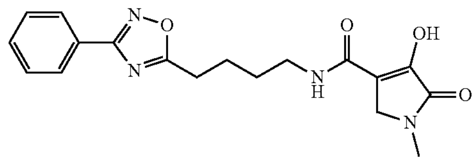 [SMILES: CN1CC(C(=O)NCCCCc2nc(-c3ccccc3)no2)=C(O)C1=O] | 4-hydroxy-1-methyl-5-oxo-N-(4-(3-phenyl-1,2,4-oxadiazol-5-yl)butyl)-2,5-dihydro-1H-pyrrole-3-carboxamide | 2.29 | 357.2 | C |
| 13 | 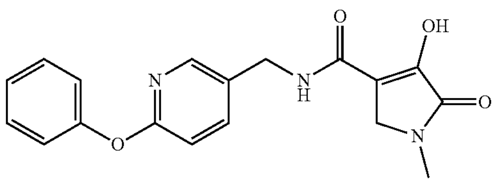 [SMILES: CN1CC(C(=O)NCc2ccc(Oc3ccccc3)nc2)=C(O)C1=O] | 4-hydroxy-1-methyl-5-oxo-N-((6-phenoxypyridin-3-yl)methyl)-2,5-dihydro-1H-pyrrole-3-carboxamide | 0.77 | 340.0 | D |
| 14 | 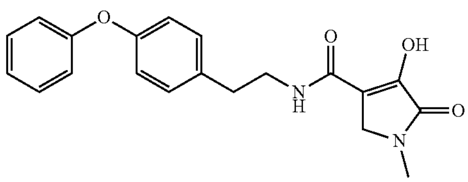 [SMILES: CN1CC(C(=O)NCCc2ccc(Oc3ccccc3)cc2)=C(O)C1=O] | 4-hydroxy-1-methyl-5-oxo-N-(4-phenoxyphenethyl)-2,5-dihydro-1H-pyrrole-3-carboxamide | 0.91 | 353.0 | D |
| 15 | 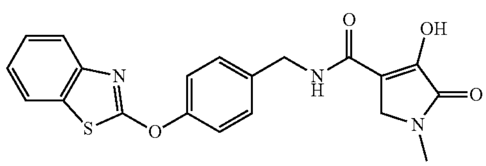 [SMILES: CN1CC(C(=O)NCc2ccc(Oc3nc4ccccc4s3)cc2)=C(O)C1=O] | N-(4-(benzo[d]thiazol-2-yloxy)benzyl)-4-hydroxy-1-methyl-5-oxo-2,5-dihydro-1H-pyrrole-3-carboxamide | 0.89 | 396.0 | D |
| 16 | 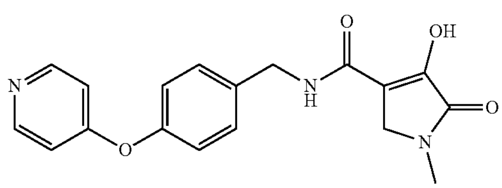 [SMILES: CN1CC(C(=O)NCc2ccc(Oc3ccncc3)cc2)=C(O)C1=O] | 4-hydroxy-1-methyl-5-oxo-N-(4-(pyridin-4-yloxy)benzyl)-2,5-dihydro-1H-pyrrole-3-carboxamide | 0.54 | 340.0 | D |
| 17 | 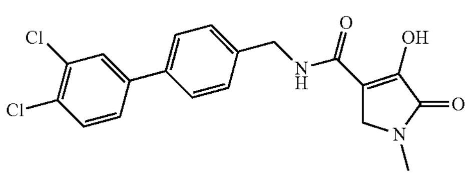 [SMILES: CN1CC(C(=O)NCc2ccc(-c3ccc(Cl)c(Cl)c3)cc2)=C(O)C1=O] | N-((3',4'-dichlorobiphenyl-4-yl)methyl)-4-hydroxy-1-methyl-5-oxo-2,5-dihydro-1H-pyrrole-3-carboxamide | 3.60 | 390.9 | N |
| 18 | 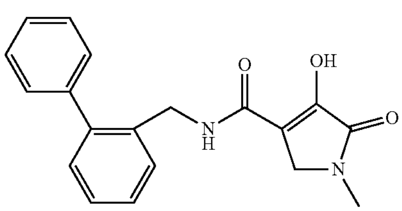 [SMILES: CN1CC(C(=O)NCc2ccccc2-c2ccccc2)=C(O)C1=O] | N-(biphenyl-2-ylmethyl)-4-hydroxy-1-methyl-5-oxo-2,5-dihydro-1H-pyrrole-3-carboxamide | 2.41 | 323.1 | A |
| 19 | 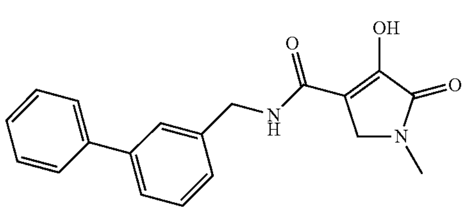 [SMILES: CN1CC(C(=O)NCc2cccc(-c3ccccc3)c2)=C(O)C1=O] | N-(biphenyl-3-ylmethyl)-4-hydroxy-1-methyl-5-oxo-2,5-dihydro-1H-pyrrole-3-carboxamide | 2.48 | 323.1 | A |

TABLE 2-continued

| Ex. # | Structure | Name | RT (min) | [M + 1]+ | LC/MS Methods |
|---|---|---|---|---|---|
| 20 | 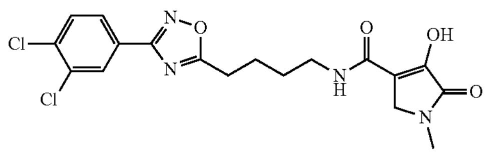 [SMILES: CN1CC(C(=O)NCCCCc2nc(-c3ccc(Cl)c(Cl)c3)no2)=C(O)C1=O] | N-(4-(3-(3,4-dichlorophenyl)-1,2,4-oxadiazol-5-yl)butyl)-4-hydroxy-1-methyl-5-oxo-2,5-dihydro-1H-pyrrole-3-carboxamide | 2.15 | 424.8 | L |
| 21 | 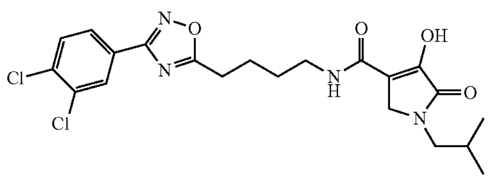 [SMILES: CC(C)CN1CC(C(=O)NCCCCc2nc(-c3ccc(Cl)c(Cl)c3)no2)=C(O)C1=O] | N-(4-(3-(3,4-dichlorophenyl)-1,2,4-oxadiazol-5-yl)butyl)-4-hydroxy-1-isobutyl-5-oxo-2,5-dihydro-1H-pyrrole-3-carboxamide | 2.30 | 466.8 | L |
| 22 | 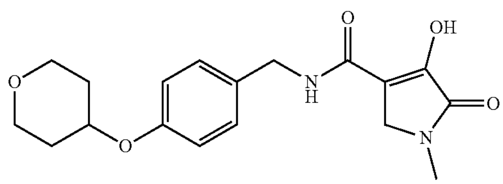 [SMILES: CN1CC(C(=O)NCc2ccc(OC3CCOCC3)cc2)=C(O)C1=O] | 4-hydroxy-1-methyl-5-oxo-N-(4-(tetrahydro-2H-pyran-4-yloxy)benzyl)-2,5-dihydro-1H-pyrrole-3-carboxamide | 1.15 | 347.0 | E |
| 23 | 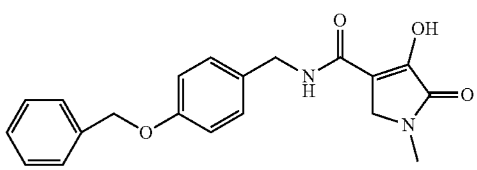 [SMILES: CN1CC(C(=O)NCc2ccc(OCc3ccccc3)cc2)=C(O)C1=O] | N-(4-(benzyloxy)benzyl)-4-hydroxy-1-methyl-5-oxo-2,5-dihydro-1H-pyrrole-3-carboxamide | 0.89 | 353 | D |
| 24 | 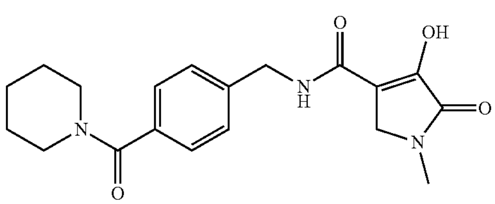 [SMILES: CN1CC(C(=O)NCc2ccc(C(=O)N3CCCCC3)cc2)=C(O)C1=O] | 4-hydroxy-1-methyl-5-oxo-N-(4-(piperidine-1-carbonyl)benzyl)-2,5-dihydro-1H-pyrrole-3-carboxamide | 0.70 | 358.0 | D |
| 25 | 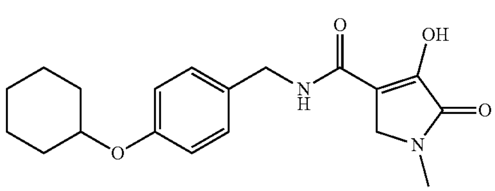 [SMILES: CN1CC(C(=O)NCc2ccc(OC3CCCCC3)cc2)=C(O)C1=O] | N-(4-(cyclohexyloxy)benzyl)-4-hydroxy-1-methyl-5-oxo-2,5-dihydro-1H-pyrrole-3-carboxamide | 0.94 | 367.0 | D |
| 26 | 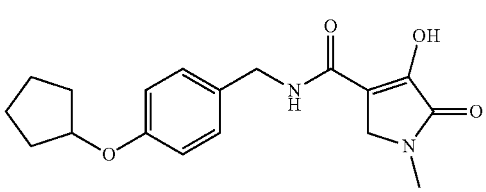 [SMILES: CN1CC(C(=O)NCc2ccc(OC3CCCC3)cc2)=C(O)C1=O] | N-(4-(cyclopentyloxy)benzyl)-4-hydroxy-1-methyl-5-oxo-2,5-dihydro-1H-pyrrole-3-carboxamide | 0.89 | 353 (+Na) | D |
| 27 | 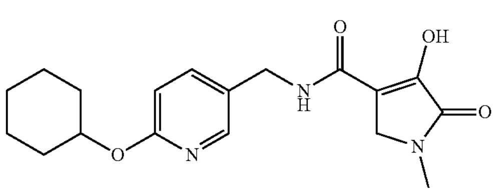 [SMILES: CN1CC(C(=O)NCc2ccc(OC3CCCCC3)nc2)=C(O)C1=O] | N-((6-(cyclohexyloxy)pyridin-3-yl)methyl)-4-hydroxy-1-methyl-5-oxo-2,5-dihydro-1H-pyrrole-3-carboxamide | 0.77 | 346 (+Na) | D |

TABLE 2-continued

| Ex. # | Structure | Name | RT (min) | [M + 1]⁺ | LC/MS Methods |
|---|---|---|---|---|---|
| 28 | 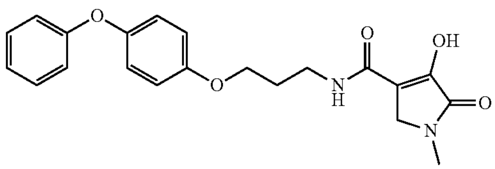 [SMILES: CN1CC(C(=O)NCCCOc2ccc(Oc3ccccc3)cc2)=C(O)C1=O] | 4-hydroxy-1-methyl-5-oxo-N-(3-(4-phenoxyphenoxy)propyl)-2,5-dihydro-1H-pyrrole-3-carboxamide | 2.09 | 382 | E |
| 29 | 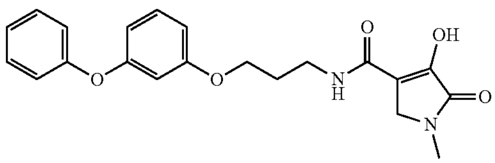 [SMILES: CN1CC(C(=O)NCCCOc2cccc(Oc3ccccc3)c2)=C(O)C1=O] | 4-hydroxy-1-methyl-5-oxo-N-(3-(3-phenoxyphenoxy)propyl)-2,5-dihydro-1H-pyrrole-3-carboxamide | 2.11 | 382 | E |
| 30 | 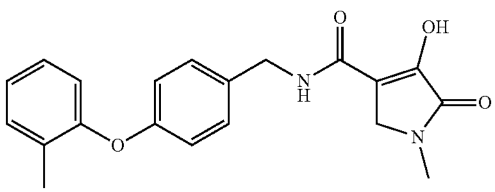 [SMILES: Cc1ccccc1Oc1ccc(CNC(=O)C2=C(O)C(=O)N(C)C2)cc1] | 4-hydroxy-1-methyl-5-oxo-N-(4-(o-tolyloxy)benzyl)-2,5-dihydro-1H-pyrrole-3-carboxamide | 2.68 | 353.0 | E |
| 31 | 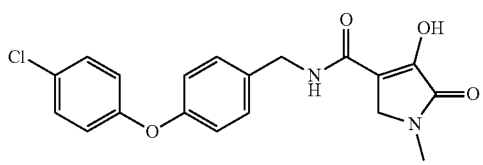 [SMILES: CN1CC(C(=O)NCc2ccc(Oc3ccc(Cl)cc3)cc2)=C(O)C1=O] | N-(4-(4-chlorophenoxy)benzyl)-4-hydroxy-1-methyl-5-oxo-2,5-dihydro-1H-pyrrole-3-carboxamide | 2.79 | 373.0 | E |
| 32 | 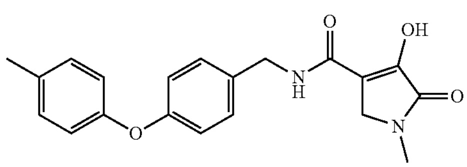 [SMILES: Cc1ccc(Oc2ccc(CNC(=O)C3=C(O)C(=O)N(C)C3)cc2)cc1] | 4-hydroxy-1-methyl-5-oxo-N-(4-(p-tolyloxy)benzyl)-2,5-dihydro-1H-pyrrole-3-carboxamide | 2.71 | 353.0 | E |
| 33 | 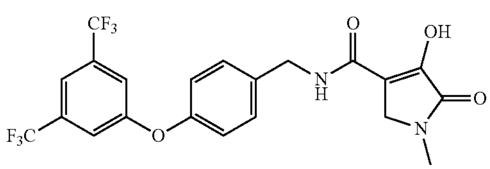 [SMILES: CN1CC(C(=O)NCc2ccc(Oc3cc(C(F)(F)F)cc(C(F)(F)F)c3)cc2)=C(O)C1=O] | N-(4-(3,5-bis(trifluoromethyl)phenoxy)benzyl)-4-hydroxy-1-methyl-5-oxo-2,5-dihydro-1H-pyrrole-3-carboxamide | 2.48 | 474.9 | E |
| 34 | 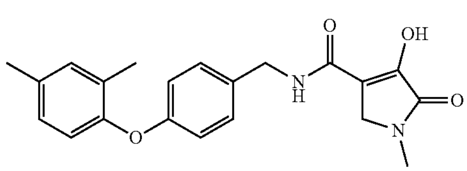 [SMILES: Cc1ccc(Oc2ccc(CNC(=O)C3=C(O)C(=O)N(C)C3)cc2)c(C)c1] | N-(4-(2,4-dimethylphenoxy)benzyl)-4-hydroxy-1-methyl-5-oxo-2,5-dihydro-1H-pyrrole-3-carboxamide | 2.93 | 366.9 | E |
| 35 | 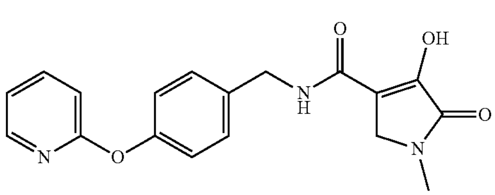 [SMILES: CN1CC(C(=O)NCc2ccc(Oc3ccccn3)cc2)=C(O)C1=O] | 4-hydroxy-1-methyl-5-oxo-N-(4-(pyridin-2-yloxy)benzyl)-2,5-dihydro-1H-pyrrole-3-carboxamide | 1.24 | 339.9 | E |

TABLE 2-continued

| Ex. # | Structure | Name | RT (min) | [M + 1]+ | LC/MS Methods |
|---|---|---|---|---|---|
| 36 | 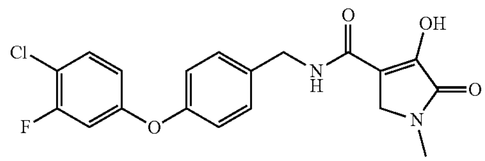 [SMILES: CN1CC(C(=O)NCc2ccc(Oc3ccc(Cl)c(F)c3)cc2)=C(O)C1=O] | N-(4-(4-chloro-3-fluorophenoxy)benzyl)-4-hydroxy-1-methyl-5-oxo-2,5-dihydro-1H-pyrrole-3-carboxamide | 2.88 | 390.9 | E |
| 37 | 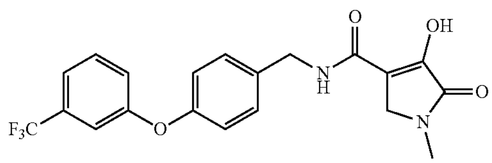 [SMILES: CN1CC(C(=O)NCc2ccc(Oc3cccc(C(F)(F)F)c3)cc2)=C(O)C1=O] | 4-hydroxy-1-methyl-5-oxo-N-(4-(3-(trifluoromethyl)phenoxy)benzyl)-2,5-dihydro-1H-pyrrole-3-carboxamide | 2.92 | 406.9 | E |
| 38 | 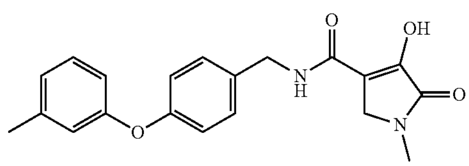 [SMILES: Cc1cccc(Oc2ccc(CNC(=O)C3=C(O)C(=O)N(C)C3)cc2)c1] | 4-hydroxy-1-methyl-5-oxo-N-(4-(m-tolyloxy)benzyl)-2,5-dihydro-1H-pyrrole-3-carboxamide | 2.70 | 352.9 | E |
| 39 | 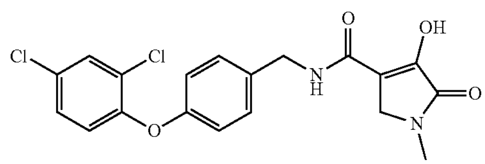 [SMILES: CN1CC(C(=O)NCc2ccc(Oc3ccc(Cl)cc3Cl)cc2)=C(O)C1=O] | N-(4-(2,4-dichlorophenoxy)benzyl)-4-hydroxy-1-methyl-5-oxo-2,5-dihydro-1H-pyrrole-3-carboxamide | 3.02 | 406.8 | E |
| 40 | 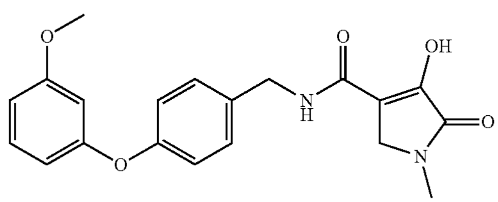 [SMILES: COc1cccc(Oc2ccc(CNC(=O)C3=C(O)C(=O)N(C)C3)cc2)c1] | 4-hydroxy-N-(4-(3-methoxyphenoxy)benzyl)-1-methyl-5-oxo-2,5-dihydro-1H-pyrrole-3-carboxamide | 2.50 | 368.9 | E |
| 41 | 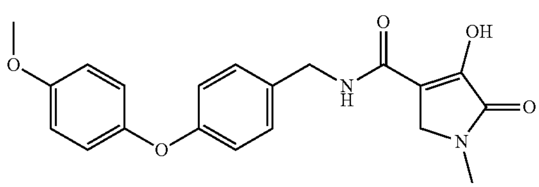 [SMILES: COc1ccc(Oc2ccc(CNC(=O)C3=C(O)C(=O)N(C)C3)cc2)cc1] | 4-hydroxy-N-(4-(4-methoxyphenoxy)benzyl)-1-methyl-5-oxo-2,5-dihydro-1H-pyrrole-3-carboxamide | 2.44 | 368.9 | E |
| 42 | 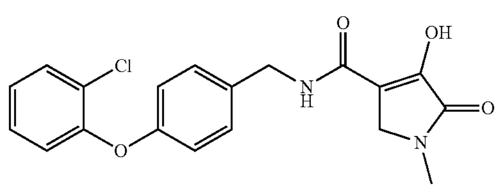 [SMILES: CN1CC(C(=O)NCc2ccc(Oc3ccccc3Cl)cc2)=C(O)C1=O] | N-(4-(2-chlorophenoxy)benzyl)-4-hydroxy-1-methyl-5-oxo-2,5-dihydro-1H-pyrrole-3-carboxamide | 2.65 | 372.9 | E |
| 43 | 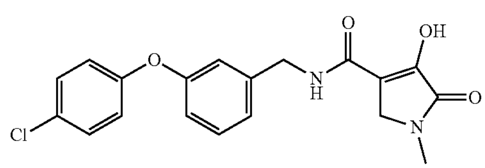 [SMILES: CN1CC(C(=O)NCc2cccc(Oc3ccc(Cl)cc3)c2)=C(O)C1=O] | N-(3-(4-chlorophenoxy)benzyl)-4-hydroxy-1-methyl-5-oxo-2,5-dihydro-1H-pyrrole-3-carboxamide | 2.77 | 372.9 | E |

TABLE 2-continued

| Ex. # | Structure | Name | RT (min) | [M + 1]+ | LC/MS Methods |
|---|---|---|---|---|---|
| 44 | 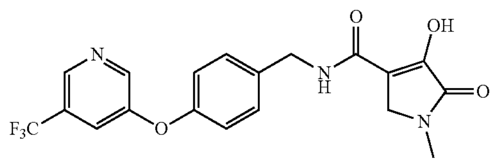 [SMILES: CN1CC(C(=O)NCc2ccc(Oc3cncc(C(F)(F)F)c3)cc2)=C(O)C1=O] | 4-hydroxy-1-methyl-5-oxo-N-(4-(5-(trifluoromethyl)pyridin-3-yloxy)benzyl)-2,5-dihydro-1H-pyrrole-3-carboxamide | 2.53 | 408.0 | E |
| 45 | 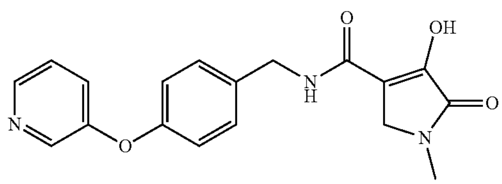 [SMILES: CN1CC(C(=O)NCc2ccc(Oc3cccnc3)cc2)=C(O)C1=O] | 4-hydroxy-1-methyl-5-oxo-N-(4-(pyridin-3-yloxy)benzyl)-2,5-dihydro-1H-pyrrole-3-carboxamide | 1.19 | 339.9 | E |
| 46 | 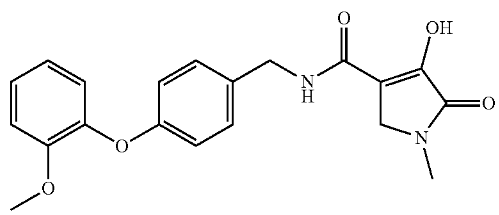 [SMILES: COc1ccccc1Oc1ccc(CNC(=O)C2=C(O)C(=O)N(C)C2)cc1] | 4-hydroxy-N-(4-(2-methoxyphenoxy)benzyl)-1-methyl-5-oxo-2,5-dihydro-1H-pyrrole-3-carboxamide | 2.35 | 369.0 | E |
| 49 | 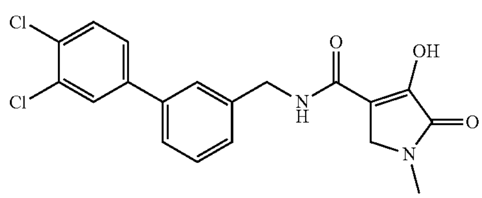 [SMILES: CN1CC(C(=O)NCc2cccc(-c3ccc(Cl)c(Cl)c3)c2)=C(O)C1=O] | N-((3',4'-dichlorobiphenyl-3-yl)methyl)-4-hydroxy-1-methyl-5-oxo-2,5-dihydro-1H-pyrrole-3-carboxamide | 2.97 | 391.1 | A |
| 50 | 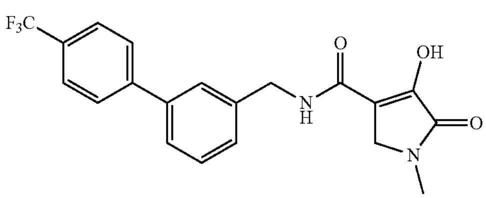 [SMILES: CN1CC(C(=O)NCc2cccc(-c3ccc(C(F)(F)F)cc3)c2)=C(O)C1=O] | 4-hydroxy-1-methyl-5-oxo-N-((4'-(trifluoromethyl)biphenyl-3-yl)methyl)-2,5-dihydro-1H-pyrrole-3-carboxamide | 2.89 | 391.1 | A |
| 51 | 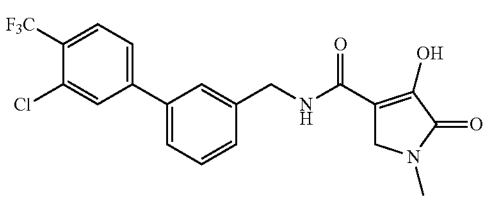 [SMILES: CN1CC(C(=O)NCc2cccc(-c3ccc(C(F)(F)F)c(Cl)c3)c2)=C(O)C1=O] | N-((3'-chloro-4'-(trifluoromethyl)biphenyl-3-yl)methyl)-4-hydroxy-1-methyl-5-oxo-2,5-dihydro-1H-pyrrole-3-carboxamide | 2.18 | 424.9 | H |
| 52 | 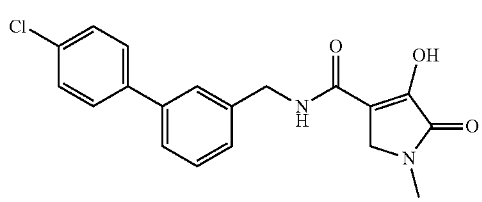 [SMILES: CN1CC(C(=O)NCc2cccc(-c3ccc(Cl)cc3)c2)=C(O)C1=O] | N-((4'-chlorobiphenyl-3-yl)methyl)-4-hydroxy-1-methyl-5-oxo-2,5-dihydro-1H-pyrrole-3-carboxamide | 2.07 | 357.0 | L |

TABLE 2-continued

| Ex. # | Structure | Name | RT (min) | [M + 1]+ | LC/MS Methods |
|---|---|---|---|---|---|
| 53 | 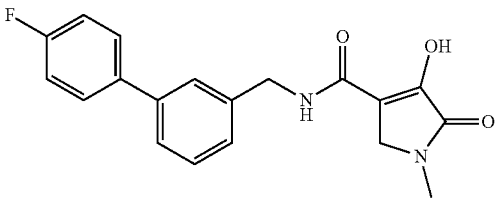 [SMILES: CN1CC(C(=O)NCc2cccc(-c3ccc(F)cc3)c2)=C(O)C1=O] | N-((4'-fluorobiphenyl-3-yl)methyl)-4-hydroxy-1-methyl-5-oxo-2,5-dihydro-1H-pyrrole-3-carboxamide | 1.95 | 340.9 | L |
| 54 | 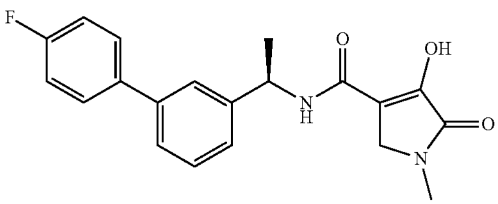 [SMILES: C[C@@H](NC(=O)C1=C(O)C(=O)N(C)C1)c1cccc(-c2ccc(F)cc2)c1] | (R)-N-(1-(4'-fluorobiphenyl-3-yl)ethyl)-4-hydroxy-1-methyl-5-oxo-2,5-dihydro-1H-pyrrole-3-carboxamide | 1.53 | 355.2 | M |
| 55 | 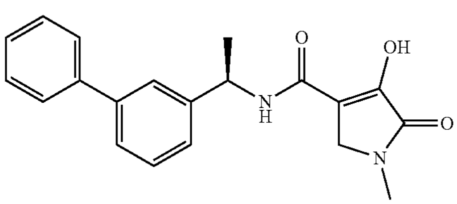 [SMILES: C[C@@H](NC(=O)C1=C(O)C(=O)N(C)C1)c1cccc(-c2ccccc2)c1] | (R)-N-(1-(biphenyl-3-yl)ethyl)-4-hydroxy-1-methyl-5-oxo-2,5-dihydro-1H-pyrrole-3-carboxamide | 2.00 | 336.0 | L |
| 56 | 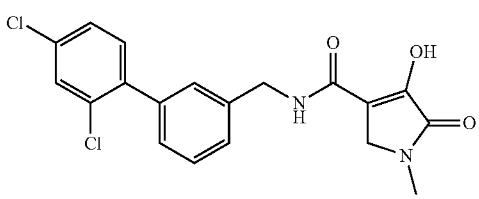 [SMILES: CN1CC(C(=O)NCc2cccc(-c3ccc(Cl)cc3Cl)c2)=C(O)C1=O] | N-((2',4'-dichlorobiphenyl-3-yl)methyl)-4-hydroxy-1-methyl-5-oxo-2,5-dihydro-1H-pyrrole-3-carboxamide | 1.79 | 391.0 | P |
| 57 | 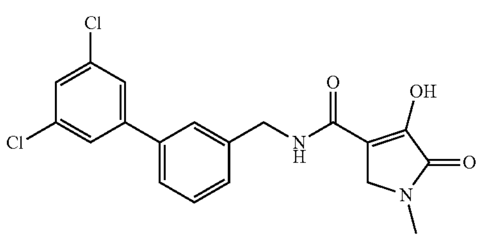 [SMILES: CN1CC(C(=O)NCc2cccc(-c3cc(Cl)cc(Cl)c3)c2)=C(O)C1=O] | N-((3',5'-dichlorobiphenyl-3-yl)methyl)-4-hydroxy-1-methyl-5-oxo-2,5-dihydro-1H-pyrrole-3-carboxamide | 1.85 | 391.0 | P |
| 58 | 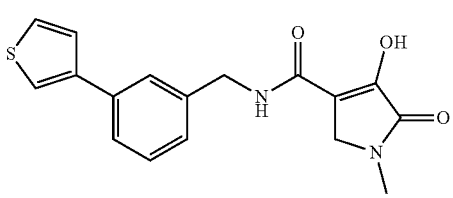 [SMILES: CN1CC(C(=O)NCc2cccc(-c3ccsc3)c2)=C(O)C1=O] | 4-hydroxy-1-methyl-5-oxo-N-(3-(thiophen-3-yl)benzyl)-2,5-dihydro-1H-pyrrole-3-carboxamide | 1.34 | 329.0 | P |
| 59 | 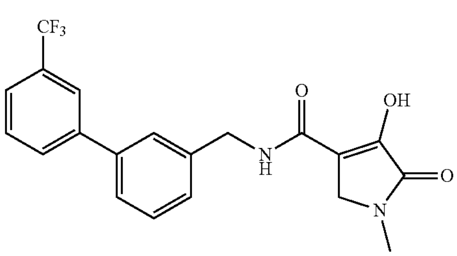 [SMILES: CN1CC(C(=O)NCc2cccc(-c3cccc(C(F)(F)F)c3)c2)=C(O)C1=O] | 4-hydroxy-1-methyl-5-oxo-N-((3'-(trifluoromethyl)biphenyl-3-yl)methyl)-2,5-dihydro-1H-pyrrole-3-carboxamide | 1.73 | 391.1 | P |

TABLE 2-continued

| Ex. # | Structure | Name | RT (min) | [M + 1]+ | LC/MS Methods |
|---|---|---|---|---|---|
| 60 | 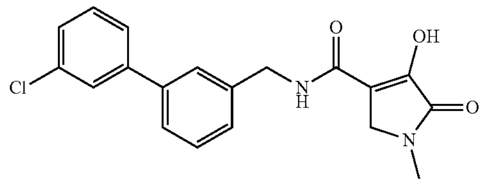 [SMILES: CN1CC(C(=O)NCc2cccc(-c3cccc(Cl)c3)c2)=C(O)C1=O] | N-((3'-chlorobiphenyl-3-yl)methyl)-4-hydroxy-1-methyl-5-oxo-2,5-dihydro-1H-pyrrole-3-carboxamide | 1.63 | 357.02 | P |
| 61 | 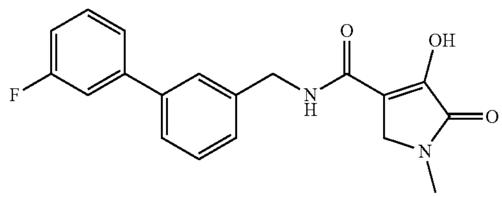 [SMILES: CN1CC(C(=O)NCc2cccc(-c3cccc(F)c3)c2)=C(O)C1=O] | N-((3'-fluorobiphenyl-3-yl)methyl)-4-hydroxy-1-methyl-5-oxo-2,5-dihydro-1H-pyrrole-3-carboxamide | 1.47 | 341.0 | P |
| 62 | 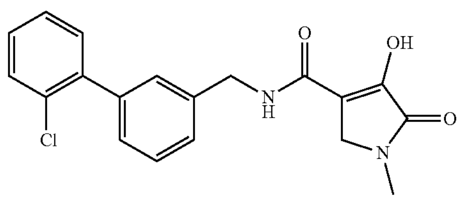 [SMILES: CN1CC(C(=O)NCc2cccc(-c3ccccc3Cl)c2)=C(O)C1=O] | N-((2'-chlorobiphenyl-3-yl)methyl)-4-hydroxy-1-methyl-5-oxo-2,5-dihydro-1H-pyrrole-3-carboxamide | 1.54 | 357.0 | P |
| 63 | 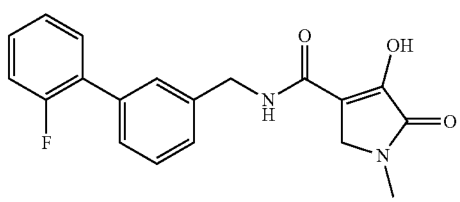 [SMILES: CN1CC(C(=O)NCc2cccc(-c3ccccc3F)c2)=C(O)C1=O] | N-((2'-fluorobiphenyl-3-yl)methyl)-4-hydroxy-1-methyl-5-oxo-2,5-dihydro-1H-pyrrole-3-carboxamide | 1.45 | 341.0 | P |
| 64 | 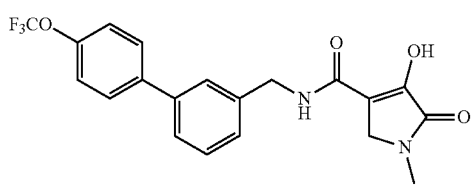 [SMILES: CN1CC(C(=O)NCc2cccc(-c3ccc(OC(F)(F)F)cc3)c2)=C(O)C1=O] | 4-hydroxy-1-methyl-5-oxo-N-((4'-(trifluoromethoxy)biphenyl-3-yl)methyl)-2,5-dihydro-1H-pyrrole-3-carboxamide | 1.81 | 407.0 | P |
| 65 | 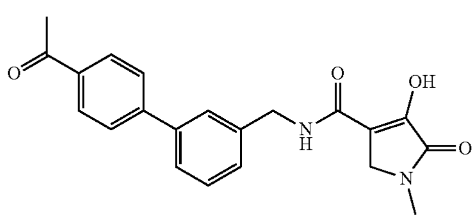 [SMILES: CC(=O)c1ccc(-c2cccc(CNC(=O)C3=C(O)C(=O)N(C)C3)c2)cc1] | N-((4'-acetylbiphenyl-3-yl)methyl)-4-hydroxy-1-methyl-5-oxo-2,5-dihydro-1H-pyrrole-3-carboxamide | 1.38 | 365.1 | P |
| 66 | 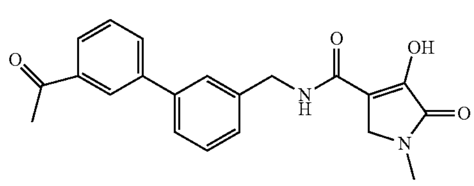 [SMILES: CC(=O)c1cccc(-c2cccc(CNC(=O)C3=C(O)C(=O)N(C)C3)c2)c1] | N-((3'-acetylbiphenyl-3-yl)methyl)-4-hydroxy-1-methyl-5-oxo-2,5-dihydro-1H-pyrrole-3-carboxamide | 1.4 | 365.1 | P |

TABLE 2-continued

| Ex. # | Structure | Name | RT (min) | [M + 1]+ | LC/MS Methods |
|---|---|---|---|---|---|
| 67 | 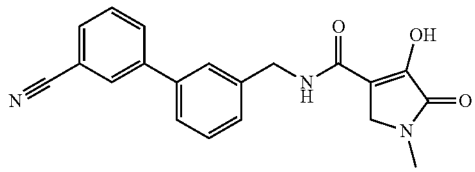 [SMILES: CN1CC(C(=O)NCc2cccc(-c3cccc(C#N)c3)c2)=C(O)C1=O] | N-((3'-cyanobiphenyl-3-yl)methyl)-4-hydroxy-1-methyl-5-oxo-2,5-dihydro-1H-pyrrole-3-carboxamide | 1.33 | 348.1 | P |
| 68 | 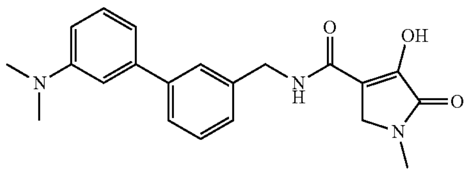 [SMILES: CN1CC(C(=O)NCc2cccc(-c3cccc(N(C)C)c3)c2)=C(O)C1=O] | N-((3'-(dimethylamino)biphenyl-3-yl)methyl)-4-hydroxy-1-methyl-5-oxo-2,5-dihydro-1H-pyrrole-3-carboxamide | 1.56 | 366.1 | P |
| 69 | 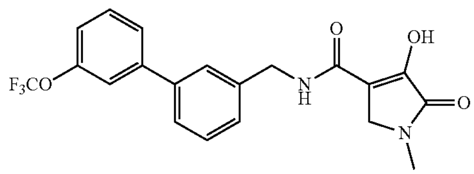 [SMILES: CN1CC(C(=O)NCc2cccc(-c3cccc(OC(F)(F)F)c3)c2)=C(O)C1=O] | 4-hydroxy-1-methyl-5-oxo-N-((3'-(trifluoromethoxy)biphenyl-3-yl)methyl)-2,5-dihydro-1H-pyrrole-3-carboxamide | 1.79 | 407.0 | P |
| 70 | 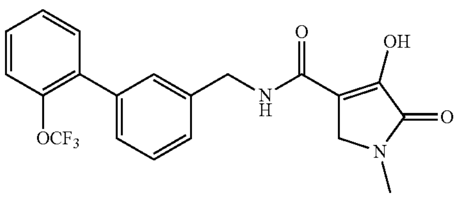 [SMILES: CN1CC(C(=O)NCc2cccc(-c3ccccc3OC(F)(F)F)c2)=C(O)C1=O] | 4-hydroxy-1-methyl-5-oxo-N-((2'-(trifluoromethoxy)biphenyl-3-yl)methyl)-2,5-dihydro-1H-pyrrole-3-carboxamide | 1.73 | 407.1 | P |
| 71 | 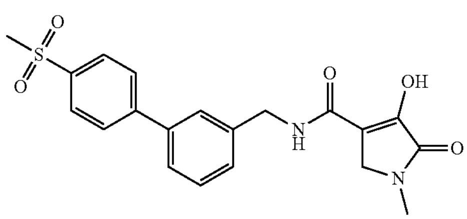 [SMILES: CN1CC(C(=O)NCc2cccc(-c3ccc(S(C)(=O)=O)cc3)c2)=C(O)C1=O] | 4-hydroxy-1-methyl-N-((4'-(methylsulfonyl)biphenyl-3-yl)methyl)-5-oxo-2,5-dihydro-1H-pyrrole-3-carboxamide | 1.14 | 401.1 | P |
| 72 | 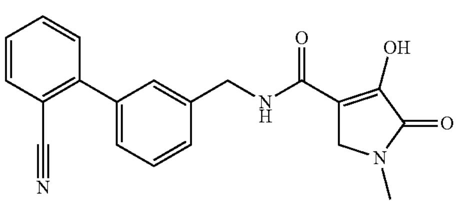 [SMILES: CN1CC(C(=O)NCc2cccc(-c3ccccc3C#N)c2)=C(O)C1=O] | N-((2'-cyanobiphenyl-3-yl)methyl)-4-hydroxy-1-methyl-5-oxo-2,5-dihydro-1H-pyrrole-3-carboxamide | 1.32 | 348.1 | P |
| 73 | 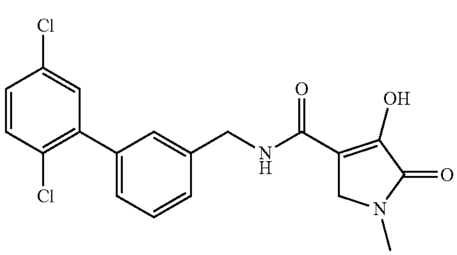 [SMILES: CN1CC(C(=O)NCc2cccc(-c3cc(Cl)ccc3Cl)c2)=C(O)C1=O] | N-((2',5'-dichlorobiphenyl-3-yl)methyl)-4-hydroxy-1-methyl-5-oxo-2,5-dihydro-1H-pyrrole-3-carboxamide | 1.75 | 391.0 | P |

TABLE 2-continued

| Ex. # | Structure | Name | RT (min) | [M + 1]+ | LC/MS Methods |
|---|---|---|---|---|---|
| 74 | 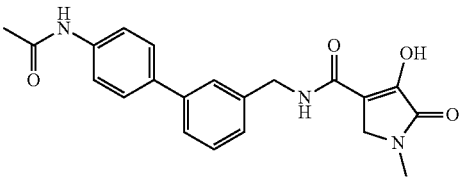 [SMILES: CC(=O)Nc1ccc(-c2cccc(CNC(=O)C3=C(O)C(=O)N(C)C3)c2)cc1] | N-((4'-acetamidobiphenyl-3-yl)methyl)-4-hydroxy-1-methyl-5-oxo-2,5-dihydro-1H-pyrrole-3-carboxamide | 1.2 | 380.1 | P |
| 75 | 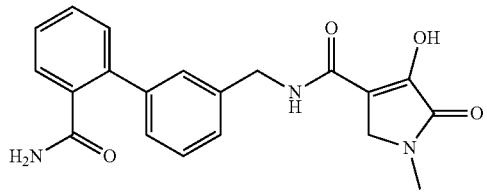 [SMILES: CN1CC(C(=O)NCc2cccc(-c3ccccc3C(N)=O)c2)=C(O)C1=O] | N-((2'-carbamoylbiphenyl-3-yl)methyl)-4-hydroxy-1-methyl-5-oxo-2,5-dihydro-1H-pyrrole-3-carboxamide | 1.01 | 366.1 | P |
| 76 | 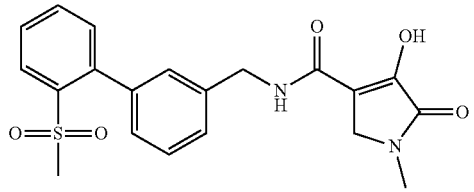 [SMILES: CN1CC(C(=O)NCc2cccc(-c3ccccc3S(C)(=O)=O)c2)=C(O)C1=O] | 4-hydroxy-1-methyl-N-((2,-(methylsulfonyl)biphenyl-3-yl)methyl)-5-oxo-2,5-dihydro-1H-pyrrole-3-carboxamide | 1.18 | 401.0 | P |
| 77 | 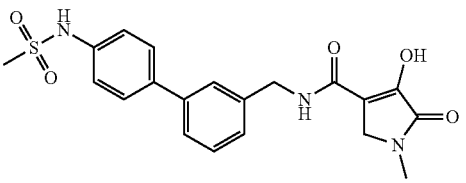 [SMILES: CN1CC(C(=O)NCc2cccc(-c3ccc(NS(C)(=O)=O)cc3)c2)=C(O)C1=O] | 4-hydroxy-1-methyl-N-((4'-(methylsulfonamido)biphenyl-3-yl)methyl)-5-oxo-2,5-dihydro-1H-pyrrole-3-carboxamide | 1.26 | 416.1 | P |
| 78 | 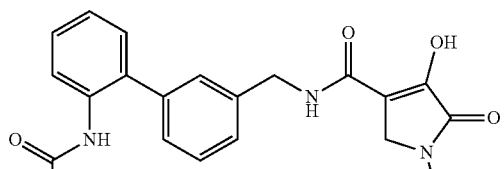 | N-((2'-acetamidobiphenyl-3-yl)methyl)-4-hydroxy-1-methyl-5-oxo-2,5-dihydro-1H-pyrrole-3-carboxamide | 1.08 | 380.1 | P |
| 79 | 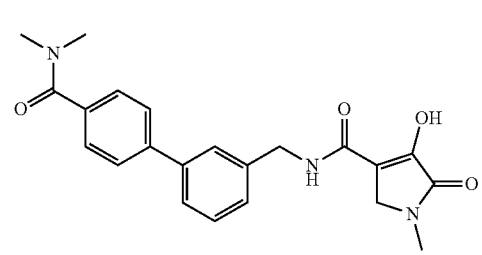 [SMILES: CN(C)C(=O)c1ccc(-c2cccc(CNC(=O)C3=C(O)C(=O)N(C)C3)c2)cc1] | N-((4'-(dimethylcarbamoyl)biphenyl-3-yl)methyl)-4-hydroxy-1-methyl-5-oxo-2,5-dihydro-1H-pyrrole-3-carboxamide | 1.19 | 394.1 | P |
| 80 | 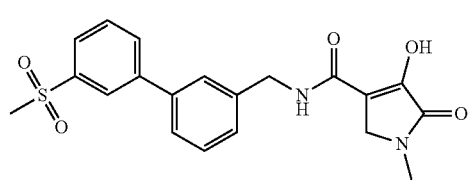 [SMILES: CN1CC(C(=O)NCc2cccc(-c3cccc(S(C)(=O)=O)c3)c2)=C(O)C1=O] | 4-hydroxy-1-methyl-N-((3'-(methylsulfonyl)biphenyl-3-yl)methyl)-5-oxo-2,5-dihydro-1H-pyrrole-3-carboxamide | 1.17 | 401.1 | P |

TABLE 2-continued

| Ex. # | Structure | Name | RT (min) | [M + 1]+ | LC/MS Methods |
|---|---|---|---|---|---|
| 81 | 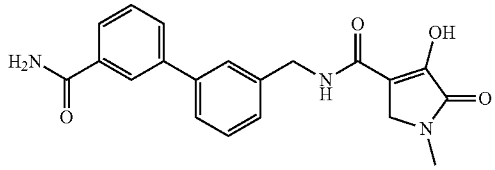 [SMILES: CN1CC(C(=O)NCc2cccc(-c3cccc(C(N)=O)c3)c2)=C(O)C1=O] | N-((3'-carbamoylbiphenyl-3-yl)methyl)-4-hydroxy-1-methyl-5-oxo-2,5-dihydro-1H-pyrrole-3-carboxamide | 1.05 | 366.1 | P |
| 82 | 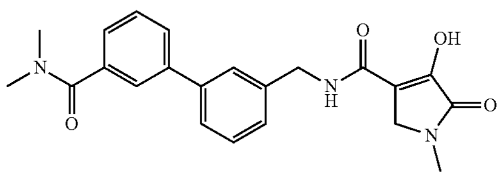 [SMILES: CN(C)C(=O)c1cccc(-c2cccc(CNC(=O)C3=C(O)C(=O)N(C)C3)c2)c1] | N-((3'-(dimethylcarbamoyl)biphenyl-3-yl)methyl)-4-hydroxy-1-methyl-5-oxo-2,5-dihydro-1H-pyrrole-3-carboxamide | 1.18 | 394.1 | P |
| 83 | 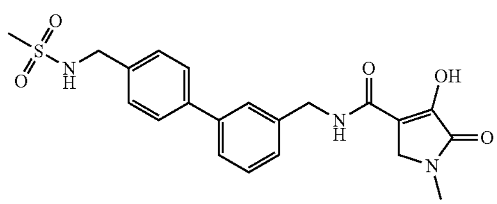 [SMILES: CN1CC(C(=O)NCc2cccc(-c3ccc(CNS(C)(=O)=O)cc3)c2)=C(O)C1=O] | 4-hydroxy-1-methyl-N-((4'-(methylsulfonamidomethyl)biphenyl-3-yl)methyl)-5-oxo-2,5-dihydro-1H-pyrrole-3-carboxamide | 1.21 | 430.1 | P |
| 84 | 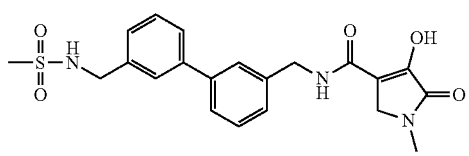 [SMILES: CN1CC(C(=O)NCc2cccc(-c3cccc(CNS(C)(=O)=O)c3)c2)=C(O)C1=O] | 4-hydroxy-1-methyl-N-((3'-(methylsulfonamidomethyl)biphenyl-3-yl)methyl)-5-oxo-2,5-dihydro-1H-pyrrole-3-carboxamide | 1.23 | 430.1 | P |
| 85 | 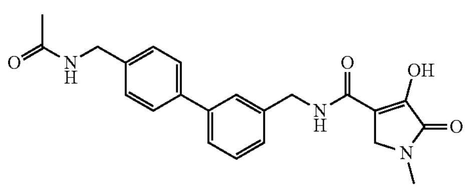 [SMILES: CC(=O)NCc1ccc(-c2cccc(CNC(=O)C3=C(O)C(=O)N(C)C3)c2)cc1] | N-((4'-(acetamidomethyl)biphenyl-3-yl)methyl)-4-hydroxy-1-methyl-5-oxo-2,5-dihydro-1H-pyrrole-3-carboxamide | 1.08 | 394.1 | P |
| 86 | 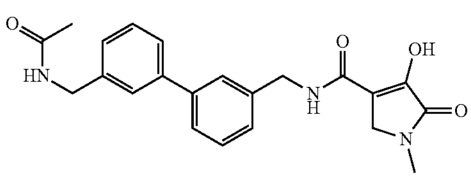 [SMILES: CC(=O)NCc1cccc(-c2cccc(CNC(=O)C3=C(O)C(=O)N(C)C3)c2)c1] | N-((3'-(acetamidomethyl)biphenyl-3-yl)methyl)-4-hydroxy-1-methyl-5-oxo-2,5-dihydro-1H-pyrrole-3-carboxamide | 1.12 | 394.1 | P |
| 87 | 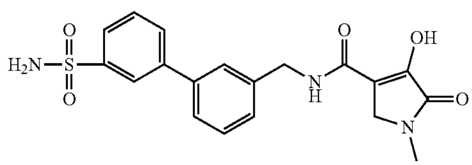 [SMILES: CN1CC(C(=O)NCc2cccc(-c3cccc(S(N)(=O)=O)c3)c2)=C(O)C1=O] | 4-hydroxy-1-methyl-5-oxo-N-((3'-sulfamoylbiphenyl-3-yl)methyl)-2,5-dihydro-1H-pyrrole-3-carboxamide | 1.05 | 402.0 | P |
| 88 | 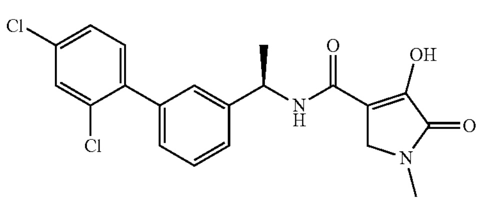 [SMILES: C[C@@H](NC(=O)C1=C(O)C(=O)N(C)C1)c1cccc(-c2ccc(Cl)cc2Cl)c1] | (R)-N-(1-(2',4'-dichlorobiphenyl-3-yl)ethyl)-4-hydroxy-1-methyl-5-oxo-2,5-dihydro-1H-pyrrole-3-carboxamide | 1.77 | 405.2 | P |

TABLE 2-continued

| Ex. # | Structure | Name | RT (min) | [M + 1]+ | LC/ MS Methods |
|---|---|---|---|---|---|
| 89 | 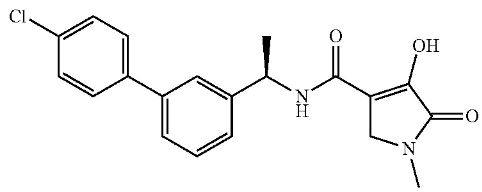 [SMILES: C[C@@H](NC(=O)C1=C(O)C(=O)N(C)C1)c1cccc(-c2ccc(Cl)cc2)c1] | (R)-N-(1-(4'-chlorobiphenyl-3-yl)ethyl)-4-hydroxy-1-methyl-5-oxo-2,5-dihydro-1H-pyrrole-3-carboxamide | 1.63 | 371.2 | P |
| 90 | 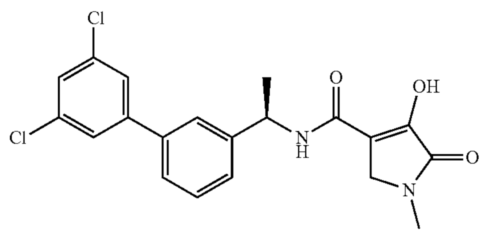 [SMILES: C[C@@H](NC(=O)C1=C(O)C(=O)N(C)C1)c1cccc(-c2cc(Cl)cc(Cl)c2)c1] | (R)-N-(1-(3',5'-dichlorobiphenyl-3-yl)ethyl)-4-hydroxy-1-methyl-5-oxo-2,5-dihydro-1H-pyrrole-3-carboxamide | 1.84 | 405.2 | P |
| 91 | 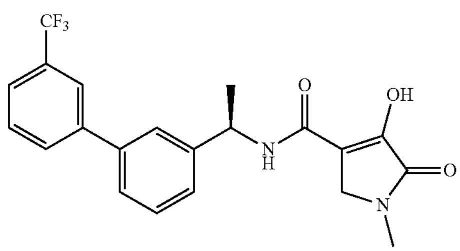 [SMILES: C[C@@H](NC(=O)C1=C(O)C(=O)N(C)C1)c1cccc(-c2cccc(C(F)(F)F)c2)c1] | (R)-4-hydroxy-1-methyl-5-oxo-N-(1-(3'-(trifluoromethyl)biphenyl-3-yl)ethyl)-2,5-dihydro-1H-pyrrole-3-carboxamide | 1.72 | 405.2 | P |
| 92 | 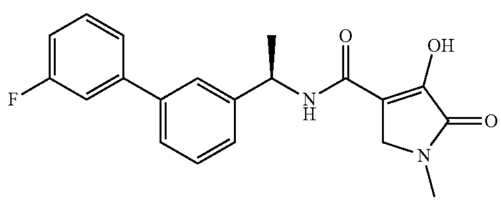 [SMILES: C[C@@H](NC(=O)C1=C(O)C(=O)N(C)C1)c1cccc(-c2cccc(F)c2)c1] | (R)-N-(1-(3'-fluorobiphenyl-3-yl)ethyl)-4-hydroxy-1-methyl-5-oxo-2,5-dihydro-1H-pyrrole-3-carboxamide | 1.47 | 355.2 | P |
| 93 | 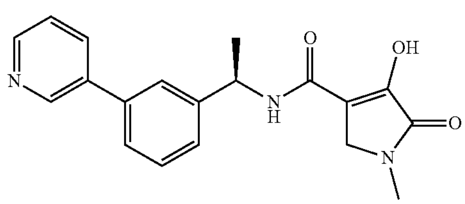 [SMILES: C[C@@H](NC(=O)C1=C(O)C(=O)N(C)C1)c1cccc(-c2cccnc2)c1] | (R)-4-hydroxy-1-methyl-5-oxo-N-(1-(3-(pyridin-3-yl)phenyl)ethyl)-2,5-dihydro-1H-pyrrole-3-carboxamide | 0.99 | 338.2 | P |
| 94 | 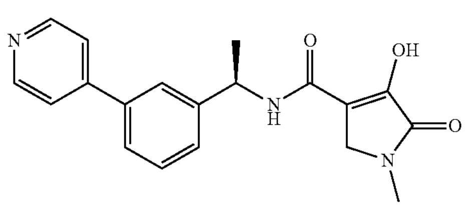 [SMILES: C[C@@H](NC(=O)C1=C(O)C(=O)N(C)C1)c1cccc(-c2ccncc2)c1] | (R)-4-hydroxy-1-methyl-5-oxo-N-(1-(3-(pyridin-4-yl)phenyl)ethyl)-2,5-dihydro-1H-pyrrole-3-carboxamide | 0.98 | 338.2 | P |
| 95 | 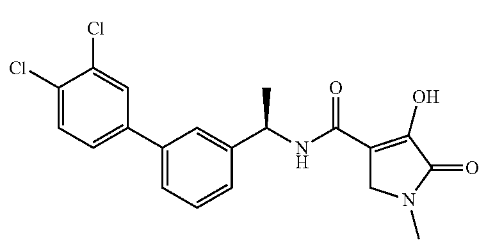 [SMILES: C[C@@H](NC(=O)C1=C(O)C(=O)N(C)C1)c1cccc(-c2ccc(Cl)c(Cl)c2)c1] | (R)-N-(1-(3',4'-dichlorobiphenyl-3-yl)ethyl)-4-hydroxy-1-methyl-5-oxo-2,5-dihydro-1H-pyrrole-3-carboxamide | 1.8 | 405.2 | P |

TABLE 2-continued

| Ex. # | Structure | Name | RT (min) | [M + 1]+ | LC/MS Methods |
|---|---|---|---|---|---|
| 96 | 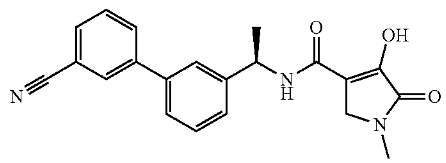 [SMILES: C[C@@H](NC(=O)C1=C(O)C(=O)N(C)C1)c1cccc(-c2cccc(C#N)c2)c1] | (R)-N-(1-(3'-cyanobiphenyl-3-yl)ethyl)-4-hydroxy-1-methyl-5-oxo-2,5-dihydro-1H-pyrrole-3-carboxamide | 1.35 | 362.2 | P |
| 97 | 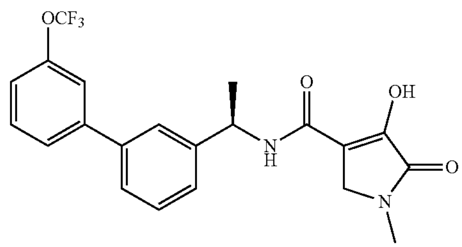 [SMILES: C[C@@H](NC(=O)C1=C(O)C(=O)N(C)C1)c1cccc(-c2cccc(OC(F)(F)F)c2)c1] | (R)-4-hydroxy-1-methyl-5-oxo-N-(1-(3'-(trifluoromethoxy)biphenyl-3-yl)ethyl)-2,5-dihydro-1H-pyrrole-3-carboxamide | 1.79 | 421.2 | P |
| 98 | 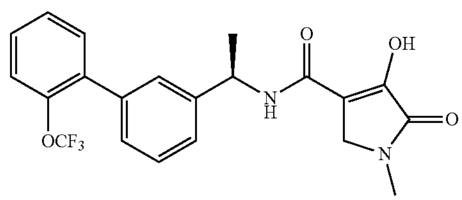 [SMILES: C[C@@H](NC(=O)C1=C(O)C(=O)N(C)C1)c1cccc(-c2ccccc2OC(F)(F)F)c1] | (R)-4-hydroxy-1-methyl-5-oxo-N-(1-(2'-(trifluoromethoxy)biphenyl-3-yl)ethyl)-2,5-dihydro-1H-pyrrole-3-carboxamide | 1.72 | 421.2 | P |
| 99 | 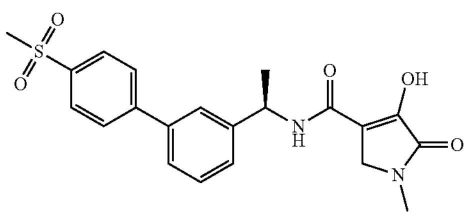 [SMILES: C[C@@H](NC(=O)C1=C(O)C(=O)N(C)C1)c1cccc(-c2ccc(S(C)(=O)=O)cc2)c1] | (R)-4-hydroxy-1-methyl-N-(1-(4'-(methylsulfonyl)biphenyl-3-yl)ethyl)-5-oxo-2,5-dihydro-1H-pyrrole-3-carboxamide | 1.14 | 415.2 | P |
| 100 | 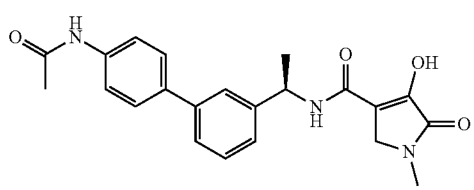 [SMILES: CC(=O)Nc1ccc(-c2cccc([C@@H](C)NC(=O)C3=C(O)C(=O)N(C)C3)c2)cc1] | (R)-N-(1-(4'-acetamidobiphenyl-3-yl)ethyl)-4-hydroxy-1-methyl-5-oxo-2,5-dihydro-1H-pyrrole-3-carboxamide | 1.09 | 394.2 | P |
| 101 | 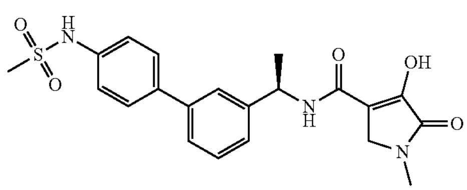 [SMILES: C[C@@H](NC(=O)C1=C(O)C(=O)N(C)C1)c1cccc(-c2ccc(NS(C)(=O)=O)cc2)c1] | (R)-4-hydroxy-1-methyl-N-(1-(4'-(methylsulfonamido)biphenyl-3-yl)ethyl)-5-oxo-2,5-dihydro-1H-pyrrole-3-carboxamide | 1.15 | 430.2 | P |
| 102 | 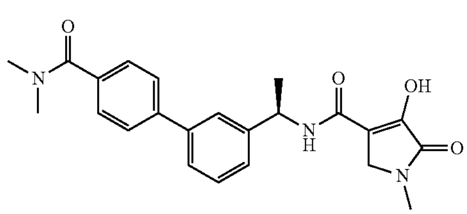 [SMILES: C[C@@H](NC(=O)C1=C(O)C(=O)N(C)C1)c1cccc(-c2ccc(C(=O)N(C)C)cc2)c1] | (R)-N-(1-(4'-(dimethylcarbamoyl)biphenyl-3-yl)ethyl)-4-hydroxy-1-methyl-5-oxo-2,5-dihydro-1H-pyrrole-3-carboxamide | 1.6 | 408.3 | P |

TABLE 2-continued

| Ex. # | Structure | Name | RT (min) | [M + 1]+ | LC/MS Methods |
|---|---|---|---|---|---|
| 103 | 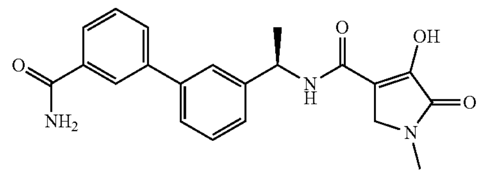 [SMILES: C[C@@H](NC(=O)C1=C(O)C(=O)N(C)C1)c1cccc(-c2cccc(C(N)=O)c2)c1] | (R)-N-(1-(3'-carbamoylbiphenyl-3-yl)ethyl)-4-hydroxy-1-methyl-5-oxo-2,5-dihydro-1H-pyrrole-3-carboxamide | 1.03 | 380.2 | P |
| 104 | 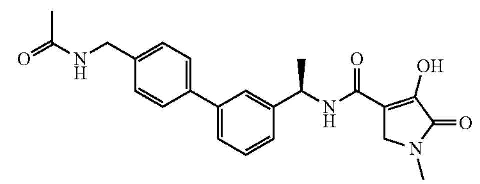 [SMILES: CC(=O)NCc1ccc(-c2cccc([C@@H](C)NC(=O)C3=C(O)C(=O)N(C)C3)c2)cc1] | (R)-N-(1-(4'-(acetamidomethyl)biphenyl-3-yl)ethyl)-4-hydroxy-1-methyl-5-oxo-2,5-dihydro-1H-pyrrole-3-carboxamide | 1.51 | 408.3 | P |
| 105 | 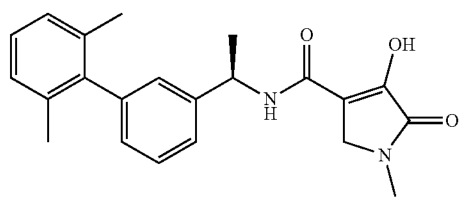 [SMILES: Cc1cccc(C)c1-c1cccc([C@@H](C)NC(=O)C2=C(O)C(=O)N(C)C2)c1] | (R)-N-(1-(2',6'-dimethylbiphenyl-3-yl)ethyl)-4-hydroxy-1-methyl-5-oxo-2,5-dihydro-1H-pyrrole-3-carboxamide | 2.35 | 365.2 | P |
| 106 | 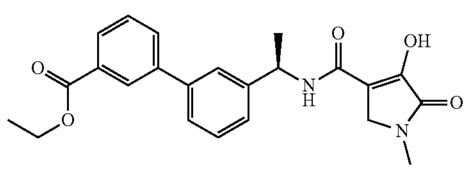 [SMILES: CCOC(=O)c1cccc(-c2cccc([C@@H](C)NC(=O)C3=C(O)C(=O)N(C)C3)c2)c1] | (R)-ethyl 3'-(1-(4-hydroxy-1-methyl-5-oxo-2,5-dihydro-1H-pyrrole-3-carboxamido)ethyl)biphenyl-3-carboxylate | 2.25 | 409.2 | P |
| 107 | 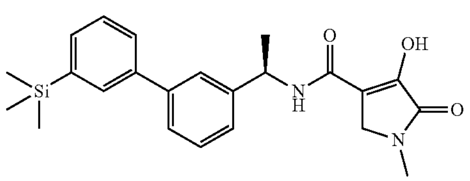 [SMILES: C[C@@H](NC(=O)C1=C(O)C(=O)N(C)C1)c1cccc(-c2cccc([Si](C)(C)C)c2)c1] | (R)-4-hydroxy-1-methyl-5-oxo-N-(1-(3'-(trimethylsilyl)biphenyl-3-yl)ethyl)-2,5-dihydro-1H-pyrrole-3-carboxamide | 2.93 | 409.3 | P |
| 108 | 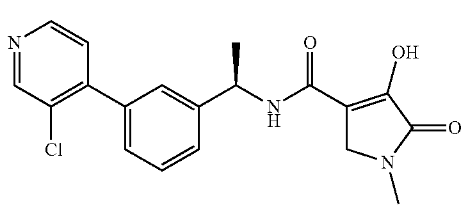 [SMILES: C[C@@H](NC(=O)C1=C(O)C(=O)N(C)C1)c1cccc(-c2ccncc2Cl)c1] | (R)-N-(1-(3-(3-chloropyridin-4-yl)phenyl)ethyl)-4-hydroxy-1-methyl-5-oxo-2,5-dihydro-1H-pyrrole-3-carboxamide | 1.62 | 372.1 | P |
| 109 | 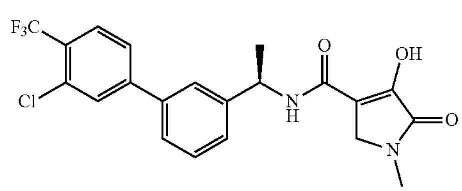 [SMILES: C[C@@H](NC(=O)C1=C(O)C(=O)N(C)C1)c1cccc(-c2ccc(C(F)(F)F)c(Cl)c2)c1] | (R)-N-(1-(3'-chloro-4'-(trifluoromethyl)biphenyl-3-yl)ethyl)-4-hydroxy-1-methyl-5-oxo-2,5-dihydro-1H-pyrrole-3-carboxamide | 2.64 | 439.2 | P |
| 110 | 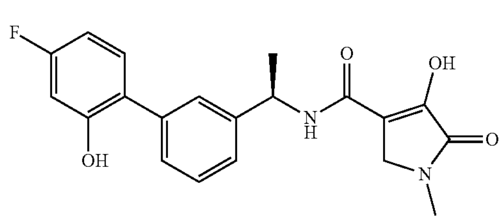 [SMILES: C[C@@H](NC(=O)C1=C(O)C(=O)N(C)C1)c1cccc(-c2ccc(F)cc2O)c1] | (R)-N-(1-(4'-fluoro-2'-hydroxybiphenyl-3-yl)ethyl)-4-hydroxy-1-methyl-5-oxo-2,5-dihydro-1H-pyrrole-3-carboxamide | 1.85 | 371.2 | P |

TABLE 2-continued

| Ex. # | Structure | Name | RT (min) | [M + 1]+ | LC/MS Methods |
|---|---|---|---|---|---|
| 111 | 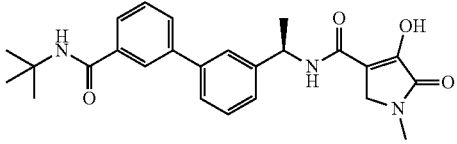 [SMILES: C[C@@H](NC(=O)C1=C(O)C(=O)N(C)C1)c1cccc(-c2cccc(C(=O)NC(C)(C)C)c2)c1] | (R)-N-(1-(3'-(tert-butylcarbamoyl)biphenyl-3-yl)ethyl)-4-hydroxy-1-methyl-5-oxo-2,5-dihydro-1H-pyrrole-3-carboxamide | 2.1 | 436.3 | P |
| 112 | 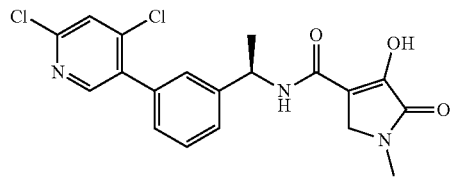 [SMILES: C[C@@H](NC(=O)C1=C(O)C(=O)N(C)C1)c1cccc(-c2cnc(Cl)cc2Cl)c1] | (R)-N-(1-(3-(4,6-dichloropyridin-3-yl)phenyl)ethyl)-4-hydroxy-1-methyl-5-oxo-2,5-dihydro-1H-pyrrole-3-carboxamide | 2.03 | 406.1 | P |
| 113 | 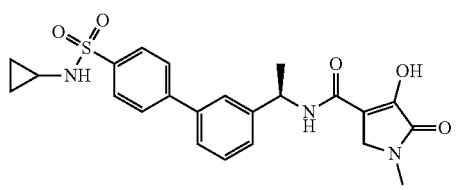 [SMILES: C[C@@H](NC(=O)C1=C(O)C(=O)N(C)C1)c1cccc(-c2ccc(S(=O)(=O)NC3CC3)cc2)c1] | (R)-N-(1-(4'-(N-cyclopropylsulfamoyl)biphenyl-3-yl)ethyl)-4-hydroxy-1-methyl-5-oxo-2,5-dihydro-1H-pyrrole-3-carboxamide | 1.87 | 456.2 | P |
| 114 | 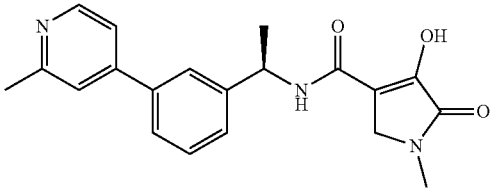 [SMILES: Cc1cc(-c2cccc([C@@H](C)NC(=O)C3=C(O)C(=O)N(C)C3)c2)ccn1] | (R)-4-hydroxy-1-methyl-N-(1-(3-(2-methylpyridin-4-yl)phenyl)ethyl)-5-oxo-2,5-dihydro-1H-pyrrole-3-carboxamide | 1.49 | 352.2 | P |
| 115 | 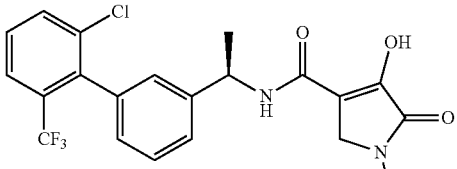 | (R)-N-(1-(2'-chloro-6'-(trifluoromethyl)biphenyl-3-yl)ethyl)-4-hydroxy-1-methyl-5-oxo-2,5-dihydro-1H-pyrrole-3-carboxamide | 2.62 | 439.2 | P |
| 116 | 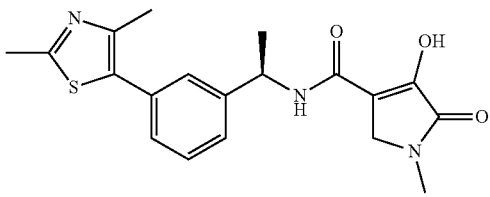 [SMILES: Cc1nc(C)c(-c2cccc([C@@H](C)NC(=O)C3=C(O)C(=O)N(C)C3)c2)s1] | (R)-N-(1-(3-(2,4-dimethylthiazol-5-yl)phenyl)ethyl)-4-hydroxy-1-methyl-5-oxo-2,5-dihydro-1H-pyrrole-3-carboxamide | 1.65 | 372.2 | P |
| 117 | 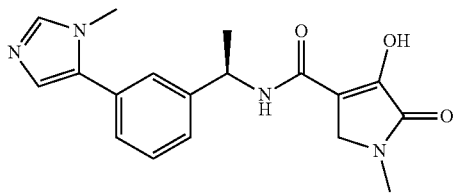 [SMILES: C[C@@H](NC(=O)C1=C(O)C(=O)N(C)C1)c1cccc(-c2cncn2C)c1] | (R)-4-hydroxy-1-methyl-N-(1-(3-(1-methyl-1H-imidazol-5-yl)phenyl)ethyl)-5-oxo-2,5-dihydro-1H-pyrrole-3-carboxamide | 1.54 | 341.0 | P |
| 118 | 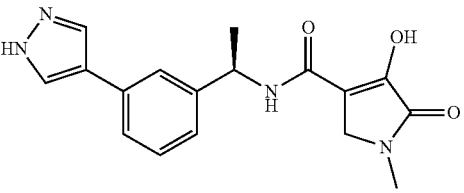 [SMILES: C[C@@H](NC(=O)C1=C(O)C(=O)N(C)C1)c1cccc(-c2cn[nH]c2)c1] | (R)-N-(1-(3-(1H-pyrazol-4-yl)phenyl)ethyl)-4-hydroxy-1-methyl-5-oxo-2,5-dihydro-1H-pyrrole-3-carboxamide | 1.19 | 327.2 | P |

TABLE 2-continued

| Ex. # | Structure | Name | RT (min) | [M + 1]+ | LC/MS Methods |
|---|---|---|---|---|---|
| 119 | 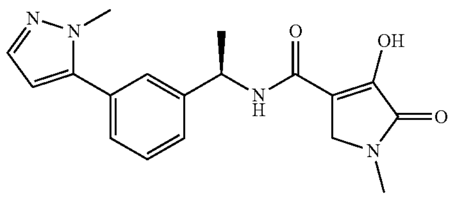 [SMILES: C[C@@H](NC(=O)C1=C(O)C(=O)N(C)C1)c1cccc(-c2ccnn2C)c1] | (R)-4-hydroxy-1-methyl-N-(1-(3-(1-methyl-1H-pyrazol-5-yl)phenyl)ethyl)-5-oxo-2,5-dihydro-1H-pyrrole-3-carboxamide | 1.38 | 341.2 | P |
| 120 | 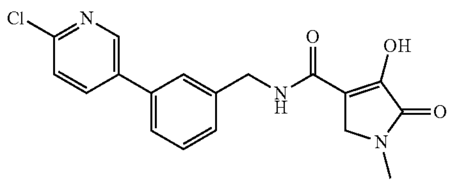 [SMILES: CN1CC(C(=O)NCc2cccc(-c3ccc(Cl)nc3)c2)=C(O)C1=O] | N-(3-(6-chloropyridin-3-yl)benzyl)-4-hydroxy-1H-methyl-5-oxo-2,5-dihydro-1H-pyrrole-3-carboxamide | 2.55 | 358.1 | Q |
| 121 | 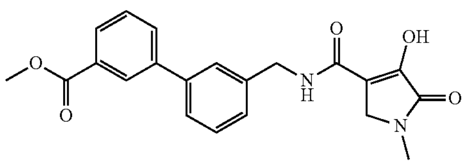 [SMILES: COC(=O)c1cccc(-c2cccc(CNC(=O)C3=C(O)C(=O)N(C)C3)c2)c1] | methyl 3'-((4-hydroxy-1-methyl-5-oxo-2,5-dihydro-1H-pyrrole-3-carboxamido)methyl)biphenyl-3-carboxylate | 2.91 | 381.2 | Q |
| 122 | 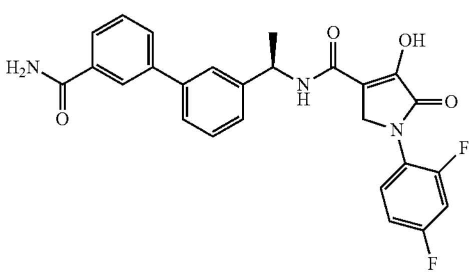 [SMILES: C[C@@H](NC(=O)C1=C(O)C(=O)N(c2ccc(F)cc2F)C1)c1cccc(-c2cccc(C(N)=O)c2)c1] | (R)-N-(1-(3'-carbamoylbiphenyl-3-yl)ethyl)-1-(2,4-difluorophenyl)-4-hydroxy-5-oxo-2,5-dihydro-1H-pyrrole-3-carboxamide | 1.95 | 478.1 | L |
| 123 | 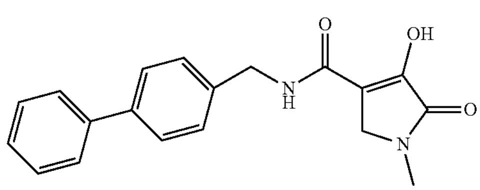 [SMILES: CN1CC(C(=O)NCc2ccc(-c3ccccc3)cc2)=C(O)C1=O] | N-(biphenyl-4-ylmethyl)-4-hydroxy-1-methyl-5-oxo-2,5-dihydro-1H-pyrrole-3-carboxamide | 2.91 | 323.0 | N |
| 124 | 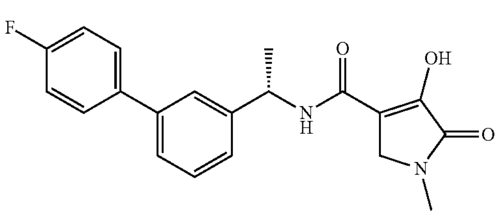 [SMILES: C[C@H](NC(=O)C1=C(O)C(=O)N(C)C1)c1cccc(-c2ccc(F)cc2)c1] | (S)-N-(1-(4'-fluorobiphenyl-3-yl)ethyl)-4-hydroxy-1-methyl-5-oxo-2,5-dihydro-1H-pyrrole-3-carboxamide | 1.54 | 355.2 | M |
| 125 | 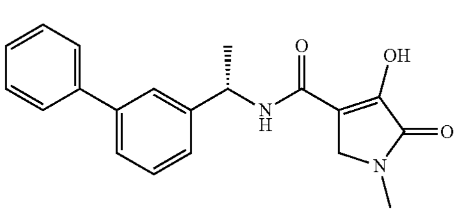 [SMILES: C[C@H](NC(=O)C1=C(O)C(=O)N(C)C1)c1cccc(-c2ccccc2)c1] | (S)-N-(1-(biphenyl-3-yl)ethyl)-4-hydroxy-1-methyl-5-oxo-2,5-dihydro-1H-pyrrole-3-carboxamide | 1.50 | 337.2 | M |

TABLE 2-continued

| Ex. # | Structure | Name | RT (min) | [M + 1]+ | LC/MS Methods |
|---|---|---|---|---|---|
| 126 | 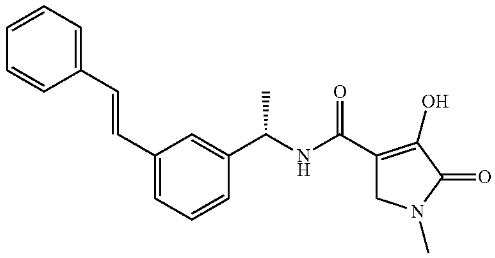 [SMILES: C[C@H](NC(=O)C1=C(O)C(=O)N(C)C1)c1cccc(/C=C/c2ccccc2)c1] | (E)-4-hydroxy-1-methyl-5-oxo-N-(3-styrylbenzyl)-2,5-dihydro-1H-pyrrole-3-carboxamide | 1.61 | 349.0 | P |
| 128 | 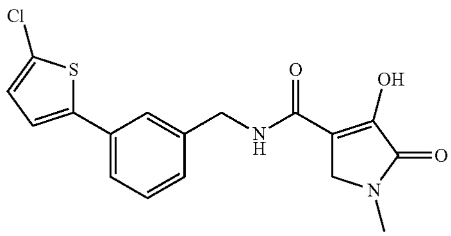 [SMILES: CN1CC(C(=O)NCc2cccc(-c3ccc(Cl)s3)c2)=C(O)C1=O] | N-(3-(5-chlorothiophen-2-yl)benzyl)-4-hydroxy-1-methyl-5-oxo-2,5-dihydro-1H-pyrrole-3-carboxamide | 1.62 | 363.0 | P |
| 129 | 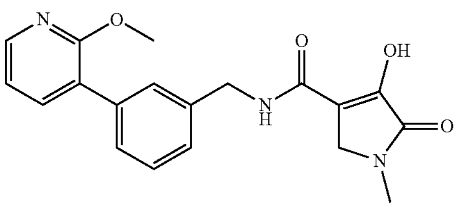 [SMILES: COc1ncccc1-c1cccc(CNC(=O)C2=C(O)C(=O)N(C)C2)c1] | 4-hydroxy-N-(3-(2-methoxypyridin-3-yl)benzyl)-1-methyl-5-oxo-2,5-dihydro-1H-pyrrole-3-carboxamide | 1.19 | 354.0 | P |
| 130 | 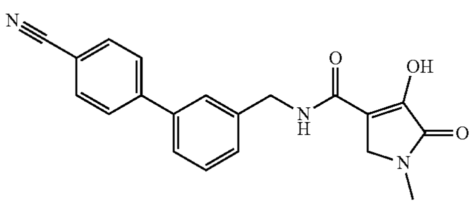 [SMILES: CN1CC(C(=O)NCc2cccc(-c3ccc(C#N)cc3)c2)=C(O)C1=O] | N-((4'-cyanobiphenyl-3-yl)methyl)-4-hydroxy-1-methyl-5-oxo-2,5-dihydro-1H-pyrrole-3-carboxamide | 1.28 | 348.0 | P |
| 131 | 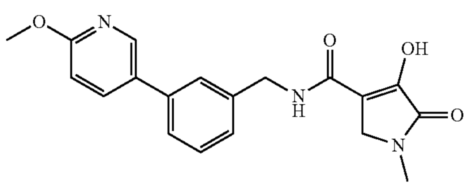 [SMILES: COc1ccc(-c2cccc(CNC(=O)C3=C(O)C(=O)N(C)C3)c2)cn1] | 4-hydroxy-N-(3-(6-methoxypyridin-3-yl)benzyl)-1-methyl-5-oxo-2,5-dihydro-1H-pyrrole-3-carboxamide | 1.23 | 354.1 | P |
| 135 | 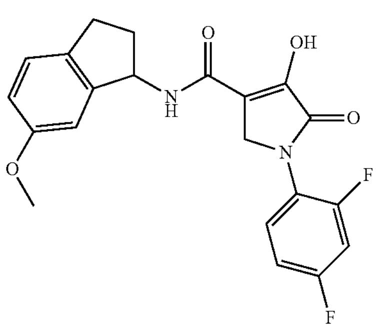 [SMILES: COc1ccc2c(c1)C(NC(=O)C1=C(O)C(=O)N(c3ccc(F)cc3F)C1)CC2] | 1-(2,4-difluorophenyl)-4-hydroxy-N-(6-methoxy-2,3-dihydro-1H-inden-1-yl)-5-oxo-2,5-dihydro-1H-pyrrole-3-carboxamide | 1.58 | 401.2 | M |

TABLE 2-continued

| Ex. # | Structure | Name | RT (min) | [M + 1]+ | LC/ MS Methods |
|---|---|---|---|---|---|
| 136 | 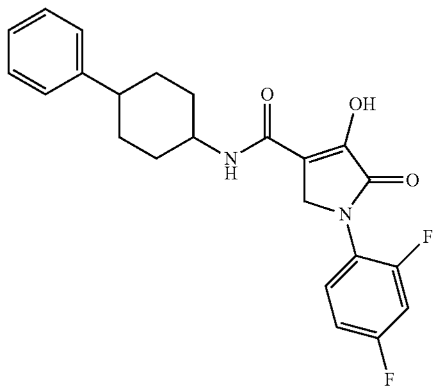 [SMILES: O=C(NC1CCC(c2ccccc2)CC1)C1=C(O)C(=O)N(c2ccc(F)cc2F)C1] | 1-(2,4-difluorophenyl)-4-hydroxy-5-oxo-N-cis-(4-phenylcyclohexyl)-2,5-dihydro-1H-pyrrole-3-carboxamide | 2.22 | 413.0 | L |
| 137 | 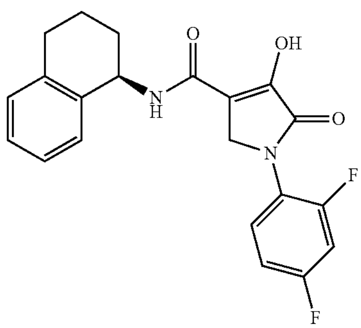 [SMILES: O=C(N[C@@H]1CCCc2ccccc21)C1=C(O)C(=O)N(c2ccc(F)cc2F)C1] | (R)-1-(2,4-difluorophenyl)-4-hydroxy-5-oxo-N-(1,2,3,4-tetrahydronaphthalen-1-yl)-2,5-dihydro-1H-pyrrole-3-carboxamide | 2.07 | 385.3 | L |
| 138 | 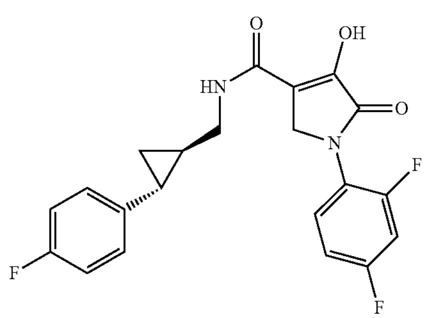 [SMILES: O=C(NC[C@@H]1C[C@H]1c1ccc(F)cc1)C1=C(O)C(=O)N(c2ccc(F)cc2F)C1] | 1-(2,4-difluorophenyl)-N-(((1R,2R)-2-(4-fluorophenyl)cyclopropyl)methyl)-4-hydroxy-5-oxo-2,5-dihydro-1H-pyrrole-3-carboxamide | 2.05 | 403.3 | O |
| 139 | 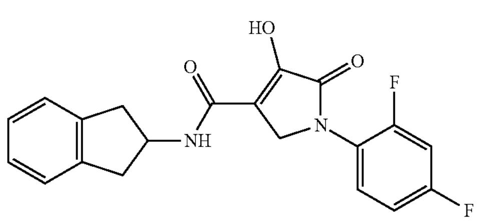 [SMILES: O=C(NC1Cc2ccccc2C1)C1=C(O)C(=O)N(c2ccc(F)cc2F)C1] | 1-(2,4-difluorophenyl)-N-(2,3-dihydro-1H-inden-2-yl)-4-hydroxy-5-oxo-2,5-dihydro-1H-pyrrole-3-carboxamide | 1.56 | 371.1 | O |
| 140 | 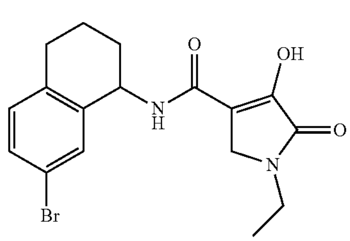 [SMILES: CCN1CC(C(=O)NC2CCCc3ccc(Br)cc32)=C(O)C1=O] | N-(7-bromo-1,2,3,4-tetrahydronaphthalen-1-yl)-1-ethyl-4-hydroxy-5-oxo-2,5-dihydro-1H-pyrrole-3-carboxamide | 2.03 | 379.3 | O |

TABLE 2-continued

| Ex. # | Name | RT (min) | [M + 1]+ | LC/MS Methods |
|---|---|---|---|---|
| 141 | N-(7-bromo-1,2,3,4-tetrahydronaphthalen-1-yl)-1-(2,4-difluorophenyl)-4-hydroxy-5-oxo-2,5-dihydro-1H-pyrrole-3-carboxamide | 2.24 | 463.3 | O |
| 142 | (R)-1-ethyl-4-hydroxy-5-oxo-N-(6-(trifluoromethyl)-2,3-dihydro-1H-inden-1-yl)-2,5-dihydro-1H-pyrrole-3-carboxamide | 2.00 | 355.2 | O |
| 143 | (R)-N-(4-bromo-2,3-dihydro-1H-inden-1-yl)-1-ethyl-4-hydroxy-5-oxo-2,5-dihydro-1H-pyrrole-3-carboxamide | 2.01 | 389.4 | O |
| 144 | (R)-N-(5-bromo-2,3-dihydro-1H-inden-1-yl)-1-ethyl-4-hydroxy-5-oxo-2,5-dihydro-1H-pyrrole-3-carboxamide | 1.99 | 389.4 | O |
| 145 | (R)-N-(6-bromo-2,3-dihydro-1H-inden-1-yl)-1-ethyl-4-hydroxy-5-oxo-2,5-dihydro-1H-pyrrole-3-carboxamide | 1.99 | 389.3 | O |
| 146 | 1-ethyl-4-hydroxy-5-oxo-N-((1R)-4-phenyl-1,2,3,4-tetrahydronaphthalen-1-yl)-2,5-dihydro-1H-pyrrole-3-carboxamide | 1.57 | 377.2 | M |

TABLE 2-continued

| Ex. # | Structure | Name | RT (min) | [M + 1]+ | LC/MS Methods |
|---|---|---|---|---|---|
| 147 | 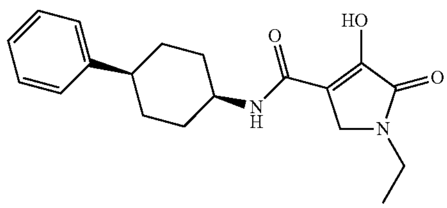 [SMILES: CCN1CC(C(=O)N[C@H]2CC[C@@H](c3ccccc3)CC2)=C(O)C1=O] | 1-ethyl-4-hydroxy-5-oxo-N-(cis-4-phenylcyclohexyl)-2,5-dihydro-1H-pyrrole-3-carboxamide | 1.52 | 329.3 | M |
| 148 | 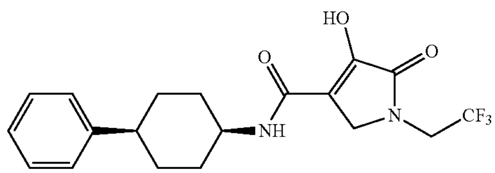 [SMILES: O=C(N[C@H]1CC[C@@H](c2ccccc2)CC1)C1=C(O)C(=O)N(CC(F)(F)F)C1] | 4-hydroxy-5-oxo-N-(cis-4-phenylcyclohexyl)-1-(2,2,2-trifluoroethyl)-2,5-dihydro-1H-pyrrole-3-carboxamide | 2.12 | 383.3 | L |
| 149 | 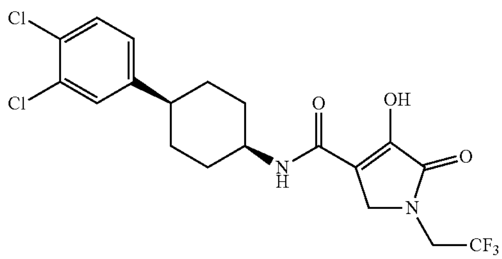 [SMILES: O=C(N[C@H]1CC[C@@H](c2ccc(Cl)c(Cl)c2)CC1)C1=C(O)C(=O)N(CC(F)(F)F)C1] | N-(cis-4-(3,4-dichlorophenyl)cyclohexyl)-4-hydroxy-5-oxo-1-(2,2,2-trifluoroethyl)-2,5-dihydro-1H-pyrrole-3-carboxamide | 2.29 | 451.2 | L |
| 150 | 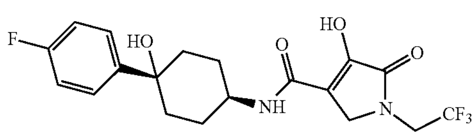 [SMILES: O=C(N[C@H]1CC[C@@](O)(c2ccc(F)cc2)CC1)C1=C(O)C(=O)N(CC(F)(F)F)C1] | N-(trans-4-(4-fluorophenyl)-4-hydroxycyclohexyl)-4-hydroxy-5-oxo-1-(2,2,2-trifluoroethyl)-2,5-dihydro-1H-pyrrole-3-carboxamide | 1.84 | 416.9 | L |
| 151 | 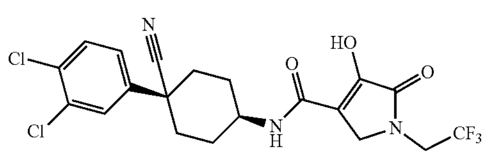 [SMILES: N#C[C@]1(c2ccc(Cl)c(Cl)c2)CC[C@@H](NC(=O)C2=C(O)C(=O)N(CC(F)(F)F)C2)CC1] | N-(trans-4-cyano-4-(3,4-dichlorophenyl)cyclohexyl)-4-hydroxy-5-oxo-1-(2,2,2-trifluoroethyl)-2,5-dihydro-1H-pyrrole-3-carboxamide | 2.17 | 476.2 | L |
| 152 | 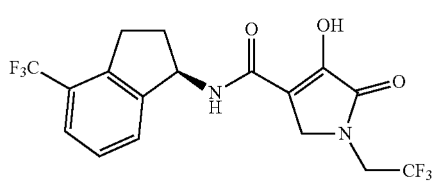 [SMILES: O=C(N[C@@H]1CCc2c1cccc2C(F)(F)F)C1=C(O)C(=O)N(CC(F)(F)F)C1] | (R)-4-hydroxy-5-oxo-1-(2,2,2-trifluoroethyl)-N-(4-(trifluoromethyl)-2,3-dihydro-1H-inden-1-yl)-2,5-dihydro-1H-pyrrole-3-carboxamide | 2.07 | 409.2 | L |
| 153 | 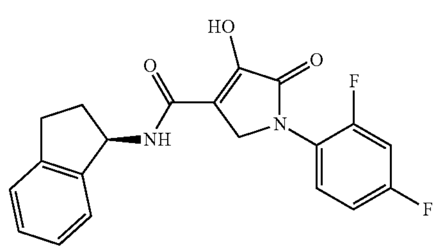 [SMILES: O=C(N[C@@H]1CCc2ccccc21)C1=C(O)C(=O)N(c2ccc(F)cc2F)C1] | (R)-1-(2,4-difluorophenyl)-N-(2,3-dihydro-1H-inden-1-yl)-4-hydroxy-5-oxo-2,5-dihydro-1H-pyrrole-3-carboxamide | 2.01 | 371.3 | L |
| 157 | 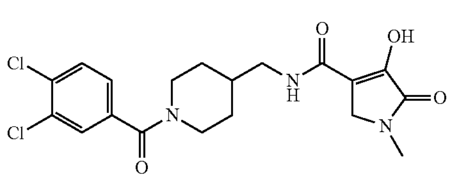 [SMILES: CN1CC(C(=O)NCC2CCN(C(=O)c3ccc(Cl)c(Cl)c3)CC2)=C(O)C1=O] | N-((1-(3,4-dichlorobenzoyl)piperidin-4-yl)methyl)-4-hydroxy-1-methyl-5-oxo-2,5-dihydro-1H-pyrrole-3-carboxamide | 0.81 | 426.1 | D |

TABLE 2-continued

| Ex. # | Structure | Name | RT (min) | [M + 1]+ | LC/MS Methods |
|---|---|---|---|---|---|
| 158 | 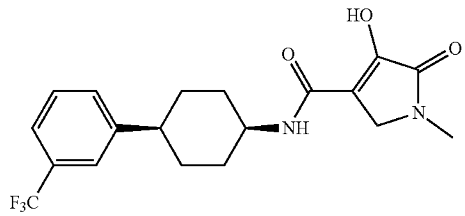 [SMILES: CN1CC(C(=O)N[C@H]2CC[C@@H](c3cccc(C(F)(F)F)c3)CC2)=C(O)C1=O] | 4-hydroxy-1-methyl-5-oxo-N-(cis-4-(3-(trifluoromethoxy)phenyl)cyclohexyl)-2,5-dihydro-1H-pyrrole-3-carboxamide | 0.97 | 399.1 | D |
| 159 | 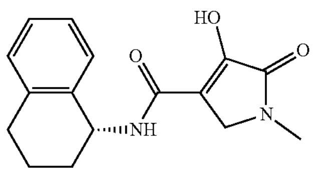 [SMILES: CN1CC(C(=O)N[C@@H]2CCCc3ccccc32)=C(O)C1=O] | (R)-4-hydroxy-1-methyl-5-oxo-N-(1,2,3,4-tetrahydronaphthalen-1-yl)-2,5-dihydro-1H-pyrrole-3-carboxamide | 0.81 | No ionization | D |
| 160 | 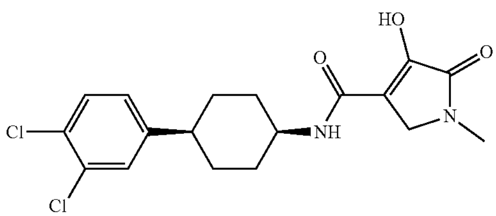 [SMILES: CN1CC(C(=O)N[C@H]2CC[C@@H](c3ccc(Cl)c(Cl)c3)CC2)=C(O)C1=O] | N-(cis-4-(3,4-dichlorophenyl)cyclohexyl)-4-hydroxy-1-methyl-5-oxo-2,5-dihydro-1H-pyrrole-3-carboxamide | 0.99 | 383.0 | D |
| 161 | 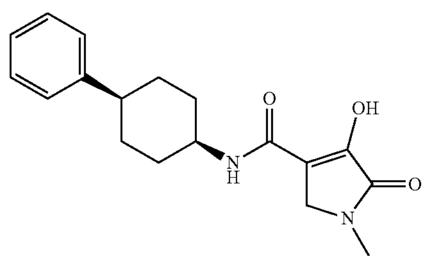 [SMILES: CN1CC(C(=O)N[C@H]2CC[C@@H](c3ccccc3)CC2)=C(O)C1=O] | 4-hydroxy-1-methyl-5-oxo-N-(cis-4-phenylcyclohexyl)-2,5-dihydro-1H-pyrrole-3-carboxamide | 0.88 | 315.3 | D |
| 162 | 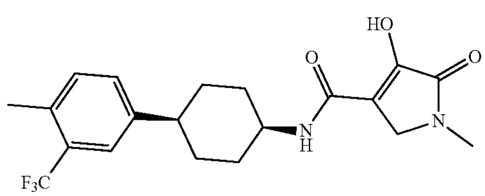 [SMILES: Cc1ccc([C@H]2CC[C@@H](NC(=O)C3=C(O)C(=O)N(C)C3)CC2)cc1C(F)(F)F] | 4-hydroxy-1-methyl-N-(cis-4-(4-methyl-3-(trifluoromethyl)phenyl)cyclohexyl)-5-oxo-2,5-dihydro-1H-pyrrole-3-carboxamide | 1.00 | 397.1 | D |
| 163 | 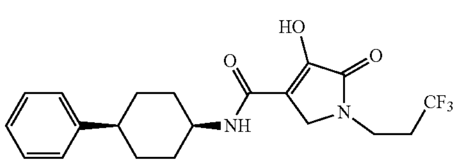 [SMILES: O=C(N[C@H]1CC[C@@H](c2ccccc2)CC1)C1=C(O)C(=O)N(CCC(F)(F)F)C1] | 4-hydroxy-5-oxo-N-(cis-4-phenylcyclohexyl)-1-(3,3,3-trifluoropropyl)-2,5-dihydro-1H-pyrrole-3-carboxamide | 0.97 | 397.2 | D |
| 164 | 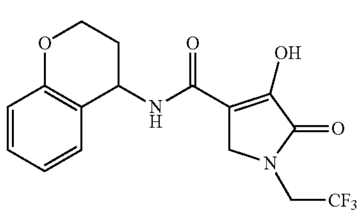 [SMILES: O=C(NC1CCOc2ccccc21)C1=C(O)C(=O)N(CC(F)(F)F)C1] | N-(chroman-4-yl)-4-hydroxy-5-oxo-1-(2,2,2-trifluoroethyl)-2,5-dihydro-1H-pyrrole-3-carboxamide | 1.81 | 357.0 | D |

TABLE 2-continued

| Ex. # | Structure | Name | RT (min) | [M + 1]+ | LC/MS Methods |
|---|---|---|---|---|---|
| 165 | 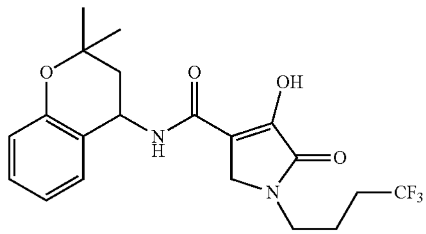 [SMILES: CC1(C)CC(NC(=O)C2=C(O)C(=O)N(CCCC(F)(F)F)C2)c2ccccc2O1] | N-(2,2-dimethylchroman-4-yl)-4-hydroxy-5-oxo-1-(4,4,4-trifluorobutyl)-2,5-dihydro-1H-pyrrole-3-carboxamide | 1.97 | 413.0 | D |
| 166 | 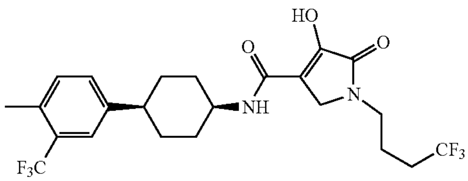 [SMILES: Cc1ccc([C@H]2CC[C@@H](NC(=O)C3=C(O)C(=O)N(CCCC(F)(F)F)C3)CC2)cc1C(F)(F)F] | 4-hydroxy-N-(cis-4-(4-methyl-3-(trifluoromethyl)phenyl)cyclohexyl)-5-oxo-1-(4,4,4-trifluorobutyl)-2,5-dihydro-1H-pyrrole-3-carboxamide | 1.09 | 493.1 | D |
| 167 | 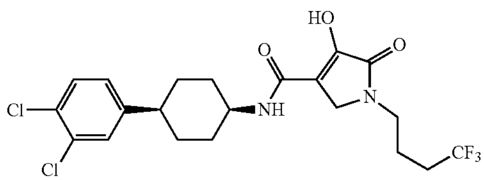 [SMILES: O=C(N[C@H]1CC[C@@H](c2ccc(Cl)c(Cl)c2)CC1)C1=C(O)C(=O)N(CCCC(F)(F)F)C1] | N-(cis-4-(3,4-dichlorophenyl)cyclohexyl)-4-hydroxy-5-oxo-1-(4,4,4-trifluorobutyl)-2,5-dihydro-1H-pyrrole-3-carboxamide | 1.09 | 479 | D |
| 168 | 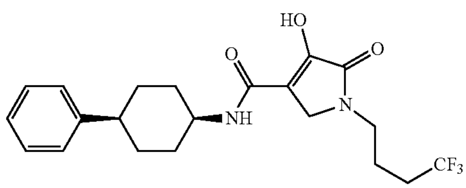 [SMILES: O=C(N[C@H]1CC[C@@H](c2ccccc2)CC1)C1=C(O)C(=O)N(CCCC(F)(F)F)C1] | 4-hydroxy-5-oxo-N-(cis-4-phenylcyclohexyl)-1-(4,4,4-trifluorobutyl)-2,5-dihydro-1H-pyrrole-3-carboxamide | 1 | 411.1 | D |
| 169 | 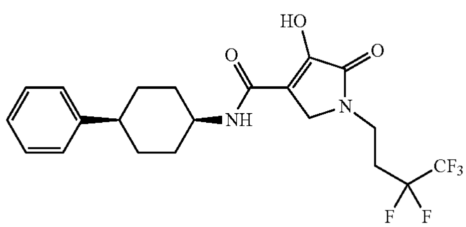 [SMILES: O=C(N[C@H]1CC[C@@H](c2ccccc2)CC1)C1=C(O)C(=O)N(CCC(F)(F)C(F)(F)F)C1] | 4-hydroxy-5-oxo-1-(2,2,3,3,3-pentafluoropropyl)-N-(cis-4-phenylcyclohexyl)-2,5-dihydro-1H-pyrrole-3-carboxamide | 1.02 | 433 | D |
| 170 | 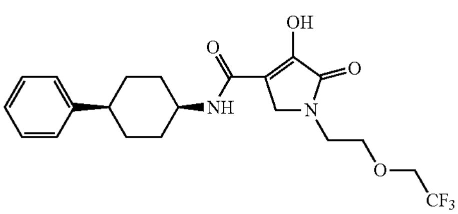 [SMILES: O=C(N[C@H]1CC[C@@H](c2ccccc2)CC1)C1=C(O)C(=O)N(CCOCC(F)(F)F)C1] | 4-hydroxy-5-oxo-N-(cis-4-phenylcyclohexyl)-1-(2-(2,2,2-trifluoroethoxy)ethyl)-2,5-dihydro-1H-pyrrole-3-carboxamide | 0.98 | 427.1 | D |
| 171 | 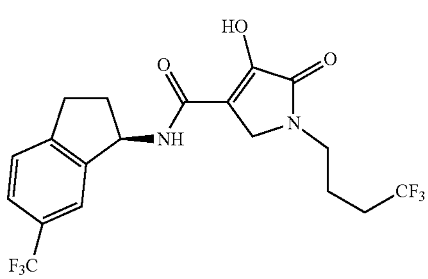 [SMILES: O=C(N[C@@H]1CCc2ccc(C(F)(F)F)cc21)C1=C(O)C(=O)N(CCCC(F)(F)F)C1] | (R)-4-hydroxy-5-oxo-1-(4,4,4-trifluorobutyl)-N-(6-(trifluoromethyl)-2,3-dihydro-1H-inden-1-yl)-2,5-dihydro-1H-pyrrole-3-carboxamide | 0.98 | No ionization | D |

TABLE 2-continued

| Ex. # | Structure | Name | RT (min) | [M + 1]+ | LC/MS Methods |
|---|---|---|---|---|---|
| 172 | 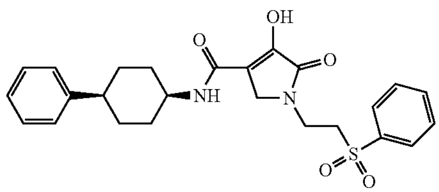 [SMILES: O=C(N[C@H]1CC[C@@H](c2ccccc2)CC1)C1=C(O)C(=O)N(CCS(=O)(=O)c2ccccc2)C1] | 4-hydroxy-5-oxo-N-(cis-4-phenylcyclohexyl)-1-(2-(phenylsulfonyl)ethyl)-2,5-dihydro-1H-pyrrole-3-carboxamide | 0.98 | No ionization | D |
| 173 | Isomer A | 4-hydroxy-1-methyl-5-oxo-N-((3S)-3-phenylcyclopentyl)-2,5-dihydro-1H-pyrrole-3-carboxamide (Isomer A) | 0.84 | 301.1 | D |
| 174 | Isomer B | 4-hydroxy-1-methyl-5-oxo-N-((3S)-3-phenylcyclopentyl)-2,5-dihydro-1H-pyrrole-3-carboxamide (Isomer B) | 0.84 | 301.1 | D |
| 175 | Isomer A | N-((3S)-3-(3,4-dichlorophenyl)cyclopentyl)-4-hydroxy-1-methyl-5-oxo-2,5-dihydro-1H-pyrrole-3-carboxamide (Isomer A) | 0.97 | 369.0 | D |
| 176 | Isomer B | N-((3S)-3-(3,4-dichlorophenyl)cyclopentyl)-4-hydroxy-1-methyl-5-oxo-2,5-dihydro-1H-pyrrole-3-carboxamide (Isomer B) | 0.97 | 369.0 | D |
| 179 | 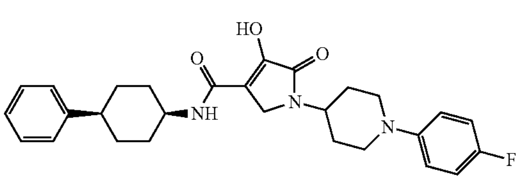 [SMILES: O=C(N[C@H]1CC[C@@H](c2ccccc2)CC1)C1=C(O)C(=O)N(C2CCN(c3ccc(F)cc3)CC2)C1] | 1-(1-(4-fluorophenyl)piperidin-4-yl)-4-hydroxy-5-oxo-N-(cis-4-phenylcyclohexyl)-2,5-dihydro-1H-pyrrole-3-carboxamide | 1.88 | 478.2 | D |
| 180 | 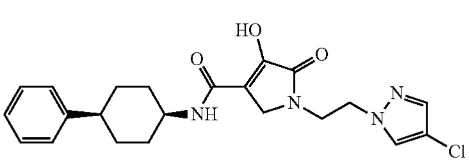 [SMILES: O=C(N[C@H]1CC[C@@H](c2ccccc2)CC1)C1=C(O)C(=O)N(CCn2cc(Cl)cn2)C1] | 1-(2-(4-chloro-1H-pyrazol-1-yl)ethyl)-4-hydroxy-5-oxo-N-(cis-4-phenylcyclohexyl)-2,5-dihydro-1H-pyrrole-3-carboxamide | 2.12 | 429.1 | D |

TABLE 2-continued

| Ex. # | Name | RT (min) | [M + 1]+ | LC/MS Methods |
|---|---|---|---|---|
| 181 | 4-hydroxy-1-(3-(methylamino)propyl)-5-oxo-N-(cis-4-phenylcyclohexyl)-2,5-dihydro-1H-pyrrole-3-carboxamide | 1.70 | 372.1 | D |
| 182 | 4-hydroxy-1-(3-(isopropylamino)propyl)-5-oxo-N-(cis-4-phenylcyclohexyl)-2,5-dihydro-1H-pyrrole-3-carboxamide | 1.73 | 400.1 | D |
| 183 | 4-hydroxy-5-oxo-N-((1s,4R)-4-phenylcyclohexyl)-1-((S)-6-(trifluoromethyl)-2,3-dihydro-1H-inden-1-yl)-2,5-dihydro-1H-pyrrole-3-carboxamide | 2.34 | 485.1 | D |
| 184 | 4-hydroxy-5-oxo-N-(cis-4-phenylcyclohexyl)-1-((R)-6-(trifluoromethyl)-2,3-dihydro-1H-inden-1-yl)-2,5-dihydro-1H-pyrrole-3-carboxamide | 2.34 | 485.1 | D |
| 185 | 4-hydroxy-5-oxo-1-(3-(2-oxopyrrolidin-1-yl)propyl)-N-(cis-4-phenylcyclohexyl)-2,5-dihydro-1H-pyrrole-3-carboxamide | 1.15 | 426.3 | W |
| 186 | ethyl 4-(3-hydroxy-2-oxo-4-(cis-4-phenylcyclohexylcarbamoyl)-2,5-dihydro-1H-pyrrol-1-yl)piperidine-1-carboxylate | 1.37 | 456.3 | W |
| 187 | 1-(1-benzylpiperidin-4-yl)-4-hydroxy-5-oxo-N-cis-4-phenylcyclohexyl)-2,5-dihydro-1H-pyrrole-3-carboxamide | 1.3 | 474.3 | W |

TABLE 2-continued

| Ex. # | Structure | Name | RT (min) | [M + 1]+ | LC/MS Methods |
|---|---|---|---|---|---|
| 188 | 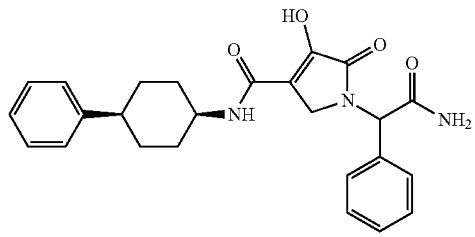 [SMILES: NC(=O)C(c1ccccc1)N1CC(C(=O)N[C@H]2CC[C@@H](c3ccccc3)CC2)=C(O)C1=O] | 1-(2-amino-2-oxo-1-phenylethyl)-4-hydroxy-5-oxo-N-(cis-4-phenylcyclohexyl)-2,5-dihydro-1H-pyrrole-3-carboxamide | 1.26 | 434.3 | W |
| 189 | 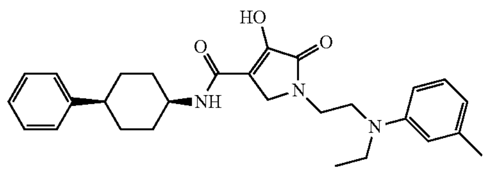 [SMILES: CCN(CCN1CC(C(=O)N[C@H]2CC[C@@H](c3ccccc3)CC2)=C(O)C1=O)c1cccc(C)c1] | 1-(2-(ethyl(m-tolyl)amino)ethyl)-4-hydroxy-5-oxo-N-(cis-4-phenylcyclohexyl)-2,5-dihydro-1H-pyrrole-3-carboxamide | 1.82 | 462.4 | W |
| 190 | 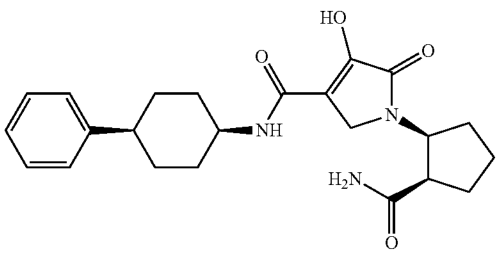 [SMILES: NC(=O)[C@@H]1CCC[C@@H]1N1CC(C(=O)N[C@H]2CC[C@@H](c3ccccc3)CC2)=C(O)C1=O] | 1-((1S,2R)-2-carbamoylcyclopentyl)-4-hydroxy-5-oxo-N-((1s,4R)-4-phenylcyclohexyl)-2,5-dihydro-1H-pyrrole-3-carboxamide | 1.11 | 412.3 | W |
| 191 | 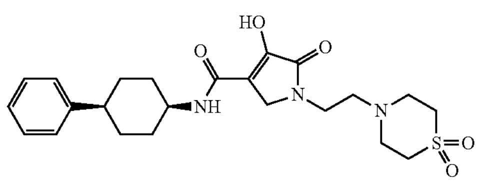 [SMILES: O=C(N[C@H]1CC[C@@H](c2ccccc2)CC1)C1=C(O)C(=O)N(CCN2CCS(=O)(=O)CC2)C1] | 1-(2-(1,1-dioxidothiomorpholin-4-yl)ethyl)-4-hydroxy-5-oxo-N-(cis-4-phenylcyclohexyl)-2,5-dihydro-1H-pyrrole-3-carboxamide | 1.11 | 462.3 | W |
| 192 | 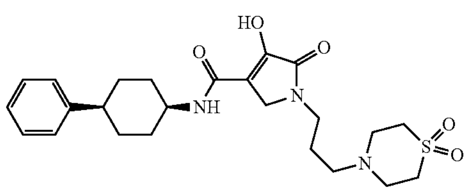 [SMILES: O=C(N[C@H]1CC[C@@H](c2ccccc2)CC1)C1=C(O)C(=O)N(CCCN2CCS(=O)(=O)CC2)C1] | 1-(3-(1,1-dioxidothiomorpholin-4-yl)propyl)-4-hydroxy-5-oxo-N-(cis-4-phenylcyclohexyl)-2,5-dihydro-1H-pyrrole-3-carboxamide | 1.13 | 476.3 | W |
| 193 | 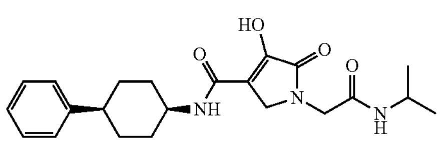 [SMILES: CC(C)NC(=O)CN1CC(C(=O)N[C@H]2CC[C@@H](c3ccccc3)CC2)=C(O)C1=O] | 4-hydroxy-1-(2-(isopropylamino)-2-oxoethyl)-5-oxo-N-(cis-4-phenylcyclohexyl)-2,5-dihydro-1H-pyrrole-3-carboxamide | 1.14 | 400.3 | W |
| 194 | 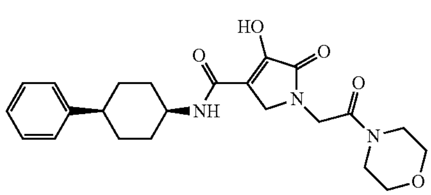 [SMILES: O=C(N[C@H]1CC[C@@H](c2ccccc2)CC1)C1=C(O)C(=O)N(CC(=O)N2CCOCC2)C1] | 4-hydroxy-1-(2-morpholino-2-oxoethyl)-5-oxo-N-(cis-4-phenylcyclohexyl)-2,5-dihydro-1H-pyrrole-3-carboxamide | 1.05 | 428.3 | W |
| 195 | 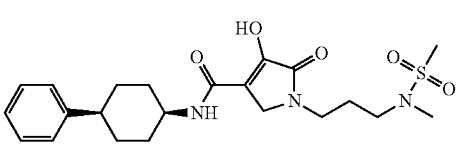 [SMILES: CN(CCCN1CC(C(=O)N[C@H]2CC[C@@H](c3ccccc3)CC2)=C(O)C1=O)S(C)(=O)=O] | 4-hydroxy-1-(3-(N-methylmethylsulfonamido)propyl)-5-oxo-N-(cis-4-phenylcyclohexyl)-2,5-dihydro-1H-pyrrole-3-carboxamide | 1.19 | 450.3 | W |

TABLE 2-continued

| Ex. # | Structure | Name | RT (min) | [M + 1]+ | LC/MS Methods |
|---|---|---|---|---|---|
| 196 | 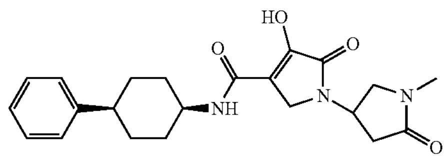 [SMILES: CN1CC(N2CC(C(=O)N[C@H]3CC[C@@H](c4ccccc4)CC3)=C(O)C2=O)CC1=O] | 4-hydroxy-1-(1-methyl-5-oxopyrrolidin-3-yl)-5-oxo-N-(cis-4-phenylcyclohexyl)-2,5-dihydro-1H-pyrrole-3-carboxamide | 1.06 | 398.3 | W |
| 197 | 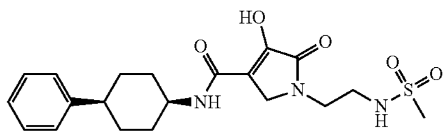 [SMILES: CS(=O)(=O)NCCN1CC(C(=O)N[C@H]2CC[C@@H](c3ccccc3)CC2)=C(O)C1=O] | 4-hydroxy-1-(2-(methylsulfonamido)ethyl)-5-oxo-N-(cis-4-phenylcyclohexyl)-2,5-dihydro-1H-pyrrole-3-carboxamide | 1.08 | 422.3 | W |
| 198 | 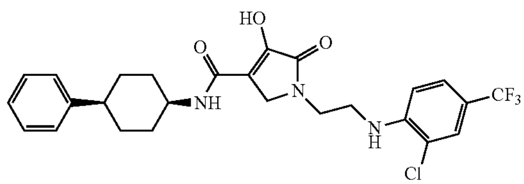 [SMILES: O=C(N[C@H]1CC[C@@H](c2ccccc2)CC1)C1=C(O)C(=O)N(CCNc2ccc(C(F)(F)F)cc2Cl)C1] | 1-(2-(3-chloro-5-(trifluoromethyl)pyridin-2-ylamino)ethyl)-4-hydroxy-5-oxo-N-(cis-4-phenylcyclohexyl)-2,5-dihydro-1H-pyrrole-3-carboxamide | 1.76 | 523.2 | W |
| 199 | 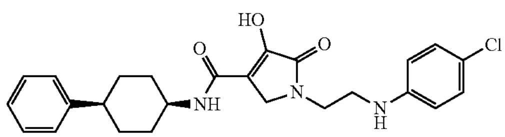 [SMILES: O=C(N[C@H]1CC[C@@H](c2ccccc2)CC1)C1=C(O)C(=O)N(CCNc2ccc(Cl)cc2)C1] | 1-(2-(4-chlorophenylamino)ethyl)-4-hydroxy-5-oxo-N-(cis-4-phenylcyclohexyl)-2,5-dihydro-1H-pyrrole-3-carboxamide | 1.63 | 454.3 | W |
| 200 | 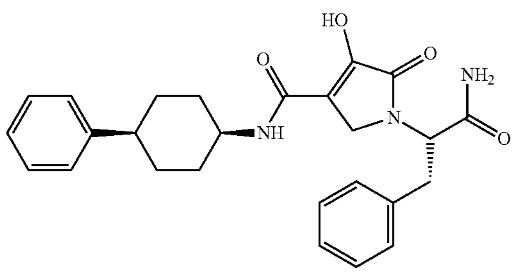 | 1-((S)-1-amino-1-oxo-3-phenylpropan-2-yl)-4-hydroxy-5-oxo-N-((1s,4R)-4-phenylcyclohexyl)-2,5-dihydro-1H-pyrrole-3-carboxamide | 1.32 | 448.3 | W |
| 201 | 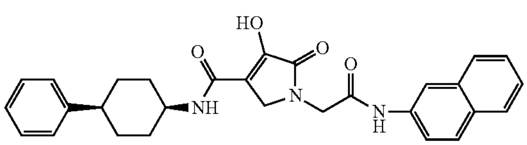 [SMILES: O=C(CN1CC(C(=O)N[C@H]2CC[C@@H](c3ccccc3)CC2)=C(O)C1=O)Nc1ccc2ccccc2c1] | 4-hydroxy-1-(2-(naphthalen-2-ylamino)-2-oxoethyl)-5-oxo-N-(cis-4-phenylcyclohexyl)-2,5-dihydro-1H-pyrrole-3-carboxamide | 1.54 | 484.3 | W |
| 202 | 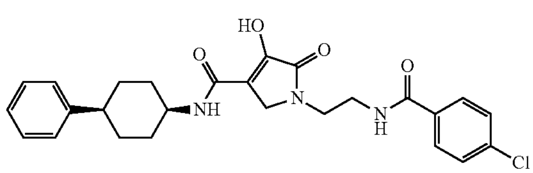 [SMILES: O=C(N[C@H]1CC[C@@H](c2ccccc2)CC1)C1=C(O)C(=O)N(CCNC(=O)c2ccc(Cl)cc2)C1] | 1-(2-(4-chlorobenzamido)ethyl)-4-hydroxy-5-oxo-N-(cis-4-phenylcyclohexyl)-2,5-dihydro-1H-pyrrole-3-carboxamide | 1.47 | 482.3 | W |
| 203 | 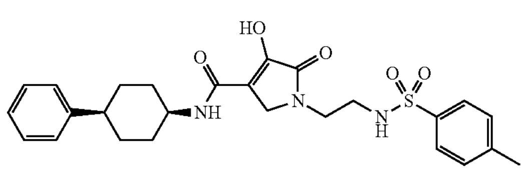 [SMILES: Cc1ccc(S(=O)(=O)NCCN2CC(C(=O)N[C@H]3CC[C@@H](c4ccccc4)CC3)=C(O)C2=O)cc1] | 4-hydroxy-1-(2-(4-methylphenylsulfonamido)ethyl)-5-oxo-N-(cis-4-phenylcyclohexyl)-2,5-dihydro-1H-pyrrole-3-carboxamide | 1.44 | 498.3 | W |

TABLE 2-continued

| Ex. # | Structure | Name | RT (min) | [M + 1]+ | LC/MS Methods |
|---|---|---|---|---|---|
| 204 | 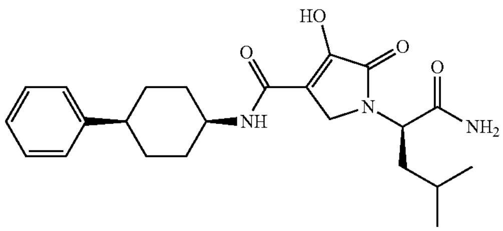 [SMILES: CC(C)C[C@H](C(N)=O)N1CC(C(=O)N[C@H]2CC[C@@H](c3ccccc3)CC2)=C(O)C1=O] | 1-((R)-1-amino-4-methyl-1-oxopentan-2-yl)-4-hydroxy-5-oxo-N-(cis-4-phenylcyclohexyl)-2,5-dihydro-1H-pyrrole-3-carboxamide | 1.32 | 414.3 | W |
| 205 | 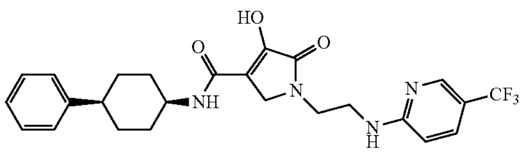 [SMILES: O=C(N[C@H]1CC[C@@H](c2ccccc2)CC1)C1=C(O)C(=O)N(CCNc2ccc(C(F)(F)F)cn2)C1] | 4-hydroxy-5-oxo-N-(cis-4-phenylcyclohexyl)-1-(2-(5-(trifluoromethyl)pyridin-2-ylamino)ethyl)-2,5-dihydro-1H-pyrrole-3-carboxamide | 1.58 | 489.3 | W |
| 206 | 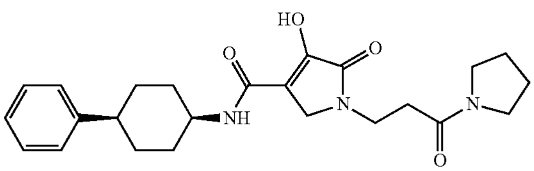 [SMILES: O=C(N[C@H]1CC[C@@H](c2ccccc2)CC1)C1=C(O)C(=O)N(CCC(=O)N2CCCC2)C1] | 4-hydroxy-5-oxo-1-(3-oxo-3-(pyrrolidin-1-yl)propyl)-N-(cis-4-phenylcyclohexyl)-2,5-dihydro-1H-pyrrole-3-carboxamide | 1.19 | 426.3 | W |
| 207 | 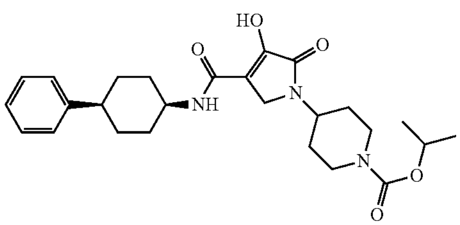 [SMILES: CC(C)OC(=O)N1CCC(N2CC(C(=O)N[C@H]3CC[C@@H](c4ccccc4)CC3)=C(O)C2=O)CC1] | isopropyl 4-(3-hydroxy-2-oxo-4-(cis-4-phenylcyclohexylcarbamoyl)-2,5-dihydro-1H-pyrrol-1-yl)piperidine-1-carboxylate | 1.48 | 470.4 | W |
| 208 | 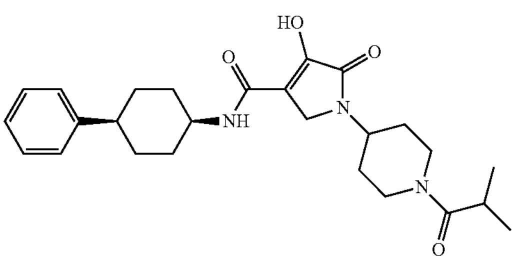 [SMILES: CC(C)C(=O)N1CCC(N2CC(C(=O)N[C@H]3CC[C@@H](c4ccccc4)CC3)=C(O)C2=O)CC1] | 4-hydroxy-1-(1-isobutyrylpiperidin-4-yl)-5-oxo-N-(cis-4-phenylcyclohexyl)-2,5-dihydro-1H-pyrrole-3-carboxamide | 1.29 | 454.4 | W |
| 209 | 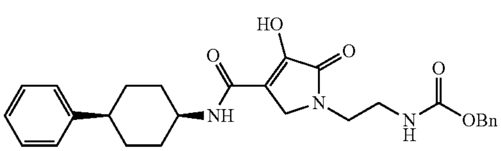 [SMILES: O=C(NCCN1CC(C(=O)N[C@H]2CC[C@@H](c3ccccc3)CC2)=C(O)C1=O)OCc1ccccc1] | benzyl 2-(3-hydroxy-2-oxo-4-(cis-4-phenylcyclohexylcarbamoyl)-2,5-dihydro-1H-pyrrol-1-yl)ethylcarbamate | 1.49 | 478.3 | W |
| 210 | 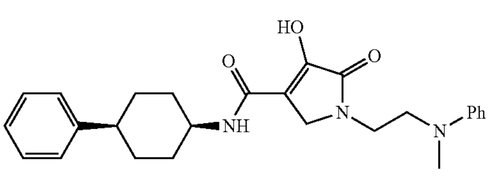 [SMILES: CN(CCN1CC(C(=O)N[C@H]2CC[C@@H](c3ccccc3)CC2)=C(O)C1=O)c1ccccc1] | 4-hydroxy-1-(2-(methyl(phenyl)amino)ethyl)-5-oxo-N-(cis-4-phenylcyclohexyl)-2,5-dihydro-1H-pyrrole-3-carboxamide | 1.84 | 434.1 | W |

TABLE 2-continued

| Ex. # | Structure | Name | RT (min) | [M + 1]+ | LC/MS Methods |
|---|---|---|---|---|---|
| 212 | 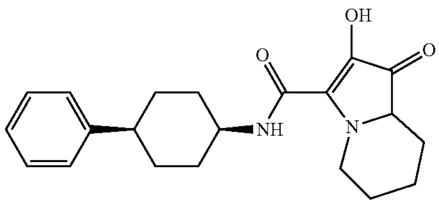 [SMILES: O=C(N[C@H]1CC[C@@H](c2ccccc2)CC1)C1=C(O)C(=O)C2CCCCN12] | 2-Hydroxy-3-oxo-N-(cis-4-phenylcyclohexyl)-3,5,6,7,8,8a-hexahydroindolizine-1-carboxamide | 2.03 | 355.1 | L |
| 213 | 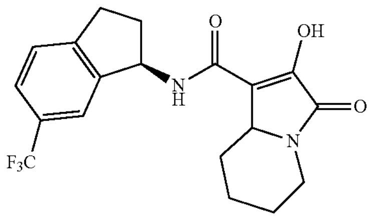 [SMILES: O=C(N[C@@H]1CCc2ccc(C(F)(F)F)cc21)C1=C(O)C(=O)N2CCCCC12] | 2-Hydroxy-3-oxo-N-((R)-6-(trifluoromethyl)-2,3-dihydro-1H-inden-1-yl)-3,5,6,7,8,8a-hexahydroindolizine-1-carboxamide Enantiomer B | 1.97 | 381.1 | L |
| 216 | 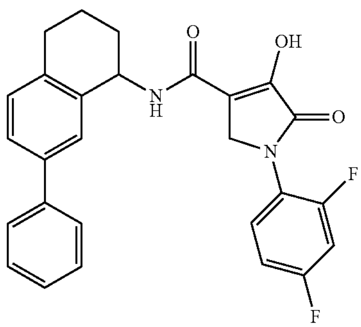 [SMILES: O=C(NC1CCCc2ccc(-c3ccccc3)cc21)C1=C(O)C(=O)N(c2ccc(F)cc2F)C1] | 1-(2,4-difluorophenyl)-4-hydroxy-5-oxo-N-(7-phenyl-1,2,3,4-tetrahydronaphthalen-1-yl)-2,5-dihydro-1H-pyrrole-3-carboxamide | 2.27 | 483.5 | O |
| 217 | 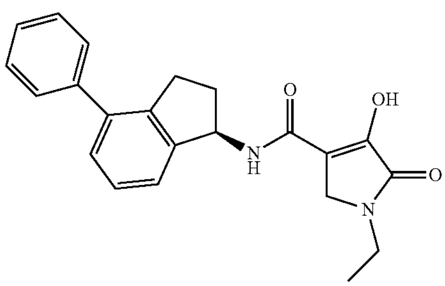 [SMILES: CCN1CC(C(=O)N[C@@H]2CCc3c(-c4ccccc4)cccc32)=C(O)C1=O] | (R)-1-ethyl-4-hydroxy-5-oxo-N-(4-phenyl-2,3-dihydro-1H-inden-1-yl)-2,5-dihydro-1H-pyrrole-3-carboxamide | 2.07 | 385.3 (M + Na) | L |
| 218 | 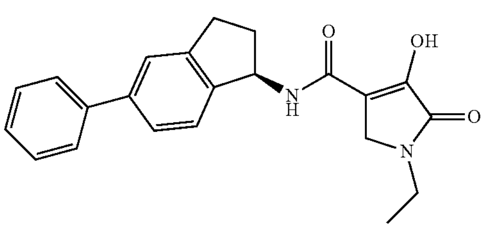 [SMILES: CCN1CC(C(=O)N[C@@H]2CCc3cc(-c4ccccc4)ccc32)=C(O)C1=O] | (R)-1-ethyl-4-hydroxy-5-oxo-N-(5-phenyl-2,3-dihydro-1H-inden-1-yl)-2,5-dihydro-1H-pyrrole-3-carboxamide | 2.09 | 385.4 (M + Na) | L |
| 219 | 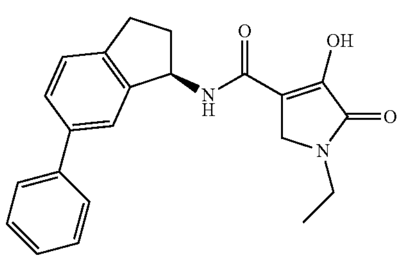 [SMILES: CCN1CC(C(=O)N[C@@H]2CCc3ccc(-c4ccccc4)cc32)=C(O)C1=O] | (R)-1-ethyl-4-hydroxy-5-oxo-N-(6-phenyl-2,3-dihydro-1H-inden-1-yl)-2,5-dihydro-1H-pyrrole-3-carboxamide | 2.08 | 385.4 (M + Na) | L |

TABLE 2-continued

| Ex. # | Structure | Name | RT (min) | [M + 1]+ | LC/MS Methods |
|---|---|---|---|---|---|
| 220 | 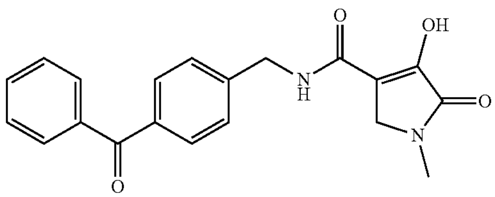 [SMILES: CN1CC(C(=O)NCc2ccc(C(=O)c3ccccc3)cc2)=C(O)C1=O] | N-(4-benzoylbenzyl)-4-hydroxy-1-methyl-5-oxo-2,5-dihydro-1H-pyrrole-3-carboxamide | 0.81 | 351 | D |
| 221 | 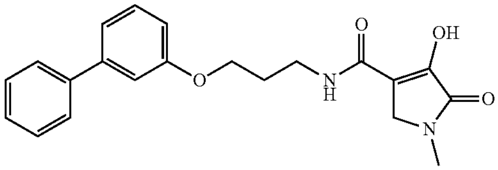 [SMILES: CN1CC(C(=O)NCCCOc2cccc(-c3ccccc3)c2)=C(O)C1=O] | N-(3-(biphenyl-3-yloxy)propyl)-4-hydroxy-1-methyl-5-oxo-2,5-dihydro-1H-pyrrole-3-carboxamide | 2.09 | 366 | E |
| 222 | 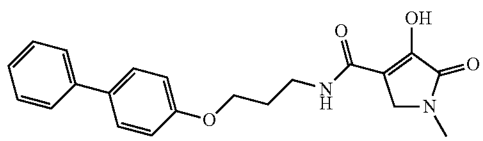 [SMILES: CN1CC(C(=O)NCCCOc2ccc(-c3ccccc3)cc2)=C(O)C1=O] | N-(3-(biphenyl-4-yloxy)propyl)-4-hydroxy-1-methyl-5-oxo-2,5-dihydro-1H-pyrrole-3-carboxamide | 2.09 | 366 | E |

What is claimed is:

1. A compound of Formula (II):

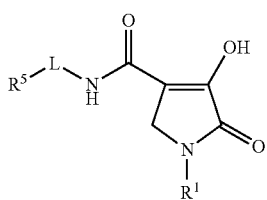

or a stereoisomer, a tautomer, or a pharmaceutically acceptable salt thereof, wherein:
  $R^1$ is independently selected from the group consisting of: $C_{1-6}$ alkyl substituted with 0-2 $R^a$, —$(CH_2)_2N(C_{1-4}$ alkyl)(—CH=CHCF$_3$), and —$(CH_2)_n$—W—$R^{1a}$;
  W is independently selected from the group consisting of: a bond, NH, N($C_{1-4}$ alkyl), CO, CONH, CON($C_{1-4}$ alkyl), SO$_2$, NHCO$_2$, and CHR$^f$;
  $R^{1a}$ is independently selected from the group consisting of: $C_{3-6}$ cycloalkyl substituted with 0-2 $R^c$, phenyl substituted with 0-2 $R^b$, naphthyl substituted with 0-2 $R^b$, dihydroindenyl substituted with 0-2 $R^c$, and a 5- to 6-membered heterocycle comprising: carbon atoms and 1-4 heteroatoms selected from N, NR$^e$, O, and S(O)$_p$; and wherein said heterocycle is substituted with 0-2 $R^c$;
  $R^5$ is independently selected from the group consisting of: $C_{5-6}$ cycloalkyl, phenyl, thienyl, pyrazolyl, imidazolyl, thiazolyl, tetrahydropyranyl, piperidinyl, pyridyl, and benzothiazolyl; and wherein each moiety is substituted with 0-2 $R^d$;
  L is $X_1$—Y—$X_2$;
  $X_1$ is independently selected from the group consisting of: a bond, —CH=CH—, O, NH, —CH$_2$O—, —CO—, —SO$_2$—;
  $X_2$ is independently selected from the group consisting of: —CH$_2$—, —(CH$_2$)$_2$—, —(CH$_2$)$_3$—, —(CH$_2$)$_4$—, —CH($C_{1-4}$ alkyl)-, —O(CH$_2$)$_2$—, and —O(CH$_2$)$_3$—;
  Y is independently selected from the group consisting of: $C_{3-6}$ cycloalkylene, $C_{4-6}$ cycloalkenylene, phenylene, pyridylene, piperidinylene, oxadiazolylene,

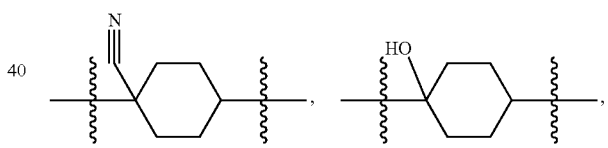

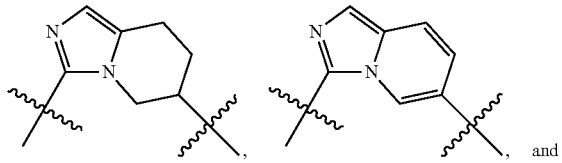

, and

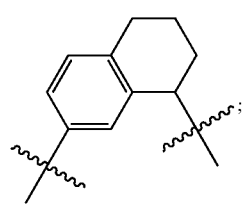

alternatively, $R^5$-L- is

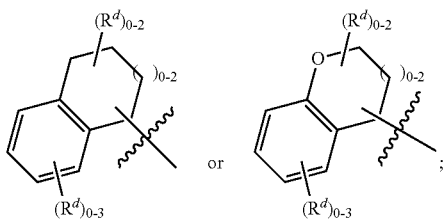

or ;

$R^a$ is, independently at each occurrence, selected from the group consisting of: halogen, $CF_3$, $CF_2CF_3$, $OCH_2CF_3$, $NH(C_{1-4}$ alkyl), $CONH_2$, $CONH(C_{1-4}$ alkyl), $NHSO_2(C_{1-4}$ alkyl), and $N(C_{1-4}$ alkyl)$SO_2(C_{1-4}$ alkyl);

$R^b$ is, independently at each occurrence, selected from the group consisting of: halogen, $C_{1-4}$ alkyl, $CF_3$, $OCF_3$, $CONH_2$, and $CONH(C_{1-4}$ alkyl);

$R^c$ is, independently at each occurrence, selected from the group consisting of: =O and $R^b$;

$R^d$ is, independently at each occurrence, selected from the group consisting of: halogen, OH, $C_{1-4}$ alkyl, $C_{1-4}$ alkoxy, $CF_3$, $OCF_3$, CN, $NH_2$, $NH(C_{1-4}$ alkyl), $N(C_{1-4}$ alkyl)$_2$, $CO(C_{1-4}$ alkyl), $CO_2(C_{1-4}$ alkyl), $NHCO(C_{1-4}$ alkyl), —$CH_2NHCO(C_{1-4}$ alkyl), $CONH_2$, $CONH(C_{1-4}$ alkyl), $CON(C_{1-4}$ alkyl)$_2$, $SO_2(C_{1-4}$ alkyl), $SO_2NH_2$, —$SO_2NH(C_{1-4}$ alkyl), —$SO_2NH(C_{3-6}$ cycloalkyl), —$NHSO_2(C_{1-4}$ alkyl), —$CH_2NHSO_2(C_{1-4}$ alkyl), and $Si(C_{1-4}$ alkyl)$_3$;

$R^e$ is, independently at each occurrence, selected from the group consisting of: H, $C_{1-4}$ alkyl, $CO_2(C_{1-4}$ alkyl), $CO_2$(benzyl), phenyl, and benzyl;

$R^f$ is, independently at each occurrence, selected from the group consisting of: $C_{1-4}$ alkyl, $CO_2(C_{1-4}$ alkyl), and $CONH_2$;

n is, independently at each occurrence, selected from 0, 1, 2, and 3; and p is, independently at each occurrence, selected from 0, 1, and 2;

wherein said 5- to 10-membered heterocycle is each independently selected from the group consisting of pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

2. A compound according to claim 1, wherein:

$R^1$ is independently selected from the group consisting of: $C_{1-4}$ alkyl substituted with 0-1 $R^a$, 4-halo-phenyl, 2-halo-4-halo-phenyl, —CH(Ph)$CONH_2$, —CH(Bn)$CONH_2$, —$(CH_2)_2N(C_{1-4}$ alkyl)(—CH=CHCF$_3$), —$(CH_2)_2NH(Ph)$, —$(CH_2)_2N(C_{1-4}$ alkyl)(Ph), —$(CH_2)_2NH(4$-halo-Ph), —$(CH_2)_2N(C_{1-4}$ alkyl)(3-$C_{1-4}$ alkyl-Ph), —$(CH_2)_2CONH(4$-halo-Ph), —$(CH_2)_2$NHCO$_2$Bn, —$(CH_2)_2SO_2$Ph, —$(CH_2)_2$NHSO$_2(4$-$C_{1-4}$ alkyl-Ph), —$CH_2CONH(2$-naphthyl), $R^5$ is independently selected from the group consisting of: $C_{5-6}$ cycloalkyl, phenyl, 2-$C_{1-4}$ alkyl-phenyl, 3-$C_{1-4}$ alkyl-phenyl, 4-$C_{1-4}$ alkyl-phenyl, 2-$C_{1-4}$ alkoxy-phenyl, 3-$C_{1-4}$ alkoxy-phenyl, 4-$C_{1-4}$ alkoxy-phenyl, 2-halo-phenyl, 3-halo-phenyl, 4-halo-phenyl, 3-$CF_3$-phenyl, 4-$CF_3$-phenyl, 2-$OCF_3$-phenyl, 3-$OCF_3$-phenyl, 4-$OCF_3$-phenyl, 2-CN-phenyl, 3-CN-phenyl, 4-CN-phenyl, 3-CO($C_{1-4}$ alkyl)-phenyl, 4-CO($C_{1-4}$ alkyl)-phenyl, 3-CO$_2(C_{1-4}$ alkyl)-phenyl, 3-N($C_{1-4}$ alkyl)-$_2$-phenyl, 2-NHCO($C_{1-4}$ alkyl)-phenyl, 4-NHCO($C_{1-4}$ alkyl)-phenyl, 3-CH$_2$NHCO($C_{1-4}$ alkyl)-phenyl, 4-CH$_2$NHCO($C_{1-4}$ alkyl)-phenyl, 2-CONH$_2$-phenyl, 3-CONH$_2$-phenyl, 3-CONH($C_{1-4}$ alkyl)-phenyl, 3-CON($C_{1-4}$ alkyl)-2-phenyl, 4-CON($C_{1-4}$ alkyl)-2-phenyl, 2-SO$_2$($C_{1-4}$ alkyl)-phenyl, 3-SO$_2$($C_{1-4}$ alkyl)-phenyl, 4-SO$_2$($C_{1-4}$ alkyl)-phenyl, 3-SO$_2$NH$_2$-phenyl, 4-SO$_2$NH(cyclopropyl)-phenyl, 4-NHSO$_2$($C_{1-4}$ alkyl)-phenyl, 3-CH$_2$NHSO$_2$($C_{1-4}$ alkyl)-phenyl, 4-CH$_2$NHSO$_2$($C_{1-4}$ alkyl)-phenyl, 3-Si(Me)$_3$-phenyl, 2-$C_{1-4}$ alkyl-4-$C_{1-4}$ alkyl-phenyl, 2-$C_{1-4}$ alkyl-6-$C_{1-4}$ alkyl-phenyl, 2-halo-4-halo-phenyl, 2-halo-5-halo-phenyl, 3-halo-4-halo-phenyl, 3-halo-5-halo-phenyl, 2-OH-4-halo-phenyl, 3-halo-4-CF$_3$-phenyl, 2-CF$_3$-6-halo-phenyl, 3-CF$_3$-4-$C_{1-4}$ alkyl-phenyl, 3,5-di(CF$_3$)-phenyl, thien-3-yl, 5-$C_{1-4}$ alkyl-thien-2-yl, 5-halo-thien-2-yl, 1H-pyrazol-4-yl, 1-$C_{1-4}$ alkyl-pyrazol-5-yl, 1-$C_{1-4}$ alkyl-imidazol-5-yl, 2-$C_{1-4}$ alkyl-4-$C_{1-4}$ alkyl-thiazol-5-yl, tetrahydro-2H-pyran-4-yl, piperidin-1-yl, pyrid-2-yl, pyrid-3-yl, pyrid-4-yl, 2-$C_{1-4}$ alkyl-pyrid-4-yl, 2-$C_{1-4}$ alkoxy-pyrid-3-yl, 6-$C_{1-4}$ alkoxy-pyrid-3-yl, 3-halo-pyrid-4-yl, 6-halo-pyrid-3-yl, 5-CF$_3$-pyrid-3-yl, 4-halo-6-halo-pyrid-3-yl, and benzothiazol-2-yl;

L is independently selected from the group consisting of: 1,2-phenylene-CH$_2$—, 1,3-phenylene-CH$_2$—, 1,4-phenylene-CH$_2$—, 1,3-phenylene-CH($C_{1-4}$ alkyl)-, —CH=CH-1,3-phenylene-CH$_2$—, —O-(1,2-phenylene)-CH$_2$—, —O-(1,3-phenylene)-CH$_2$—, —O-(1,4-phenylene)-CH$_2$—, —O-(1,4-phenylene)-(CH$_2$)$_2$—, —O-(1,4-phenylene)-(CH$_2$)$_3$—, —CH$_2$O-(1,4-phenylene)-CH$_2$—, —O-(1,3-phenylene)-O(CH$_2$)$_3$—, —O-(1,4-phenylene)-O(CH$_2$)$_3$—, —CO-(1,4-phenylene)-CH$_2$—,

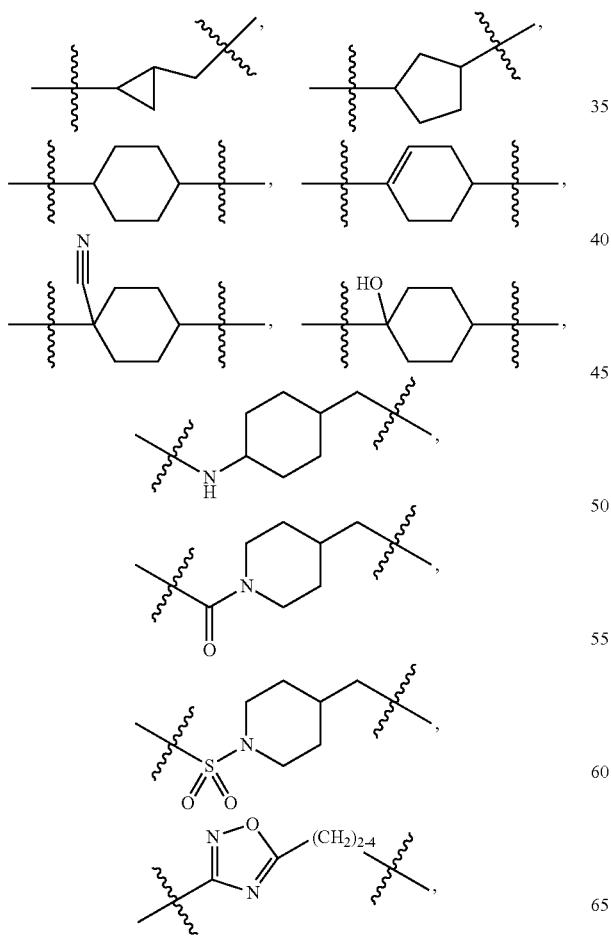

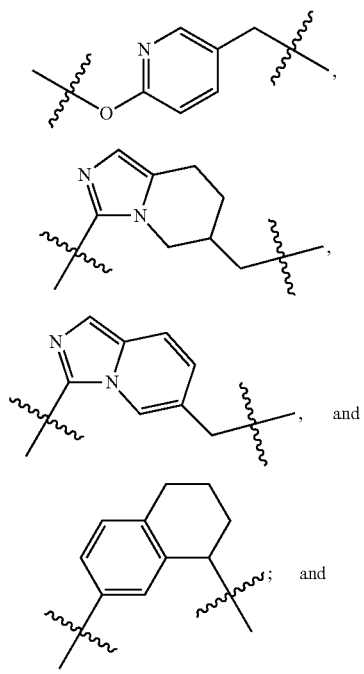

$R^a$ is, independently at each occurrence, selected from the group consisting of: CF$_3$, CF$_2$CF$_3$, OCH$_2$CF$_3$, NH($C_{1-4}$ alkyl), CONH$_2$, CONH($C_{1-4}$ alkyl), NHSO$_2$($C_{1-4}$ alkyl), and N($C_{1-4}$ alkyl)SO$_2$($C_{1-4}$ alkyl).

3. A compound according to claim 2, wherein:

$R^1$ is independently selected from the group consisting of: $C_{1-4}$ alkyl substituted with 0-1 $R^a$, 4-halo-phenyl, 2-halo-4-halo-phenyl, —(CH$_2$)$_2$NH(4-halo-Ph), —(CH$_2$)$_2$N($C_{1-4}$ alkyl)(3-$C_{1-4}$ alkyl-Ph), —(CH$_2$)$_2$CONH(4-Cl-Ph), —CH$_2$CONH(2-naphthyl),

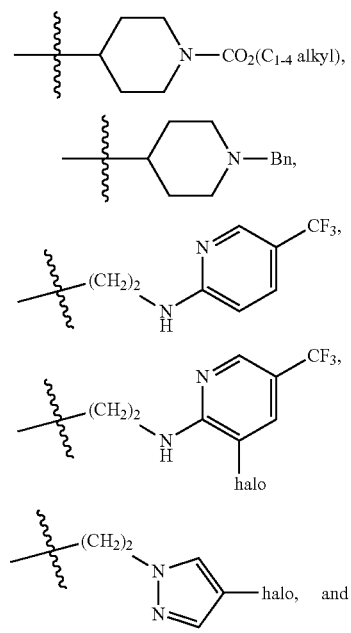

155
-continued

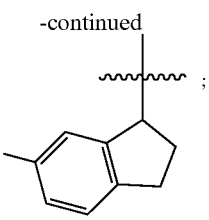

R⁵ is independently selected from the group consisting of:
C$_{5-6}$ cycloalkyl, phenyl, 2-C$_{1-4}$ alkyl-phenyl, 3-C$_{1-4}$ alkyl-phenyl, 4-C$_{1-4}$ alkyl-phenyl, 2-C$_{1-4}$ alkoxy-phenyl, 3-C$_{1-4}$ alkoxy-phenyl, 4-C$_{1-4}$ alkoxy-phenyl, 2-halo-phenyl, 3-halo-phenyl, 4-halo-phenyl, 3-CF$_3$-phenyl, 4-CF$_3$-phenyl, 2-OCF$_3$-phenyl, 3-OCF$_3$-phenyl, 4-OCF$_3$-phenyl, 2-CN-phenyl, 3-CN-phenyl, 4-CN-phenyl, 3-CO(C$_{1-4}$ alkyl)-phenyl, 4-CO(C$_{1-4}$ alkyl)-phenyl, 3-CO$_2$(C$_{1-4}$ alkyl)-phenyl, 3-N(C$_{1-4}$ alkyl)-$_2$-phenyl, 4-NHCO(C$_{1-4}$ alkyl)-phenyl, 3-CH$_2$NHCO(C$_{1-4}$ alkyl)-phenyl, 4-CH$_2$NHCO(C$_{1-4}$ alkyl)-phenyl, 3-CONH$_2$-phenyl, 3-CONH(C$_{1-4}$ alkyl)-phenyl, 3-CON(C$_{1-4}$ alkyl)-2-phenyl, 4-CON(C$_{1-4}$ alkyl)-2-phenyl, 3-SO$_2$(C$_{1-4}$ alkyl)-phenyl, 4-SO$_2$(C$_{1-4}$ alkyl)-phenyl, 4-SO$_2$NH(cyclopropyl)-phenyl, 4-NHSO$_2$(C$_{1-4}$ alkyl)-phenyl, 3-CH$_2$NHSO$_2$(C$_{1-4}$ alkyl)-phenyl, 4-CH$_2$NHSO$_2$(C$_{1-4}$ alkyl)-phenyl, 3-Si(Me)$_3$-phenyl, 2-C$_{1-4}$ alkyl-4-C$_{1-4}$ alkyl-phenyl, 2-C$_{1-4}$ alkyl-6-C$_{1-4}$ alkyl-phenyl, 2-halo-4-halo-phenyl, 2-halo-5-halo-phenyl, 3-halo-4-halo-phenyl, 3-halo-5-halo-phenyl, 2-OH-4-halo-phenyl, 3-halo-4-CF$_3$-phenyl, 2-CF$_3$-6-halo-phenyl, 3-CF$_3$-4-C$_{1-4}$ alkyl-phenyl, 3,5-di(CF$_3$)-phenyl, thien-3-yl, 5-C$_{1-4}$ alkyl-thien-2-yl, 5-halo-thien-2-yl, 1H-pyrazol-4-yl, 1-C$_{1-4}$ alkyl-pyrazol-5-yl, 2-C$_{1-4}$ alkyl-4-C$_{1-4}$ alkyl-thiazol-5-yl, tetrahydro-2H-pyran-4-yl, pyrid-3-yl, pyrid-4-yl, 2-C$_{1-4}$ alkyl-pyrid-4-yl, 2-C$_{1-4}$ alkoxy-pyrid-3-yl, 6-C$_{1-4}$ alkoxy-pyrid-3-yl, 3-halo-pyrid-4-yl, 5-CF$_3$-pyrid-3-yl, 4-halo-6-halo-pyrid-3-yl, and benzothiazol-2-yl;

L is independently selected from the group consisting of: 1,2-phenylene-CH$_2$—, 1,3-phenylene-CH$_2$—, 1,4-phenylene-CH$_2$—, 1,3-phenylene-CH(C$_{1-4}$ alkyl)-, —CH=CH-1,3-phenylene-CH$_2$—, —O-(1,2-phenylene)-CH$_2$—, —O-(1,3-phenylene)-CH$_2$—, —O-(1,4-phenylene)-CH$_2$—, —O-(1,4-phenylene)-(CH$_2$)$_2$—, —O-(1,4-phenylene)-(CH$_2$)$_3$—, -(1,3-phenylene)-O(CH$_2$)$_3$—, -(1,4-phenylene)-O(CH$_2$)$_3$—, —CH$_2$O-(1,4-phenylene)-CH$_2$—, —O-(1,4-phenylene)-O(CH$_2$)$_2$—, —O-(1,3-phenylene)-O(CH$_2$)$_3$—, —O-(1,4-phenylene)-O(CH$_2$)$_3$—,

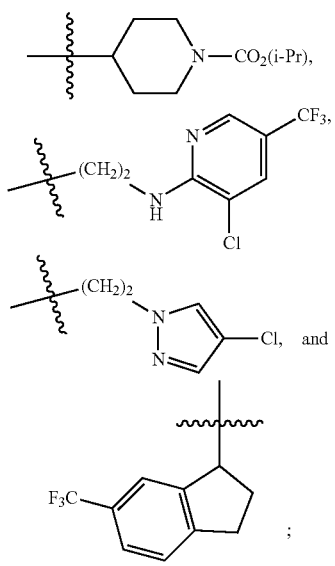

156
-continued

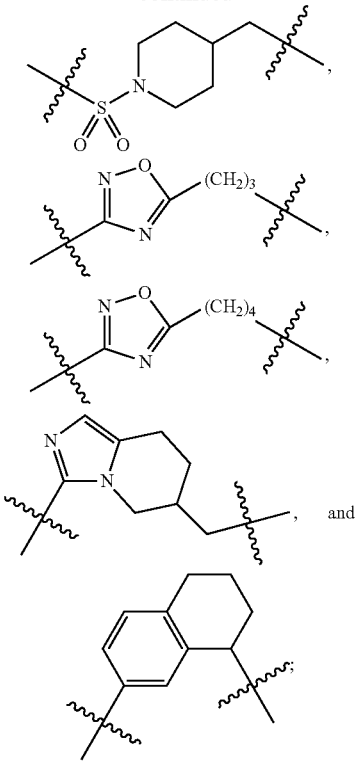

and
R$^a$ is, independently at each occurrence, selected from the group consisting of: CF$_3$ and CONH$_2$.

4. A compound according to claim 3, wherein:
R$^1$ is independently selected from the group consisting of: methyl, ethyl, i-butyl, —CH$_2$CF$_3$, —(CH$_2$)$_3$CF$_3$, 4-F-phenyl, 2,4-diF-phenyl, —(CH$_2$)$_2$NH(4-Cl-Ph), —(CH$_2$)$_2$N(Et)(3-Me-Ph), R⁵ is independently selected from the group consisting of: cyclopentyl, cyclohexyl, phenyl, 2-Me-phenyl, 3-Me-phenyl, 4-Me-phenyl, 2-OMe-phenyl, 3-OMe-phenyl, 4-OMe-phenyl, 2-F-phenyl, 3-F-phenyl, 4-F-phenyl, 2-Cl-phenyl, 3-Cl-phenyl, 4-Cl-phenyl, 3-CF$_3$-phenyl, 4-CF$_3$-phenyl, 2-OCF$_3$-phenyl, 3-OCF$_3$-phenyl, 4-OCF$_3$-phenyl, 3-CN-phenyl, 4-CN-phenyl, 3-COMe-phenyl, 4-COMe-phenyl, 3-CO$_2$Me-phenyl, 3-CO$_2$Et-phenyl, 3-N(Me)-$_2$-phenyl, 4-NHCOMe-phenyl, 3-CH$_2$NHCOMe-phenyl, 4-CH$_2$NHCOMe-phenyl, 3-CONH$_2$-phenyl, 3-CONH(t-Bu)-phenyl, 3-CON(Me)-$_2$-phenyl, 4-CON(Me)-$_2$-phenyl, 3-SO$_2$Me-phenyl, 4-SO$_2$Me-phenyl, 4-SO$_2$NH(cyclopropyl)-phenyl, 4-NHSO$_2$Me-phenyl, 3-CH$_2$NHSO$_2$Me-phenyl, 4-CH$_2$NHSO$_2$Me-phenyl, 2,4-diMe-phenyl, 2,6-diMe-phenyl, 2,4-diCl-phenyl, 2,5-diCl-phenyl, 3,4-diCl-phenyl, 3,5-diCl-phenyl, 2-OH-4-F-phenyl, 4-Cl-3-F-phenyl, 3-C$_{1-4}$-CF$_3$-phenyl, 3-CF$_3$-4-Me-phenyl, 3,5-di(CF$_3$)-phenyl, thien-3-yl, 5-Me-thien-2-yl, 5-Cl-thien-2-yl, 1H-pyrazol-4-yl, 1-Me-pyrazol-5-yl, 2,4,-di-Me-thiazol-5-yl, tetrahydro-2H-pyran-4-yl, pyrid-3-yl, 2-Me-pyrid-4-yl, 2-OMe-pyrid-3-yl, 6-OMe-pyrid-3-yl, 5-CF$_3$-pyrid-3-yl, and 4,6-diCl-pyrid-3-yl; and L is independently selected from the group consisting of: 1,2-phenylene-CH$_2$—, 1,3-phenylene-CH$_2$—, 1,4-phenylene-CH$_2$—, 1,3-phenylene-CHMe-, —CH═CH-1,3-phenylene-CH$_2$—, —O-(1,2-phenylene)-CH$_2$—, —O-(1,3-phenylene)-CH$_2$—, —O-(1,4-phenylene)-CH$_2$—, —O-(1,4-phenylene)-(CH$_2$)$_2$—, —O-(1,4-phenylene)-(CH$_2$)$_3$—, —CH$_2$O-(1,4-phenylene)-CH$_2$—, —O-(1,3-phenylene)-O(CH$_2$)$_3$—, —O-(1,4-phenylene)-O(CH$_2$)$_3$—,

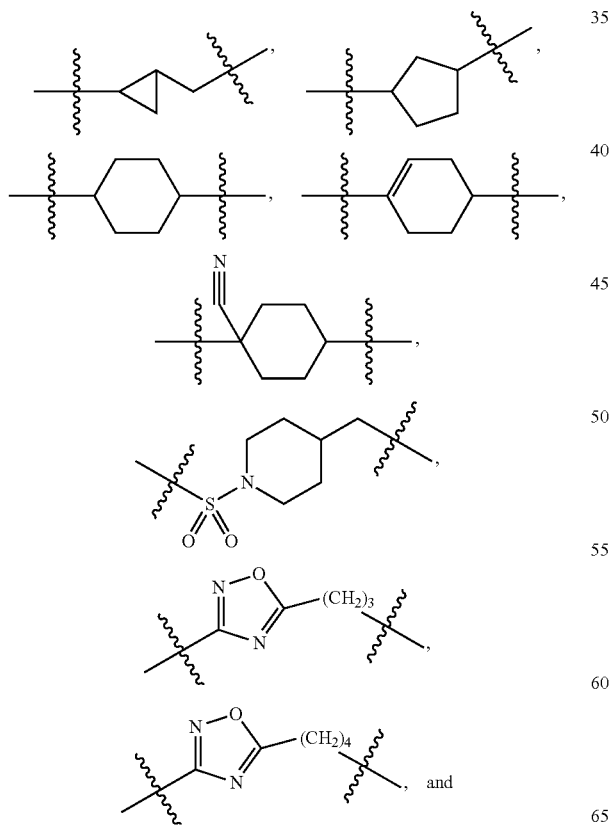

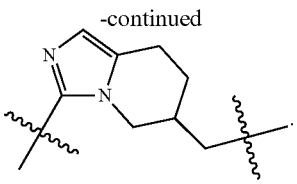

5. A compound according to claim 4, wherein:
R$^1$ is independently selected from the group consisting of: methyl, ethyl, i-butyl, —(CH$_2$)$_3$CF$_3$, 2,4-diF-phenyl, and

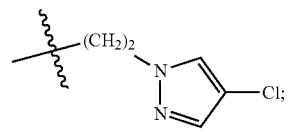

R$^5$ is independently selected from the group consisting of: cyclohexyl, phenyl, 3-Me-phenyl, 4-Me-phenyl, 4-OMe-phenyl, 2-F-phenyl, 3-F-phenyl, 4-F-phenyl, 4-Cl-phenyl, 3-CF$_3$-phenyl, 4-CF$_3$-phenyl, 2-OCF$_3$-phenyl, 3-OCF$_3$-phenyl, 4-NHCOMe-phenyl, 3-CONH$_2$-phenyl, 4-NHSO$_2$Me-phenyl, 2,4-diMe-phenyl, 2,4-diCl-phenyl, 3,4-diCl-phenyl, 5-Me-thien-2-yl, and 6-OMe-pyrid-3-yl; and L is independently selected from the group consisting of: 1,2-phenylene-CH$_2$—, 1,3-phenylene-CH$_2$—, 1,4-phenylene-CH$_2$—, 1,3-phenylene-CHMe-, —O-(1,3-phenylene)-CH$_2$—, —O-(1,4-phenylene)-CH$_2$—, —O-(1,4-phenylene)-(CH$_2$)$_2$—, —O-(1,4-phenylene)-(CH$_2$)$_3$—, —O-(1,3-phenylene)-O(CH$_2$)$_3$—, —O-(1,4-phenylene)-O(CH$_2$)$_3$—,

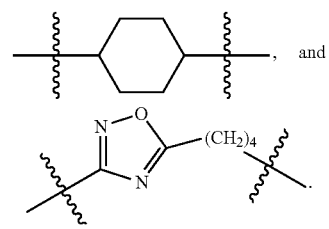

6. A compound according to claim 1, wherein the compound is selected from:
4-hydroxy-1-methyl-5-oxo-N-(2-phenoxybenzyl)-2,5-dihydro-1H-pyrrole-3-carboxamide;
N-((4'-fluorobiphenyl-3-yl)methyl)-1-(4-fluorophenyl)-4-hydroxy-5-oxo-2,5-dihydro-1H-pyrrole-3-carboxamide;
(R)-N-(1-(4'-acetamidobiphenyl-3-yl)ethyl)-1-(2,4-difluorophenyl)-4-hydroxy-5-oxo-2,5-dihydro-1H-pyrrole-3-carboxamide;
4-hydroxy-1-methyl-N-(3-(5-methylthiophen-2-yl)benzyl)-5-oxo-2,5-dihydro-1H-pyrrole-3-carboxamide;
1-ethyl-4-hydroxy-5-oxo-N-(3-(4-phenoxyphenyl)propyl)-2,5-dihydro-1H-pyrrole-3-carboxamide;
N-((3-(3,4-dichlorophenyl)imidazo[1,5-a]pyridin-6-yl)methyl)-1-ethyl-4-hydroxy-5-oxo-2,5-dihydro-1H-pyrrole-3-carboxamide;
(R)-4-hydroxy-5-oxo-1-(2,2,2-trifluoroethyl)-N-(6-(trifluoromethyl)-2,3-dihydro-1H-inden-1-yl)-2,5-dihydro-1H-pyrrole-3-carboxamide;

N-(4-(4-fluorophenyl)cyclohex-3-enyl)-4-hydroxy-5-oxo-1-(2,2,2-trifluoroethyl)-2,5-dihydro-1H-pyrrole-3-carboxamide;

N-(cis-4-(4-fluorophenyl)cyclohexyl)-4-hydroxy-5-oxo-1-(2,2,2-trifluoroethyl)-2,5-dihydro-1H-pyrrole-3-carboxamide;

N-((1-(3,4-dichlorophenylsulfonyl)piperidin-4-yl)methyl)-4-hydroxy-1-methyl-5-oxo-2,5-dihydro-1H-pyrrole-3-carboxamide;

4-hydroxy-1-methyl-5-oxo-N-((trans-4-(pyridin-2-ylamino)cyclohexyl)methyl)-2,5-dihydro-1H-pyrrole-3-carboxamide;

4-hydroxy-5-oxo-N-(cis-4-phenylcyclohexyl)-1-(2-((E)-4,4,4-trifluoro-N-methylbut-2-enamido)ethyl)-2,5-dihydro-1H-pyrrole-3-carboxamide;

2-hydroxy-3-oxo-N-((R)-6-(trifluoromethyl)-2,3-dihydro-1H-inden-1-yl)-3,5,6,7,8,8a-hexahydroindolizine-1-carboxamide;

N-((3-(3,4-Dichlorophenyl)-5,6,7,8-tetrahydroimidazo[1,5-a]pyridin-6-yl)methyl)-1-ethyl-4-hydroxy-5-oxo-2,5-dihydro-1H-pyrrole-3-carboxamide;

N-(7-(4-acetamidophenyl)-1,2,3,4-tetrahydronaphthalen-1-yl)-1-(2,4-difluorophenyl)-4-hydroxy-5-oxo-2,5-dihydro-1H-pyrrole-3-carboxamide;

4-hydroxy-1-methyl-5-oxo-N-(4-phenoxybenzyl)-2,5-dihydro-1 H-pyrrole-3-carboxamide;

4-hydroxy-1-methyl-5-oxo-N-(3-phenoxybenzyl)-2,5-dihydro-1H-pyrrole-3-carboxamide;

N-(2-(4-fluorophenoxy)benzyl)-4-hydroxy-1-methyl-5-oxo-2,5-dihydro-1H-pyrrole-3-carboxamide;

N-(3-(4-fluorophenoxy)benzyl)-4-hydroxy-1-methyl-5-oxo-2,5-dihydro-1H-pyrrole-3-carboxamide;

N-(4-(2-fluorophenoxy)benzyl)-4-hydroxy-1-methyl-5-oxo-2,5-dihydro-1H-pyrrole-3-carboxamide;

N-(4-(3-fluorophenoxy)benzyl)-4-hydroxy-1-methyl-5-oxo-2,5-dihydro-1H-pyrrole-3-carboxamide ;

N-(4-(4-fluorophenoxy)benzyl)-4-hydroxy-1-methyl-5-oxo-2,5-dihydro-1H-pyrrole-3-carboxamide;

N-(4-(3,4-dichlorophenoxy)benzyl)-4-hydroxy-1-methyl-5-oxo-2,5-dihydro-1H-pyrrole-3-carboxamide;

4-hydroxy-1-methyl-5-oxo-N-(2-(3-phenyl-1,2,4-oxadiazol-5-yl)ethyl)-2,5-dihydro-1H-pyrrole-3-carboxamide;

4-hydroxy-1-methyl-5-oxo-N-(3-(3-phenyl-1,2,4-oxadiazol-5-yl)propyl)-2,5-dihydro-1H-pyrrole-3-carboxamide;

4-hydroxy-1-methyl-5-oxo-N-(4-(3-phenyl-1,2,4-oxadiazol-5-yl)butyl)-2,5-dihydro-1H-pyrrole-3-carboxamide;

4-hydroxy-1-methyl-5-oxo-N-((6-phenoxypyridin-3-yl)methyl)-2,5-dihydro-1H-pyrrole-3-carboxamide;

4-hydroxy-1-methyl-5-oxo-N-(4-phenoxyphenethyl)-2,5-dihydro-1H-pyrrole-3-carboxamide;

N-(4-(benzo[d]thiazol-2-yloxy)benzyl)-4-hydroxy-1-methyl-5-oxo-2,5-dihydro-1H-pyrrole-3-carboxamide;

4-hydroxy-1-methyl-5-oxo-N-(4-(pyridin-4-yloxy)benzyl)-2,5-dihydro-1H-pyrrole-3-carboxamide;

N-((3',4'-dichlorobiphenyl-4-yl)methyl)-4-hydroxy-1-methyl-5-oxo-2,5-dihydro-1H-pyrrole-3-carboxamide;

N-(biphenyl-2-ylmethyl)-4-hydroxy-1-methyl-5-oxo-2,5-dihydro-1H-pyrrole-3-carboxamide;

N-(biphenyl-3-ylmethyl)-4-hydroxy-1-methyl-5-oxo-2,5-dihydro-1H-pyrrole-3-carboxamide;

N-(4-(3-(3,4-dichlorophenyl)-1,2,4-oxadiazol-5-yl)butyl)-4-hydroxy-1-methyl-5-oxo-2,5-dihydro-1H-pyrrole-3-carboxamide;

N-(4-(3-(3,4-dichlorophenyl)-1,2,4-oxadiazol-5-yl)butyl)-4-hydroxy-1-isobutyl-5-oxo-2,5-dihydro-1H-pyrrole-3-carboxamide;

4-hydroxy-1-methyl-5-oxo-N-(4-(tetrahydro-2H-pyran-4-yloxy)benzyl)-2,5-dihydro-1H-pyrrole-3-carboxamide;

N-(4-(benzyloxy)benzyl)-4-hydroxy-1-methyl-5-oxo-2,5-dihydro-1H-pyrrole-3-carboxamide;

4-hydroxy-1-methyl-5-oxo-N-(4-(piperidine-1-carbonyl)benzyl)-2,5-dihydro-1H-pyrrole-3-carboxamide;

N-(4-(cyclohexyloxy)benzyl)-4-hydroxy-1-methyl-5-oxo-2,5-dihydro-1H-pyrrole-3-carboxamide;

N-(4-(cyclopentyloxy)benzyl)-4-hydroxy-1-methyl-5-oxo-2,5-dihydro-1H-pyrrole-3-carboxamide;

N-((6-(cyclohexyloxy)pyridin-3-yl)methyl)-4-hydroxy-1-methyl-5-oxo-2,5-dihydro-1H-pyrrole-3-carboxamide;

4-hydroxy-1-methyl-5-oxo-N-(3-(4-phenoxyphenoxy)propyl)-2,5-dihydro-1H-pyrrole-3-carboxamide;

4-hydroxy-1-methyl-5-oxo-N-(3-(3-phenoxyphenoxy)propyl)-2,5-dihydro-1H-pyrrole-3-carboxamide;

4-hydroxy-1-methyl-5-oxo-N-(4-(o-tolyloxy)benzyl)-2,5-dihydro-1H-pyrrole-3-carboxamide;

N-(4-(4-chlorophenoxy)benzyl)-4-hydroxy-1-methyl-5-oxo-2,5-dihydro-1H-pyrrole-3-carboxamide;

4-hydroxy-1-methyl-5-oxo-N-(4-(p-tolyloxy)benzyl)-2,5-dihydro-1H-pyrrole-3-carboxamide;

N-(4-(3,5-bis(trifluoromethyl)phenoxy)benzyl)-4-hydroxy-1-methyl-5-oxo-2,5-dihydro-1H-pyrrole-3-carboxamide;

N-(4-(2,4-dimethylphenoxy)benzyl)-4-hydroxy-1-methyl-5-oxo-2,5-dihydro-1H-pyrrole-3-carboxamide;

4-hydroxy-1-methyl-5-oxo-N-(4-(pyridin-2-yloxy)benzyl)-2,5-dihydro-1H-pyrrole-3-carboxamide;

N-(4-(4-chloro-3-fluorophenoxy)benzyl)-4-hydroxy-1-methyl-5-oxo-2,5-dihydro-1H-pyrrole-3-carboxamide;

4-hydroxy-1-methyl-5-oxo-N-(4-(3-(trifluoromethyl)phenoxy)benzyl)-2,5-dihydro-1H-pyrrole-3-carboxamide;

4-hydroxy-1-methyl-5-oxo-N-(4-(m-tolyloxy)benzyl)-2,5-dihydro-1H-pyrrole-3carboxamide;

N-(4-(2,4-dichlorophenoxy)benzyl)-4-hydroxy-1-methyl-5-oxo-2,5-dihydro-1H-pyrrole-3-carboxamide;

4-hydroxy-N-(4-(3-methoxyphenoxy)benzyl)-1-methyl-5-oxo-2,5-dihydro-1H-pyrrole-3-carboxamide;

4-hydroxy-N-(4-(4-methoxyphenoxy)benzyl)-1-methyl-5-oxo-2,5-dihydro-1H-pyrrole-3-carboxamide;

N-(4-(2-chlorophenoxy)benzyl)-4-hydroxy-1-methyl-5-oxo-2 ,5-dihydro-1H-pyrrole-3-carboxamide;

N-(3-(4-chlorophenoxy)benzyl)-4-hydroxy-1-methyl-5-oxo-2,5-dihydro-1H-pyrrole-3-carboxamide 4-hydroxy-1-methyl-5-oxo-N-(4-(5-(trifluoromethyl)pyridin-3-yloxy)benzyl)-2,5-dihydro-1H-pyrrole-3-carboxamide;

4-hydroxy-1-methyl-5-oxo-N-(4-(pyridin 3-yloxy)benzyl)-2,5-dihydro-1H-pyrrole-3-carboxamide;

4-hydroxy-N-(4-(2-methoxyphenoxy)benzyl)-1-methyl-5-oxo-2,5-dihydro-1H-pyrrole-3-carboxamide;

N-((3',4'-dichlorobiphenyl-3-yl)methyl)-4-hydroxy-1-methyl-5-oxo-2,5-dihydro-1H-pyrrole-3-carboxamide;

4-hydroxy-1-methyl-5-oxo-N-((4'-(trifluoromethyl)biphenyl-3-yl)methyl)-2,5-dihydro-1H-pyrrole-3-carboxamide;

N-((3'-chloro-4'-(trifluoromethyl)biphenyl-3-yl)methyl)-4-hydroxy-1-methyl-5-oxo-2,5-dihydro-1H-pyrrole-3-carboxamide;

N-((4'-chlorobiphenyl-3-yl)methyl)-4-hydroxy-1-methyl-5-oxo-2,5-dihydro-1H-pyrrole-3-carboxamide;
N-((4'-fluorobiphenyl-3-yl)methyl)-4-hydroxy-1-methyl-5-oxo-2,5-dihydro-1H-pyrrole-3-carboxamide;
(R)-N-(1-(4'-fluorobiphenyl-3-yl)ethyl)-4-hydroxy-1-methyl-5-oxo-2,5-dihydro-1H-pyrrole-3-carboxamide;
(R)-N-(1-(biphenyl-3-yl)ethyl)-4-hydroxy-1-methyl-5-oxo-2,5-dihydro-1H-pyrrole-3-carboxamide;
N-((2',4'-dichlorobiphenyl-3-yl)methyl)-4-hydroxy-1-methyl-5-oxo-2,5-dihydro-1H-pyrrole-3-carboxamide;
N-((3',5'-dichlorobiphenyl-3-yl)methyl)-4-hydroxy-1-methyl-5-oxo-2,5-dihydro-1H-pyrrole-3-carboxamide;
4-hydroxy-1-methyl-5-oxo-N-(3 (thiophen-3yl)benzyl)-2,5-dihydro-1H-pyrrole-3-carboxamide;
4-hydroxy-1-methyl-5-oxo-N-((3'-(trifluoromethyl)biphenyl-3-yl)methyl)-2,5-dihydro-1H-pyrrole-3-carboxamide;
N-((3'chlorobiphenyl-3-yl)methyl)-4-hydroxy-1-methyl-5-oxo-2,5-dihydro-1H-pyrrole-3-carboxamide;
N-((3'-fluorobiphenyl-3-yl)methyl)-4-hydroxy-1-methyl-5-oxo-2,5-dihydro-1H-pyrrole-3-carboxamide;
N-((2'-chlorobiphenyl-3-yl)methyl)-4-hydroxy-1-methyl-5-oxo-2,5-dihydro-1H-pyrrole-3-carboxamide;
N-((2'-fluorobiphenyl-3-yl)methyl)-4-hydroxy-1-methyl-5-oxo-2,5-dihydro-1H-pyrrole-3-carboxamide;
4-hydroxy-1-methyl-5-oxo-N-((4'-(trifluoromethoxy)biphenyl-3-yl)methyl)-2,5-dihydro-1H-pyrrole-3-carboxamide;
N-((4'-acetylbiphenyl-3-yl)methyl)-4-hydroxy-1-methyl-5-oxo-2,5-dihydro-1H-pyrrole-3-carboxamide,
N-((3'-acetylbiphenyl-3-yl)methyl)-4-hydroxy-1-methyl-5-oxo-2,5-dihydro-1H-pyrrole-3-carboxamide;
N-((3'-cyanobiphenyl-3-yl)methyl)-4-hydroxy-1-methyl-5-oxo-2,5-dihydro-1H-pyrrole-3-carboxamide;
N-((3'-(dimethylamino)biphenyl-3-yl)methyl)-4-hydroxy-1-methyl-5-oxo-2,5-dihydro-1H-pyrrole-3-carboxamide;
4-hydroxy-1-methyl-5-oxo-N-((3 '-(trifluoromethoxy)biphenyl-3-yl)methyl)-2,5-dihydro-1H-pyrrole-3-carboxamide;
4-hydroxy-1-methyl-5-oxo-N-((2'-(trifluoromethoxy)biphenyl-3-yl)methyl)-2,5-dihydro-1H-pyrrole-3-carboxamide;
4-hydroxy-1-methyl-N-((4'-(methylsulfony)biphenyl-3-yl)methyl)-5-oxo-2,5-dihydro-1H-pyrrole-3-carboxamide;
N-((2'-cyanobiphenyl-3-yl)methyl)-4-hydroxy-1-methyl-5-oxo-2,5-dihydro-1H-pyrrole-3-carboxamide;
N-((2',5'-dichlorobiphenyl-3-yl)methyl)-4-hydroxy-1-methyl-5-oxo-2,5-dihydro-1H-pyrrole-3-carboxamide;
N-((4'-acetamidobiphenyl-3-yl)methyl)-4-hydroxy-1-methyl-5-oxo-2,5-dihydro-1H-pyrrole-3-carboxamide;
N-((2'-carbamoylbiphenyl-3-yl)methyl)-4-hydroxy-1-methyl-5-oxo-2,5-dihydro-1H-pyrrole-3-carboxamide;
4-hydroxy-1-methyl-N-((2'-(methylsulfonyl)biphenyl-3-yl)methyl)-5-oxo-2,5-dihydro-1H-pyrrole-3-carboxamide;
4-hydroxy-1-methyl-N-((4'-(methylsulfonamido)biphenyl-3-yl)methyl)-5-oxo-2,5-dihydro-1H-pyrrole-3-carboxamide;
N-((2'-acetamidobiphenyl-3-yl)methyl)-4-hydroxy-1-methyl-5-oxo-2,5-dihydro-1H-pyrrole-3-carboxamide;
N-((4'-(dimethylcarbamoyl)biphenyl-3-yl)methyl)-4-hydroxy-1-methyl-5-oxo-2,5-dihydro-1H-pyrrole-3-carboxamide;
4-hydroxy-1-methyl-N-((3'-(methylsulfonyl)biphenyl-3-yl)methyl)-5-oxo-2,5-dihydro-1H-pyrrole-3-carboxamide;
N-((3'-carbamoylbiphenyl-3-yl)methyl)-4-hydroxy-1-methyl-5-oxo-2,5-dihydro-1H-pyrrole-3-carboxamide;
N-((3'-(dimethylcarbamoyl)biphenyl-3-yl)methyl)-4-hydroxy-1-methyl-5-oxo-2,5-dihydro-1H-pyrrole-3-carboxamide;
4-hydroxy-1-methyl-N-((4'-(methylsulfonamidomethyl)biphenyl-3-yl)methyl)-5-oxo-2,5-dihydro-1H-pyrrole-3-carboxamide;
4-hydroxy-1-methyl-N-((3'-(methylsulfonamidomethyl)biphenyl-3-yl)methyl)-5-oxo-2,5-dihydro-1H-pyrrole-3-carboxamide;
N-((4'-(acetamidomethyl)biphenyl-3-yl)methyl)-4-hydroxy-1-methyl-5-oxo-2,5-dihydro-1H-pyrrole-3-carboxamide;
N-((3'-(acetamidomethyl)biphenyl-3-yl)methyl)-4-hydroxy-1-methyl-5-oxo-2,5-dihydro-1H-pyrrole-3-carboxamide;
4-hydroxy-1-methyl-5-oxo-N-((3'-sulfamoylbiphenyl-3-yl)methyl)-2,5-dihydro-1H-pyrrole-3-carboxamide;
(R)-N-(1-(2',4'-dichlorobiphenyl-3-yl)ethyl)-4-hydroxy-1-methyl-5-oxo-2,5-dihydro-1H-pyrrole-3-carboxamide;
(R)-N-(1-(4'-chlorobiphenyl-3-yl)ethyl)-4-hydroxy-1-methyl-5-oxo-2,5-dihydro-1H-pyrrole-3-carboxamide;
(R)-N-(1-(3',5'-dichlorobiphenyl-3-yl)ethyl)-4-hydroxy-1-methyl-5-oxo-2,5-dihydro-1H-pyrrole-3-carboxamide;
(R)-4-hydroxy-1-methyl-5-oxo-N-(1-(3'-(trifluoromethyl)biphenyl-3-yl)ethyl)-2,5-dihydro-1H-pyrrole-3-carboxamide;
(R)-N-(1-(3'-fluorobiphenyl-3-yl)ethyl)-4-hydroxy-1-methyl-5-oxo-2,5-dihydro-1H-pyrrole-3-carboxamide;
(R)-4-hydroxy-1-methyl-5-oxo-N-(1-(3-(pyridin-3-yl)phenyl)ethyl)-2,5-dihydro-1H-pyrrole-3-carboxamide;
(R)-4-hydroxy-1-methyl-5-oxo-N-(1-(3-(pyridin-4-yl)phenyl)ethyl)-2,5-dihydro-1H-pyrrole-3-carboxamide;
(R)-N-(1-(3',4'-dichlorobiphenyl-3-yl)ethyl)-4-hydroxy-1-methyl-5-oxo-2,5-dihydro-1H-3-carboxamide;
(R)-N-(1-(3'-cyanobiphenyl-3-yl)ethyl)-4-hydroxy-1-methyl-5-oxo-2,5-dihydro-1H-pyrrole-3-carboxamide;
(R)-4-hydroxy-1-methyl-5-oxo-N-(1-(3 '-(trifluoromethoxy)biphenyl-3-yl)ethyl)-2,5-dihydro-1H-pyrrole-3-carboxamide;
(R)-4-hydroxy-1-methyl-5-oxo-N-(1-(2'-(trifluoromethoxy)biphenyl-3-yl)ethyl)-2,5-dihydro-1H-pyrrole-3-carboxamide;
(R)-4-hydroxy-1-methyl-N-(1-(4'-(methylsulfonyl)biphenyl-3-yl)ethyl)-5-oxo-2,5-dihydro-1H-pyrrole-3-carboxamide;
(R)-N-(1-(4'-acetamidobiphenyl-3-yl)ethyl)-4-hydroxy-1-methyl-5-oxo-2,5-dihydro-1H-pyrrole-3-carboxamide;
(R)-4-hydroxy-1-methyl-N-(1-(4'-(methylsulfonamido)biphenyl-3-yl)ethyl)-5-oxo-2,5-dihydro-1H-pyrrole-3-carboxamide;
(R)-N-(1-(4'-(dimethylcarbamoyl)biphenyl-3-yl)ethyl)-4-hydroxy-1-methyl-5-oxo-2,5-dihydro-1H-pyrrole-3-carboxamide;
(R)-N-(1-(3'-carbamoylbiphenyl-3-yl)methyl)-4-hydroxy-1-methyl-5-oxo-2,5-dihydro-1H-pyrrole-3-carboxamide;
(R)-N-(1-(4'-(acetamidomethyl)biphenyl-3-yl)ethyl)-4-hydroxy-1-methyl-5-oxo-2,5-dihydro-1H-pyrrole-3-carboxamide;

(R)-N-(1-(2',6'-dimethylbiphenyl-3-yl)ethyl)-4-hydroxy-1-methyl-5-oxo-2,5-dihydro-1H-pyrrole-3-carboxamide;
(R)-ethyl 3'-(1-(4-hydroxy-1-methyl-5-oxo-2,5-dihydro-1H-pyrrole-3-carboxamido)ethyl)biphenyl-3-carboxylate;
(R)-4-hydroxy-1-methyl-5-oxo-N-(1-(3'-(trimethylsilyl)biphenyl-3-yl)ethyl)-2,5-dihydro-1H-pyrrole-3-carboxamide;
(R)-N-(1-(3-(3-chloropyridin-4-yl)phenyl)ethyl)-4-hydroxy-1-methyl-5-oxo-2,5-dihydro-1H-pyrrole-3-carboxamide;
(R)-N-(1-(3'-chloro-4'-(trifluoromethyl)biphenyl-3-yl)ethyl)-4-hydroxy-1-methyl-5-oxo-2,5-dihydro-1-pyrrole-3-carboxamide;
(R)-N-(1-(4'-fluoro-2'-hydroxybiphenyl-3-yl)ethyl)-4-hydroxy-1-methyl-5-oxo-2,5-dihydro-1H-pyrrole-3-carboxamide
(R)-N-(1-(3-(tert-butylcarbamoyl)biphenyl-3-yl)ethyl)-4-hydroxy-1-methyl-5-oxo-2,5-dihydro-1H-pyrrole-3-carboxamide;
(R)-N-(1-(3-(4,6-dichloropyridin-3-yl)phenyl)ethyl)-4-hydroxy-1-methyl-5-oxo-2,5-dihydro-1H-pyrrole-3-carboxamide;
(R)-N-(1-(4'-(N-cyclopropylsulfamoyl)biphenyl-3-yl)ethyl)-4-hydroxy-1-methyl-5-oxo-2,5-dihydro-1H-pyrrole-3-carboxamide;
(R)-4-hydroxy-1-methyl-N-(1-(3-(2-methylpyridin-4-yl)phenyl)ethyl)-5-oxo-2,5-dihydro-1H-pyrrole-3-carboxamide;
(R)-N-1-2'-chloro-6'-(trifluoromethyl)biphenyl-3-yl)ethyl)-4-hydroxy-1-methyl-5-oxo-2,5-dihydro-1H-pyrrole-3-carboxamide;
(R)-N-(1-(3-(2,4-dimethylthiazol-5-yl)phenyl)ethyl)-4-hydroxy-1-methyl-5-oxo-2,5-dihydro-1H-pyrrole-3-carboxamide;
(R)-4-hydroxy-1-methyl-N-(1-(3-(1-methyl-1H-imidazol-5-yl)phenyl)ethyl)-5-oxo-2,5-dihydro-1H-pyrrole-3-carboxamide;
(R)-N-(1-(3-(1H-pyrazol-4-yl)phenyl)ethyl)-4-hydroxy-1-methyl-5-oxo-2,5-dihydro-1H-pyrrole-3-carboxamide;
(R)-4-hydroxy-1-methyl-N-(1-(3-(1-methyl-1H-pyrazol-5-yl)phenyl)ethyl)-5-oxo-2,5-dihydro-1H-pyrrole-3-carboxamide;
N-(3-(6-chloropyridin-3-yl)benzyl)-4-hydroxy-1-methyl-5-oxo-2,5-dihydro-1H-pyrrole-3-carboxamide;
methyl 3'((4-hydroxy-1-methyl-5-oxo-2,5-dihydro-1H-pyrrole-3carboxamido)methyl)biphenyl-3-carboxylate;
(R)-N-(1-(3'-carbamoylbiphenyl-3-yl)ethyl)-1-(2,4-difluorophenyl)-4-hydroxy-5-oxo-2,5-dihydro-1H-pyrrole-3-carboxamide;
N-(biphenyl-4-ylmethyl)-4-hydroxy-1-methyl-5-oxo-2,5-dihydro-1H-pyrrole-3-carboxamide;
(S)-N-1-4'-fluorobiphenyl -3yl)ethyl 4hydroxy-1-methyl-5-oxo-2,5-dihydro-1H-pyrrole-3-carboxamide;
(S)-N-(1-(biphenyl-3-yl)ethyl)-4-hydroxy-1-methyl-5-oxo-2,5-dihydro-1H-pyrrole-3-carboxamide;
(E)-4-hydroxy-1-methyl-5-oxo-N-(3-styrylbenzyl)-2,5-dihydro-1H-pyrrole-3-carboxamide;
N-(3-(5-chlorothiophen-2-yl)benzyl)-4-hydroxy-1-methyl-5-oxo-2,5-dihydro-1H-pyrrole-3-carboxamide;
4-hydroxy-N-(3-(2-methoxypyridin-3-yl)benzyl)-1-methyl-5-oxo-2,5-dihydro-1H-pyrrole-3-carboxamide;
N-((4'-cyanobiphenyl-3-yl)methyl)-4-hydroxy-1-methyl-5-oxo-2,5-dihydro-1H-pyrrole-3-carboxamide;
4-hydroxy-N-(3-(6-methoxypyridin-3-yl)benzyl)-1-methyl-5-oxo-2,5-dihydro-1H-pyrrole-3-carboxamide;
1-(2,4-difluorophenyl)-4-hydroxy-(6-methoxy-2,3-dihydro-1H-inden-1-yl)-5-oxo-2,5-dihydro-1H-pyrrole-3-carboxamide;
1-(2,4-difluorophenyl)-4-hydroxy-5-oxo-N-cis-(4-phenylcyclohexyl)-2,5-dihydro-1H-pyrrole-3-carboxamide;
(R)-1-(2,4-difluorophenyl)-4-hydroxy-5-oxo-N-(1,2,3,4-tetrahydronaphthalen-1-yl)-2,5-dihydro-1H-pyrrole-3-carboxamide;
1-(2,4-difluorophenyl)-N-(((1R,2R)-2-(4-fluorophenyl)cyclopropyl)methyl)-4-hydroxy-5-oxo-2,5-dihydro-1H-pyrrole-3-carboxamide;
1-(2,4-difluorophenyl)-N-(2,3-dihydro-1H-inden-2-yl)-4-hydroxy-5-oxo-2,5-dihydro-1H-pyrrole-3-carboxamide;
N-(7-bromo-1,2,3,4-tetrahydronaphthalen-1-yl)-1-ethyl-4-hydroxy-5-oxo-2,5-dihydro-1H-pyrrole-3-carboxamide;
N-(7-bromo-1,2,3,4-tetrahydronaphthalen-1-yl)-1-(2,4-difluorophenyl)-4-hydroxy-5-oxo-2,5-dihydro-1H-pyrrole-3-carboxamide;
(R)-1-ethyl-4-hydroxy-5-oxo-N-(6-(trifluoromethyl)-2,3-dihydro-1H-inden-1-yl)-2,5-dihydro-1H-pyrrole-3-carboxamide;
(R)-N-(4-bromo-2,3-dihydro-1H-inden-1-yl)-1-ethyl-4-hydroxy-5-oxo-2,5-dihydro-1H-pyrrole-3-carboxamide;
(R)-N-(5-bromo-2,3-dihydro-1H-inden-1-yl)-1-ethyl-4-hydroxy-5-oxo-2,5-dihydro-1H-pyrrole-3-carboxamide;
(R)-N-(6-bromo-2,3-dihydro-1H-inden-1-yl)-1-ethyl-4-hydroxy-5-oxo-2,5-dihydro-1H-pyrrole-3-carboxamide;
1-ethyl-4-hydroxy-5-oxo-N-((1R)-4-phenyl-1,2,3,4-tetrahydronaphthalen-1-yl)-2,5-dihydro-1H-pyrrole-3-carboxamide;
1-ethyl-4-hydroxy-5-oxo-N-(cis-4-phenylcyclohexyl)-2,5-dihydro-1H-pyrrole-3-carboxamide;
4-hydroxy-5-oxo-N-(cis-4-phenylcyclohexyl 1)-1-(2,2,2-trifluoroethyl)-2,5-dihydro-1H-pyrrole-3-carboxamide;
N-(cis-4-(3,4-dichlorophenyl)cyclohexyl)-4-hydroxy-5-oxo-1-(2,2,2-trifluoroethyl)-2,5-dihydro-1H-pyrrole-3-carboxamide;
N-(trans-4-(4-fluorophenyl)-4-hydroxycyclohexyl)-4-hydroxy-5-oxo-1-(2,2,2-trifluoroethyl)-2,5-dihydro-1H-pyrrole-3-carboxamide;
N-(trans-4-cyano-4-(3,4-dichlorophenyl)cyclohexyl)-4-hydroxy-5-oxo-1-(2,2,2-trifluoroethyl)-2,5-dihydro-1H-pyrrole-3-carboxamide;
(R)-4-hydroxy-5-oxo-1-(2,2,2-trifluoroethyl)-N4-(trifluoromethyl)-2,3-dihydro-1H-inden-1-yl)-2,5-dihydro-1H-pyrrole-3-carboxamide;
(R)-1-(2,4-difluorophenyl)-N-(2,3-dihydro-1H-inden-1-yl)-4-hydroxy-5-oxo-2,5-dihydro-1H-pyrrole-3-carboxamide;
N-((1-(3,4-dichlorobenzoyl)piperidin-4-yl)methyl)-4-hydroxy-1-methyl-5-oxo-2,5-dihydro-1H-pyrrole-3-carboxamide;
4-hydroxy-1-methyl-5-oxo-N-(cis-4-(3-(trifluoromethoxy)phenyl)cyclohexyl)-2,5-dihydro-1H-pyrrole-3-carboxamide;
(R)-4-hydroxy-1-methyl-5-oxo-N-(1,2,3,4-tetrahydronaphthalen-1-yl)-2,5-dihydro-1-H-pyrrole-3-carboxamide;

N-(cis-4-(3,4-dichlorophenyl)cyclohexyl)-4-hydroxy-1-methyl-5-oxo-2,5-dihydro-1H-pyrrole-3-carboxamide;
4-hydroxy-1-methyl-5-oxo-N-(cis-4-phenylcyclohexyl)-2,5-dihydro-1H-pyrrole-3-carboxamide;
4-hydroxy-1-methyl-N-(cis-4-(4-methyl-3-(trifluoromethyl)phenyl)cyclohexyl)-5-oxo-2,5-dihydro-1H-pyrrole-3-carboxamide;
4-hydroxy-5-oxo-N-(cis-4-phenylcyclohexyl)-1-(3,3,3-trifluoropropyl)-2,5-dihydro-1H-pyrrole-3-carboxamide;
N-(chroman-4-yl)-4-hydroxy-5-oxo-1-(2,2,2-trifluoroethyl)-2,5-dihydro-1H-pyrrole-3-carboxamide;
N-(2,2-dimethylchroman-4-yl)-4-hydroxy-5-oxo-1-(4,4,4-trifluorobutyl)-2,5-dihydro-1H-pyrrole-3-carboxamide;
4-hydroxy-N-(cis-4-(4-methyl-3-(trifluoromethyl)phenyl)cyclohexyl)-5-oxo-1-(4,4,4-trifluorobutyl)-2,5-dihydro-1H-pyrrole-3-carboxamide;
N-(cis-4-(3,4-dichlorophenyl)cyclohexyl)-4-hydroxy-5-oxo-1-(4,4,4-trifluorobutyl)-2,5-dihydro-1H-pyrrole-3-carboxamide;
4-hydroxy-5-oxo-N-(cis-4-phenylcyclohexyl)-1-(4,4,4-trifluorobutyl)-2,5-dihydro-1H-pyrrole-3-carboxamide;
4-hydroxy-5-oxo-1-(2,2,3,3,3-pentafluoropropyl)-N4 cis-4-phenylcyclohexyl)-2,5-dihydro-1H-pyrrole-3-carboxamide;
4-hydroxy-5-oxo-N-(cis-4-phenylcyclohexyl)-1-(2-(2,2,2-trifluoroethoxy)ethyl)-2,5-dihydro-1H-pyrrole-3-carboxamide;
(R)-4-hydroxy-5-oxo-1-(4,4,4-trifluorobutyl)-N-(6-(trifluoromethyl)-2,3-dihydro-1H-inden-1-yl)-2,5-dihydro-1H-pyrrole-3-carboxamide;
4-hydroxy-5-oxo-N-(cis-4-phenylcyclohexyl)-1-(2-(phenylsulfonyl)ethyl)-2,5-dihydro-1H-pyrrole-3-carboxamide;
4-hydroxy-1-methyl-5-oxo-N-((3S)-3-phenylcyclopentyl)-2,5-dihydro-1H-pyrrole-3-carboxamide;
4-hydroxy-1-methyl-5-oxo-N-((3S)-3-phenylcyclopentyl)-2,5-dihydro-1H-pyrrole-3-carboxamide;
N-((3S)-3-(3,4-dichlorophenyl)cyclopentyl)-4-hydroxy-1-methy 1-5-oxo-2,5-dihydro-1H-pyrrole-3-carboxamide;
N-((3S)-3-(3,4-dichlorophenyl)cyclopentyl)-4-hydroxy-1-methyl-5-oxo-2,5-dihydro-1H-pyrrole-3-carboxamide;
1-(1-(4-fluorophenyl)piperidin-4-yl)-4-hydroxy-5-oxo-N-(cis-4-phenylcyclohexyl)-2,5-dihydro-1H-pyrrole-3-carboxamide;
1-(2-(4-chloro-1H-pyrazol-1-yl)ethyl)-4-hydroxy-5-oxo-N-(cis-4-phenylcyclohexyl)-2,5-dihydro-1H-pyrrole-3-carboxamide;
4-hydroxy-1-(3-(methylamino)propyl)-5-oxo-N-(cis-4-phenylcyclohexyl)-2,5-dihydro-1H-pyrrole-3-carboxamide;
4-hydroxy-1-(3-(isopropylamino)propyl)-5-oxo-N-(cis-4-phenylcyclohexyl)-2,5-dihydro-1H-pyrrole-3-carboxamide;
4-hydroxy-5-oxo-N-((1S,4R)-4-phenylcyclohexyl)-1(S)-6-(trifluoromethyl)-2,3 -dihydro-1H-inden-1-yl)-2,5-dihydro-1H-pyrrole-3-carboxamide;
4-hydroxy-5-oxo-N-(cis-4-phenylcyclohexyl)-1((R)-6-(trifluoromethyl)-2,3-dihydro-1H-inden-1-yl)-2,5-dihydro-1H-pyrrole-3-carboxamide;
4-hydroxy-5-oxo-1-(3-(2-oxopyrrolidin-1yl)propyl)-N-(cis-4-phenylcyclohexyl)-2,5-dihydro-1H-pyrrole-3-carboxamide;
ethyl 4-(3-hydroxy-2-oxo-4-(cis-4-phenylcyclohexylcarbamoyl)-2,5-dihydro-1H-pyrrol-1-yl)piperidine-1-carboxylate;
1-(1-benzylpiridin-4-yl)-4-hydroxy-5-oxo-N-(cis-4-phenylcyclohexyl)-2,5-dihydro-1H-pyrrole-3-carboxamide;
1-(2-amino-2-oxo-1-phenylethyl)-4-hydroxy-5-oxo-N-(cis-4-phenylcyclohexyl)-2,5-dihydro-1H-pyrrole-3-carboxamide;
1-(2-(ethyl(m-tolyl)amino)ethyl)-4-hydroxy-5-oxo-N-(cis-4-phenylcyclohexyl 1)-2,5-dihydro-1H-pyrrole-3-carboxamide;
((1S,2R)-2-carbamoycyclopenty)-4-oxo-N-hydroxy-5-oxo-N((1S,4R)-4-phenylcyclohexyl)-2,5-dihydro-1H-1-pyrrole-3-carboxamide;
1(2-(1,1-dioxidothiomorpholin-4-yl)ethyl)-4-hydroxy-5-oxo-N-(cis-4-phenylcyclohexyl)-2,5-dihydro-1H-pyrrole-3-carboxamide;
1-(3-(1,1-dioxidothiomorpholin-4-yl)propyl)-4-hydroxy-5-oxo-N-(cis-4-phenylcyclohexyl)-2,5-dihydro-1H-pyrrole-3-carboxamide;
4-hydroxy-1-(2-(isopropylamino)-2-oxoethyl)-5-oxo-N-(cis-4-phenylcyclohexyl)-2,5-dihydro-1H-pyrrole-3-carboxamide;
4-hydroxy-1-(2-morpholino-2-oxoethyl)-5-oxo-N4cis-4-phenylcyclohexyl)-2,5-dihydro-1H-pyrrole-3-carboxamide;
4-hydroxy-1-(3-(N-methylmethylsulfonamido)propyl)-5-oxo-N-(cis-4-phenylcyclohexy 1)-2,5-dihydro-1H-pyrrole-3-carboxamide;
4-hydroxy-1-(1-methyl-5-oxopyrrolidin-3-yl)-5-oxo-N-(cis-4-phenylcyclohexyl)-2,5-dihydro-1H-pyrrole-3-carboxamide;
4-hydroxy-1-(2-(methylsulfonamido)ethyl)-5-oxo-N-(cis-4-phenylcyclohexyl)-2,5-dihydro-1H-pyrrole-3-carboxamide;
1-(2-(3-chloro-5-(trifluoromethyl)pyridin-2-ylamino)ethyl)-4-hydroxy-5-oxo-N-(cis-4-phenylcyclohexyl)-2,5-dihydro-1H-pyrrole-3-carboxamide;
1-(2-(4-chlorophenylamino)ethyl)-4-hydroxy-5-oxo-N-(cis-4-phenylcyclohexyl)-2,5-dihydro-1H-pyrrole-3-carboxamide;
1-((S)-1-amino-1-oxo-3-phenylpropan-2-yl)-4-hydroxy-5-oxo-N-((1S,4R)-4-phenylcyclohexyl)-2,5-dihydro-1H-pyrrole-3-carboxamide;
4-hydroxy-1-(2-(naphthalen-2-ylamino)-2-oxoethyl)-5-oxo-N-(cis-4-phenylcyclohexyl)-2,5-dihydro-1H-pyrrole-3-carboxamide;
1-(2-(4-chlorobenzamido)ethyl)-4-hydroxy-5-oxo-N-(cis-4-phenylcyclohexyl)-2,5-dihydro-1H-pyrrole-3-carboxamide;
4-hydroxy-1-(2-(4-methylphenylsulfonamido)ethyl)-5-oxo-N-(cis-4-phenylcyclohexyl)-2,5-dihydro-1H-pyrrole-3-carboxamide;
1-((R)-1-amino-4-methyl-1-oxopentan-2-yl)-4-hydroxy-5-oxo-N-(cis-4-phenylcyclohexyl)-2,5-dihydro-1H-pyrrole-3-carboxamide;
4-hydroxy-5-oxo-N-(cis-4-phenylcyclohexyl)-1-(2-(5-(trifluoromethyl)pyridin-2-ylamino)ethyl)-2,5-dihydro-1H-pyrrole-3-carboxamide;
4-hydroxy-5-oxo-1-(3-oxo-3-(pyrrolidin-1-yl)propyl)-N-(cis-4-phenylcyclohexyl)-2,5-dihydro-1H-pyrrole-3-carboxamide;
isopropyl 4-(3-hydroxy-2-oxo-4-(cis-4-phenylcyclohexylcarbamoyl)-2,5-dihydro-1H-pyrrol-1-yl)piperidine-1-carboxylate;

4-hydroxy-1-(1-isobutyrylpiperidin-4-yl)-5-oxo-N-(cis-4-phenylcyclohexyl)-2,5dihydro-1H-pyrrole-3-carboxamide;

benzyl 2-(3-hydroxy-2-oxo-4-phenylcyclohexylcarbamoyl)-2,5-dihydro-1H-pyrrol-1-yl)ethylcarbamate;

4-hydroxy-1-(2-(methyl(phenyl)amino)ethyl)-5-oxo-N-(cis-4-phenylcyclohexyl)-2,5-dihydro-1H-pyrrole-3-carboxamide;

2-Hydroxy-3-oxo-N-(cis-4-phenylcyclohexyl)-3,5,6,7,8,8a-hexahydroindolizine-1-carboxamide;

2-Hydroxy-3-oxo-N-((R)-6-(trifluoromethyl)-2,3-dihydro-1H-inden-1-yl)-3,5,6,7,8,8a-hexahydroindolizine-1-carboxamide 1-(2,4-difluorophenyl)-4-hydroxy-5-oxo-N-(7-phenyl-1,2,3,4-tetrahydronaphthalen-1-yl)-2,5-dihydro-1H-pyrrole-3-carboxamide;

(R)-1-ethyl-4-hydroxy-5-oxo-N-(4-phenyl-2,3-dihydro-1H-inden-1-yl)-2,5-dihydro-1H-pyrrole-3-carboxamide;

(R)-1-ethyl-4-hydroxy-5-oxo-N-(5-phenyl-2,3-dihydro-1H-inden-1-yl)-2,5-dihydro-1H-pyrrole-3-carboxamide;

(R)-1-ethyl-4-hydroxy-5-oxo-N-(6-phenyl-2,3-dihydro-1H-inden-1-yl)-2,5-dihydro-1H-pyrrole-3-carboxamide;

N-(4-benzoylbenzyl)-4-hydroxy-1-methyl-5-oxo-2,5-dihydro-1H-pyrrole-3-carboxamide;

N-(3-(biphenyl-3-yloxy)propyl)-4-hydroxy-1-methyl-5-oxo-2,5-dihydro-1H-pyrrole-3-carboxamide;

N-(3-(biphenyl-4-yloxy)propyl)-4-hydroxy-1-methyl-5-oxo-2,5-dihydro-1H-pyrrole-3-carboxamide, or a stereoisomer, a tautomer, or a pharmaceutically acceptable salt thereof.

7. A pharmaceutical composition, comprising: a pharmaceutically acceptable carrier and a compound of claim 1.

* * * * *